(12) United States Patent
Cázares-Körner et al.

(10) Patent No.: US 12,338,226 B2
(45) Date of Patent: *Jun. 24, 2025

(54) SUBSTITUTED BENZODIAZOLES AND USE THEREOF IN THERAPY

(71) Applicant: THOMAS HELLEDAYS STIFTELSE FÖR MEDICINSK FORSKNING, Stockholm (SE)

(72) Inventors: Armando Cázares-Körner, Johanneshov (SE); Thomas Helleday, Danderyd (SE); Torkild Visnes, Trondheim (NO); Olov Wallner, Solna (SE); Tobias Koolmeister, Stockholm (SE)

(73) Assignee: THOMAS HELLEDAYS STIFTELSE FOR MEDICINSK FORSKNING, Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 18/614,086

(22) Filed: Mar. 22, 2024

(65) Prior Publication Data

US 2024/0287020 A1    Aug. 29, 2024

Related U.S. Application Data

(63) Continuation of application No. 16/975,130, filed as application No. PCT/EP2019/055178 on Mar. 1, 2019, now Pat. No. 11,970,474.

(60) Provisional application No. 62/636,983, filed on Mar. 1, 2018.

(51) Int. Cl.

| *C07D 401/04* | (2006.01) |
|---|---|
| *A61K 45/06* | (2006.01) |
| *A61P 35/00* | (2006.01) |
| *C07D 235/26* | (2006.01) |
| *C07D 401/14* | (2006.01) |
| *C07D 403/04* | (2006.01) |
| *C07D 405/14* | (2006.01) |
| *C07D 413/12* | (2006.01) |
| *C07D 471/04* | (2006.01) |
| *C07D 471/08* | (2006.01) |
| *C07D 487/04* | (2006.01) |

(52) U.S. Cl.
CPC ............ *C07D 401/04* (2013.01); *A61P 35/00* (2018.01); *C07D 235/26* (2013.01); *C07D 401/14* (2013.01); *C07D 403/04* (2013.01); *C07D 405/14* (2013.01); *C07D 413/12* (2013.01); *C07D 471/04* (2013.01); *C07D 471/08* (2013.01); *C07D 487/04* (2013.01); *A61K 45/06* (2013.01)

(58) Field of Classification Search
CPC .. C07D 401/04; C07D 401/14; C07D 235/26; C07D 405/14; C07D 413/12; C07D 471/04; C07D 471/08; A61K 45/06
See application file for complete search history.

(56) References Cited

U.S. PATENT DOCUMENTS

| 9,018,222 B2 | 4/2015 | Buschmann et al. |
| 2003/0073842 A1 | 4/2003 | Urbanski et al. |
| 2008/0058376 A1 | 3/2008 | Gross et al. |

FOREIGN PATENT DOCUMENTS

| WO | 2002055514 A2 | 7/2002 |
| WO | 2006114706 A1 | 11/2006 |
| WO | 2007076055 A2 | 7/2007 |
| WO | 2017011384 A1 | 1/2017 |

OTHER PUBLICATIONS

Nitta et al. Discovery and structure-activity relationships of urea derivatives as potent and novel CCR3 antagonists. Bioorganic & Medicinal Chemistry Letters, vol. 22, 4951-4954. (Year: 2012).*
International Search Report and Written Opinion for International Application No. PCT/EP2019/055178 dated Apr. 26, 2019.
Bacsi et al., "Down-regulation of 8-oxoguanine DNA glycosylase 1 expression in the airway epithelium ameliorates allergic lung inflammation," Elsevier, DNA Repair, 2013, pp. 18-26.

(Continued)

*Primary Examiner* — Sikarl A Witherspoon
(74) *Attorney, Agent, or Firm* — Renner, Otto, Boisselle & Sklar, LLP

(57) ABSTRACT

There is provided herein a compound of formula I

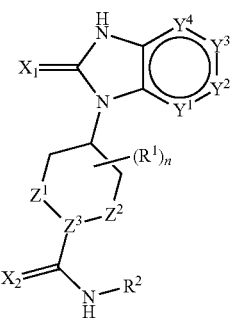

or a pharmaceutically acceptable salt thereof, wherein $R^1$, $R^2$, $X^1$, $X^2$, $Y^1$ to $Y^4$, $Z^1$ to $Z^3$, and n have meanings provided in the description.

20 Claims, 7 Drawing Sheets
Specification includes a Sequence Listing.

(56) References Cited

OTHER PUBLICATIONS

Klungland et al., "Accumulation of premutagenic DNA lesions in mice defective in removal of oxidative base damage," PNAS, Nov. 9, 1999, vol. 96, No. 23.
Lee et al., "Ras Proteins Induce Senescence by Altering the Intracellular Levels of Reactive Oxygen Species," The Journal of Biochemical Chemistry, vol. 274, No. 12, Issue of Mar. 19, 1999, pp. 7936-7940.
Malayappan et al., "Urinary analysis of 8-oxoguanine, 8-oxoguanosine, fapy-guanine and 8-oxo-2'-deoxyguanosine by high-performance liquid chromatography-electrospray tandem mass spectrometry as a measure of oxidative stress," Elsevier, Journal of Chromatography A, 1167 (2007) pp. 54-62.
Hasbal et al., "DNA damage and glutathione level in children with asthma bronchiale: Effect of antiasthmatic therapy," Pediatric Allergy and Immunology 2010: 21: e674-e678 DOI: 10.1111/j. 1399-3038. 2009.00959.x.
Nathan et al., "Beyond oxidative stress: an immunologist's guide to reactive oxygen species," Nat Rev Immunol. May 2013 ; 13(5): 349-361. doi: 10.1038/nri3423.
Touati et al., "Deficiency in OGG1 Protects against Inflammation and Mutagenic Effects Associated with H. pylori Infection in Mouse," 2006 Blackwell Publishing Ltd, Helicobacter 11: 494-505; Helicobacter ISSN 1523-5378.
Deslee et al., "Oxidative Damage to Nucleic Acids in Severe Emphysema," Chest 2009; 135: 965-974.
Li et al, "8-Oxoguanine-DNA glycosylase 1 deficiency modifies allergic airway inflammation by regulating STAT6 and IL-4 in cells and in mice," Elsevier, Free Radical Biology & Medicine 52 (2012) 392-401.
Krokan et al, "Base Excision Repair," Cold Spring Harb Perspect Biol 2013;5:a012583.
Huang et al, "MIR-4673 Modulates Paclitaxel-Induced Oxidative Stress and Loss of Mitochondrial Membrane Potential by Targeting 8-Oxoguanine-DNA Glycosylase-1," Cellular Pellular Physiology and Biochemistry, 2017;42:889-900, DOI: 10.1159/000478644 Published online: Jun. 26, 2017.
Mabley et al, "Potential role for 8-oxoguanine DNA glycosylase in regulating inflammation," The FASEB Journal express article 10.1096/fj.04-2278fje. Published online Dec. 1, 2004.
Jacob et al., "Markers of Oxidant Stress that are Clinically Relevant in Aging and Age-related Disease," Mech Ageing Dev. Mar. 2013 ; 134(0): 139-157. doi: 10.1016/j.mad.2013.02.008.
Kettle et al, "Potent and Selective Inhibitors of MTH1 Probe Its Role in Cancer Cell Survival," Journal of Medicinal Chemistry, 2016, 59, 2346-2361, DOI: 10.1021/acs.jmedchem.5b01760.
Aguilera-Aguirre, "Innate Inflammation Induced by the 8-Oxoguanine DNA Glycosylase-1-KRAS-NF-κB Pathway," The Journal of Immunology, 2014; 193:4643-4653; Prepublished online Sep. 29, 2014;doi: 10.4049/jimmunol.1401625http://www.jimmunol.org/content/193/9/4643.
Pan et al., "Oxidized Guanine Base Lesions Function in 8-Oxoguanine DNA Glycosylase-1-mediated Epigenetic Regulation of Nuclear Factor κB-driven Gene Expression," The Journal of Biological Chemistry vol. 291, No. 49, p. 25553-25566, Dec. 2, 2016 , The American Society for Biochemistry and Molecular Biology, Inc.
Pan et al. "OGG1-DNA interactions facilitate NF-κB binding to DNA targets," Scientific Reports, 7:43297; DOI: 10.1038/srep43297.
Ohno et al., 8-oxoguanine causes spontaneous de novo germline mutations in mice, Scientific Reports, 4: 4689 DOI: 10.1038/srep04689.
Romanowska et al., "DNA damage, superoxide, and mutant K-ras in human lung adenocarcinoma cells," Elsevier, Free Radical Biology & Medicine 43 (2007) 1145-1155.
Donley et al., "Small Molecule Inhibitors of 8-Oxoguanine DNA Glycosylase-1 (OGG1)," ACS Chem Biol. Oct. 16, 2015; 10(10): 2334-2343. doi:10.1021/acschembio.5b00452.
Minowa et al, "Mmh/Ogg1 gene inactivation results in accumulation of 8-hydroxyguanine in mice," PNAS, Apr. 11, 2000, vol. 97, No. 8.
Vafa et al., c-Myc Can Induce DNA Damage, Increase Reactive Oxygen Species, and Mitigate p53 Function: A Mechanism for Oncogene-Induced Genetic Instability, Molecular Cell, vol. 9, 1031-1044, May 2002.
Oka et al., "Two distinct pathways of cell death triggered by oxidative damage to nuclear and mitochondrial DNAs," The EMBO Journal vol. 27, No. 2, 2008.
Igishi et al, "Elevated urinary 8-hydroxydeoxyguanosine, a biomarker of oxidative stress, and lack of association with antioxidant vitamins in chronic obstructive pulmonary disease," Respirology (2003) 8, 455-460.
Halazonetis et al, "An Oncogene-Induced DNA Damage Model for Cancer Development," Science, Mar. 7, 2008, vol. 319.
Tahara et al., "Potent and Selective Inhibitors of 8-Oxoguanine DNA Glycosylase," J Am Chem Soc. Feb. 14, 2018; 140(6): 2105-2114. doi:10.1021/jacs.7b09316.
Warpman et al., "Validation and development of MTH1 inhibitors for treatment of cancer," Annals of Oncology 00: 1-9, 2016 doi: 10.1093/annonc/mdw429.
Ba et al, "The Role of 8-Oxoguanine DNA Glycosylase-1 in Inflammation," International Journal of Molecular Sciences 2014, 15, 16975-16997; doi:10.3390/ijms150916975.
Ba et al., 8-Oxoguanine DNA Glycosylase-1 Augments Proinflammatory Gene Expression by Facilitating the Recruitment of Site-Specific Transcription Factors, The Journal of Immunology, 2014, 192:2384-2394; Prepublished online Jan. 31, 2014; doi: 10.4049/jimmunol.1302472http://www.jimmunol.org/content/192/5/2384.
Tsurudome et al., "Changes in levels of 8-hydroxyguanine in DNA, its repair and OGG1 mRNA in rat lungs after intratracheal administration of diesel exhaust particles," Carcinogenesis, vol. 20, No. 8, pp. 1573-1576, 1999.
Zhang et al., "Redox Control of the Survival of Healthy and Diseased Cells," Antioxidants & Redox Signaling, vol. 15, No. 11, 2011, Mary Ann Liebert, Inc, DOI: 10.1089/ars.2010.3685.
Ramdzan et al., "RAS Transformation Requires CUX1-Dependent Repair of Oxidative DNA Damage," PLOS Biology, 12(3): e1001807. doi: 10.1371/journal.pbio.1001807.
Ichihara et al., "Development of Self-Indicating Resin" Combinatorial Chemistry & High Throughput Screening, 2007, 10, 261-267.
Nguyen et al., Calcitonin gene-related peptide (CGRP) receptor antagonists: Investigations of a pyridinone template, Bioorganic & Medicinal Chemistry Letters, 2008, vol. 18, 755-758.

\* cited by examiner

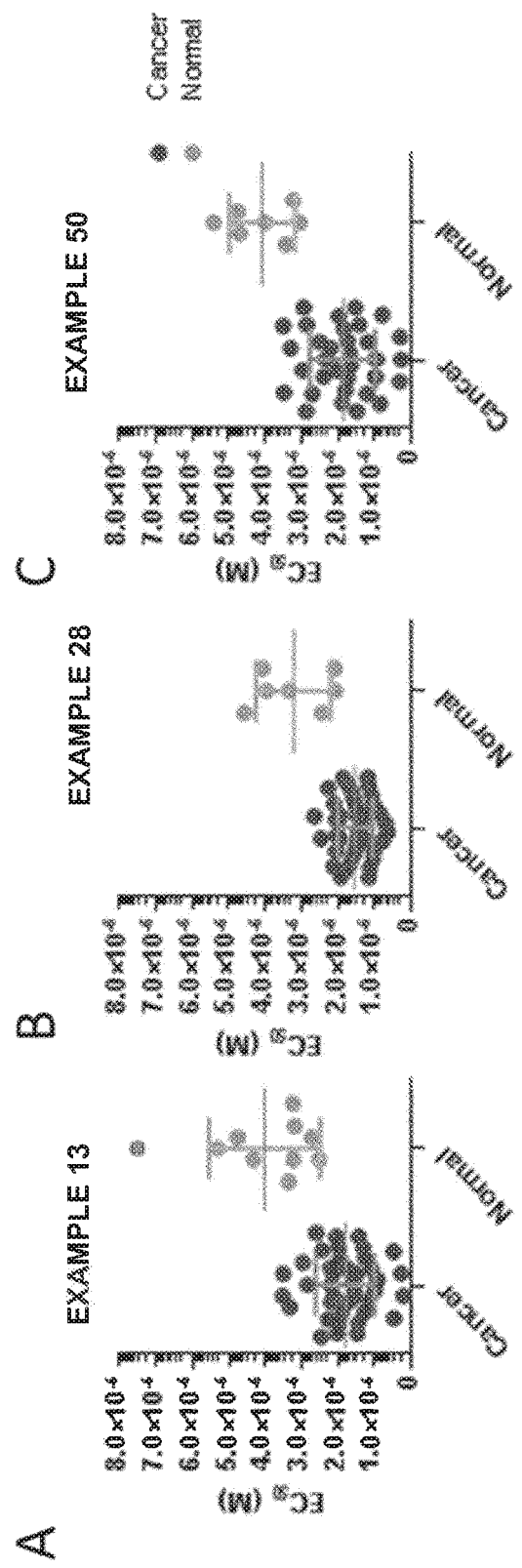
Figure 1 A to C

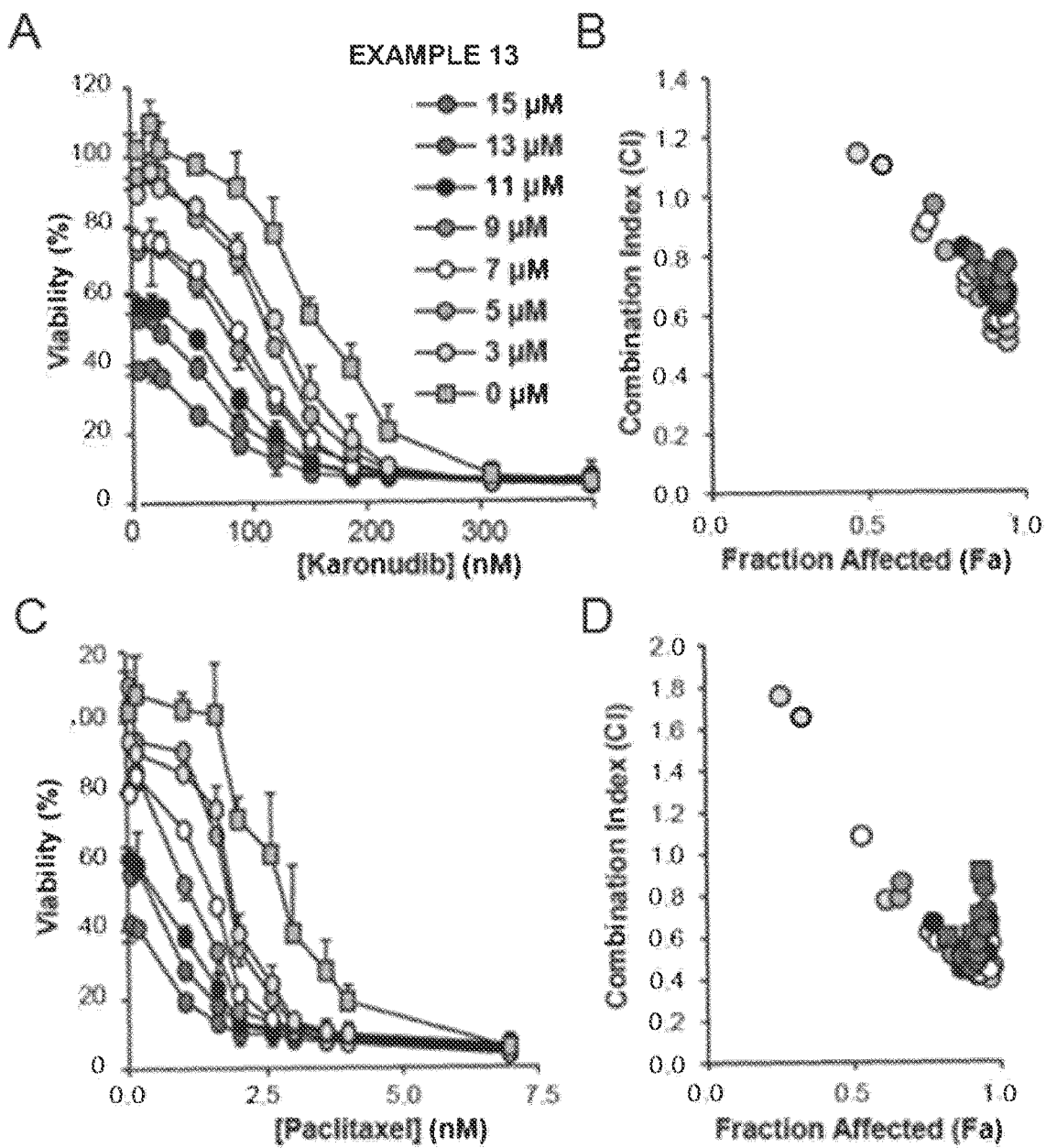
Figure 2 A to D

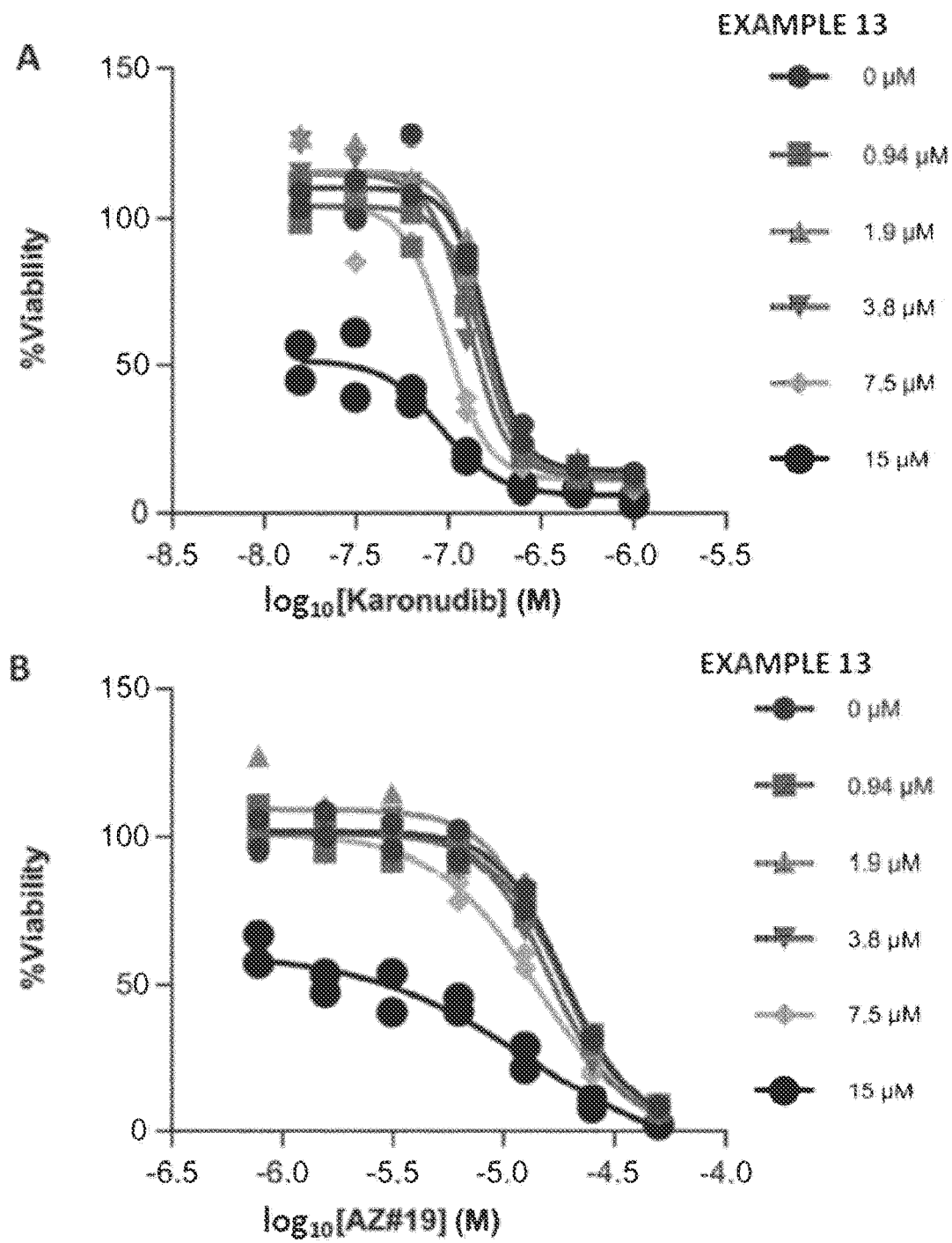
Figure 3 A and B

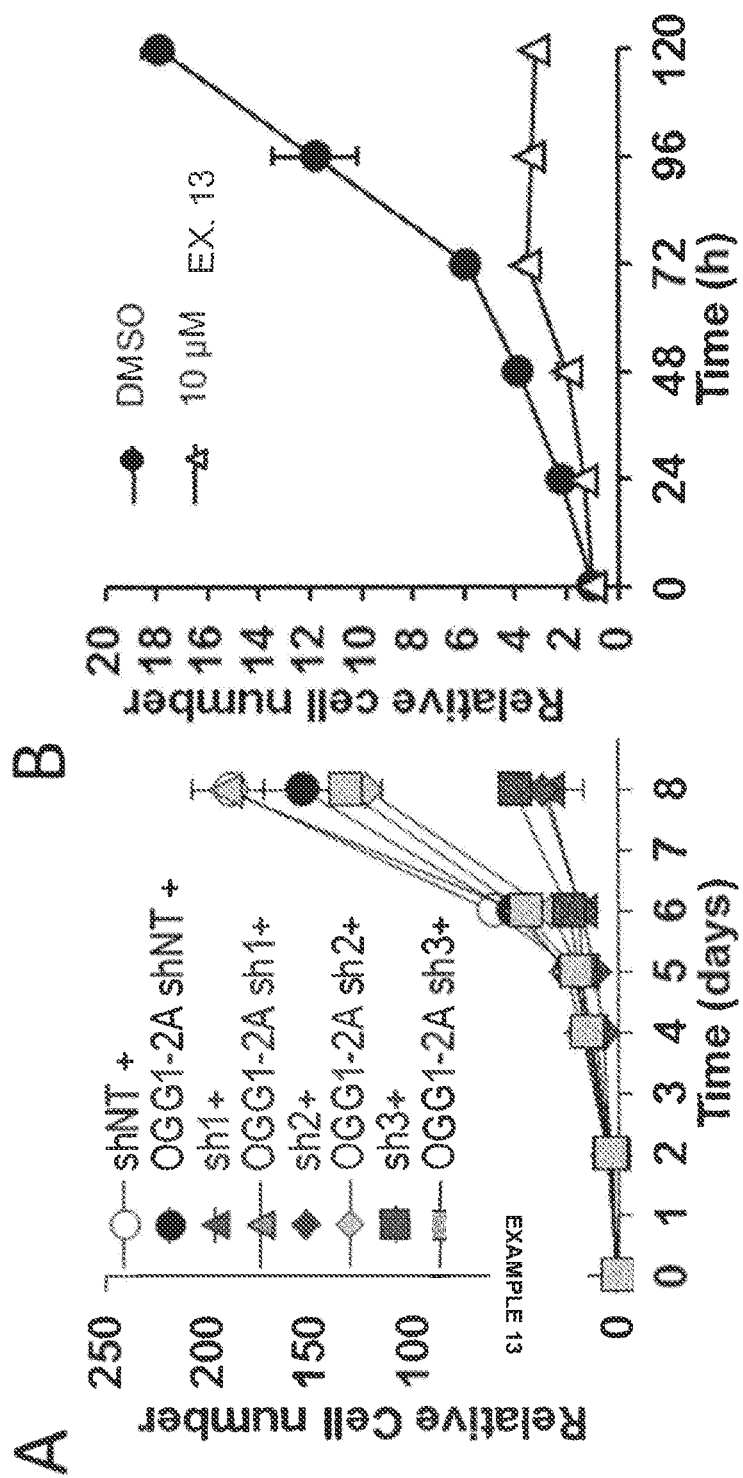
Figure 4 A and B

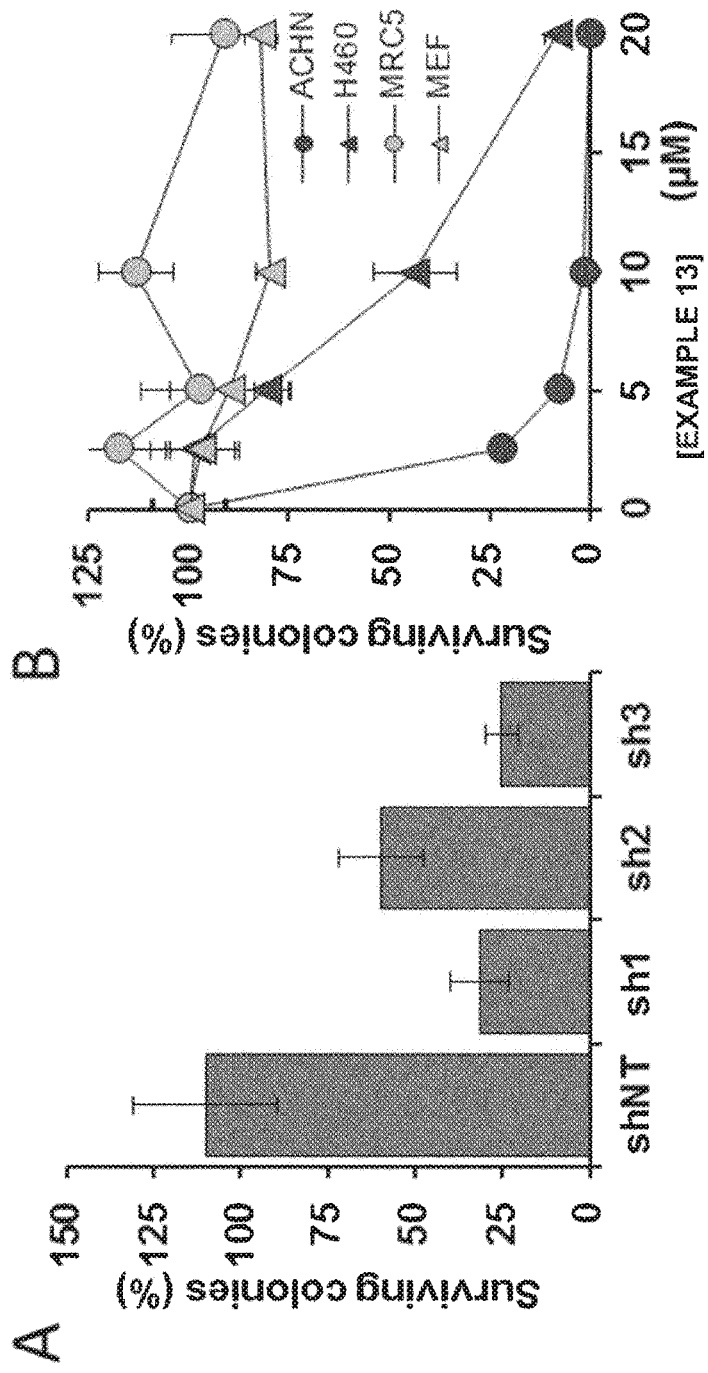
Figure 5 A and B

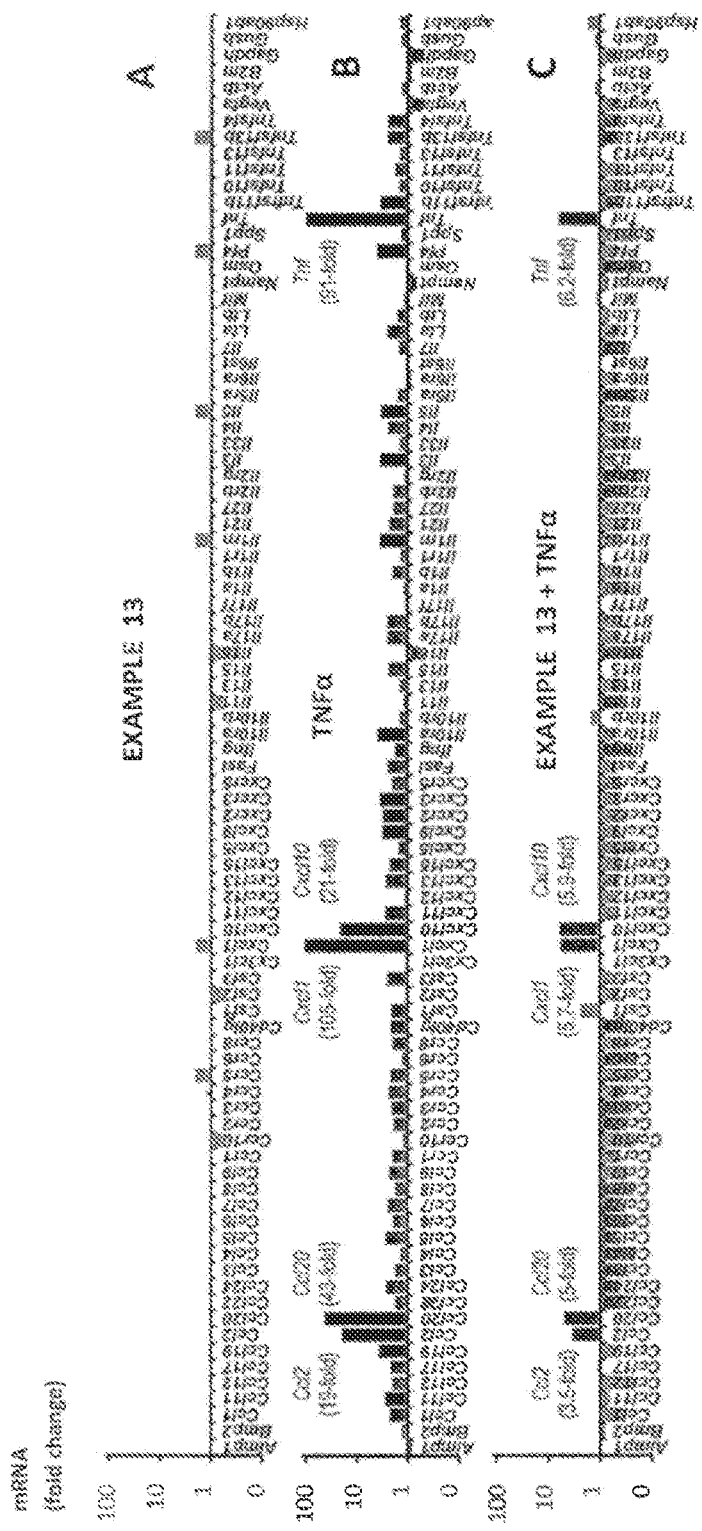
Figure 6 A to C

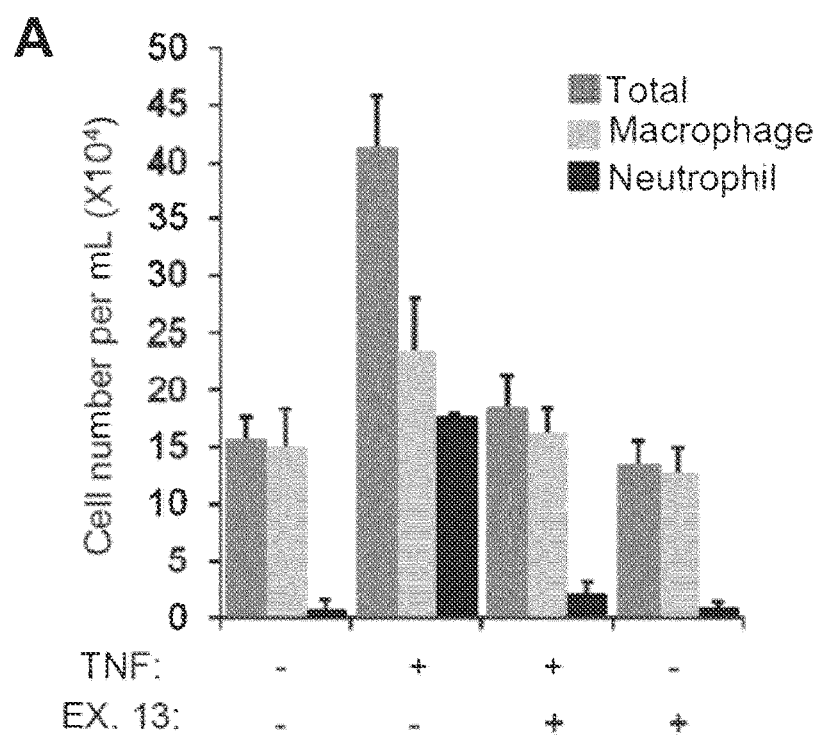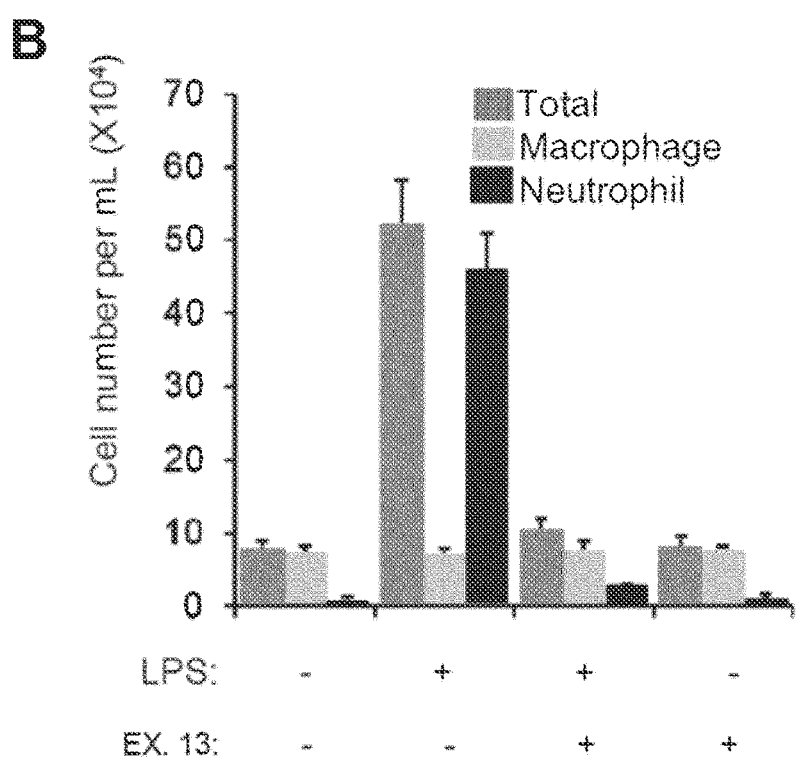
Figure 7 A and B

SUBSTITUTED BENZODIAZOLES AND USE THEREOF IN THERAPY

This application is a Continuation and claims priority of U.S. application Ser. No. 16/975,130, filed Aug. 23, 2020, which is a national phase of International Application No. PCT/EP2019/055178, filed Mar. 1, 2019, which claims the benefit of U.S. Provisional Application No. 62/636,983, filed Mar. 1, 2018, each of which is hereby incorporated herein by reference in its entirety.

INCORPORATION BY REFERENCE

The material in the Sequence Listing XML file named "BRNN14PUS03CON_Sequence-Listing.xml", created on Feb. 19, 2025, and having a size of 18,107 bytes, is incorporated herein by reference in its entirety.

FIELD OF THE INVENTION

The present invention relates to novel compounds, compositions comprising such compounds, and the use of such compounds and compositions in medicine. In particular, the present invention relates to the use of such compounds and compositions in methods for the treatment of cell proliferation disorders, such as in the treatment of inflammation and cancers, which treatment is thought to occur through inhibition of OGG1.

BACKGROUND OF THE INVENTION

The listing or discussion of an apparently prior-published document in this specification should not necessarily be taken as an acknowledgement that the document is part of the state of the art or is common general knowledge.

Reactive oxygen species (ROS) are involved in a range of human pathologies (see, for example, C. Nathan, and A. Cunningham-Bussel, Nat. Rev. Immunol. 13 (2013) 349-361). While ROS are important signalling molecules that stimulate cell growth and are necessary for normal cellular processes, excessive generation of ROS as a result of inflammation or cancer leads to damage to macromolecules. In DNA, guanine is particularly prone to oxidation, resulting in 7,8-dihydro-8-oxoguanine (8-oxoG) in DNA—a well-established biomarker for ROS-mediated pathologies (see: X. Ba, et al., Int. J. Mol. Sci. 15 (2014) 16975-16997; and K. D. Jacob, et al., Mech. Ageing Dev. 134 (2013) 139-157). DNA repair pathways allow cells to cope with high ROS and are highly sought-after therapeutic targets. In mammals, 8-oxoG is primarily recognized and repaired by 8-oxoguanine-DNA glycosylase 1 (OGG1), which is the quantitatively dominant repair activity for oxidized guanines in mammals (see: A. Klungland, et al., Proc. Natl. Acad. Sci. USA. 96 (1999) 13300-5; and E. C. Friedberg, DNA repair and mutagenesis, 2nd ed., ASM Press, Washington, D.C., 2006).

In cancer, activation of oncogenes contributes to genomic instability through replication stress at an early step in carcinogenesis (see T. D. Halazonetis, V. G. Gorgoulis, and J. Bartek, Science. 319 (2008) 1352-1355). While the mechanistic details underlying replication stress are far from clear, we know that at least a subset of oncogenes such as c-Myc and Ras confer an increase in reactive oxygen species and DNA damage (see: O. Vafa, et al., Mol. Cell. 9 (2002) 1031-1044; and A. C. Lee, et al., J. Biol. Chem. 274 (1999) 7936-7940). Multiple lines of evidence show that a high load of reactive oxygen species drive cancer cell proliferation and metastasis at the cost of suffering oxidative damage to macromolecules (see Y. Zhang, et al., Antioxid. Redox Signal. 15 (2011) 2867-2908). Deficiencies in this repair system may lead to increased mutagenesis or cell death after oxidative stress (see: S. Oka, et al., EMBO J. 27 (2008) 421-432; and M. Ohno, et al., Sci. Rep. 4 (2014)).

Mice knockout for Ogg1 are not particularly prone to cancer (see A. Klungland, et al., Proc. Natl. Acad. Sci. USA. 96 (1999) 13300-5), suggesting that functional 8-oxodG avoidance pathways protect cancer cells against the negative effects of the oxidative stress phenotype. OGG1 overexpression protects cells against Ras-induced senescence (see Z. M. Ramdzan, et al., PLoS Biol. 12 (2014)) and OGG1 expression is correlated with lower genomic instability in a panel of adenocarcinoma cell lines (see M. Romanowska, et al., Free Radic. Biol. Med. 43 (2007) 1145-1155) as well as the cellular response to ROS-inducing chemotherapeutics such as paclitaxel (see H.-L. Huang, et al., Cell. Physiol. Biochem. 42 (2017) 889-900). In tumour cells, reducing the capacity to eliminate oxidized guanines from DNA by inhibiting OGG1 activity will reduce cancer cell survival and hence will represent promising novel anticancer therapy, either as monotherapy in cancer forms with high oxidative stress levels and/or in combination with radiotherapy and chemotherapy drugs.

Current treatments of cancer are not effective for all patients with diagnosed disease, including a large proportion of patients that experience adverse effects from treatments with existing therapies or where resistance to on-going therapy is developed over time. The present invention aims at providing new cancer treatments, based on the inhibition of the OGG1 enzyme. OGG1 inhibitors may be used as treatment alone or in combination with other established chemotherapeutics.

Acute and chronic inflammation causes an elevation of ROS and an accumulation of oxidative DNA damage, primarily 8-oxoG (see: C. Nathan, and A. Cunningham-Bussel, Nat. Rev. Immunol. 13 (2013) 349-361; and X. Ba, et al., Int. J. Mol. Sci. 15 (2014) 16975-16997) and in particular at promoter regions (see: L. Pan, et al., J. Biol. Chem. (2016); and L. Pan, et al., Sci. Rep. 7 (2017) 43297). This DNA lesion, present in the genome or as a free repair product in blood and urine, is a biomarker for ongoing lung exposure to pollutants (see: Y. Tsurudome, et al., Carcinogenesis. 20 (1999) 1573-1576; and B. Malayappan, et al., J. Chromatogr. A. 1167 (2007) 54-62) and lung inflammations such as asthma (see C. Hasbal, et al., Pediatr. Allergy Immunol. 21 (2010) e674-e678) and chronic obstructive pulmonary disease (COPD) (see: G. Deslee, et al., Chest. 135 (2009) 965-974; and T. Igishi, et al., Respirology. 8 (2003) 455-460).

Cells depend on OGG1 as the most important repair enzyme for removing 8-oxoG from DNA (see H. E. Krokan, and M. Bjorns, Perspect. Biol. 5 (2013)) and the absence of ROS (see C. Nathan, and A. Cunningham-Bussel, Nat. Rev. Immunol. 13 (2013) 349-361) or OGG1 (see: L. Pan, et al., J. Biol. Chem. (2016); E. Touati, et al., *Helicobacter.* 11 (2006) 494-505; A. Bacsi, et al., DNA Repair. 12 (2013) 18-26; G. Li, et al., Free Radic. Biol. Med. 52 (2012) 392-401; L. Aguilera-Aguirre, et al., J. Immunol. 193 (2014) 4643-4653; X. Ba, et al., J. Immunol. 192 (2014) 2384-2394; and J. G. Mabley, et al., C., FASEB J. (2004)) reduces the inflammatory response in cells and animals.

Since Ogg1$^{-/-}$ mice are protected against inflammation (see: E. Touati, et al., *Helicobacter.* 11 (2006) 494-505; A. Bacsi, et al., DNA Repair. 12 (2013) 18-26; G. Li, et al., Free Radic. Biol. Med. 52 (2012) 392-401; and J. G. Mabley, et al., FASEB J. (2004)), but otherwise viable and largely healthy (see: A. Klungland, et al., Proc. Natl. Acad. Sci. USA. 96 (1999) 13300-5; and O. Minowa, et al., Proc. Natl. Acad. Sci. USA. 97 (2000) 4156-61), a small molecule inhibitor of OGG1 would be expected to alleviate excessive chronic and/or acute inflammations without inducing toxic side effects.

Various disclosures (for example: N. Donley, et al., ACS Chem. Biol. 10 (2015) 2334-2343; Tahara et al., J. Am. Chem. Soc., 140(6) (2018) 2105-2114; and WO 2017/011834 A1) describe screening campaigns for small molecule OGG1 inhibitors.

Nevertheless, at present treatment of diseases caused by excessive inflammation is inefficient for many patients. These patients may suffer from a failure to alleviate the inflammation or serious adverse effects of current treatments.

Thus, there exists a clear and significant need for new treatments for inflammatory diseases based on immunomodulatory effects that can be achieved by inhibition of the OGG1 enzyme. Such methods for the alleviation of inflammation may be achieved by a mechanism that is distinct from any other established or experimental treatment for inflammation and may be used alone or in combination with established medicines. Moreover, such methods may also be broadly applicable to the treatment of a range of disorders relating to abnormal cell proliferation, such as in the treatment of cancers.

SUMMARY OF THE INVENTION

It has now been unexpectedly found that certain substituted benzodiazoles are able to act as inhibitors of OGG1, and thus have properties rendering them useful for the treatment or prevention of cell proliferation disorders.

In a first aspect of the invention, therefore, there is provided a compound of formula I

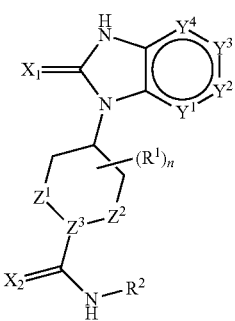

or a pharmaceutically acceptable salt thereof, wherein:
  $X^1$ and $X^2$ each independently represent O or S;
  each of $Y^1$ to $Y^4$ independently represents CH or $CR^3$, or any one of $Y^1$ to $Y^4$ may alternatively represent N;
  either $Z^1$ and $Z^2$ both represent methylene optionally linked by an additional ethylene group,
  or $Z^1$ represents ethylene and $Z^2$ represents methylene;
  $Z^3$ represents CH, $CR^1$ or N;
  each $R^1$ independently represents, where possible
  (i) halo, oxy, —$NO_2$, —CN, —$R^{1a}$, —$OR^{1b}$, —$S(O)_q R^{1c}$, —$S(O)_r N(R^{1d})(R^{1e})$, —$N(R^{1f})S(O)_s R^{1g}$, —$N(R^{1h})(R^{1i})$, —$C(O)OR^{1j}$, or —$C(O)NR^{1k}R^{1l}$,
  (ii) aryl optionally substituted by one or more (e.g. 1-3) groups independently selected from $A^1$,
  (iii) heteroaryl optionally substituted by one or more (e.g. 1-3) groups selected from $A^2$, or
  (iv) heterocyclyl optionally substituted by one or more (e.g. 1-3) groups independently selected from $A^3$;
  n represents 0 to 11, as appropriate;
  $R^2$ represents
  (i) phenyl optionally substituted by one or more (e.g. 1-3) groups independently selected from $A^4$,
  (ii) 5- or 6-membered monocyclic heteroaryl optionally substituted by one or more (e.g. 1-3) groups selected from oxy and $A^5$, or
  (iii) phenyl substituted with two adjacent groups which, together with the ring to which they are attached, form a bicyclic heteroaryl optionally substituted by one or more (e.g. 1-3) groups selected from oxy and $A^6$;
  each $R^3$ independently represents
  (i) halo, —$NO_2$, —CN, —$R^{2a}$, —$OR^{2b}$, —$S(O)_q R^{2c}$, —$S(O)_r N(R^{2d})(R^{2e})$, —$N(R^{2f})S(O)_s R^{2g}$, —$N(R^{2h})(R^{2i})$, —$C(O)OR^{2j}$, or —$C(O)NR^{2k}R^{2l}$,
  (ii) aryl optionally substituted by one or more (e.g. 1-3) groups independently selected from $A^7$,
  (iii) heteroaryl optionally substituted by one or more (e.g. 1-3) groups selected from $A^8$, or
  (iv) heterocyclyl optionally substituted by one or more (e.g. 1-3) groups independently selected from $A^9$;
  each $R^{1a}$ and $R^{2a}$ independently represent
  (i) $C_{1-6}$ alkyl, $C_{2-6}$ alkenyl or $C_{2-6}$ alkynyl, wherein each such alkyl, alkenyl or alkynyl group is optionally substituted by one or more (e.g. 1-3) groups independently selected from oxy and $B^1$;
  (ii) aryl optionally substituted by one or more (e.g. 1-3) groups independently selected from oxy and $B^2$,
  (iii) heteroaryl optionally substituted by one or more (e.g. 1-3) groups selected from oxy and $B^3$, or
  (iv) heterocyclyl optionally substituted by one or more (e.g. 1-3) groups independently selected from oxy and $B^4$;
  each $R^{1b}$ to $R^{1l}$ and $R^{2b}$ to $R^{2l}$ independently represents H or
  (i) $C_{1-6}$ alkyl, $C_{2-6}$ alkenyl or $C_{2-6}$ alkynyl, wherein each such alkyl, alkenyl or alkynyl group is optionally substituted by one or more (e.g. 1-3) groups independently selected from oxy and $B^1$;
  (ii) aryl optionally substituted by one or more (e.g. 1-3) groups independently selected from oxy and $B^2$,
  (iii) heteroaryl optionally substituted by one or more (e.g. 1-3) groups selected from oxy and $B^3$, or
  (iv) heterocyclyl optionally substituted by one or more (e.g. 1-3) groups independently selected from oxy and $B^4$;
  each of $A^1$ to $A^9$ independently represents
  (i) halo, $NO_2$, —CN, —$R^{3a}$, —$OR^{3b}$, —$S(O)_q R^{3c}$, —$S(O)_r N(R^{3d})(R^{3e})$, —$N(R^{3f})S(O)_s R^{3g}$, —$N(R^{3h})(R^{3i})$, —$C(O)OR^{3j}$, or —$C(O)NR^{3k}R^{3l}$,
  (ii) aryl optionally substituted by one or more (e.g. 1-3) groups independently selected from oxy and $D^1$,
  (iii) heteroaryl optionally substituted by one or more (e.g. 1-3) groups selected from oxy and $D^2$, or
  (iv) heterocyclyl optionally substituted by one or more (e.g. 1-3) groups independently selected from oxy and $D^3$;
  each $B^1$ independently represents
  (i) halo, $NO_2$, —CN, —$OR^{4b}$, —$S(O)_q R^{4c}$, —$S(O)_r N(R^{4d})(R^{4e})$, —$N(R^{4f})S(O)_s R^{4g}$, —$N(R^{4h})(R^{4i})$, —$C(O)OR^{4j}$, or —$C(O)NR^{4k}R^{4l}$,
  (ii) aryl optionally substituted by one or more (e.g. 1-3) groups independently selected from $D^4$, (iii) heteroaryl optionally substituted by one or more (e.g. 1-3) groups selected from $D^5$, or
(iv) heterocyclyl optionally substituted by one or more (e.g. 1-3) groups independently selected from $D^6$;

each $B^2$ to $B^4$ independently represents
(i) halo, $NO_2$, —CN, —$R^{4a}$, —$OR^{4b}$, —$S(O)_qR^{4c}$, —$S(O)_rN(R^{4d})(R^{4e})$, —$N(R^{4f})S(O)_sR^{4g}$, —$N(R^{4h})(R^{4i})$, —$C(O)OR^{4j}$, or —$C(O)NR^{4k}R^{4l}$,
(ii) aryl optionally substituted by one or more (e.g. 1-3) groups independently selected from oxy and $D^4$,
(iii) heteroaryl optionally substituted by one or more (e.g. 1-3) groups selected from oxy and $D^5$, or
(iv) heterocyclyl optionally substituted by one or more (e.g. 1-3) groups independently selected from oxy and $D^6$;

each $R^{3a}$ and $R^{4a}$ represent
(i) $C_{1-6}$ alkyl, $C_{2-6}$ alkenyl or $C_{2-6}$ alkynyl, wherein each such alkyl, alkenyl or alkynyl group is optionally substituted by one or more (e.g. 1-3) groups independently selected from oxy and $E^1$;
(ii) aryl optionally substituted by one or more (e.g. 1-3) groups independently selected from oxy and $E^2$,
(iii) heteroaryl optionally substituted by one or more (e.g. 1-3) groups selected from oxy and $E^3$, or
(iv) heterocyclyl optionally substituted by one or more (e.g. 1-3) groups independently selected from oxy and $E^4$;

each $R^{3b}$ to $R^{3l}$, and $R^{4b}$ to $R^{4l}$ independently represents H or
(i) $C_{1-6}$ alkyl, $C_{2-6}$ alkenyl or $C_{2-6}$ alkynyl, wherein each such alkyl, alkenyl or alkynyl group is optionally substituted by one or more (e.g. 1-3) groups independently selected from oxy and $E^1$;
(ii) aryl optionally substituted by one or more (e.g. 1-3) groups independently selected from oxy and $E^2$,
(iii) heteroaryl optionally substituted by one or more (e.g. 1-3) groups selected from oxy and $E^3$, or
(iv) heterocyclyl optionally substituted by one or more (e.g. 1-3) groups independently selected from oxy and $E^4$;

each $D^1$ to $D^6$ independently represents
(i) halo, $NO_2$, —CN, —$R^{5a}$, —$OR^{5b}$, —$S(O)_qR^{5c}$, —$S(O)_rN(R^{5d})(R^{5e})$, —$N(R^{5f})S(O)_sR^{5g}$, —$N(R^{5h})(R^{5i})$, —$C(O)OR^{5j}$, or —$C(O)NR^{5k}R^{5l}$,
(ii) aryl optionally substituted by one or more (e.g. 1-3) groups independently selected from oxy and $G^1$,
(iii) heteroaryl optionally substituted by one or more (e.g. 1-3) groups selected from oxy and $G^2$, or
(iv) heterocyclyl optionally substituted by one or more (e.g. 1-3) groups independently selected from oxy and $G^3$;

each $E^1$ independently represents
(i) halo, $NO_2$, —CN, —$OR^{6b}$, —$S(O)_qR^{6c}$, —$S(O)_rN(R^{6d})(R^{6e})$, —$N(R^{6f})S(O)_sR^{6g}$, —$N(R^{6h})(R^{6i})$, —$C(O)OR^{6j}$, or —$C(O)NR^{6k}R^{6l}$,
(ii) aryl optionally substituted by one or more (e.g. 1-3) groups independently selected from $G^4$,
(iii) heteroaryl optionally substituted by one or more (e.g. 1-3) groups selected from $G^5$, or
(iv) heterocyclyl optionally substituted by one or more (e.g. 1-3) groups independently selected from $G^6$;

each $E^2$ to $E^4$ independently represents
(i) halo, $NO_2$, —CN, —$R^{6a}$, —$OR^{6b}$, —$S(O)_qR^{6c}$, —$S(O)_rN(R^{6d})(R^{6e})$, —$N(R^{6f})S(O)SR^{6g}$, —$N(R^{6h})(R^{6i})$, —$C(O)OR^{6j}$, or —$C(O)NR^{6k}R^{6l}$,
(ii) aryl optionally substituted by one or more (e.g. 1-3) groups independently selected from oxy and $G^4$,
(iii) heteroaryl optionally substituted by one or more (e.g. 1-3) groups selected from oxy and $G^5$, or
(iv) heterocyclyl optionally substituted by one or more (e.g. 1-3) groups independently selected from oxy and $G^6$;

each $R^{5a}$ and $R^{6a}$ represent
(i) $C_{1-6}$ alkyl, $C_{2-6}$ alkenyl or $C_{2-6}$ alkynyl, wherein each such alkyl, alkenyl or alkynyl group is optionally substituted by one or more (e.g. 1-3) groups independently selected from oxy and $J^1$;
(ii) aryl optionally substituted by one or more (e.g. 1-3) groups independently selected from oxy and $J^2$,
(iii) heteroaryl optionally substituted by one or more (e.g. 1-3) groups selected from oxy and $J^3$, or
(iv) heterocyclyl optionally substituted by one or more (e.g. 1-3) groups independently selected from oxy and $J^4$;

each $R^{5b}$ to $R^{5l}$, and $R^{6b}$ to $R^{6l}$ independently represents H or
(i) $C_{1-6}$ alkyl, $C_{2-6}$ alkenyl or $C_{2-6}$ alkynyl, wherein each such alkyl, alkenyl or alkynyl group is optionally substituted by one or more (e.g. 1-3) groups independently selected from oxy and $J^1$;
(ii) aryl optionally substituted by one or more (e.g. 1-3) groups independently selected from oxy and $J^2$,
(iii) heteroaryl optionally substituted by one or more (e.g. 1-3) groups selected from oxy and $J^3$, or
(iv) heterocyclyl optionally substituted by one or more (e.g. 1-3) groups independently selected from oxy and $J^4$;

each $G^1$ to $G^6$ independently represents
(i) halo, $NO_2$, —CN, —$R^{7a}$, —$OR^{7b}$, —$S(O)_qR^{7c}$, —$S(O)_rN(R^{7d})(R^{7e})$, —$N(R^{7f})S(O)_sR^{7g}$, —$N(R^{7h})(R^{7i})$, —$C(O)OR^{7j}$, or —$C(O)NR^{7k}R^{7l}$,
(ii) aryl optionally substituted by one or more (e.g. 1-3) groups independently selected from oxy and $L^1$,
(iii) heteroaryl optionally substituted by one or more (e.g. 1-3) groups selected from oxy and $L^2$, or
(iv) heterocyclyl optionally substituted by one or more (e.g. 1-3) groups independently selected from oxy and $L^3$;

each $J^1$ independently represents
(i) halo, $NO_2$, —CN, —$OR^{8b}$, —$S(O)_qR^{8c}$, —$S(O)_rN(R^{8d})(R^{8e})$, —$N(R^{8f})S(O)_sR^{8g}$, —$N(R^{8h})(R^{8i})$, —$C(O)OR^{8j}$, or —$C(O)NR^{8k}R^{8l}$,
(ii) aryl optionally substituted by one or more (e.g. 1-3) groups independently selected from $L^1$,
(iii) heteroaryl optionally substituted by one or more (e.g. 1-3) groups selected from $L^2$, or
(iv) heterocyclyl optionally substituted by one or more (e.g. 1-3) groups independently selected from $L^3$;

each $J^2$ to $J^4$ independently represents
(i) halo, $NO_2$, —CN, —$R^{8a}$, —$OR^{8b}$, —$S(O)_qR^{8c}$, —$S(O)_rN(R^{8d})(R^{8e})$, —$N(R^{8f})S(O)_sR^{8g}$, —$N(R^{8h})(R^{8i})$, —$C(O)OR^{8j}$, or —$C(O)NR^{8k}R^{8l}$,
(ii) aryl optionally substituted by one or more (e.g. 1-3) groups independently selected from oxy and $L^1$,
(iii) heteroaryl optionally substituted by one or more (e.g. 1-3) groups selected from oxy and $L^2$, or
(iv) heterocyclyl optionally substituted by one or more (e.g. 1-3) groups independently selected from oxy and $L^3$;

each $R^{7a}$ and $R^{8a}$ represent $C_{1-3}$ alkyl optionally substituted with one or more fluoro; each $R^{7b}$ to $R^{7l}$, and $R^{8b}$ to $R^{8l}$ independently represents H or $C_{1-3}$ alkyl optionally substituted with one or more fluoro;

each $L^1$ to $L^3$ independently represents halo, $NO_2$, —CN, —$R^{9a}$, —$OR^{9b}$, —$S(O)_qR^{9c}$, —$S(O)_rN(R^{9d})(R^{9e})$, —$N(R)S(O)_sR^{9g}$, —$N(R^{9h})(R^{9i})$, —$C(O)OR^{9j}$, or —$C(O)NR^{9k}R^{9l}$, each $R^{9a}$ independently represents $C_{1-3}$ alkyl optionally substituted with one or more fluoro;

each $R^{9b}$ to $R^{9l}$ independently represents H or $C_{1-3}$ alkyl optionally substituted with one or more fluoro; and each q, r and s independently represents 0, 1 or 2, which compounds (including pharmaceutically acceptable salts) may be referred to herein as the "compounds of the invention".

BRIEF DESCRIPTION OF THE DRAWINGS

FIG. 1: OGG1 inhibitors selectively decrease the viability of cancer cells

The cell lines from Table 3 are grouped according to pathology and plotted. A. EC50 values for Example 13. The difference between EC50 values of cancer and normal cell lines is significant (P<1E-7, Student's T-test). B. EC50 values for Example 28. The difference between EC50 values of cancer and normal cell lines is significant (P<1E-7, Student's T-test). C. EC50 values for Example 50. The difference between EC50 values of cancer and normal cell lines is significant (P<1E-5, Student's T-test). All values are derived using the method 2 or 3, after a five day incubation.

FIG. 2: OGG1 inhibitor synergize with MTH1 inhibitors and paclitaxel

A3 T-cell leukemia cell line was incubated with the indicated concentrations of Example 13 together with a dilution series of the MTH1 inhibitor Karonudib, as well as paclitaxel. Viability was assessed after a three-day incubation using method 4. A. Viability of A3 cells exposed to the OGG1 inhibitor Example 13 and/or the MTH1 inhibitor Karonudib (Berglund, U., et al. "Validation and Development of MTH1 Inhibitors for Treatment of Cancer." *Annals of Oncology*, (2016)). B. Combination index calculation of the results in panel A. A combination index <0.7 indicates synergism. C. Viability of A3 cells exposed to the OGG1 inhibitor Example 13 and/or the tubulin poison paclitaxel. D. Combination index calculation of the results in panel C. A combination index <0.7 indicates synergism.

FIG. 3: OGG1 inhibitor synergize with MTH1 inhibitors Karonudib and AZ #19

A3 T-cell leukemia cell line was incubated with the indicated concentrations of Example 13 together with a dilution series of the MTH1 inhibitor Karonudib or the MTH1 inhibitor AZ #19 (4-((4-Chloro-2-fluorophenyl)amino)-6,7-dimethoxy-N-methylquinoline-3-carboxamide) (Kettle et. al., J. Med. Chem. 2016, 59, 2346-2361). Viability was assessed after a three-day incubation using method 4. A. Viability of A3 cells exposed to the OGG1 inhibitor Example 13 and/or the MTH1 inhibitor Karonudib. B. Viability of A3 cells exposed to the OGG1 inhibitor Example 13 and/or the MTH1 inhibitor AZ #19.

FIG. 4: OGG1 deficiency inhibits cell proliferation in A3 cells

A. A3 cells harbouring doxycycline-inducible shRNA constructs targeting the endogenous OGG1 (sh1, sh2 and sh3) and/or expressing an exogenous OGG1 isoform targeted to mitochondria (OGG1-2A) were added doxycycline and counted at the indicated times. B. Native A3 cells were grown in the presence of 10 µM Example 13 or vehicle and counted at the indicated times. Relative cell numbers were determined according to Method 4.

FIG. 5: OGG1 deficiency and inhibition is toxic in cancer cells

A. OGG1 knockdown inhibits colony formation in H460 lung cancer cells. B. Example 13 inhibits colony formation in the cancer cell lines ACHN and H460, but not in the normal cell lines MRC5 and Ogg1$^{-/-}$ mouse embryonic fibroblasts. Surviving colonies were determined according to Method 6.

FIG. 6: Example 13 reduces pro-inflammatory gene regulation induced by the cytokine TNFα in MLE-12 cells Individual genes encoding pro-inflammatory cytokines and chemokines are plotted along the horizontal axis, and the fold change of the indicated treatment compared to non-treated cells is shown on the vertical axes. A. gene regulatory signature of Example 13 compared to non-treated cells. B. gene regulatory signature of 20 ng/ml TNFα. C. gene regulatory signature of 20 ng/ml TNFα and 5 µM Example 13.

FIG. 7: Example 13 reduces recruitment of neutrophils to mouse airways

A. 20 ng TNFα was delivered into each mouse lung intranasally and 25 mg/kg Example 13 was injected intraperitoneally. Lungs were lavaged after 16 h and the number of macrophages and neutrophils was counted. B. 20 ng lipopolysaccharide was delivered intranasally into each mouse lung intranasally and 25 mg/kg Example 13 was injected intraperitoneally. Lungs were lavaged after 16 h and the number of macrophages and neutrophils was counted.

DETAILED DESCRIPTION OF THE INVENTION

For the avoidance of doubt, the skilled person will understand that references herein to compounds of particular aspects of the invention (such as the first aspect of the invention, i.e. referring to compounds of formula I as defined in the first aspect of the invention) will include references to all embodiments and particular features thereof, which embodiments and particular features may be taken in combination to form further embodiments and features of the invention.

Unless indicated otherwise, all technical and scientific terms used herein will have their common meaning as understood by one of ordinary skill in the art to which this invention pertains.

Pharmaceutically acceptable salts include acid addition salts and base addition salts. Such salts may be formed by conventional means, for example by reaction of a free acid or a free base form of a compound of the invention with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared using techniques known to those skilled in the art, such as by exchanging a counter-ion of a compound of the invention in the form of a salt with another counter-ion, for example using a suitable ion exchange resin.

Particular acid addition salts that may be mentioned include carboxylate salts (e.g. formate, acetate, trifluoroacetate, propionate, isobutyrate, heptanoate, decanoate, caprate, caprylate, stearate, acrylate, caproate, propiolate, ascorbate, citrate, glucuronate, glutamate, glycolate, α-hydroxybutyrate, lactate, tartrate, phenylacetate, mandelate, phenylpropionate, phenylbutyrate, benzoate, chlorobenzoate, methylbenzoate, hydroxybenzoate, methoxybenzoate, dinitrobenzoate, o-acetoxy-benzoate, salicylate, nicotinate, isonicotinate, cinnamate, oxalate, malonate, succinate, suberate, sebacate, fumarate, malate, maleate, hydroxymaleate, hippurate, phthalate or terephthalate salts), halide salts (e.g. chloride, bromide or iodide salts), sulphonate salts (e.g. benzenesulphonate, methyl-, bromo- or chloro-benzenesulphonate, xylenesulphonate, methanesulphonate, ethanesulphonate, propanesulphonate, hydroxy-ethanesulphonate, 1- or 2-naphthalene-sulphonate or 1,5-naphthalene-disulphonate salts) or sulphate, pyrosulphate, bisulphate, sulphite, bisulphite, phosphate, monohydrogenphosphate, dihydrogenphosphate, metaphosphate, pyrophosphate or nitrate salts, and the like.

Particular base addition salts that may be mentioned include salts formed with alkali metals (such as Na and K salts), alkaline earth metals (such as Mg and Ca salts), organic bases (such as ethanolamine, diethanolamine, triethanolamine, tromethamine and lysine) and inorganic bases (such as ammonia and aluminium hydroxide). More particularly, base addition salts that may be mentioned include Mg, Ca and, most particularly, K and Na salts.

For the avoidance of doubt, compounds of the invention may exist as solids, and thus the scope of the invention includes all amorphous, crystalline and part crystalline forms thereof, and may also exist as oils. Where compounds of the invention exist in crystalline and part crystalline forms, such forms may include solvates, which are included in the scope of the invention.

For the avoidance of doubt, compounds of the invention may also exist in solution (i.e. in solution in a suitable solvent). For example, compounds of the invention may exist in aqueous solution, in which case compounds of the invention may exist in the form of hydrates thereof.

Compounds of the invention may contain double bonds and, unless otherwise indicated, may thus exist as E (entgegen) and Z (zusammen) geometric isomers about each individual double bond. Unless otherwise specified, all such isomers and mixtures thereof are included within the scope of the invention.

Compounds of the invention may also exhibit tautomerism. All tautomeric forms and mixtures thereof are included within the scope of the invention (particularly those of sufficient stability to allow for isolation thereof).

Compounds of the invention may also contain one or more asymmetric carbon atoms and may therefore exhibit optical and/or diastereoisomerism (i.e. existing in enantiomeric or diastereomeric forms). Diastereoisomers may be separated using conventional techniques, e.g. chromatography or fractional crystallisation. The various stereoisomers (i.e. enantiomers) may be isolated by separation of a racemic or other mixture of the compounds using conventional, e.g. fractional crystallisation or HPLC, techniques. Alternatively the desired enantiomer or diastereoisomer may be obtained from appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution; for example, with a homochiral acid followed by separation of the diastereomeric derivatives by conventional means such as chromatography), or by reaction with an appropriate chiral reagent or chiral catalyst, all of which methods and processes may be performed under conditions known to the skilled person. Unless otherwise specified, all stereoisomers and mixtures thereof are included within the scope of the invention.

For the avoidance of doubt, the skilled person will understand that where a particular group is depicted herein as being bound to a ring system via a floating bond (i.e. a bond not shown as being bound to a particular atom within the ring), the relevant group may be bound to any suitable atom within the relevant ring system (i.e. the ring within which the floating bond terminates).

Unless otherwise specified, C-z alkyl groups (where z is the upper limit of the range) defined herein may be straight-chain or, when there is a sufficient number (i.e. a minimum of two or three, as appropriate) of carbon atoms, be branched-chain, and/or cyclic (so forming a $C_{3-z}$ cycloalkyl group). When there is a sufficient number (i.e. a minimum of four) of carbon atoms, such groups may also be part cyclic (so forming a $C_{4-z}$ partial cycloalkyl group). For example, cycloalkyl groups that may be mentioned include cyclopropyl, cyclopentyl and cyclohexyl. Similarly, part cyclic alkyl groups (which may also be referred to as "part cycloalkyl" groups) that may be mentioned include cyclopropylmethyl. When there is a sufficient number of carbon atoms, such groups may also be multicyclic (e.g. bicyclic or tricyclic) and/or spirocyclic. For the avoidance of doubt, particular alkyl groups that may be mentioned include straight chain (i.e. not branched and/or cyclic) alkyl groups. Other alkyl groups that may be mentioned include straight chain and branched (i.e. non-cyclic) alkyl groups.

Unless otherwise specified, $C_{2-z}$ alkenyl groups (where z is the upper limit of the range) defined herein may be straight-chain or, when there is a sufficient number (i.e. a minimum of three) of carbon atoms, be branched-chain, and/or cyclic (so forming a $C_{4-z}$ cycloalkenyl group). When there is a sufficient number (i.e. a minimum of five) of carbon atoms, such groups may also be part cyclic. For example, part cyclic alkenyl groups (which may also be referred to as "part cycloalkenyl" groups) that may be mentioned include cyclopentenylmethyl and cyclohexenylmethyl. When there is a sufficient number of carbon atoms, such groups may also be multicyclic (e.g. bicyclic or tricyclic) or spirocyclic. For the avoidance of doubt, particular alkenyl groups that may be mentioned include straight chain (i.e. not branched and/or cyclic) alkenyl groups. Other alkenyl groups that may be mentioned include straight chain and branched (i.e. non-cyclic) alkenyl groups.

Unless otherwise specified, $C_{2-z}$ alkynyl groups (where z is the upper limit of the range) defined herein may be straight-chain or, when there is a sufficient number (i.e. a minimum of four) of carbon atoms, be branched-chain. For the avoidance of doubt, particular alkynyl groups that may be mentioned include straight chain (i.e. not branched and/or cyclic) alkynyl groups. Other alkynyl groups that may be mentioned include straight chain and branched (i.e. non-cyclic) alkynyl groups.

For the avoidance of doubt, unless otherwise specified, groups referred to herein as "alkyl", "alkenyl" and/or "alkynyl" will be taken as referring to the highest degree of unsaturation in a bond present in such groups. For example, such a group having a carbon-carbon double bond and, in the same group, a carbon-carbon triple bond will be referred to as "alkynyl". Alternatively, it may be particularly specified that that such groups will comprise only the degree of unsaturation specified (i.e. in one or more bond therein, as appropriate; e.g. in in one bond therein).

For the avoidance of doubt, alkyl, alkenyl and alkynyl groups as described herein may also act as linker groups (i.e. groups joining two or more parts of the compound as described), in which case such groups may also be referred to as "alkylene", "alkenylene" and/or "alkynylene" groups, respectively.

In some embodiments, any alkyl, alkenyl or alkynyl, more particularly is alkyl (i.e. a saturated, linear branched or cyclic aliphatic moiety, such as methyl, ethyl, n-propyl, isopropyl, cyclopropyl, n-butyl etc).

Furthermore, in some embodiments, any $C_{1-6}$ alkyl more particularly is $C_{1-4}$alkyl, any $C_{2-6}$ alkenyl more particularly is $C_{2-4}$ alkenyl, and any $C_{2-6}$ alkynyl more particularly is $C_{2-4}$ alkynyl. In some further of the above embodiments, any $C_{1-6}$ alkyl more particularly is $C_{1-3}$ alkyl, any $C_{2-6}$ alkenyl more particularly is $C_{2-3}$ alkenyl, and any $C_{2-6}$ alkynyl more particularly is $C_{2-3}$ alkynyl.

For the avoidance of doubt, as used herein, references to heteroatoms will take their normal meaning as understood by one skilled in the art. Particular heteroatoms that may be mentioned include phosphorus, selenium, tellurium, silicon, boron, oxygen, nitrogen and sulfur (e.g. oxygen, nitrogen and sulfur, such as oxygen and nitrogen).

As used herein, the term heterocyclyl may refer to non-aromatic monocyclic and polycyclic (e.g. bicyclic) heterocyclic groups (which groups may, where containing a sufficient number of atoms, also be bridged) in which at least one (e.g. one to four) of the atoms in the ring system is other than carbon (i.e. a heteroatom), and in which the total number of atoms in the ring system is between three and twelve (e.g. between five and ten, such as between three and eight; for example, forming a 5- or 6-membered heterocyclyl group). Further, such heterocyclyl groups may be saturated, forming a heterocycloalkyl, or unsaturated containing one or more carbon-carbon or, where possible, carbon-heteroatom or heteroatom-heteroatom double and/or triple bonds, forming for example a $C_{2-z}$ (e.g. $C_{4-z}$) heterocycloalkenyl (where z is the upper limit of the range) or a $C_{7-z}$ heterocycloalkynyl group.

For the avoidance of doubt, the skilled person will understand that heterocyclyl groups that may form part of compounds of the invention are those that are chemically obtainable, as known to those skilled in the art. Various heterocyclyl groups will be well-known to those skilled in the art, such as 7-azabicyclo-[2.2.1]heptanyl, 6-azabicyclo[3.1.1]heptanyl, 6-azabicyclo[3.2.1]-octanyl, 8-azabicyclo[3.2.1]octanyl, aziridinyl, azetidinyl, 2,3-dihydroisothiazolyl, dihydropyranyl, dihydropyridinyl, dihydropyrrolyl (including 2,5-dihydropyrrolyl), dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), imidazolidinyl, imidazolinyl, isothiazolidinyl, morpholinyl, 7-oxabicyclo[2.2.1]heptanyl, 6-oxabicyclo[3.2.1]-octanyl, oxetanyl, oxiranyl, piperazinyl, piperidinyl, pyranyl, pyrazolidinyl, pyrrolidinonyl, pyrrolidinyl, pyrrolinyl, quinuclidinyl, sulfolanyl, 3-sulfolenyl, tetrahydropyranyl, tetrahydrofuryl, tetrahydropyridinyl (such as 1,2,3,4-tetrahydropyridinyl and 1,2,3,6-tetrahydropyridinyl), thietanyl, thiiranyl, thiolanyl, tetrahydrothiopyranyl, thiomorpholinyl, trithianyl (including 1,3,5-trithianyl), tropanyl and the like.

Particular heterocyclyl groups that may be mentioned include morpholinyl (e.g. morpholin-4-yl).

Substituents on heterocyclyl groups may, where appropriate, be located on any atom in the ring system including a heteroatom. Further, in the case where the substituent is another cyclic compound, then the cyclic compound may be attached through a single atom on the heterocyclyl group, forming a spirocyclic compound. The point of attachment of heterocyclyl groups may be via any suitable atom in the ring system, including (where appropriate) a further heteroatom (such as a nitrogen atom), or an atom on any fused carbocyclic ring that may be present as part of the ring system. Heterocyclyl groups may also be in the N or S-oxidized forms, as known to those skilled in the art.

At each occurrence when mentioned herein, particular heterocyclyl groups that may be mentioned include 3- to 8-membered heterocyclyl groups (e.g. a 4- to 6-membered heterocyclyl group, such as a 5- or 6-membered heterocyclyl group). Any such heterocyclyl will include at least one heteroatom, e.g. from 1 to 4 heteroatoms, e.g. from 1 to 3 heteroatoms, in particular 1 or 2 heteroatoms, which heteroatoms preferably are selected from N, O and S, e.g. from N and O.

For the avoidance of doubt, references to polycyclic (e.g. bicyclic or tricyclic) groups (for example when employed in the context of heterocyclyl or cycloalkyl groups (e.g. heterocyclyl)) will refer to ring systems wherein at least two scissions would be required to convert such rings into a non-cyclic (i.e. straight or branched) chain, with the minimum number of such scissions corresponding to the number of rings defined (e.g. the term bicyclic may indicate that a minimum of two scissions would be required to convert the rings into a straight chain). For the avoidance of doubt, the term bicyclic (e.g. when employed in the context of alkyl groups) may refer to groups in which the second ring of a two-ring system is formed between two adjacent atoms of the first ring, to groups in which two non-adjacent atoms are linked by an alkyl (which, when linking two moieties, may be referred to as alkylene) group (optionally containing one or more heteroatoms), which later groups may be referred to as bridged, or to groups in which the second ring is attached to a single atom, which latter groups may be referred to as spiro compounds.

As may be used herein, the term aryl may refer to $C_{6-14}$ (e.g. $C_{6-10}$) aromatic groups. Such groups may be monocyclic or bicyclic and, when bicyclic, be either wholly or partly aromatic. $C_{6-10}$ aryl groups that may be mentioned include phenyl, naphthyl, 1,2,3,4-tetrahydronaphthyl, indanyl, and the like (e.g. phenyl, naphthyl, and the like). For the avoidance of doubt, the point of attachment of substituents on aryl groups may be via any suitable carbon atom of the ring system. For the avoidance of doubt, the skilled person will understand that aryl groups that may form part of compounds of the invention are those that are chemically obtainable, as known to those skilled in the art. Particular aryl groups that may be mentioned include phenyl. In some embodiments, any "aryl" mentioned herein refers to phenyl.

As may be used herein, references to heteroaryl (with may also be referred to as heteroaromatic) groups may refer to 5- to 14- (e.g. 5- to 10-membered heteroaromatic groups containing one or more heteroatoms (such as one or more heteroatoms selected from oxygen, nitrogen and/or sulfur). Such heteroaryl groups may comprise one, two, or three rings, of which at least one is aromatic. Certain heteroaryl groups that may be mentioned include those in which all rings forming such groups are aromatic.

Substituents on heteroaryl/heteroaromatic groups may, where appropriate, be located on any suitable atom in the ring system, including a heteroatom (e.g. on a suitable N atom). For the avoidance of doubt, the skilled person will understand that heteroaryl groups that may form part of compounds of the invention are those that are chemically obtainable, as known to those skilled in the art.

The point of attachment of heteroaryl/heteroaromatic groups may be via any atom in the ring system including (where appropriate) a heteroatom. Bicyclic heteroaryl/heteroaromatic groups may comprise a benzene ring fused to one or more further aromatic or non-aromatic heterocyclic rings, in which instances, the point of attachment of the polycyclic heteroaryl/heteroaromatic group may be via any ring including the benzene ring or the heteroaryl/heteroaromatic or heterocyclyl ring.

For the avoidance of doubt, the skilled person will understand that heteroaryl groups that may form part of compounds of the invention are those that are chemically obtainable, as known to those skilled in the art. Various heteroaryl groups will be well-known to those skilled in the art, such as pyridinyl, pyrrolyl, furanyl, thiophenyl, oxadiazolyl, thiadiazolyl, thiazolyl, oxazolyl, pyrazolyl, triazolyl, tetrazolyl, isoxazolyl, isothiazolyl, imidazolyl, imidazopyrimidinyl, imidazothiazolyl, thienothiophenyl, pyrimidinyl, furopyridinyl, indolyl, azaindolyl, pyrazinyl, pyrazolopyrimidinyl, indazolyl, quinolinyl, isoquinolinyl, quinazolinyl, benzofuranyl, benzothiophenyl, benzoimidazolyl, benzoxazolyl, benzothiazolyl, benzotriazolyl, pyrazolopyridinyl, pyrrolopyrazolyl and purinyl.

For the avoidance of doubt, the oxides of heteroaryl/heteroaromatic groups are also embraced within the scope of the invention (e.g. the N-oxide).

As stated above, heteroaryl includes polycyclic (e.g. bicyclic) groups in which one ring is aromatic (and the other may or may not be aromatic). Hence, other heteroaryl groups that may be mentioned include groups such as benzo[1,3]dioxolyl, benzo[1,4]dioxinyl, dihydrobenzo[d]isothiazole, 3,4-dihydrobenz[1,4]oxazinyl, dihydrobenzothiophenyl, indolinyl, 5H,6H,7H-pyrrolo[1,2-b]pyrimidinyl, 1,2,3,4-tetrahydroquinolinyl, thiochromanyl, pyrazolo[3,4-b]pyridinyl, pyrrolo[3,4-c]pyrazolyl, methylenedioxyphenyl, and the like.

Particular heteroaryl groups that may be mentioned include pyrazolo[3,4-b]pyridinyl (e.g. pyrazolo[3,4-b]pyridine-5-yl), pyrrolo[3,4-c]pyrazolyl (e.g. pyrrolo[3,4-c]pyrazol-5-yl), 1,2,4 triazolyl (e.g. 1,2,4 triazol-1-yl), pyrimidinyl (e.g. pyrimidin-5-yl), pyrazolyl (e.g. pyrazol-1-yl), pyridinyl (e.g. pyridine-3-yl and pyridine-4-yl), indolyl (e.g. indol-6-yl and indol-7-yl), imidazolyl (e.g. imidazol-5-yl), isoxazolyl (e.g. isoxazol-3-yl), 1,2-methylenedioxyphenyl (e.g. 1,2-methylenedioxyphen-1-yl) and pyrazolyl (e.g. pyrazol-3-yl).

For the avoidance of doubt, where a ring is depicted having a circle therein, its presence shall indicate that the relevant ring is aromatic. Alternatively, aromatic groups may be depicted as cyclic groups comprising therein a suitable number of double bonds to allow for aromaticity.

The present invention also embraces isotopically-labelled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Hence, the compounds of the invention also include deuterated compounds, i.e. compounds of the invention in which one or more hydrogen atoms are replaced by the hydrogen isotope deuterium.

For the avoidance of doubt, in cases in which the identity of two or more substituents in a compound of the invention may be the same, the actual identities of the respective substituents are not in any way interdependent. For example, in the situation in which two or more $R^3$ groups are present, those $R^3$ groups may be the same or different. Similarly, where two or more $R^3$ groups are present and each represent $R^{2a}$, the $R^{2a}$ groups in question may be the same or different.

Also for the avoidance of doubt, when a term such as "$A^1$ to $A^9$" is employed herein, this will be understood by the skilled person to mean $A^1, A^2, A^3, A^4, A^5, A^6, A^7, A^8$ and $A^9$, inclusively. Unless otherwise stated, the same reasoning will apply to other such terms used herein.

Further for the avoidance of doubt, when it is specified that a substituent is itself optionally substituted by one or more substituents (e.g. $A^1$ represents aryl optionally substituted by one or more (e.g. 1-3) groups independently selected from $D^1$), these substituents where possible may be positioned on the same or different atoms. Such optional substituents may be present in any suitable number thereof (e.g. the relevant group may be substituted with one or more such substituents, such as one such substituent).

For the avoidance of doubt, where groups are referred to herein as being optionally substituted it is specifically contemplated that such optional substituents may be not present (i.e. references to such optional substituents may be removed), in which case the optionally substituted group may be referred to as being unsubstituted.

Where used herein, a dashed bond (i.e. "- - -", or the like) may indicate the position of attachment of the relevant substituent to the core molecule (i.e. the compound of the compound of formula I to which the substituent is attached).

For the avoidance of doubt, when in structures provided herein a ring is represented as having a circle therein (e.g. in the case of the ring comprising $Y^1$ to $Y^4$ in formula I), the skilled person will understand that the relevant ring is aromatic.

For the avoidance of doubt, the skilled person will appreciate that compounds of the invention that are the subject of this invention include those that are obtainable, i.e. those that may be prepared in a stable form. That is, compounds of the invention include those that are sufficiently robust to survive isolation, e.g. from a reaction mixture, to a useful degree of purity.

In certain embodiments (i.e. certain embodiments of the first aspect of the invention) that may be mentioned, where $Z^3$ represents N and/or (e.g. and) $X^2$ represents O, at least one $R^3$ group is present. In certain embodiments, where $Z^3$ represents N, at least one $R^3$ group is present.

In further embodiments, there is the proviso that where $Z^3$ represents N at least one $R^3$ group is present, which proviso may be referred to herein as proviso (a).

In yet further embodiments, proviso (a) may require (in all instances) that at least one $R^3$ group is present.

In certain embodiments, there is the proviso that the compound of formula I is not a compound selected from the following list:
4-(5-chloro-2-oxo-2,3-dihydro-1H-1,3-benzodiazol-1-yl)-N-(4-chlorophenyl)piperidine-1-carbothioamide;
N-(4-chlorophenyl)-4-(5-fluoro-2-oxo-2,3-dihydro-1H-1,3-benzodiazol-1-yl)piperidine-1-carbothioamide;
4-(5-chloro-2-oxo-2,3-dihydro-1H-1,3-benzodiazol-1-yl)-N-(3-chlorophenyl)piperidine-1-carboxamide;
ethyl 4-{[4-(5-chloro-2-oxo-2,3-dihydro-1H-1,3-benzodiazol-1-yl)piperidine-1-carbonyl]amino}benzoate;
4-(5-chloro-2-oxo-2,3-dihydro-1H-1,3-benzodiazol-1-yl)-N-(2,6-dichloropyridin-4-yl)piperidine-1-carboxamide,
which may be referred to herein as proviso (b).

In particular embodiments (i.e. particular embodiments of the first aspect of the invention), the compound of formula I is such that: $X^1$ and $X^2$ each represent O; or $X^1$ represents O and $X^2$ represents S.

Thus, in particular embodiments, $X^1$ represents O. For example, in certain embodiments $X^1$ and $X^2$ each represent O.

In particular embodiments, the compound of formula I is such that: each of $Y^1$ to $Y^4$ independently represents CH or $CR^3$, or $Y^1$ may alternatively represent N.

Preferably, $Y^1$, $Y^2$, $Y^3$ and $Y^4$ are not all CH. For example, in some embodiments, three of $Y^1$, $Y^2$, $Y^3$ and $Y^4$ are CH, and the remaining one is N or $CR^3$; e.g. three of $Y^1$, $Y^2$, $Y^3$ and $Y^4$ are CH, and the remaining one is $CR^3$.

In some further embodiments, $Y^1$, $Y^2$ and $Y^3$ represent CH, or two of $Y^1$, $Y^2$ and $Y^3$ represent CH, and one of $Y^1$, $Y^2$ and $Y^3$ represents N; and $Y^4$ represents $CR^3$.

In some further embodiments, $Y^1$ and $Y^2$ represent CH, and one of $Y^3$ and $Y^4$ represents N or $CR^3$, while the other one represents CH.

In particular embodiments, the compound of formula I is a compound of formula Ia

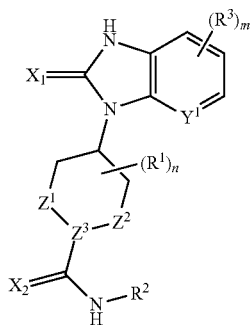

Ia wherein:
$Y^1$ represents N, CH or $CR^3$;
m represents 0 to 3; and
$R^1$ to $R^3$, $X^1$, $X^2$, $Z^1$ to $Z^3$, and n are as defined herein (i.e. for compounds of formula I, including all embodiments thereof).

In particular such embodiments, either
$Y^1$ represents N or CH (e.g. N) and m represents 1 to 3 (e.g. 1); or
$Y^1$ represents $CR^3$ and m represents 0 to 3 (e.g. 0).

In certain embodiments, $Y^1$ represents N or CH.

In yet more particular embodiments, the compound of formula I is a compound of formula Ib

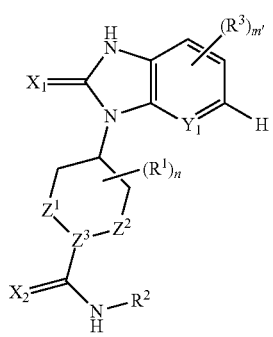

Ib wherein:
$Y^1$ represents N, CH or $CR^3$;
m' represents 0 to 2; and
$R^1$ to $R^3$, $X^1$, $X^2$, $Z^1$ to $Z^3$, and n are as defined herein (i.e. for compounds of formula I, including all embodiments thereof).

In particular such embodiments, $Y^1$ represents N or CH (e.g. N) and m' represents 1 or 2 (e.g. 1).

In certain embodiments that may be mentioned, the compound of formula I is a compound of formula Ic

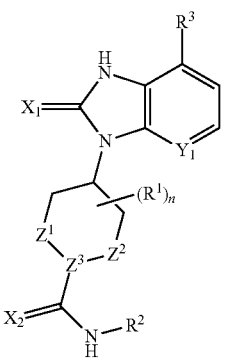

Ic wherein:
$Y^1$ represents N or CH; and
$R^1$ to $R^3$, $X^1$, $X^2$, $Z^1$ to $Z^3$, and n are as defined herein (i.e. for compounds of formula I, including all embodiments thereof).

In certain embodiments, $Y^1$ represents CH.

In particular embodiments, either:
$Z^1$ and $Z^2$ both represent methylene;
$Z^1$ and $Z^2$ both represent methylene linked by an additional ethylene group; or
$Z^1$ represents ethylene and $Z^2$ represents methylene.

In certain embodiments that may be mentioned, $Z^1$ and $Z^2$ both represent methylene.

In particular embodiments, $Z^3$ represents CH or N. In certain embodiments, $Z^3$ represents N.

In further embodiments, $Z^3$ represents CH or $CR^1$. In yet further embodiments, $Z^3$ represents CH.

Thus, in certain embodiments, the compound of formula I is a compound of formula Id

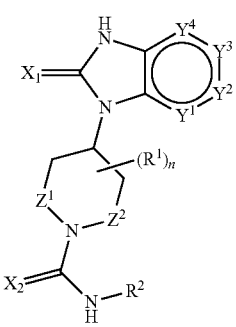

Id wherein $R^1$ to $R^3$, $X^1$, $X^2$, $Y^1$ to $Y^4$, $Z^1$ to $Z^3$, and n are as defined herein (i.e. for compounds of formula I, including all embodiments thereof).

In further embodiments, the compound of formula I is a compound of formula Ie

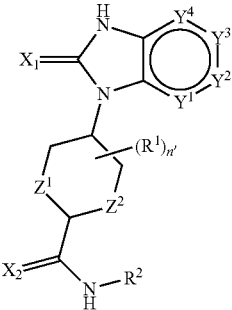

Ie wherein $R^1$ to $R^3$, $X^1$, $X^2$, $Y^1$ to $Y^4$, and $Z^1$ to $Z^3$ are as defined herein (i.e. for compounds of formula I, including all embodiments thereof), and n' represents 0 to 12, as appropriate.

In yet further embodiments, the compound of formula I is a compound of formula If

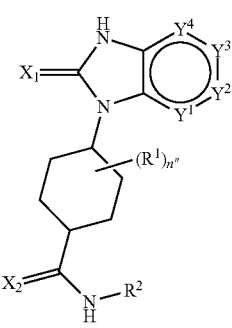

If wherein $R^1$ to $R^3$, $X^1$, $X^2$, $Y^1$ to $Y^4$, and $Z^1$ to $Z^3$ are as defined herein (i.e. for compounds of formula I, including all embodiments thereof), and n" represents 0 to 10.

In yet further embodiments, the compound of formula I is a compound of formula Ig

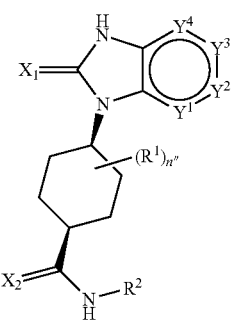

Ig wherein $R^1$ to $R^3$, $X^1$, $X^2$, $Y^1$ to $Y^4$, and $Z^1$ to $Z^3$ are as defined herein (i.e. for compounds of formula I, including all embodiments thereof), and n" represents 0 to 10.

For the avoidance of doubt, the skilled person will understand that the stereochemistry shown in formula Ig is relative, thus showing that the substituents on the cyclohexane are in the cis configuration. In such instances, compounds may be defined as being provided such that the required diastereoisomer is present in an excess when compared to the relative amounts of other possible diastereoisomers, such as being present in a diastereomeric excess (d.e.) of at least 60% (such as at least 70%, 80%, 85%, 90% or 95%, e.g. at least 99% or at least 99.9%).

In particular embodiments, n (and, similarly, n' and n") represents 0 or 1.

In particular embodiments, each $R^1$ independently represents, where possible: halo, oxy, $—NO_2$, $—CN$, $—R^{1a}$, $—OR^{1b}$, $—S(O)_qRC$, $—S(O)_r(R^{1d})(R^{1e})$, $—N(R^{1f})S(O)_sR^{1g}$, $—N(R^{1h})(R^{1i})$, $—C(O)OR^{1j}$, or $—C(O)NR^{1k}R^{1l}$. In more particular embodiments, each $R^1$ independently represents halo (e.g. fluoro), $—R^{1a}$ or $—OR^{1b}$. In yet more particular embodiments, each $R^1$ independently represents $—R^{1a}$ or $—OR^{1b}$, such as wherein $R^{1a}$ represents $C_{1-6}$ alkyl (e.g. methyl); and $R^{1b}$ represents H. In more particular embodiments, each $R^1$ independently represents fluoro, methyl or hydroxy, e.g. fluoro or methyl, in particular fluoro.

In particular embodiments, where n represents 1, the $R^1$ group is present in a position that is alpha or beta to the point of attachment of the ring on which such groups are present to the essential benzimidazole ring.

In certain embodiments, n represents 0.

In a compound of formula I, $R^2$ represents
(i) phenyl optionally substituted by one or more (e.g. 1-3, or 1-2) groups independently selected from $A^4$, ("option a(i)")
(ii) 5- or 6-membered monocyclic heteroaryl optionally substituted by one or more (e.g. 1-3, or 1-2) groups selected from oxy and $A^6$ ("option a(ii)"), or
(iii) phenyl substituted with two adjacent groups which, together with the ring to which they are attached, form a bicyclic heteroaryl optionally substituted by one or more (e.g. 1-3, or 1-2) groups selected from oxy and $A^6$ ("option a(iii)")

In some embodiments, $R^2$ represents option a(i) or option a(ii). In some embodiments, $R^2$ represents option a(i) or option a(iii). In some embodiments, $R^2$ represents option a(ii) or option a(iii).

In some embodiments, $R^2$ represents option a(i). In some embodiments, $R^2$ represents option a(ii). In some embodiments, $R^2$ represents option a(iii).

For the avoidance of doubt, it is pointed out that, for example, the indication that "$R^2$ represents option a(i)" is equivalent to an indication that "$R^2$ represents (i) phenyl optionally substituted by one or more (e.g. 1-3, or 1-2) groups independently selected from $A^4$", and consequently these two types of expression may replace each other herein.

In some embodiments, in option a(i) the phenyl is substituted by one or two groups independently selected from $A^4$. (For the avoidance of doubt, it is pointed out that this means that, in some embodiments, when $R^2$ represents option a(i), $R^2$ more particularly represents phenyl substituted by one or two groups independently selected from $A^4$).

In some embodiments, in option a(i) the phenyl is substituted by one group independently selected from $A^4$.

In some embodiments, in option a(i), one $A^4$ in the meta position relative to the point of attachment to the essential amide group, e.g. the phenyl is substituted by one group independently selected from $A^4$, which is in meta position on the phenyl ring.

In some further embodiments, in option a(i), one $A^4$ in the para position relative to the point of attachment to the essential amide group.

In some embodiments, in option a(i), the phenyl is substituted by at least 2 groups independently selected from $A^4$, (in particular 2 or 3 groups, e.g. 2 groups), of which one group is in the para position relative to the point of attachment of the phenyl ring to the essential amide group, and one is in the meta position relative to the point of attachment of the phenyl ring to the essential amide group. Thus, in some embodiments, the compound of formula I is as represented by formula Ih

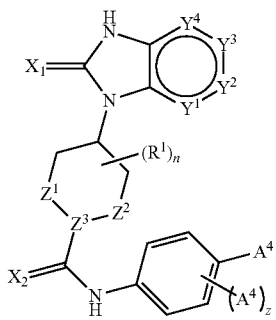

Ih wherein each $R^1$, n $X^1$, $X^2$, $Y^1$ to $Y^4$, $Z^1$ to $Z^3$, each $A^4$, and n are as defined herein, and z is an integer of from 0 to 2, e.g. z is 0 or 1. In some embodiments, z is 0. In some other embodiments, z is 1. In some particular embodiments, when z is 1, the compound of formula I is as represented by formula Ii

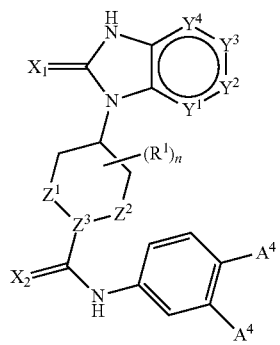

Ii wherein $X^1$, $X^2$, $Y^1$ to $Y^4$, $Z^1$ to $Z^3$, and each $A^4$, and n are as defined herein.

In some embodiments, $R^2$ cannot be unsubstituted phenyl, i.e. in option a(i), the phenyl is substituted by at least one group $A^4$.

In some preferred embodiments, the compound of formula I is as illustrated by formula Ij

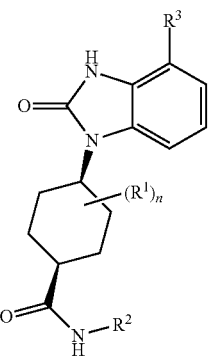

Ij wherein $R^1$, $R^2$, $R^3$ and n are as defined herein. In some of these embodiments, n is 0, i.e. the compound more particularly is as represented by formula Ik

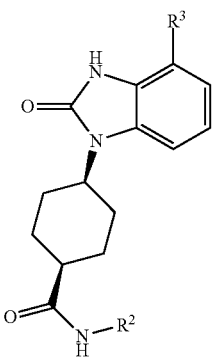

Ik wherein $R^2$ and $R^3$ are as represented herein.

In some of these preferred embodiments, the compound of formula Ik is also a compound of formula Ih, i.e. a compound as represented by formula Im

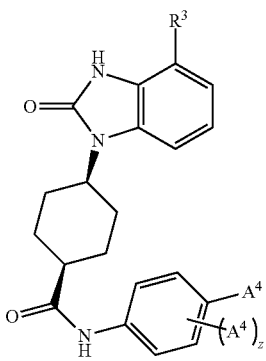

Im wherein $R^3$, each $A^4$ and z are as defined herein, e.g. z is 0 or 1. In some embodiments, z is 0. In some other particular embodiments, z is 1. In some of these embodiments, the compound is as represented by formula In

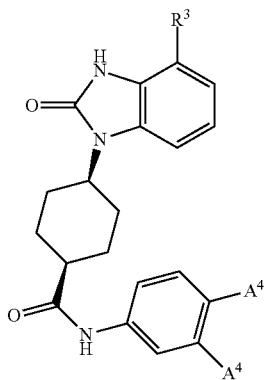

wherein R³ and each A⁴ are as defined herein.

In some embodiments, in option a(i), R² represents a moiety selected from 3-(dimethylamino)phenyl, 3-(hydroxymethyl)phenyl, 3-(trifluoromethyl)phenyl, 3-aminophenyl, 3-chlorophenyl, 3-hydroxyphenyl, 3-methoxyphenyl, 3-methylphenyl, 4-chlorophenyl, 4-(dimethylamino)phenyl, 4-(trifluoromethyl)phenyl, 4-carbamoylphenyl, 4-cyanophenyl, 4-ethylphenyl, 4-fluorophenyl, 4-hydroxyphenyl, 4-iodophenyl, 4-methoxyphenyl, 4-methylphenyl, 2,3-dimethylphenyl, 2,4-dichlorophenyl, 2-fluoro-4-methoxyphenyl, 2-fluoro-4-methylphenyl, 2-hydroxy-4-methylphenyl, 3,4-dichlorophenyl, 3,4-difluorophenyl, 3,4-dimethoxyphenyl, 3,4-dimethylphenyl, 3-chloro-4-(trifluoromethoxy)phenyl, 3-chloro-4-cyanophenyl, 3-chloro-4-fluorophenyl, 3-chloro-4-hydroxyphenyl, 3-chloro-4-iodophenyl, 3-chloro-4-methoxyphenyl, 3-chloro-5-methoxyphenyl, 3-cyano-4-methoxyphenyl, 3-fluoro-4-(trifluoromethyl)phenyl, 3-fluoro-4-methoxyphenyl, 3-fluoro-5-methoxyphenyl, 3-hydroxy-4-methylphenyl, 3-methoxy-4-methylphenyl, 3-methoxy-5-(trifluoromethyl)phenyl, 4-bromo-3-chlorophenyl, 4-bromo-3-methylphenyl, 4-chloro-3-(trifluoromethyl)phenyl, 4-chloro-3-cyanophenyl, 4-chloro-3-fluorophenyl, 4-chloro-3-methoxyphenyl, 4-chloro-3-methylphenyl, 4-cyano-3-methoxyphenyl, 4-fluoro-3-methoxyphenyl, 4-fluoro-3-methylphenyl, 4-hydroxy-3-methylphenyl, 4-iodo-3-methylphenyl, 4-methoxy-3-(methoxycarbonyl)phenyl, 4-methoxy-3-(trifluoromethyl)phenyl, 4-methoxy-3-methylphenyl, 4-methyl-3-(trifluoromethyl)phenyl, 2-amino-4,5-dimethylphenyl, 2,3-difluoro-4-methoxyphenyl, 3,4,5-trimethoxyphenyl, and 3,5-difluoro-4-methoxyphenyl. In some embodiments, e.g. of a compound of formula Ig, R₂ is 3-methoxy-4-methylphenyl.

In some embodiments, in option a(ii), the 5- or 6-membered monocyclic heteroaryl is unsubstituted or substituted by 1, 2 or 3 (in particular 1 or 2, more particularly 1) group(s) A⁵. In some embodiments, in option a(ii), the 5- or 6-membered monocyclic heteroaryl is unsubstituted, i.e. carries no group A⁵. In some other embodiments, in option a(ii), the 5- or 6-membered monocyclic heteroaryl substituted by 1, 2 or 3 (in particular 1 or 2, more particularly 1) group(s) A⁵.

In some embodiments, in option a(ii), the 5- or 6-membered monocyclic heteroaryl more particularly is 6-membered monocyclic heteroaryl. In some other embodiments, in option a(ii), the 5- or 6-membered monocyclic heteroaryl more particularly is 5-membered monocyclic heteroaryl. In some embodiments, in option a(ii), the monocyclic heteroaryl, when 5-membered, contains 1-3, or 1-2, or 1, heteroatom(s) selected from N, O and S, e.g. from N and O. In some embodiments, in option a(ii), the monocyclic heteroaryl, when 6-membered, contains 1 or 2 nitrogen atoms.

In some embodiments, in option a(ii), the heteroaryl is selected from imidazolyl, pyrazolyl, oxazolyl, and pyridinyl. In some particular embodiments, the heteroraryl is pyridinyl, e.g. pyridin-2-yl or pyridin-3-yl, in particular pyridin-3-yl.

In some embodiments, when in option a(ii) the heteroaryl is pyridin-2-yl or pyridin-3-yl, in particular pyridin-3-yl, said pyridinyl is substituted in para position relative to the point of attachment of the pyridinyl ring to the essential amide group. In some of these embodiments, the pyridinyl is substituted with one group A⁵. In some other embodiments, the pyridinyl is substituted with two groups A⁵, one of which is in para position, and the other one of which is in meta position, relative to the point of attachment of the pyridinyl ring to the essential amide group.

In some embodiments, in option a(ii), R² represents a moiety selected from 5-chloropyridin-3-yl, 5-methylpyridin-2-yl, 6-chloropyridin-3-yl, 6-methoxypyridin-3-yl, 6-methylpyridin-3-yl, 5,6-dichloropyridin-3-yl, 5-chloro-6-methoxypyridin-3-yl, 5-chloro-6-methylpyridin-2-yl, 6-chloro-5-methylpyridin-3-yl, and 6-methoxy-5-methylpyridin-3-yl.

In some embodiments, in option a(iii), the bicyclic heteroaryl is unsubstituted, i.e. carries no group A⁶. In some other embodiments, in option a(iii), the bicyclic heteroaryl is substituted by one or more (e.g. 1-3) groups selected from A⁶, e.g. 1, 2 or 3 groups selected from A⁶, or 1 or 2 groups selected from A⁶, e.g. one group A⁶. In some embodiments, the bicyclic heteroaryl is unsubstituted or substituted by one group A⁶.

In option a(iii), the bicyclic heteroaryl contains one benzene ring fused to a heterocyclic ring, e.g. a 5- or 6-membered heterocyclic ring, which may be saturated or unsaturated and aromatic or non-aromatic, and contain one or more heteroatoms, e.g. 1 or 2 heteroatoms. In some embodiments, the heterocyclic ring is 5- or 6-membered and aromatic, e.g. 5- or 6-membered and aromatic and containing 1 or 2 heteroatoms selected from N, O and S, e.g. from N and O.

It should be pointed out that the bicyclic heteroaryl may be attached to the essential amide group by a bond to either the benzene ring or the heterocyclic ring. In some embodiments, the bicyclic heteroaryl is attached to the essential amide group by a bond to the benzene ring of the bicyclic heteroaryl.

In some embodiments, in option a(iii), the bicyclic heteroaryl is selected from benzodioxolyl, benzodioxinyl, indolyl, indazolyl, benzoxazolyl, quinolinyl, and benzodiazolyl. In some of these embodiments, the bicyclic heteroaryl more particularly is indolyl, indazolyl, benzoxazolyl, quinolinyl, or benzodiazolyl.

In some particular embodiments, in option a(iii), R² represents a moiety selected from 1H-indolyl, 1H-indolyl, 1H-indazolyl, 1H-indazolyl, 1-methyl-1H-indazolyl, 3-methyl-1H-indazolyl, 1-methyl-1H-1,3-benzodiazolyl, 2-methyl-1,3-benzoxazolyl, quinolinyl, 2,3-dihydro-1,4-benzodioxinyl, and 2H-1,3-benzodioxolyl; e.g. from 1H-indol-4-yl, 1H-indol-5-yl, 1H-indazol-6-yl, 1H-indazol-7-yl, 1-methyl-1H-indazol-5-yl, 3-methyl-1H-indazol-5-yl, 1-methyl-1H-1,3-benzodiazol-2-yl, 2-methyl-1,3-benzoxazol-6-yl, quinolin-6-yl, 2,3-dihydro-1,4-benzodioxin-6-yl, and 2H-1,3-benzodioxol-5-yl.

In a compound of formula I, each $R^3$ independently represents
  (i) halo, —NO$_2$, —CN, —R$^{2a}$, —OR$^{2b}$, —S(O)$_q$R$^{2c}$, —S(O)$_r$N(R$^{2d}$)(R$^{2e}$), —N(R$^{2f}$)S(O)$_s$R$^{2g}$, —N(R$^{2h}$)(R$^{2i}$), —C(O)OR$^{2j}$, or —C(O)NR$^{2k}$R$^{2l}$ ("option b(i)"),
  (ii) aryl optionally substituted by one or more (e.g. 1-3) groups independently selected from A$^7$ ("option b(ii)"),
  (iii) heteroaryl optionally substituted by one or more (e.g. 1-3) groups selected from A$^8$, ("option b(ii)"), or
  (iv) heterocyclyl optionally substituted by one or more (e.g. 1-3) groups independently selected from A$^9$ ("option b(iv)").

In some embodiments, $R^3$ represents option b(i), option b(ii) or option b(iii). In some embodiments, $R^3$ represents option b(i) or option b(iv). In some embodiments, $R^3$ represents option b(i), option b(ii), or option b(iv). In some embodiments, $R^3$ represents option b(i), option b(ii), or option b(iv).

In some particular embodiments, $R^3$ represents option b(i). In some other particular embodiments, $R^3$ represents option b(ii). In still other embodiments, $R^3$ represents option b(iii). In some further embodiments, $R^3$ represents option b(iv).

In some embodiments, in option b(i), $R^3$ more particularly represents a moiety selected from halo, —CN, —R$^{2a}$, —OR$^{2b}$, —S(O)$_q$R$^{2c}$, —N(R$^{2h}$)(R$^{2i}$), —C(O)OR$^{2j}$, and —C(O)NR$^{2k}$R$^{2l}$. In some further embodiments, in option b(i), the moiety is selected from halo, CN, —R$^{2a}$, —OR$^{2b}$, —N(R$^{2h}$)(R$^{2i}$), —C(O)OR$^{2j}$, and —C(O)NR$^{2k}$R$^{2l}$. In still some further embodiments, in option b(i), the moiety is selected from halo, —OR$^{2b}$, N(R$^{2h}$)(R$^{2i}$), and —C(O)NR$^{2k}$R$^{2l}$. In still some further embodiments, in option b(i), the moiety is selected from halo, —N(R$^{2h}$)(R$^{2i}$), and —C(O)NR$^{2k}$R$^{2l}$. In still some further embodiments, in option b(i), the moiety is selected from halo.

In still some further embodiments, in option b(i), the moiety is selected from —OR$^{2b}$, —N(R$^{2h}$)(R$^{2i}$), and —C(O)NR$^{2k}$R$^{2l}$. In still some further embodiments, in option b(i), the moiety is selected from —N(R$^{2h}$)(R$^{2i}$), and —C(O)NR$^{2k}$R$^{2l}$. In still some further embodiments, in option b(i), the moiety is —C(O)NR$^{2k}$R$^{2l}$. In still some further embodiments, in option b(i), the moiety is —N(R$^{2h}$)(R$^{2i}$).

In still some further embodiments, in option b(i), the moiety is —OR$^{2b}$ or —C(O)NR$^{2k}$R$^{2l}$. In still some further embodiments, in option b(i), the moiety is —OR$^{2b}$.

In still some further embodiments, in option b(i), the moiety is selected from halo, —R$^{2a}$, —OR$^{2b}$, N(R$^{2h}$)(R$^{2i}$), and —C(O)NR$^{2k}$R$^{2l}$. In still some further embodiments, in option b(i), the moiety is selected from halo, —R$^{2a}$, —N(R$^{2h}$)(R$^{2i}$), and —C(O)NR$^{2k}$R$^{2l}$. In still some further embodiments, in option b(i), the moiety is selected from halo and —R$^{2a}$.

In still some further embodiments, in option b(i), the moiety is selected from —R$^{2a}$, —OR$^{2b}$, —N(R$^{2h}$)(R$^{2i}$), and —C(O)NR$^{2k}$R$^{2l}$. In still some further embodiments, in option b(i), the moiety is selected from —R$^{2a}$, N(R$^{2h}$)(R$^{2i}$), and —C(O)NR$^{2k}$R$^{2l}$. In still some further embodiments, in option b(i), the moiety is —R$^{2a}$ or —C(O)NR$^{2k}$R$^{2l}$. In still some further embodiments, in option b(i), the moiety is —R$^{2a}$ or —N(R$^{2h}$)(R$^{2i}$). In still some further embodiments, in option b(i), the moiety is —R$^{2a}$, —OR$^{2b}$ or —C(O)NR$^{2k}$R$^{2l}$. In still some further embodiments, in option b(i), the moiety is —R$^{2a}$ or —OR$^{2b}$. In still some further embodiments, in option b(i), the moiety is —R$^{2a}$.

In some embodiments, in option b(i), the moiety —S(O)$_q$R$^{2c}$ more particularly is a moiety selected from —S(O)$_2$R$^{2c}$ and —SR$^{2c}$. In some embodiments, the moiety —S(O)$_q$R$^{2c}$ is —SR$^{2c}$. In some other embodiments, the moiety —S(O)$_q$R$^{2c}$ is —S(O)R$^{2c}$ or —S(O)$_2$R$^{2c}$, in particular —S(O)$_2$R$^{2c}$.

In certain embodiments, each $R^3$ independently represents halo (e.g. F or Br, such as Br).

In further embodiments, where $Z^3$ represents CH or CR$^1$, each $R^3$ represents F (such as wherein one $R^3$ group is present).

In some embodiments, in option b(ii), $R^3$ represents phenyl optionally substituted by one or more (e.g. 1-3) groups independently selected from A$^7$. In some of these embodiments, the phenyl is substituted by 1-3 groups independently selected from A$^7$, e.g. 1 or 2 groups independently selected from A7, or one group independently selected from A$^7$.

In some particular embodiments, in option b(ii), $R^3$ represents a moiety selected from 2-aminophenyl, 2-((dimethylamino)methyl)phenyl, 3-aminophenyl, 3-((2-methoxyethyl)carbamoyl)phenyl, 3-(2-(dimethylamino)ethoxy)phenyl, 3-(aminomethyl)phenyl, 3-(carbamoylmethyl)phenyl, 3-(methoxycarbonyl)phenyl, 3-(morpholine-4-carbonyl)phenyl, 3,5-bis(trifluoromethyl)phenyl, 3-[2-(dimethylamino)ethoxy]phenyl, 3-carboxyphenyl, 3-fluorophenyl, 4-(2-(dimethylamino)ethoxy)phenyl, 4-(2,2,2-trifluoroacetyl)phenyl, 4-(aminomethyl)phenyl, 4-carboxyphenyl, and 4-sulfamoylphenyl.

In option b(iii), the heteroaryl is optionally substituted by one or more (e.g. 1, 2 or 3) groups selected from A$^6$, in particular by 1 or 2 groups selected from A$^8$. In some embodiments, in option b(iii), the heteroaryl is unsubstituted or substituted by one group A$^8$.

In option b(iii), the required heteroaryl is as generally described herein above. For example, the heteroaryl may be monocyclic and 5- or 6-membered and contain one or more (e.g. 1, 2 or 3) heteroatoms selected from N, O and S; or bicyclic and 8- to 10-membered (or 9- or 10-membered) and contain one or more (e.g. 1, 2, 3 or 4) heteroatoms selected from N, O and S. For example, the heteroaryl may be selected from 1H-pyrrolyl, 1H-pyrazolyl, triazolyl (such as 1H-1,2,4-triazolyl) pyridinyl, pyrimidinyl, 1H-pyrazolopyridinyl (e.g. 1H-pyrazolo[3,4-b]pyridinyl, and 1H,4H,5H,6H-pyrrolopyrazolyl, (e.g. 1H,4H,5H,6H-pyrrolo[3,4-c]pyrazolyl).

In some embodiments, in option b(iii), $R^3$ represents a moiety selected from 1H-pyrrol-2-yl, 1H-pyrazol-1-yl, 4-bromo-1H-pyrazol-1-yl, 4-(ethylcarbamoyl)-1H-pyrazol-1-yl, 4-(diethylcarbamoyl)-1H-pyrazol-1-yl, 4-(2-(dimethylamino)ethyl)carbamoyl)-1H-pyrazol-1-yl, 4-((2,3-dihydroxypropyl)carbamoyl)-1H-pyrazol-1-yl, 1H-1,2,4-triazol-1-yl, pyridin-3-yl, pyridin-4-yl, 2-ethoxypyridin-3-yl, 2-(trifluoromethyl)pyridin-4-yl, pyridin-4-yl, 5-aminopyridin-3-yl, 6-aminopyridin-3-yl, 6-(hydroxymethyl)pyridin-3-yl, 6-methoxypyridin-3-yl, pyrimidin-5-yl, 1H-pyrazolo[3,4-b]pyridin-5-yl, and 1H,4H,5H,6H-pyrrolo[3,4-c]pyrazol-5-yl.

In option b(iv), the heterocyclyl is optionally substituted by one or more (e.g. 1-3, or 1-2) groups selected from A$^9$, in particular by 1 or 2 groups selected from A$^9$, e.g. 1 group selected from A$^9$. In some embodiments, in option b(iv), the heterocyclyl is unsubstituted or substituted by one group A$^9$.

In option b(iv), the heterocyclyl is a ring as generally described herein. For example, the heterocyclyl may be a monocyclic, saturated or unsaturated (non-aromatic) 4- to 8-membered, more particularly 4- to 6-membered (e.g. 5- or 6-membered) ring containing 1, 2 or 3 (e.g. 1 or 2) heteroatoms selected from N, O and S. In some embodiments, the heterocyclyl is 5- or 6-membered and contains 1 or 2 heteroatoms selected from N, O and S, in particular N or O. In some embodiments, said heterocyclyl contains at least one N in the ring. In some of these embodiments, the heterocyclyl containing at least one N in the ring is attached to the benzene ring of the compound of formula I by a bond to said N.

In some embodiments, in option b(iv), the heterocyclyl is selected from pyrrolidinyl, piperidinyl, piperazinyl, morpholinyl, and 1,2,3,6-tetrahydropyridinyl; e.g. from pyrrolidin-1-yl, piperidin-1-yl, piperazin-1-yl, morpholin-4-yl, and 1,2,3,6-tetrahydropyridin-4-yl.

In some particular embodiments, in option b(iv), $R^3$ represents a moiety selected from pyrrolidin-1-yl, 3-aminopyrrolidin-1-yl, 3-(dimethylamino)pyrrolidin-1-yl, 3-acetamidopyrrolidin-1-yl, 3-((tert-butoxycarbonyl)amino)pyrrolidin-1-yl, piperazin-1-yl, 4-aminopiperidin-1-yl, 1,2,3,6-tetrahydropyridin-4-yl, 1-methyl-1,2,3,6-tetrahydropyridin-4-yl, and morpholin-4-yl.

In a compound of formula I, each $R^{2a}$ represents:
(i) $C_{1-6}$ alkyl, $C_{2-6}$ alkenyl or $C_{2-6}$ alkynyl, wherein each such alkyl, alkenyl or alkynyl group is optionally substituted by one or more (e.g. 1-3) groups independently selected from oxy and $B^1$ ("option c(i)"),
(ii) aryl optionally substituted by one or more (e.g. 1-3) groups independently selected from oxy and $B^2$ ("option c(ii)"),
(iii) heteroaryl optionally substituted by one or more (e.g. 1-3) groups selected from oxy and $B^3$ ("option c(iii)"), or
(iv) heterocyclyl optionally substituted by one or more (e.g. 1-3) groups independently selected from oxy and $B^4$ ("option c(iv)"); and each $R^{2b}$ to $R^{2l}$ independently represents H, or
(i) $C_{1-6}$ alkyl, $C_{2-6}$ alkenyl or $C_{2-6}$ alkynyl, wherein each such alkyl, alkenyl or alkynyl group is optionally substituted by one or more (e.g. 1-3) groups independently selected from oxy and $B^1$ ("option d(i)"),
(ii) aryl optionally substituted by one or more (e.g. 1-3) groups independently selected from oxy and $B^2$ ("option d(ii)"),
(iii) heteroaryl optionally substituted by one or more (e.g. 1-3) groups selected from oxy and $B^3$ ("option d(iii)"), or
(iv) heterocyclyl optionally substituted by one or more (e.g. 1-3) groups independently selected from oxy and $B^4$ ("option d(iv)").

In some embodiments, each $R^{2a}$ represents option c(i), option c(iii), or option c(iv), and each $R^{2b}$ to $R^{2l}$ independently represents H, option d(i), option d(iii) or option d(iv). In some embodiments, each $R^{2a}$ represents option c(i) or option c(iv), and each $R^{2b}$ to $R^{2l}$ independently represents H, option d(i) or option d(iv). In some further embodiments, each $R^{2a}$ represents option c(i) and each $R^{2b}$ to $R^{2l}$ independently represents H or option d(i).

In some embodiments, in any one of $R^{2a}$ to $R^{2l}$, any $C_{1-6}$ alkyl, $C_{2-6}$ alkenyl or $C_{2-6}$ alkynyl more particularly is (saturated) $C_{1-6}$ alkyl, e.g. $C_{1-4}$ alkyl, or $C_{1-3}$ alkyl (including linear and, when there are a sufficient number of carbon atoms, branched alkyl and cycloalkyl).

In some of the above embodiments, when any one of $R^{2a}$ to $R^{2l}$ represents (optionally substituted) $C_{1-6}$ alkyl, $C_{2-6}$ alkenyl, or $C_{2-6}$ alkynyl, any such alkyl, alkynyl or alkenyl more particularly is $C_{1-4}$ alkyl, any $C_{2-6}$ alkenyl more particularly is $C_{2-4}$ alkenyl, and any $C_{2-6}$ alkynyl more particularly is $C_{2-4}$ alkynyl. In some further of the above embodiments, any such alkyl more particularly is $C_{1-3}$ alkyl, any such alkenyl more particularly is $C_{2-3}$ alkenyl, and any such alkynyl more particularly is $C_{2-3}$ alkynyl.

When any one of $R^{2a}$ to $R^{2l}$ represents (optionally substituted) aryl, such aryl preferably is phenyl.

When any one of $R^{2a}$ to $R^{2l}$ represents (optionally substituted) heteroaryl, such heteroaryl is as defined herein above, e.g. it may be 5- or 6-membered and contain from 1 to 3 heteroatoms, such as 1 to 3 heteroatoms selected from N, O and S, in particular from N and O.

When any one of any one of $R^{2a}$ to $R^{2l}$ represents (optionally substituted) heterocyclyl, such heterocyclyl is as defined herein above, and e.g. may be selected from 4- to 6-membered heterocyclyl containing one or more heteroatoms selected from N, O and S, e.g. 1 or 3 heteroatoms selected from N, O and S, e.g. from N and O. For example, the heterocyclyl may be selected from piperazinyl, morpholinyl, piperidinyl, pyrrolidinyl, and azetidinyl.

In particular embodiments:
$R^{2a}$ represents $C_{1-6}$ alkyl (e.g. $C_{1-3}$ alkyl) optionally substituted by one or more (e.g. 1-3) groups independently selected from oxy and $B^1$;
$R^{2b}$ represents H or $C_{1-6}$ alkyl (e.g. $C_{1-2}$ alkyl);
$R^{2c}$ represents H or $C_{1-6}$ alkyl (e.g. $C_1$ alkyl), such as $C_{1-6}$ alkyl (e.g. $C_1$ alkyl); and
$R^{2h}$ and $R^{2i}$ independently represent H or $C_{1-6}$ alkyl (e.g. $C_1$ alkyl).

In some embodiments, $R^{2a}$ represents $C_{1-6}$ alkyl, e.g. $C_{1-3}$ alkyl, such as methyl, ethyl, propyl or cyclopropyl; or $R^{2a}$ represents $C_{1-6}$ alkyl (e.g. $C_{1-3}$ alkyl, such as methyl, ethyl, propyl or cyclopropyl), substituted by one or more moieties selected from oxy and $B^1$, e.g. one oxy and/or 1, 2 or 3 moieties $B^1$.

In some embodiments, $R^{2a}$ represents $C_{1-6}$ alkyl (e.g. $C_{1-3}$ alkyl, such as methyl, ethyl, propyl or cyclopropyl), said alkyl being substituted by one or more moieties selected from oxy and $B^1$, e.g. one oxy and/or 1, 2 or 3 moieties $B^1$, or said alkyl being substituted by one or more (e.g. 1, 2 or 3) moieties $B^1$.

In some embodiments, when $R^{2a}$ represents $C_{1-6}$ alkyl (e.g. $C_{1-3}$ alkyl, such as methyl, ethyl, propyl or cyclopropyl) substituted by one or more moieties $B^1$, such moieties are selected from halogen (e.g. fluoro), —$OR^{4b}$, —$N(R^{4h})(R^{4i})$, and —$C(O)OR^{4j}$, e.g. from OH, $NH_2$, and methoxycarbonyl.

In some embodiments, when $R^{2a}$ represents $C_{1-6}$ alkyl substituted by one or more moieties selected from oxy and $B^1$, $R^{2a}$ more particularly represents —$C(O)B^1$, wherein $B^1$ is as described herein. For example, in some embodiments, in —$C(O)B^1$, $B^1$ represents heterocyclyl as described herein (e.g. 4- to 8 membered heterocyclyl, or 4- to 6-membered heterocyclyl, e.g. heterocyclyl containing 1 or 2 heteroatoms) optionally substituted by one or more (e.g. 1-3) groups independently selected from $D^6$, said heterocyclyl containing at least one nitrogen atom in the ring, and said heterocyclyl being attached to the C(O) moiety by a bond to said nitrogen atom. In some of these embodiments, the heterocyclyl is selected from pyrrolidinyl, piperidinyl, piperazinyl, and morpholinyl.

In some embodiments, when $R^{2a}$ represents a moiety —$C(O)B^1$, said moiety is selected from 3-(dimethylamino)pyrrolidine-1-carbonyl, 2-(pyrrolidin-1-ylmethyl)pyrrolidin-1-yl, 2-carbamoylpyrrolidine-1-carbonyl, 4-(dimethylamino)piperidine-1-carbonyl, piperazine-1-carbonyl, 4-methylpiperazine-1-carbonyl, 3-(trifluoromethyl)piperazine-1-carbonyl, 4-(2-(dimethylamino)ethyl)piperazine-1-carbonyl, or morpholine-4-carbonyl.

In some embodiments, $R^{2a}$ represents a moiety selected from methyl, 2-methoxy-2-oxoethyl, 2-hydroxyethyl, cyclopropyl, aminomethyl, 3-(dimethylamino)pyrrolidine-1-carbonyl, 2-(pyrrolidin-1-ylmethyl)pyrrolidin-1-yl, 2-carbamoylpyrrolidine-1-carbonyl, 4-(dimethylamino)piperidine-1-carbonyl, piperazine-1-carbonyl, 4-methylpiperazine-1- carbonyl, 3-(trifluoromethyl)piperazine-1-carbonyl, 4-(2-(dimethylamino)ethyl)piperazine-1-carbonyl, and morpholine-4-carbonyl.

In the moiety —OR$^{2b}$, R$^{2b}$ is as defined herein above. In some particular embodiments, R$^{2b}$ represents a moiety selected from H and C$_{1-6}$ alkyl, wherein the alkyl is optionally substituted by one or more (e.g. 1-3) groups independently selected from B$^1$, or R$^{2b}$ represents a heterocyclyl as defined herein.

In some embodiments, R$^{2b}$ is as defined herein, but does not represent H.

When R$^{2b}$ represents an alkyl substituted by one or more (e.g. one) B$^1$, each B$^1$ is as defined herein. In some embodiments, each B$^1$, when part of R$^{2b}$, independently represents a moiety selected from halo (e.g. F), —OR$^{4b}$, —N(R$^{4h}$)(R$^{4i}$), —C(O)OR$^{4j}$, and —C(O)NR$^{4k}$R$^{4l}$; e.g. from halo (e.g. F), —OR$^{4b}$, —N(R$^{4h}$)(R$^{4i}$), and —C(O)OR$^{4j}$; in particular from —OR$^{4b}$ and —N(R$^{4h}$)(R$^{4i}$).

In the moiety —S(O)$_q$R$^{2c}$, R$^{2c}$ is as defined herein above. In some embodiments, R$^{2c}$ represents a moiety selected from H and C$_{1-6}$ alkyl (e.g. H and C$_{1-3}$ alkyl, or H and C$_1$ alkyl), wherein the alkyl is optionally substituted by one or more (e.g. 1-3) groups independently selected from B$^1$, as defined herein. In some embodiments, R$^{2c}$ represents H, methyl, (4-methoxyphenyl)methyl, or carboxymethyl, in particular H or methyl, e.g. H. In still other embodiments, R$^{2c}$ is as defined herein, but does not represent H; e.g. R$^{2c}$ represents a moiety selected from C$_{1-6}$ alkyl (e.g. C$_{1-3}$ alkyl, or C$_1$ alkyl), wherein the alkyl is optionally substituted by one or more (e.g. 1-3) groups independently selected from B$^1$, as defined herein.

In the moiety —N(R$^{2h}$)(R$^{2i}$), each one of R$^{2h}$ and R$^{2i}$ is as defined herein above. In some embodiments, R$^{2h}$ represents H or C$_{1-6}$ alkyl, e.g. H or C$_{1-3}$ alkyl, or H or C$_{1-2}$ alkyl, e.g. H or methyl, and R$^{2i}$ is as defined herein. In some embodiments, R$^{2i}$ is as defined herein, but does not represent H.

In some embodiments, R$^{2i}$ represents H, C$_{1-6}$ alkyl optionally substituted by one or more (e.g. 1-3) groups independently selected from oxy and B$^1$, heteroaryl optionally substituted by one or more (e.g. 1-3) groups selected from oxy and B$^3$ (in particular from B$^3$), and heterocyclyl optionally substituted by one or more (e.g. 1-3) groups independently selected from oxy and B$^4$ (in particular from B$^4$).

In some of these embodiment, each B$^1$, when part of R$^{2i}$, independently represents a moiety selected from halo, —OR$^{4b}$, —N(R$^{4h}$)(R$^{4i}$), —C(O)NR$^{4k}$R$^{4l}$, heteroaryl optionally substituted by one or more (e.g. 1-3) groups independently selected from D$^5$, and heterocyclyl optionally substituted by one or more (e.g. 1-3) groups independently selected from oxy and D$^6$.

In some further of these embodiment, each such B$^1$ independently represents a moiety selected from halo, —OR$^{4b}$, —N(R$^{4h}$)(R$^{4i}$), heteroaryl optionally substituted by one or more (e.g. 1-3) groups independently selected from D$^5$, and heterocyclyl optionally substituted by one or more (e.g. 1-3) groups independently selected from oxy and D$^6$.

In some embodiments, when R$^{2i}$ represents C$_{1-6}$alkyl optionally substituted by one or more (e.g. 1-3) groups independently selected from oxy and B$^1$, R$^{2i}$ more particularly represents C$_{1-6}$ alkyl substituted by one oxy and optionally substituted by one or more (e.g. 1-3) groups independently selected from B$^1$. In some of these embodiments, R$^{2i}$ represents:

(a) —C(O)C$_{1-5}$ alkyl, wherein the alkyl is optionally substituted by one or more (e.g. 1-3) groups independently selected from B$^1$, wherein B$^1$ is as defined herein, or (b) —C(O)B$^1$, wherein the B$^1$ attached to the C(O) is as defined herein, e.g. said B$^1$ represents:
aryl optionally substituted by one or more (e.g. 1-3) groups independently selected from D$^4$,
heteroaryl optionally substituted by one or more (e.g. 1-3) groups selected from D$^5$, or heterocyclyl optionally substituted by one or more (e.g. 1-3) groups independently selected from D$^6$.

In some more particular embodiments, R$^{2i}$ represents:
(a) —C(O)C$_{1-3}$ alkyl, wherein the alkyl is optionally substituted by one or more (e.g. 1-3) groups independently selected from B$^1$, wherein B$^1$ is as defined herein, or
(b) —C(O)B$^1$, wherein the B$^1$ attached to the C(O) is as defined herein, e.g. said B$^1$ represents:
aryl optionally substituted by one or more (e.g. 1-3) groups independently selected from D$^4$,
heteroaryl optionally substituted by one or more (e.g. 1-3) groups selected from D$^5$, or heterocyclyl optionally substituted by one or more (e.g. 1-3) groups independently selected from D$^6$.

In some of the above embodiments, R$^{2i}$ represents —C(O)C$_{1-3}$ alkyl, wherein the alkyl is optionally substituted by one or more (e.g. 1-3) groups independently selected from B$^1$, wherein B$^1$ is as defined herein.

In some of the above embodiments, R$^{2i}$ represents —C(O)B$^1$, wherein the B$^1$ attached to the C(O) represents:
aryl optionally substituted by one or more (e.g. 1-3) groups independently selected from D$^4$,
heteroaryl optionally substituted by one or more (e.g. 1-3) groups selected from D$^5$, or heterocyclyl optionally substituted by one or more (e.g. 1-3) groups independently selected from D$^6$.

In some of the above embodiments, when R$^2$ represents —C(O)B$^1$, the B$^1$ attached to the C(O) represents heteroaryl optionally substituted by one or more (e.g. 1-3) groups selected from D$^5$, or heterocyclyl optionally substituted by one or more (e.g. 1-3) groups independently selected from D$^6$.

In some of the above embodiments, when R$^2$ represents —C(O)B$^1$, the B$^1$ attached to the C(O) represents heterocyclyl optionally substituted by one or more (e.g. 1-3) groups independently selected from D$^6$.

In some of the above embodiments, when R$^{2i}$ represents —C(O)B$^1$, the B$^1$ attached to the C(O) represents heteroaryl optionally substituted by one or more (e.g. 1-3) groups selected from D$^5$.

In some embodiments, R$^{2i}$ represents a moiety selected from H, methyl, ethyl, propyl, 2,2-difluoroethyl, 2,2,2-trifluoroethyl, benzyl, pyrimidin-2-yl, 1-methylpyrrolidin-3-yl, 2-aminoethyl, 3-aminopropyl, 2-(methylamino)ethyl, 2-(dimethylamino)ethyl, 3-((tert-butoxycarbonyl)amino)propyl, acetyl, 2-methoxyacetyl, 2-aminoacetyl, 2-(dimethylamino)acetyl, 3-aminopropanoyl, 2-morpholinoacetyl, morpholine-2-carbonyl, 4-hydroxypyrrolidine-2-carbonyl, azetidine-2-carbonyl, 1H-pyrazole-3-carbonyl, 1-methyl-1H-pyrazole-5-carbonyl, oxazole-5-carbonyl, 2-aminooxazole-4-carbonyl, 5-methylisoxazole-3-carbonyl, 1-methyl-1H-imidazole-2-carbonyl, and 1-methyl-1H-imidazole-4-carbonyl.

In some of the above embodiments, R$^{2h}$ represents H or methyl, in particular H.

In the moiety —C(O)N(R$^{2k}$)(R$^{2l}$) each one of R$^{2k}$ and R$^{2l}$ is as defined herein above. In some embodiments, R$^{2k}$ represents H or C$_{1-6}$alkyl, e.g. H or C$_{1-3}$ alkyl, or H or C$_{1-2}$ alkyl, e.g. H or methyl, in particular H; and R$^{2l}$ is as defined herein. In some embodiments, R$^{2l}$ does not represent H.

In some embodiments, $R^{2l}$ represents H, $C_{1-6}$ alkyl optionally substituted by one or more $B^1$, heteroaryl optionally substituted by one or more groups selected from $B^3$, or heterocyclyl optionally substituted by one or more groups independently selected from $B^4$. In some of these embodiments, any $B^1$, when part of $R^{2l}$, represents a moiety selected from —$OR^{4b}$, —$N(R^{4h})(R^{4i})$, —$C(O)NR^{4k}R^{4l}$, heteroaryl optionally substituted by one or more groups selected from $D^5$, and heterocyclyl optionally substituted by one or more groups independently selected from $D^6$. For example, in some embodiments, any such $B^1$ represents a moiety selected from hydroxy, amino, methylamino, dimethylamino, acetamido, carbamoyl, methylsulfonamido, pyrrolidinyl (e.g. pyrrolidin-2-yl), piperazinyl (e.g. piperazin-1-yl), morpholinyl (e.g. morpholin-3-yl, or morpholin-4-yl), oxolanyl (e.g. oxolan-2-yl), 1H-imidazol-2-yl (e.g. 1H-imidazol-2-yl), and pyrimidinyl (e.g. pyrimidin-2-yl).

In some particular embodiments, $R^{2k}$ represents a moiety selected from H, methyl, 2-hydroxyethyl, 2-aminoethyl, 2-(dimethylamino)ethyl, 2-(methylamino)ethyl, 3-aminopropyl, 2-acetamidoethyl, 2,3-dihydroxypropyl, 2-(methylsulfonamido)ethyl, 3-amino-3-oxopropyl, (pyrrolidin-2-yl)methyl, 2-(piperazin-1-yl)ethyl, 2-(morpholin-4-yl)ethyl, (oxolan-2-yl)methyl, (1H-imidazol-2-yl)methyl, pyrimidin-2-yl)methyl, (morpholin-3-yl)methyl, azetidin-3-yl, pyrrolidin-3-yl, and 1-methylpyrrolidin-3-yl.

In a compound of formula I, each one of $A^1$ to $A^9$ independently represents
  (i) halo, $NO_2$, —CN, —$R^{3a}$, —$OR^{3b}$, —$S(O)_qR^{3c}$, —$S(O)_rN(R^{3d})(R^{3e})$, —$N(R^{3f})S(O)_sR^{3g}$, —$N(R^{3h})(R^{3i})$, —$C(O)OR^{3j}$, or —$C(O)NR^{3k}R^{3l}$ ("option e(i)"),
  (ii) aryl optionally substituted by one or more (e.g. 1-3) groups independently selected from oxy and $D^1$ ("option e(ii)"),
  (iii) heteroaryl optionally substituted by one or more (e.g. 1-3) groups selected from oxy and $D^2$ ("option e(iii)"), or
  (iv) heterocyclyl optionally substituted by one or more (e.g. 1-3) groups independently selected from oxy and $D^3$ ("option e(iv)").

In some embodiments, each $A^1$ to $A^9$ independently represents option e(i) or option e(iv). In some embodiments, each $A^1$ to $A^9$ independently represents option e(i).

In some embodiments, $A^1$, $A^2$ and $A^3$ are absent, and each one of $A^4$ to $A^9$ is as defined herein above.

In some embodiments, in option e(i), each $A^1$ to $A^9$ (e.g. $A^4$ to $A^9$) independently represents a moiety selected from halo, —CN, —$R^{3a}$, —$OR^{3b}$, —$S(O)_rN(R^{3d})(R^{3e})$, —$N(R^{3h})(R^{3i})$, —$C(O)OR^{3j}$, and —$C(O)NR^{3k}R^{3l}$. In some further embodiments, in option e(i), each such moiety is selected from halo, —CN, —$R^{3a}$, —$OR^{3b}$, —$N(R^{3h})(R^{3i})$, —$C(O)OR^{3j}$, and —$C(O)NR^{3k}R^{3l}$.

In some further embodiments, in option e(i) each such moiety is selected from halo, —$R^{3a}$, —$OR^{3b}$, —$N(R^{3h})(R^{3i})$, —$C(O)OR^{3j}$, and —$C(O)NR^{3k}R^{3l}$.

Particular $A^4$ groups that may be mentioned include halo, $NO_2$, —CN, —$R^{3a}$, —$OR^{3b}$, —$S(O)_qR^{3c}$, —$S(O)_rN(R^{3d})(R^{3e})$, —$N(R^{3f})S(O)_sR^{3g}$, —$N(R^{3h})(R^{3i})$, —$C(O)OR^{3j}$, and —$C(O)NR^{3k}R^{3l}$. More particular $A^4$ groups that may be mentioned include halo (e.g. Cl, F, Br and I), —CN, —$R^{3a}$, —$OR^{3b}$, and —$C(O)OR^{3j}$. For example, $A^4$ may represent halo (e.g. I).

In some embodiments, any $A^4$ group represents a moiety selected from halo, —CN, —$R^{3a}$, —$OR^{3b}$, —$N(R^{3h})(R^{3i})$, —$C(O)OR^{3j}$, and —$C(O)NR^{3k}R^{3l}$; e.g. from halo, —CN, —$R^{3a}$, —$OR^{3b}$, and —$N(R^{3h})(R^{3i})$.

In some embodiments, any $A^4$ group represents a moiety selected from halo, —$R^{3a}$, and —$OR^{3b}$, e.g. from halo, $C_{1-6}$ alkyl, and $C_{1-6}$ alkoxy, such as from halo, $C_{1-3}$ alkyl, and $C_{1-3}$ alkoxy, in particular halo, methyl and methoxy, e.g. halo.

In some embodiments, any $A^4$ group represents a moiety selected from halo, and —$R^{3a}$, e.g. from halo, and $C_{1-6}$ alkyl, such as from halo, and $C_{1-3}$ alkyl, in particular halo, and methyl.

In some embodiments, any $A^4$ group represents a moiety selected from —$R^{3a}$, and —$OR^{3b}$, e.g. from $C_{1-6}$ alkyl, and $C_{1-6}$ alkoxy, such as from $C_{1-3}$ alkyl, and $C_{1-3}$ alkoxy, in particular methyl and methoxy.

In some embodiments, any $A^4$ group represents —$OR^{3b}$, e.g. $C_{1-6}$ alkoxy, or $C_{1-3}$ alkoxy, in particular methoxy. In some other embodiments, any $A^4$ group represents a moiety selected from —CN, —$R^{3a}$, —$OR^{3b}$, —$N(R^{3h})(R^{3i})$, —$C(O)OR^{3j}$, and —$C(O)NR^{3k}R^{3l}$; e.g. from —CN, —$R^{3a}$, —$OR^{3b}$, and —$N(R^{3h})(R^{3i})$; or from —$R^{3a}$, —$OR^{3b}$, —$N(R^{3h})(R^{3i})$, and —$C(O)OR^{3j}$; in particular from —$R^{3a}$, —$OR^{3b}$, and —$N(R^{3h})(R^{3i})$. In some particular embodiments, any $A^4$ group represents a moiety selected from $R^{3a}$, and —$OR^{3b}$; e.g. methyl and methoxy.

In some embodiments, when $A^4$ is or comprises an alkyl group (such as $A^4$ being methyl or methoxy), such alkyl group may be substituted by one or more halo, e.g. one or more fluoro, such as in trifluoromethyl or trifluoromethoxy. Thus, in some embodiments, $A^4$ may represent a moiety selected from halo, methyl, trifluoromethyl, methoxy and trifluoromethoxy, e.g. from methyl, trifluoromethyl, methoxy and trifluoromethoxy.

In some embodiments, when any $A^4$ is halo, such halo more particularly is selected from chloro, bromo and iodo, e.g. chloro and iodo. In some embodiments, when any $A^4$ is halo, such halo is iodo. In some embodiments, when any $A^4$ is halo, such halo is chloro.

Particular $A^5$ groups that may be mentioned include halo, $NO_2$, —CN, —$R^{3a}$, —$OR^{3b}$, —$S(O)_qR^{3c}$, —$S(O)_rN(R^{3d})(R^{3e})$, —$N(R^{3f})S(O)_sR^{3g}$, —$N(R^{3h})(R^{3i})$, and —$C(O)NR^{3k}R^{3l}$. More particular $A^5$ groups that may be mentioned include halo (e.g. Cl) —$R^{3a}$(e.g. methyl) and —$OR^{3b}$(e.g. —OMe).

Particular $A^6$ groups that may be mentioned include halo, $NO_2$, —CN, —$R^{3a}$, —$OR^{3b}$, —$S(O)_qR^{3c}$, —$S(O)_rN(R^{3d})(R^{3e})$, —$N(R^{3a})S(O)_sR^{3g}$, —$N(R^{3h})(R^{3i})$, —$C(O)OR^{3j}$, and —$C(O)NR^{3k}R^{3l}$. More particular $A^6$ groups that may be mentioned include halo (e.g. Cl) —$R^{3a}$(e.g. methyl) and —$OR^{3b}$ (e.g. —OMe). More particular $A^6$ groups that may be mentioned include —$R^{3a}$Particular $A^7$ groups that may be mentioned include halo, $NO_2$, —CN, —$R^{3a}$, —$OR^{3b}$, —$S(O)_qR^{3c}$, —$S(O)_rN(R^{3d})(R^{3e})$, —$N(R^{3f})S(O)_sR^{3g}$, —$N(R^{3h})(R^{3i})$, —$C(O)OR^{3j}$, and —$C(O)NR^{3k}R^{3l}$. More particular $A^7$ groups that may be mentioned include halo (e.g. F), —$R^{3a}$, —$OR^{3b}$, —$S(O)_2N(R^{3d})(R^{3e})$, —$N(R^{3h})(R^{3i})$, —$C(O)OR^{3j}$, and —$C(O)NR^{3k}R^{3l}$.

Particular $A^8$ groups that may be mentioned include halo, $NO_2$, —CN, —$R^{3a}$, —$OR^{3b}$, —$S(O)_qR^{3c}$, —$S(O)_rN(R^{3d})(R^{3e})$, —$N(R^{3f})S(O)_sR^{3g}$, —$N(R^{3h})(R^{3i})$, —$C(O)OR^{3j}$, and —$C(O)NR^{3k}R^{3l}$. More particular $A^8$ groups that may be mentioned include halo (e.g. Br), —$R^{3a}$, —$OR^{3b}$, —$N(R^{3h})(R^{3i})$, —$C(O)OR^{3j}$, and —$C(O)NR^{3k}R^{3l}$; e.g. halo (e.g. Br), —$R^{3a}$, —$OR^{3b}$, —$N(R^{3h})(R^{3i})$, and —$C(O)NR^{3k}R^{3l}$.

Particular $A^9$ groups that may be mentioned include halo, $NO_2$, —CN, —$R^{3a}$, —$OR^{3b}$, —$S(O)_qR^{3c}$, —$S(O)_rN(R^{3d})(R^{3e})$, —$N(R^{3f})S(O)_sR^{3g}$, —$N(R^{3h})(R^{3i})$, —$C(O)OR^{3j}$, and —$C(O)NR^{3k}R^{3l}$. More particular $A^9$ groups that may be mentioned include —$R^{3a}$, and —$N(R^{3h})(R^{3i})$.

In a compound of formula I, each $B^1$ independently represents:

(i) halo, $NO_2$, —CN, —$OR^{4b}$, —$S(O)_rR^{4c}$, —$S(O)_rN(R^{4d})(R^{4e})$, $N(R^{4f})S(O)_sR^{4g}$, —$N(R^{4h})(R^{4i})$, —$C(O)OR^{4j}$, or —$C(O)NR^{4k}R^{4l}$ ("option f(i)"), (ii) aryl optionally substituted by one or more (e.g. 1-3) groups independently selected from $D^4$ ("option f(ii)"), (iii) heteroaryl optionally substituted by one or more (e.g. 1-3) groups selected from $D^5$ ("option f(iii)"), or (iv) heterocyclyl optionally substituted by one or more (e.g. 1-3) groups independently selected from $D^6$ ("option f(iv)").

In some embodiments, each $B^1$ represents a moiety selected from option f(i) and option f(iv). In some particular embodiments, each $B^1$ represents option f(i). In some other particular embodiments, each $B^1$ represents option f(iv). In some further embodiments, each $B^1$ represents a moiety selected from option f(ii), option f(iii) and option f(iv), in particular option f(iii) and option f(iv). In some further embodiments, each $B^1$ independently represents option f(ii). In still further embodiments, each $B^1$ independently represents option f(iii).

In some embodiments, in option f(i), each $B^1$ independently represents a moiety selected from halo, $NO_2$, —CN, —$OR^{4b}$, —$N(R^{4f})S(O)_sR^{4g}$, —$N(R^{4h})(R^{4i})$, —$C(O)OR^{4j}$, and —$C(O)NR^{4k}R^{4l}$. In some embodiments, in option f(i), each such moiety is selected from halo, —$OR^{4b}$, —$N(R^{4f})S(O)_sR^{4g}$, —$N(R^{4h})(R^{4i})$, —$C(O)OR^{4j}$, and —$C(O)NR^{4k}R^{4l}$. In some further embodiments, in option f(i), each such moiety is selected from —$OR^{4b}$, —$N(R^{4f})S(O)_sR^{4g}$, —$N(R^{4h})(R^{4i})$, —$C(O)OR^{4j}$, and —$C(O)NR^{4k}R^{4l}$. In some further embodiments, in option f(i), each moiety is selected from —$OR^{4b}$, —$N(R^{4h})(R^{4i})$, —$C(O)OR^{4j}$, and —$C(O)NR^{4k}R^{4l}$. In some further embodiments, in option f(i), each such moiety is selected from —$OR^{4b}$, —$N(R^{4h})(R^{4i})$, and —$C(O)OR^{4j}$. In some further embodiments, in option f(i), each such moiety is selected from —$OR^{4b}$ and —$N(R^{4h})(R^{4i})$. In some further embodiments, in option f(i), each such moiety is selected from —$OR^{4b}$. In some further embodiments, in option f(i), each such moiety is —$N(R^{4h})(R^{4i})$.

In some embodiments, when $B^1$ represents —$N(R^{4h})(R^{4i})$, $R^{4h}$ is H or $C_{1-6}$ alkyl, e.g. H or $C_{1-3}$ alkyl, in particular H or methyl, and $R^{4i}$ is $C_{1-6}$ alkyl optionally substituted by one or more groups independently selected from oxy and $E^1$.

In some embodiments, when $R^{4i}$ represents $C_{1-6}$ alkyl optionally substituted by one or more (e.g. 1-3) groups independently selected from oxy and $E^1$, $R^{4i}$ more particularly represents $C_{1-6}$ alkyl substituted by one oxy and optionally substituted by one or more (e.g. 1-3) groups independently selected from $E^1$. In some of these embodiments, $R^{4i}$ represents:

(a) —$C(O)C_{1-6}$ alkyl, wherein the alkyl is optionally substituted by one or more (e.g. 1-3) groups independently selected from $E^1$, wherein $E^1$ is as defined herein, or (b) —$C(O)E^1$, wherein the $E^1$ attached to the C(O) is as defined herein, e.g. said $E^1$ represents:

aryl optionally substituted by one or more (e.g. 1-3) groups independently selected from $G^4$, heteroaryl optionally substituted by one or more (e.g. 1-3) groups selected from $G^5$, or heterocyclyl optionally substituted by one or more (e.g. 1-3) groups independently selected from $G^6$.

In some more particular embodiments, $R^{4i}$ represents:

(a) —$C(O)C_{1-3}$ alkyl, wherein the alkyl is optionally substituted by one or more (e.g. 1-3) groups independently selected from $E^1$, wherein $E^1$ is as defined herein, or (b) —$C(O)E^1$, wherein the $E^1$ attached to the C(O) is as defined herein, e.g. said $E^1$ represents:

—$OR^{6b}$, wherein $R^{6b}$ is as defined herein, aryl optionally substituted by one or more (e.g. 1-3) groups independently selected from $G^4$, heteroaryl optionally substituted by one or more (e.g. 1-3) groups selected from $G^5$, or heterocyclyl optionally substituted by one or more (e.g. 1-3) groups independently selected from $G^6$.

In some of the above embodiments, $R^{4i}$ represents —$C(O)C_{1-3}$ alkyl, wherein the alkyl is optionally substituted by one or more (e.g. 1-3) groups independently selected from $E^1$, wherein $E^1$ is as defined herein.

In some of the above embodiments, $R^{4i}$ represents $C_{1-6}$ alkoxycarbonyl (e.g. tert-butoxycarbonyl) or $C_{1-6}$ alkylcarbonyl (e.g. acetoxy).

In some particular embodiments, $R^{4h}$ represents H or $C_{1-6}$ alkyl (in particular H or $C_{1-3}$ alkyl, or H or methyl, e.g. H) and $R^{4i}$ represents H, $C_{1-6}$ alkyl, $C_{1-6}$ alkoxycarbonyl or $C_{1-6}$ alkylcarbonyl.

Some further particular $B^1$ groups that may be mentioned include —$OR^{4b}$ and —$C(O)OR^{4j}$, such as wherein $R^{4b}$ represents H and $R^{4j}$ represents $C_{1-6}$ alkyl (e.g. $C_1$ alkyl).

In some embodiments, in option f(i), $B^1$ represents a moiety selected from halo (e.g. fluoro), hydroxy, $C_{1-6}$ alkoxy (e.g. methoxy or cyclohexyloxy), $C_{1-6}$ alkylsulfonsulfonamido (e.g. methylsulfonamido), N—($C_{1-6}$alkyl)($C_{1-6}$ alkyl) sulfonamido (e.g. N-methylmethylsulfonamido), amino, $C_{1-6}$ alkylamino (e.g. methylamino), di-$C_{1-6}$ alkylamino (e.g. dimethylamino), carboxy, $C_{1-6}$ alkoxycarbonyl (e.g. methoxycarbonyl), carbamoyl, $C_{1-6}$ alkylcarbamoyl (e.g. methylcarbamoyl), and di-$C_{1-6}$ alkylcarbamoyl (e.g. dimethylcarbamoyl), wherein each alkyl is optionally substituted by one or more groups independently selected from oxy and $E^1$.

In some embodiments, in option f(ii), the phenyl optionally is substituted by 1 or 2 group(s) independently selected from $D^4$, e.g. 1 group independently selected from $D^4$; e.g. the phenyl is substituted with one group $D^4$, which is in para position on the phenyl ring.

In some embodiments, in option f(iii), the heteroaryl is 5- or 6-membered monocyclic heteroaryl. In some embodiments, in option f(iii), the heteroaryl is 5- or 6-membered monocyclic heteroaryl containing from 1 to 3 (e.g. 1 or 2) heteroatoms selected from N, O and S, e.g. from N and O. For example, the heteroaryl may be selected from pyrazolyl, imidazolyl, oxazolyl, pyridinyl, and pyrimidinyl, or from pyrazolyl, imidazolyl, oxazolyl, and pyrimidinyl.

In some embodiments, in option f(iii), the heteroaryl optionally is substituted by 1 or 2 group(s) independently selected from $D^5$, e.g. 1 group independently selected from $D^5$.

In some embodiments, in option f(iv), the heterocyclyl is selected from 4- to 6-membered heterocyclyl containing one or more heteroatoms selected from N, O and S, e.g. 1 or 3 heteroatoms selected from N, O and S, e.g. from N and O. For example, the heterocyclyl may be selected from piperazinyl, morpholinyl, piperidinyl, pyrrolidinyl, and azetidinyl.

In some embodiments, in option f(iv), the heterocyclyl optionally is substituted by 1 or 2 group(s) independently selected from $D^6$, e.g. 1 group independently selected from $D^6$.

In a compound of formula I, each $B^2$ to $B^4$ independently represents
- (i) halo, $NO_2$, —CN, —$R^{4a}$, —$OR^{4b}$, —$S(O)_qR^{4c}$, —$S(O)_rN(R^{4d})(R^{4e})$, —$N(R^{4f})S(O)_sR^{4g}$, —$N(R^{4h})(R^{4i})$, —$C(O)OR^{4j}$, or —$C(O)NR^{4k}R^{4l}$ ("option g(i)"),
- (ii) aryl optionally substituted by one or more (e.g. 1-3) groups independently selected from oxy and $D^4$ ("option g(ii)"),
- (iii) heteroaryl optionally substituted by one or more (e.g. 1-3) groups selected from oxy and $D^5$ ("option g(iii)"), or
- (iv) heterocyclyl optionally substituted by one or more (e.g. 1-3) groups independently selected from oxy and $D^6$ ("option g(iv)"), In some embodiments, each $B^2$ to $B^4$ independently represents option g(i) or option g(iv). In some embodiments, each $B^2$ to $B^4$ independently represents option g(i).

In some embodiments, in option g(i), $B^2$ to $B^4$ independently represents a moiety selected from halo, $NO_2$, —CN, —$R^{4a}$, —$OR^{4b}$; e.g. halo or —$R^{4a}$; in particular —$R^{4a}$.

In some embodiments, $B^2$ and $B^3$ are absent and $B^4$ is as defined herein above.

In a compound of formula I, each $R^{3a}$ and $R^{4a}$ represents
- (i) $C_{1-6}$ alkyl, $C_{2-6}$ alkenyl or $C_{2-6}$ alkynyl, wherein each such alkyl, alkenyl or alkynyl group is optionally substituted by one or more (e.g. 1-3) groups independently selected from oxy and $E^1$ ("option h(i)"),
- (ii) aryl optionally substituted by one or more (e.g. 1-3) groups independently selected from oxy and $E^2$ ("option h(ii)"),
- (iii) heteroaryl optionally substituted by one or more (e.g. 1-3) groups selected from oxy and $E^3$ ("option h(iii)"), or
- (iv) heterocyclyl optionally substituted by one or more (e.g. 1-3) groups independently selected from oxy and $E^4$ ("option h(iv)").

In some embodiments, each $R^{3a}$ and $R^{4a}$ independently represents option h(i) or option h(iv). In some embodiments, each $R^{3a}$ and $R^{4a}$ independently represents option h(i).

In some embodiments, in option h(i) each $R^{3a}$ and $R^{4a}$ more particularly represents a moiety selected from $C_{1-6}$ alkyl, optionally substituted by one or more (e.g. 1-3) groups independently selected from oxy and $E^1$; more particularly a moiety selected from $C_{1-3}$ alkyl, optionally substituted by one or more (e.g. 1-3) groups independently selected from oxy and $E^1$. In some embodiments, in option h(i), the moiety is selected from $C_{1-6}$ alkyl, optionally substituted by one or more (e.g. 1-3) groups independently selected from $E^1$; e.g. $C_{1-3}$ alkyl, optionally substituted by one or more (e.g. 1-3) groups independently selected from $E^1$. In some embodiments, in option h(i) each moiety is selected from methyl and ethyl, in particular methyl, optionally substituted by one or more (e.g. 1-3) groups independently selected from $E^1$.

In some particular embodiments, each $R^{3a}$ is as defined herein above and each $R^{4a}$ is selected from $C_{1-6}$ alkyl, in particular $C_{1-3}$ alkyl, more particularly methyl, optionally substituted by one or more (e.g. 1-3) groups independently selected from $E^1$. In some particular embodiments, each $R^{3a}$ is as defined herein above and each $R^{4a}$ is selected from $C_{1-6}$ alkyl, in particular $C_{1-3}$ alkyl, more particularly methyl.

In some embodiments, when $R^{3a}$ is selected from $C_{1-6}$ alkyl, e.g. $C_{1-3}$ alkyl, or $C_1$ alkyl, optionally substituted by one or more $E^1$, $E^1$ represents a moiety selected from halo, —$OR^{6b}$, —$N(R^{6h})(R^{6i})$, and —$C(O)NR^{6k}R^{6l}$, e.g. from fluoro, OH, $NH_2$, $N(CH_3)_2$, and $C(O)NH_2$.

In some particular embodiments, when any one of $A^1$-$A^6$ (in particular $A^4$-$A^6$) represents a moiety $R^{3a}$, such $R^{3a}$ is selected from $C_{1-6}$ alkyl, e.g. $C_{1-3}$ alkyl, or $C_1$ alkyl, optionally substituted by one or more $E^1$, e.g. one or more halo, —$OR^{6b}$ or —$N(R^{6h})(R^{6i})$, in particular one or more halo or —$OR^{6b}$, such as one or more fluoro or OH.

In some embodiments, when any one of $A^7$-$A^9$ represents a moiety $R^{3a}$, such $R^{3a}$ is selected from $C_{1-6}$ alkyl, e.g. $C_{1-3}$ alkyl, or $C_1$ alkyl, wherein said alkyl is optionally substituted by one or more $E^1$, e.g. one or more halo, —$OR^{6b}$, —$N(R^{6h})(R^{6i})$, or —$C(O)NR^{6k}R^{6l}$, such as one or more fluoro, OH, $NH_2$, $N(CH_3)_2$, or $C(O)NH_2$.

Thus, in some embodiments, each $R^{3a}$:
- when present in any of $A^1$-$A^6$ (e.g. $A^4$-$A^6$) independently represents $C_{1-6}$ alkyl, e.g. $C_{1-3}$ alkyl, or $C_1$ alkyl, optionally substituted by one or more (e.g. 1-3) $E^1$, e.g. one or more halo, —$OR^{6b}$ or —$N(R^{6h})(R^{6i})$, such as one or more moieties selected from fluoro and OH; in particular one or more fluoro; and,
- when present in any of $A^7$-$A^9$, independently represents $C_{1-6}$ alkyl, e.g. $C_{1-3}$alkyl, or $C_1$ alkyl, wherein said alkyl is optionally substituted by one or more (e.g. 1-3) $E^1$, e.g. one or more moieties selected from halo, —$OR^{6b}$, —$N(R^{6h})(R^{6i})$, and —$C(O)NR^{6k}R^{6l}$, such as one or more fluoro, hydroxy, amino, dimethylamino, and carbamoyl.

In a compound of formula I, each $R^{3b}$ to $R^{3l}$, and each $R^{4b}$ to $R^{4l}$ independently represents H, or
- (i) $C_{1-6}$ alkyl, $C_{2-6}$ alkenyl or $C_{2-6}$ alkynyl, wherein each such alkyl, alkenyl or alkynyl group is optionally substituted by one or more (e.g. 1-3) groups independently selected from oxy and $E^1$ ("option i(i)"),
- (ii) aryl optionally substituted by one or more (e.g. 1-3) groups independently selected from oxy and $E^2$ ("option i(ii)"),
- (iii) heteroaryl optionally substituted by one or more (e.g. 1-3) groups selected from oxy and $E^3$ ("option i(iii)"), or
- (iv) heterocyclyl optionally substituted by one or more (e.g. 1-3) groups independently selected from oxy and $E^4$ ("option i(iv)").

In some embodiments, each $R^{3b}$ to $R^{3l}$, and each $R^{4b}$ to $R^{4l}$ independently represents H, option i(i), or option i(iv). In some further embodiments, each $R^{3b}$ to $R^{3l}$, and each $R^{4b}$ to $R^{4l}$ independently represents H, or option i(i).

In some embodiments, in option i(i), each $R^{3b}$ to $R^{3l}$, and each $R^{4b}$ to $R^{4l}$ more particularly represents a moiety selected from $C_{1-6}$ alkyl, optionally substituted by one or more (e.g. 1-3) groups independently selected from oxy and $E^1$; e.g. from $C_{1-3}$ alkyl, optionally substituted by one or more (e.g. 1-3) groups independently selected from oxy and $E^1$. In some embodiments, such moiety is selected from $C_{1-6}$ alkyl, optionally substituted by one or more (e.g. 1-3) groups independently selected from $E^1$; e.g. from $C_{1-3}$ alkyl, optionally substituted by one or more (e.g. 1-3) groups independently selected from $E^1$. In some embodiments, $R^{3b}$ to $R^{3l}$ and $R^{4b}$ to $R^{4l}$ represent methyl or ethyl, optionally substituted by one or more (e.g. 1-3) groups independently selected from $E^1$.

In some embodiments, any $R^{3b}$ to $R^{3l}$ present in a group represented by $A^1$ to $A^6$ (e.g. $A^4$ to $A^6$) is selected from H and $C_{1-6}$ alkyl (e.g. H or $C_{1-3}$ alkyl, or H or $C_1$ alkyl), wherein the alkyl is optionally substituted by one or more fluoro.

In some embodiments, when any one of $A^7$-$A^9$ represents a moiety —$OR^{3b}$, $R^{3b}$ in any such $A^7$-$A^9$ is H or $C_{1-6}$ alkyl (e.g. H or $C_{1-3}$ alkyl), wherein the alkyl is optionally substituted by one or more (e.g. 1-3) groups independently selected from oxy and $E^1$, e.g. one or more (e.g. 1-3) groups (in particular one group) independently selected from $E^1$.

For example, $R^{3b}$ in any such $A^7$-$A^9$ may be selected from H and $C_{1-6}$ alkyl (in particular H and $C_{1-3}$ alkyl), wherein the alkyl is optionally substituted by —$OR^{6b}$ or —$N(R^{6h})(R^{6i})$, in particular —$N(R^{6h})(R^{6i})$.

Thus, in some embodiments, each $R^{3b}$:
when present in any of $A^1$-$A^6$ (e.g. $A^4$-$A^6$), independently represents H or $C_{1-6}$ alkyl (e.g. H or $C_{1-3}$ alkyl, or H or $C_1$ alkyl), wherein the alkyl is optionally substituted by one or more fluoro; and,
when present in any of $A^7$-$A^9$, independently represents H or $C_{1-6}$ alkyl (e.g. H or $C_{1-3}$ alkyl), wherein the alkyl is optionally substituted by one or more (e.g. 1-3) groups independently selected from oxy and $E^1$, e.g. one or more (e.g. 1-3) groups (in particular one group) independently selected from $E^1$; e.g. H and $C_{1-6}$ alkyl (in particular H and $C_{1-3}$ alkyl), wherein the alkyl is optionally substituted by —$OR^{6b}$ or —$N(R^{6h})(R^{6i})$, in particular —$N(R^{6h})(R^{6i})$.

In some embodiments, when any one of $A^7$-$A^9$ represents a moiety —$N(R^{3h})(R^{3i})$, $R^{3h}$ in such $A^7$-$A^9$ independently represents H or $C_{1-6}$ alkyl, and
$R^{3i}$ in such $A^7$-$A^9$ independently represents H or
(a) $C_{1-6}$ alkyl (e.g. $C_{1-3}$ alkyl), optionally substituted by one or more (e.g. 1-3) groups independently selected from $E^1$,
(b) —$C(O)C_{1-6}$ alkyl (e.g. —$C(O)C_{1-3}$ alkyl), optionally substituted by one or more (e.g. 1-3) groups independently selected from $E^1$, wherein $E^1$ is as defined herein, or (c) —$C(O)E^1$, wherein $E^1$ is —$OR^{6b}$.

In some of these embodiments, in such $A^7$-$A^9$, $R^{3h}$ independently represents H or $C_{1-3}$ alkyl, e.g. H or methyl, or H.

Thus, in some embodiments, each $R^{3h}$ and $R^{3i}$:
when present in any of $A^1$-$A^6$ (e.g. $A^4$-$A^6$), independently represents H or $C_{1-6}$ alkyl (e.g. H or $C_{1-3}$ alkyl, or H or $C_1$ alkyl); and,
when present in any of $A^7$-$A^9$, $R^{3h}$ independently represents H or $C_{1-6}$ alkyl (e.g. H or $C_{1-3}$ alkyl, or H or $C_1$ alkyl), and $R^{3i}$ independently represents H or
(a) $C_{1-6}$ alkyl (e.g. $C_{1-3}$ alkyl), optionally substituted by one or more (e.g. 1-3) groups independently selected from $E^1$,
(b) —$C(O)C_{1-6}$alkyl (e.g. —$C(O)C_{1-3}$alkyl), optionally substituted by one or more (e.g. 1-3) groups independently selected from $E^1$, wherein $E^1$ is as defined herein, or
(c) —$C(O)E^1$, wherein $E^1$ is —$OR^{6b}$.

In some embodiments, when any one of $A^7$-$A^9$ represents a moiety —$C(O)NR^{3k}R^{3l}$, $R^{3k}$ and $R^{3l}$ in such $A^7$-$A^9$ independently represents H or $C_{1-6}$ alkyl, optionally substituted by one or more (e.g. 1-3) groups independently selected from $E^1$.

In some further embodiments, when any one of $A^7$-$A^9$ represents a moiety —$C(O)NR^{3k}R^{3l}$, $R^{3k}$ in such $A^7$-$A^9$ independently represents H or $C_{1-6}$ alkyl, and $R^{3l}$ in such $A^7$-$A^9$ independently represents H or $C_{1-6}$ alkyl (e.g. $C_{1-3}$ alkyl), wherein the alkyl is optionally substituted by one or more (e.g. 1-3) groups independently selected from $E^1$, e.g. one or more (e.g. 1-3) groups independently selected from —$OR^{6b}$ and —$N(R^{6h})(R^{6i})$.

In some of these embodiments, in such $A^7$-$A^9$, $R^{3k}$ independently represents H or $C_{1-3}$ alkyl, e.g. H or methyl, or H.

Thus, in some embodiments, each $R^{3h}$ and $R^{3i}$:
when present in any of $A^1$-$A^6$, independently represents H or $C_{1-6}$ alkyl (e.g. H or $C_{1-3}$ alkyl, or H or $C_1$ alkyl); and, when present in any of $A^7$-$A^9$, independently represents H or $C_{1-6}$ alkyl (e.g. H or $C_{1-3}$ alkyl, or H or $C_1$ alkyl), wherein the alkyl is optionally substituted by one or more (e.g. 1-3) groups independently selected from $E^1$, e.g. from —$OR^{6b}$ and —$N(R^{6h})(R^{6i})$.

In some further particular embodiments:
$R^{3a}$ represents $C_{1-2}$ alkyl optionally substituted with one or more F;
$R^{3b}$ represents $C_1$ alkyl optionally substituted with one or more F; and
$R^{3j}$ represents $C_1$ alkyl.

In a compound of formula I, each $D^1$ to $D^6$ independently represents
(i) halo, $NO_2$, —CN, —$R^{5a}$, —$OR^{5b}$, —$S(O)_qR^{5c}$, —$S(O)_rN(R^{5d})(R^{5e})$, —$N(R^{5d})S(O)_sR^{5g}$, —$N(R^{5h})(R^{5i})$, —$C(O)OR^{5j}$, or —$C(O)NR^{5k}R^{5l}$ ("option j(i)"),
(ii) aryl optionally substituted by one or more (e.g. 1-3) groups independently selected from oxy and $G^1$ ("option j(ii)"),
(iii) heteroaryl optionally substituted by one or more (e.g. 1-3) groups selected from oxy and $G^2$ ("option j(iii)"), or
(iv) heterocyclyl optionally substituted by one or more (e.g. 1-3) groups independently selected from oxy and $G^3$ ("option j(iv)")

In some embodiments, each $D^1$ to $D^6$ independently represents option j(i) or option j(iv). In some further embodiments, each $D^1$ to $D^6$ independently represents option j(i).

In some embodiments, in option j(i), each $D^1$ to $D^6$ independently represents a moiety selected from halo, $NO_2$, —CN, —$R^{5a}$, —$OR^{5b}$, or —$N(R^{5h})(R^{5i})$; e.g. —$R^{5a}$, —$OR^{5b}$, and —$N(R^{5h})(R^{5i})$.

In still further embodiments, $D^1$ to $D^3$ are absent and each $D^4$ to $D^6$ is as indicated herein above.

In some embodiments, $D^4$ represents —$OR^{5b}$.

In some embodiments, $D^5$ represents —$R^{5a}$ or —$N(R^{5h})(R^{5i})$, in particular —$R^{5a}$.

In some embodiments, $D^6$ represents —$N(R^{5h})(R^5)$.

In a compound of formula I each $E^1$ independently represents
(i) halo, $NO_2$, —CN, —$OR^{6b}$, —$S(O)_qR^{6c}$, —$S(O)_rN(R^{6d})(R^{6e})$, —$N(R^{6f})S(O)_sR^{6g}$, —$N(R^{6h})(R^{6i})$, —$C(O)OR^{6j}$, or —$C(O)NR^{6k}R^{6l}$ ("option k(i)"),
(ii) aryl optionally substituted by one or more (e.g. 1-3) groups independently selected from $G^4$ ("option k(ii)"),
(iii) heteroaryl optionally substituted by one or more (e.g. 1-3) groups selected from $G^5$ ("option k(iii)"), or
(iv) heterocyclyl optionally substituted by one or more (e.g. 1-3) groups independently selected from $G^6$ ("option k(iv)").

In some embodiments, each $E^1$ independently represents option k(i) or option k(iv). In some further embodiments, each $E^1$ independently represents option k(i).

In some embodiments, in option k(i), $E^1$ more particularly represents a moiety selected from halo, —$OR^{6b}$, —$N(R^{6h})(R^{6i})$, and —$C(O)NR^{6k}R^{6l}$. In some embodiments, in option k(i), the moiety more particularly represents —$N(R^{6h})(R^{6i})$ or —$C(O)NR^{6k}R^{6l}$, e.g. —$C(O)NR^{6k}R^{6l}$.

When $E^1$ is halo, such halo e.g. may be F or Cl, more particularly F.

In some embodiments, each $E^1$ is selected from halo, hydroxy, $C_{1-6}$ alkoxy, amino, $C_{1-6}$ alkylamino, di-$C_{1-6}$ alkylamino, carbamoyl, $C_{1-6}$ alkylcarbamoyl (e.g. methylcarbamoyl), and di-$C_{1-6}$ alkylcarbamoyl (e.g. dimethylcarbamoyl); e.g. from halo, hydroxy, $C_{1-6}$ alkoxy, amino, $C_{1-6}$ alkylamino, di-$C_{1-6}$ alkylamino, and carbamoyl.

In a compound of formula I, each $E^2$ to $E^4$ independently represents
- (i) halo, $NO_2$, —CN, —$R^{6a}$, —$OR^{6b}$, —$S(O)_qR^{6c}$, —$S(O)_rN(R^{6d})(R^{6e})$, —$N(R^{6f})S(O)_sR^{6g}$, —$N(R^{6h})(R^{6i})$, —$C(O)OR^{6j}$, or —$C(O)NR^{6k}R^{6l}$ ("option l(i)"),
- (ii) aryl optionally substituted by one or more (e.g. 1-3) groups independently selected from $G^4$ ("option l(ii)"),
- (iii) heteroaryl optionally substituted by one or more (e.g. 1-3) groups selected from $G^5$ ("option l(iii)"), or
- (iv) heterocyclyl optionally substituted by one or more (e.g. 1-3) groups independently selected from $G^6$ ("option l(iv)").

In some embodiments, each $E^2$ to $E^4$ independently represents option l(i) or option l(iv). In some further embodiments, each $E^2$ to $E^4$ independently represents option l(i).

In some embodiments, in option l(i), each $E^2$ to $E^4$ more particularly represents a moiety selected from halo, —Ra, —$OR^{6b}$, —$N(R^{6h})(R^{6i})$, -and —$C(O)NR^{6k}R^{6l}$; e.g. from halo and —$R^{6a}$. In some embodiments, when any one of $E^2$ to $E^4$ is halo, such halo e.g. may be F or Cl, more particularly F.

In some embodiments, $E^2$ to $E^4$ are absent.

In a compound of formula I, each $R^{5a}$ and $R^{6a}$ represents
- (i) $C_{1-6}$ alkyl, $C_{2-6}$ alkenyl or $C_{2-6}$ alkynyl, wherein each such alkyl, alkenyl or alkynyl group is optionally substituted by one or more (e.g. 1-3) groups independently selected from oxy and $J^1$ ("option m(i)"),
- (ii) aryl optionally substituted by one or more (e.g. 1-3) groups independently selected from oxy and $J^2$ ("option m(ii)"),
- (iii) heteroaryl optionally substituted by one or more (e.g. 1-3) groups selected from oxy and $J^3$ ("option m(iii)"), or
- (iv) heterocyclyl optionally substituted by one or more (e.g. 1-3) groups independently selected from oxy and $J^4$ ("option m(iv)").

In some embodiments, each $R^{5a}$ and $R^{6a}$ independently represents option m(i) or option m(iv). In some embodiments, each $R^{5a}$ and $R^{6a}$ represents independently represents option m(i).

In some embodiments, in option m(i), each $R^{5a}$ and $R^{6a}$ independently represents a moiety selected from $C_{1-6}$ alkyl, optionally substituted by one or more (e.g. 1-3) groups independently selected from oxy and $J^1$; e.g. each $R^{5a}$ and $R^{6a}$ independently represents a moiety selected from $C_{1-3}$ alkyl, optionally substituted by one or more (e.g. 1-3) groups independently selected from oxy and $J^1$. In some embodiments, such moiety is selected from $C_{1-6}$ alkyl, optionally substituted by one or more (e.g. 1-3) groups independently selected from $J^1$; e.g. from $C_{1-3}$ alkyl, optionally substituted by one or more (e.g. 1-3) groups independently selected from $J^1$. In some embodiments, each $R^{5a}$ and $R^{6a}$ independently represents methyl or ethyl, optionally substituted by one or more (e.g. 1-3) groups independently selected from $J^1$. In some embodiments, each $R^{5a}$ and $R^{6a}$ independently represents $C_{1-6}$ alkyl, e.g. $C_3$alkyl, e.g. methyl.

In some embodiments, $R^{5a}$ is as defined herein above and $R^{6a}$ is absent.

In a compound of formula I, each $R^{5b}$ to $R^{5l}$, and $R^{6b}$ to $R^{6l}$ independently represents H or
- (i) $C_{1-6}$ alkyl, $C_{2-6}$ alkenyl or $C_{2-6}$ alkynyl, wherein each such alkyl, alkenyl or alkynyl group is optionally substituted by one or more (e.g. 1-3) groups independently selected from oxy and $J^1$ ("option n(i)"),
- (ii) aryl optionally substituted by one or more (e.g. 1-3) groups independently selected from oxy and $J^2$ ("option n(ii)"),
- (iii) heteroaryl optionally substituted by one or more (e.g. 1-3) groups selected from oxy and $J^3$ ("option n(iii)"), or
- (iv) heterocyclyl optionally substituted by one or more (e.g. 1-3) groups independently selected from oxy and $J^4$ ("option n(iv)").

In some embodiments, each $R^{5b}$ to $R^{5l}$, and each $R^{6b}$ to $R^{6l}$ independently represents H, option n(i), or option n(iv). In some embodiments, each $R^{5b}$ to $R^{5l}$, and each $R^{6b}$ to $R^{6l}$ independently represents H, or option n(i). In some embodiments, each $R^{5b}$ to $R^{5l}$, and each $R^{6b}$ to $R^{6l}$ independently represents H.

In some embodiments, in option n(i), each $R^{5b}$ to $R^{5l}$, and each $R^{6b}$ to $R^{6l}$ more particularly represents a moiety selected from $C_{1-6}$ alkyl, optionally substituted by one or more (e.g. 1-3) groups independently selected from oxy and $J^1$; e.g. from $C_{1-3}$ alkyl, optionally substituted by one or more (e.g. 1-3) groups independently selected from oxy and $J^1$. In some embodiments, such moiety is selected from $C_{1-6}$ alkyl, optionally substituted by one or more (e.g. 1-3) groups independently selected from $J^1$; e.g. from $C_{1-3}$ alkyl, optionally substituted by one or more (e.g. 1-3) groups independently selected from $J^1$. In some embodiments, such moiety is selected from methyl and ethyl, said methyl and ethyl optionally being substituted by one or more (e.g. 1-3) groups independently selected from $J^1$. In some embodiments, such moiety is methyl optionally substituted by one or more (e.g. 1-3) groups independently selected from $J^1$. In some embodiments, $J^1$ is absent. Thus, in some of particular embodiments, each $R^{5b}$ to $R^{5l}$, and $R^{6b}$ to $R^{6l}$ represents H or $C_{1-6}$ alkyl, e.g. H or $C_{1-4}$ alkyl, or H or $C_{1-3}$ alkyl, in particular H or methyl, e.g. H.

In a compound of formula I, each $G^1$ to $G^6$ independently represents
- (i) halo, $NO_2$, —CN, —$R^{7a}$, —$OR^{7b}$, —$S(O)_qR^{7c}$, —$S(O)_rN(R^{7d})(R^{7e})$, —$N(R^{7f})S(O)_sR^{7g}$, —$N(R^{7h})(R^{7i})$, —$C(O)OR^{7j}$, or —$C(O)NR^{7k}R^{7l}$ ("option o(i)"),
- (ii) aryl optionally substituted by one or more (e.g. 1-3) groups independently selected from oxy and $L^1$ ("option o(ii)"),
- (iii) heteroaryl optionally substituted by one or more (e.g. 1-3) groups selected from oxy and $L^2$ ("option o(iii)"), or
- (iv) heterocyclyl optionally substituted by one or more (e.g. 1-3) groups independently selected from oxy and $L^3$ ("option o(iv)").

In some embodiments, each $G^1$ to $G^6$ independently represents option o(i) or option o(iv).

In some embodiments, each $G^1$ to $G^6$ independently represents option o(i).

In some embodiments, in option o(i), each $G^1$ to $G^8$ independently represents halo, $NO_2$, —CN, —$R^{7a}$, or —$OR^{7b}$; in particular halo, or —$R^{7a}$. In still further embodiments, $G^1$ to $G^6$ are absent.

In a compound of formula I, each $J^1$ independently represents
- (i) halo, $NO_2$, —CN, —$OR^{8b}$, —$S(O)_qR^{8c}$, —$S(O)_rN(R^{8d})(R^{8e})$, —$N(R^{8f})S(O)_sR^{8g}$, —$N(R^{8h})(R^{8i})$, —$C(O)OR^{8j}$, or —$C(O)NR^{8k}R^{8l}$ ("option p(i)"),
- (ii) aryl optionally substituted by one or more (e.g. 1-3) groups independently selected from $L^1$ ("option p(ii)"),
- (iii) heteroaryl optionally substituted by one or more (e.g. 1-3) groups selected from $L^2$ ("option p(iii)"), or
- (iv) heterocyclyl optionally substituted by one or more (e.g. 1-3) groups independently selected from $L^3$ ("option p(iv)").

In some embodiments, each $J^1$ independently represents option p(i) or option p(iv). In some embodiments, each $J^1$ independently represents option p(i).

In some embodiments, in option p(i), each $J^1$ more particularly may represent halo, $NO_2$, —CN, —$OR^{8b}$, or —$N(R^{8h})(R^{8i})$, in particular halo (e.g. F) or —$N(R^{8h})(R^{8i})$.

In a compound of formula I, each $J^2$ to $J^4$ independently represents
 (i) halo, $NO_2$, —CN, —$R^{8a}$, —$OR^{8b}$, —$S(O)_qR^{8c}$, —$S(O)_rN(R^{8d})(R^{8e})$, —$N(R^{8f})S(O)SR^{8g}$, —$N(R^{8h})(R^{8i})$, —$C(O)OR^{8j}$, or —$C(O)NR^{8k}R^{8l}$ ("option q(i)"),
 (ii) aryl optionally substituted by one or more (e.g. 1-3) groups independently selected from oxy and $L^1$ ("option q(ii)"),
 (iii) heteroaryl optionally substituted by one or more (e.g. 1-3) groups selected from oxy and $L^2$ ("option q(iii)"),
 (iv) heterocyclyl optionally substituted by one or more (e.g. 1-3) groups independently selected from oxy and $L^3$ ("option q(iv)").

In some embodiments, each $J^1$ independently represents option q(i) or option q(iv). In some embodiments, each $J^1$ independently represents option q(i).

In some embodiments, in option q(i), each $J^2$ to $J^4$ more particularly may represent halo, $NO_2$, —CN, —$R^{8a}$, —$OR^{8b}$, or —$N(R^{8h})(R^{8i})$, in particular halo (e.g. F), —$R^{8a}$, or —$N(R^{8h})(R^{8i})$, or halo or —$R^{8a}$. In still further embodiments, $J^2$ to $J^4$ are absent.

In a compound of formula I, each $L^1$ to $L^3$ independently represents halo, $NO_2$, —CN, —$R^{9a}$, —$OR^{9b}$, —$S(O)_qR^{9c}$, —$S(O)_rN(R^{9d})(R^{9e})$, —$N(R^{9f})S(O)_sR^{9g}$, —$N(R^{9h})(R^{9i})$, —$C(O)OR^{9j}$, or —$C(O)NR^{9k}R^{9l}$. In some embodiments, each $L^1$ to $L^3$ independently represents halo, $NO_2$, —CN, —$R^{9a}$, or —$OR^{9b}$, e.g. halo or —$R^{9a}$. In some embodiments, $L^1$ to $L^3$ are absent.

In a compound of formula I, each $R^{7a}$, $R^{8a}$ and $R^{9a}$ represents $C_{1-3}$ alkyl optionally substituted with one or more fluoro; and each $R^{7b}$ to $R^{7l}$, $R^{8b}$ to $R^{8l}$ and $R^{9b}$ to $R^{9l}$ independently represents H or $C_{1-3}$ alkyl optionally substituted with one or more fluoro. In some embodiments, each $R^{7a}$, $R^{8a}$ and $R^{9a}$ represents methyl optionally substituted with one or more fluoro; and each $R^{7b}$ to $R^{7l}$, $R^{8b}$ to $R^{8l}$ and $R^{9b}$ to $R^{9l}$ independently represents H or methyl optionally substituted with one or more fluoro.

In a compound of formula I each q, r and s independently represents 0, 1 or 2. In some embodiments, each q, r and s independently represents 0 or 2. In some embodiments, each q, r and s represents 2. In some embodiments, q represents 0 or 2, and r and s represent 2.

In some particular embodiments of a compound of formula I:
 $R^2$ represents any one of options a(i) to a(iii);
 each $R^3$ independently represents any one of options b(i) to b(iv);
 each $R^{2a}$ independently represents any one of options c(i) and c(iv);
 each $R^{2b}$ to $R^{2l}$ independently represents H or any one of options d(i) and d(iv);
 each $A^4$ to $A^9$ independently represents option e(i);
 each $B^1$ independently represents any one of options f(i) to f(iv);
 each $B^4$ independently represents option g(i);
 each $R^{3a}$ and $R^{4a}$ independently represents option h(i);
 each $R^{3b}$ to $R^{3l}$, and $R^{4b}$ to $R^{4l}$ independently represents H or option i(i);
 each $D^4$ to $D^6$ independently represents option j(i);
 each $E^1$ independently represents options k(i) or k(iv);
 each $R^{5a}$ and $R^{6a}$ independently represents option l(i);
 each $R^{5b}$ to $R^{5l}$, and $R^{6b}$ to $R^{6l}$ independently represents H or option m(i);
 each $J^1$ independently represents any one of options n(i) and n(iv);
 each $R^{8a}$ represents $C_{1-3}$ alkyl optionally substituted with one or more fluoro;
 each $R^{8b}$ to $R^{8l}$ independently represents H or $C_{1-3}$ alkyl optionally substituted with one or more fluoro;
 each $L^3$ independently represents halo, $NO_2$, —CN, —$R^{9a}$, —$OR^{9b}$, —$S(O)_qR^{9c}$, —$S(O)_rN(R^{9d})(R^{9e})$, —$N(R^{9f})S(O)_sR^{9g}$, —$N(R^{9h})(R^{9i})$, —$C(O)OR^{9j}$, or —$C(O)NR^{9k}R^{9l}$;
 each $R^{9a}$ independently represents $C_{1-3}$ alkyl optionally substituted with one or more fluoro;
 each $R^{9b}$ to $R^{9l}$ independently represents H or $C_{1-3}$ alkyl optionally substituted with one or more fluoro; and
 each q, r and s independently represents 0, 1 or 2.

In some of these particular embodiments:
 $R^2$ represents any one of options a(i) to a(iii);
 each $R^3$ independently represents any one of options b(i) to b(iv);
 each $R^{2a}$ independently represents option c(i);
 each $R^{2b}$ to $R^{2l}$ independently represents H or option d(i);
 each $A^4$ to $A^9$ independently represents option e(i);
 each $B^1$ independently represents any one of options f(i) to f(iv);
 each $B^4$ independently represents option g(i);
 each $R^{3a}$ and $R^{4a}$ independently represents option h(i);
 each $R^{3b}$ to $R^{3l}$, and $R^{4b}$ to $R^{4l}$ independently represents H or option i(i);
 each $D^4$ to $D^6$ independently represents option j(i);
 each $E^1$ independently represents option k(i);
 each $R^{5a}$ and $R^{6a}$ independently represents option l(i);
 each $R^{5b}$ to $R^{5l}$, and $R^{6b}$ to $R^{6l}$ independently represents H or option m(i); and
 each $J^1$ independently represents option n(i).

In some further of these particular embodiments:
 $R^2$ represents option a(i);
 $R^3$ represents option b(i);
 each $R^{2a}$ independently represents option c(i);
 each $R^{2b}$ to $R^{2l}$ independently represents H or option d(i);
 $A^4$ represents option e(i);
 each $B^1$ independently represents any one of options f(i) to f(iv);
 each $R^{3a}$ and $R^{4a}$ independently represents option h(i);
 each $R^{3b}$ to $R^{3l}$, and $R^{4b}$ to $R^{4l}$ independently represents H or option i(i);
 each $D^4$ to $D^6$ independently represents option j(i);
 each $E^1$ independently represents option k(i);
 each $R^{5a}$ and $R^{6a}$ independently represents option l(i);
 each $R^{5b}$ to $R^{5l}$, and $R^{6b}$ to $R^{6l}$ independently represents H or option m(i); and
 each $J^1$ independently represents option n(i).

In some further of these particular embodiments:
 $R^2$ represents option a(i);
 $R^3$ represents option b(i);
 each $R^{2a}$ independently represents option c(i);
 each $R^{2b}$ to $R^{2l}$ independently represents H or option d(i);
 $A^4$ represents option e(i);
 each $B^1$ independently represents any one of options f(i) and f(iv); in particular option f(i);
 each $R^{3a}$ and $R^{4a}$ independently represents option h(i);
 each $R^{3b}$ to $R^{3l}$, and $R^{4b}$ to $R^{4l}$ independently represents H or option i(i);
 each $D^4$ to $D^6$ independently represents option j(i);
 each $E^1$ independently represents option k(i);
 each $R^{5a}$ and $R^{6a}$ independently represents option l(i);

each $R^{5b}$ to $R^{5l}$, and $R^{6b}$ to $R^{6l}$ independently represents H or option m(i); and each $J^1$ independently represents option n(i).

For the avoidance of doubt, it is pointed out that, for example, the indication that "$R^3$ represents option b(i)" should be understood to mean that "$R^3$ represents (i) halo, —$NO_2$, —CN, —$R^{2a}$, —$OR^{2b}$, —$S(O)_qR^{2c}$, —$S(O)_rN(R^{2d})(R^{2e})$, —$N(R^{2f})S(O)_sR^{2g}$, —$N(R^{2h})(R^{2i})$, —$C(O)OR^{2j}$, or —$C(O)NR^{2k}R^{2l}$", and thus such two expressions may replace each other.

As a further illustrating example, the indication that "each $B^1$ independently represents any one of options f(i) and f(iv)" should be understood to mean that "each $B^1$ independently represents (i) halo, $NO_2$, —CN, —$OR^{4b}$, —$S(O)_qR^{4c}$, —$S(O)_rN(R^{4d})(R^{4e})$, —$N(R^4)S(O)_sR^{4g}$, —$N(R^{4h})(R^{4i})$, —$C(O)OR^{4j}$, or —$C(O)NR^{4k}R^{4l}$, or (iv) heterocyclyl optionally substituted by one or more groups independently selected from $D^6$", and thus such two expressions may replace each other.

In some particular embodiments of a compound of formula I:

each $R^1$ independently represents fluoro, methyl or hydroxy;

n represents 0, 1 or 2; preferably 0 or 1, more preferably 0;

$R^2$ represents (i) phenyl optionally substituted by one or more groups independently selected from $A^4$, (ii) 5- or 6-membered monocyclic heteroaryl optionally substituted by one or more groups selected from oxy and $A^5$, or (iii) phenyl substituted with two adjacent groups which, together with the ring to which they are attached, form a bicyclic heteroaryl optionally substituted by one or more groups selected from oxy and $A^6$;

each $R^3$ independently represents (i) halo, —$NO_2$, —CN, —$R^{2a}$, —$OR^{2b}$, —$S(O)_qR^{2c}$, —$S(O)_rN(R^{2d})(R^{2e})$, —$N(R^{2f})S(O)SR^{2g}$, —$N(R^{2h})(R^{2i})$, —$C(O)OR^{2j}$, or —$C(O)NR^{2k}R^{2l}$, (ii) aryl optionally substituted by one or more groups independently selected from $A^7$, (iii) heteroaryl optionally substituted by one or more groups selected from $A^8$, or (iv) heterocyclyl optionally substituted by one or more groups independently selected from $A^9$;

each $R^{2a}$ independently represents (i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $B^1$;

each $R^{1b}$ to $R^{1l}$ and $R^{2b}$ to $R^{2l}$ independently represents H or (i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $B^1$;

(ii) aryl optionally substituted by one or more groups independently selected from oxy and $B^2$, (iii) heteroaryl optionally substituted by one or more groups selected from oxy and $B^3$, or (iv) heterocyclyl optionally substituted by one or more groups independently selected from oxy and $B^4$;

each $A^4$ to $A^9$ independently represents (ii) halo, $NO_2$, —CN, —$R^{3a}$, —$OR^{3b}$, —$S(O)_qR^{3c}$, —$S(O)_rN(R^{3d})(R^{3e})$, —$N(R^{3f})S(O)SR^{3g}$, —$N(R^{3h})(R^{3i})$, —$C(O)OR^{3j}$, or —$C(O)NR^{3k}R^{3l}$, each $B^1$ independently represents (i) halo, $NO_2$, —CN, —$OR^{4b}$, —$S(O)_qR^{4c}$, —$S(O)_rN(R^{4d})(R^{4e})$, —$N(R^{4f})S(O)_sR^{4g}$, —$N(R^{4h})(R^{4i})$, —$C(O)OR^{4j}$, or —$C(O)NR^{4k}R^{4l}$, (ii) aryl optionally substituted by one or more groups independently selected from $D^4$, (iii) heteroaryl optionally substituted by one or more groups selected from $D^5$, or (iv) heterocyclyl optionally substituted by one or more groups independently selected from $D^6$;

each $B^2$ to $B^4$ independently represents (ii) halo, $NO_2$, —CN, —$R^{4a}$, —$OR^{4b}$, —$S(O)_qR^{4c}$, —$S(O)_rN(R^{4d})(R^{4e})$, —$N(R^{4f})S(O)SR^{4g}$, —$N(R^{4h})(R^{4i})$, —$C(O)OR^{4j}$, or —$C(O)NR^{4k}R^{4l}$;

each $R^{3a}$ and $R^{4a}$ independently represents (i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $E^1$;

each $R^{3b}$ to $R^{3l}$, and $R^{4b}$ to $R^{4l}$ independently represents H or (i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $E^1$;

each $D^4$ to $D^6$ independently represents (i) halo, $NO_2$, —CN, —$R^{5a}$, —$OR^{5b}$, —$S(O)_qR^{5c}$, —$S(O)_rN(R^{5d})(R^{5e})$, —$N(R^{5f})S(O)_sR^{5g}$, —$N(R^{5h})(R^{5i})$, —$C(O)OR^{5j}$, or —$C(O)NR^{5k}R^{5l}$, each $E^1$ independently represents (i) halo, $NO_2$, —CN, —$OR^{6b}$, —$S(O)_qR^{6c}$, —$S(O)_rN(R^{6d})(R^{6e})$, —$N(R^{6f})S(O)_sR^{6g}$, —$N(R^{6h})(R^{6i})$, —$C(O)OR^{6j}$, or —$C(O)NR^{6k}R^{6l}$, or (iv) heterocyclyl;

each $R^{5a}$ represents (i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $J^1$;

each $R^{5b}$ to $R^{5l}$, and $R^{6b}$ to $R^{6l}$ independently represents H or (i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $J^1$;

each $J^1$ independently represents (i) halo, $NO_2$, —CN, —$OR^{8b}$, —$S(O)_qR^{8c}$, —$S(O)_rN(R^{8d})(R^{8e})$, —$N(R^{8f})S(O)_sR^{8g}$, $N(R^{8h})(R^{8i})$, —$C(O)OR^{8j}$, or —$C(O)NR^{8k}R^{8l}$, (iv) heterocyclyl optionally substituted by one or more groups independently selected from $L^3$;

each $R^{8b}$ to $R^{8l}$ independently represents H or $C_{1-3}$ alkyl optionally substituted with one or more fluoro;

each $L^3$ independently represents halo, $NO_2$, —CN, —$R^{9a}$, —$OR^{9b}$, —$S(O)_qR^{9c}$, —$S(O)_rN(R^{9d})(R^{9e})$, —$N(R^{9f})S(O)_sR^{9g}$, —$N(R^{9h})(R^{9i})$, —$C(O)OR^{9j}$, or —$C(O)NR^{9k}R^{9l}$, each $R^{9a}$ independently represents $C_{1-3}$ alkyl optionally substituted with one or more fluoro;

each $R^{9b}$ to $R^{9l}$ independently represents H or $C_{1-3}$ alkyl optionally substituted with one or more fluoro; and each q, r and s independently represents 0, 1 or 2.

In some further particular embodiments of a compound of formula I:

each $R^1$ independently represents fluoro, methyl or hydroxy;

n represents 0, 1 or 2; preferably 0 or 1, more preferably 0;

$R^2$ represents
(i) phenyl optionally substituted by one or more groups independently selected from $A^4$,
(ii) 5- or 6-membered monocyclic heteroaryl optionally substituted by one or more groups selected from oxy and $A^1$, or
(iii) phenyl substituted with two adjacent groups which, together with the ring to which they are attached, form a bicyclic heteroaryl optionally substituted by one or more groups selected from oxy and $A^6$;

each $R^3$ independently represents
(i) halo, $-NO_2$, $-CN$, $-R^{2a}$, $-OR^{2b}$, $-S(O)_qR^{2c}$, $-S(O)_rN(R^{2d})(R^{2e})$, $-N(R^{2f})S(O)_sR^{2g}$, $-N(R^{2h})(R^{2i})$, $-C(O)OR^{2j}$, or $-C(O)NR^{2k}R^{2l}$,
(ii) aryl optionally substituted by one or more groups independently selected from $A^7$,
(iii) heteroaryl optionally substituted by one or more groups selected from $A^8$, or
(iv) heterocyclyl optionally substituted by one or more groups independently selected from $A^9$;

each $R^{2a}$ independently represents
(i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $B^1$;

each $R^{2b}$ to $R^{2l}$ independently represents H or
(i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $B^1$;
(iii) heteroaryl optionally substituted by one or more groups selected from oxy and $B^3$, or
(iv) heterocyclyl optionally substituted by one or more groups independently selected from oxy and $B^4$;

each $A^4$ to $A^9$ independently represents
(i) halo, $-NO_2$, $-CN$, $-R^{3a}$, $-OR^{3b}$, $-S(O)_qR^{3c}$, $-S(O)_rN(R^{3d})(R^{3e})$, $-N(R^{3f})S(O)_sR^{3g}$, $-N(R^{3h})(R^{3i})$, $-C(O)OR^{3j}$, or $-C(O)NR^{3k}R^{3l}$, each $B^1$ independently represents
(i) halo, $NO_2$, $-CN$, $-OR^{4b}$, $-S(O)_qR^{4c}$, $-S(O)_rN(R^{4d})(R^{4e})$, $-N(R^{4f})S(O)_sR^{4g}$, $-N(R^{4h})(R^{4i})$, $-C(O)OR^{4j}$, or $-C(O)NR^{4k}R^{4l}$,
(ii) aryl optionally substituted by one or more groups independently selected from $D^4$,
(iii) heteroaryl optionally substituted by one or more groups selected from $D^5$, or
(iv) heterocyclyl optionally substituted by one or more groups independently selected from $D^6$;

each $B^3$ to $B^4$ independently represents
(i) halo, $NO_2$, $-CN$, $-R^{4a}$, $-OR^{4b}$, $-S(O)_gR^{4c}$, $-S(O)_rN(R^{4d})(R^{4e})$, $-N(R^{4f})S(O)_sR^{4g}$, $-N(R^{4h})(R^{4i})$, $-C(O)OR^{4j}$, or $-C(O)NR^{4k}R^{4l}$;

each $R^{3a}$ and $R^{4a}$ represent
(i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $E^1$;

each $R^{3b}$ to $R^{3l}$, and $R^{4b}$ to $R^{4l}$ independently represents H or
(i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $E^1$;

each $D^4$ to $D^6$ independently represents
(i) halo, $NO_2$, $-CN$, $-R^{5a}$, $-OR^{5b}$, $-S(O)_qR^{5c}$, $-S(O)_rN(R^{5d})(R^{5e})$, $-N(R^{5f})S(O)_sR^{5g}$, $-N(R^{5h})(R^{5i})$, $-C(O)OR^{5j}$, or $-C(O)NR^{5k}R^{5l}$, each $E^1$ independently represents
(i) halo, $NO_2$, $-CN$, $-OR^{6b}$, $-S(O)_qR^{6c}$, $-S(O)_rN(R^{6d})(R^{6e})$, $-N(R^{6f})S(O)_sR^{6g}$, $-N(R^{6h})(R^{6i})$, $-C(O)OR^{6j}$, or $-C(O)NR^{6k}R^{6l}$, or
(iv) heterocyclyl;

each $R^{5a}$ represents
(i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $J^1$;

each $R^{5b}$ to $R^{5l}$, and $R^{6b}$ to $R^{6l}$ independently represents H or
(i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $J^1$;

each $J^1$ independently represents
(i) halo, $NO_2$, $-CN$, $-OR^{8b}$, $-S(O)_qR^{8c}$, $-S(O)_rN(R^{8d})(R^{8e})$, $-N(R^{8f})S(O)SR^{8g}$, $-N(R^{8h})(R^{8i})$, $-C(O)OR^{8j}$, or $-C(O)NR^{8k}R^{8l}$,
(iv) heterocyclyl optionally substituted by one or more groups independently selected from $L^3$;

each $R^{8b}$ to $R^{8l}$ independently represents H or $C_{1-3}$ alkyl optionally substituted with one or more fluoro;

each $L^3$ independently represents halo, $NO_2$, $-CN$, $-Rea$, $-OR^{9b}$, $-S(O)_qR^{9c}$, $-S(O)_rN(R^{9d})(R^{9e})$, $-N(R^{9f})S(O)_sR^{9g}$, $-N(R^{9h})(R^{9i})$, $-C(O)OR^{9j}$, or $-C(O)NR^{9k}R^{9l}$, each $R^{9a}$ independently represents $C_{1-3}$ alkyl optionally substituted with one or more fluoro;

each $R^{9b}$ to $R^{9l}$ independently represents H or $C_{1-3}$ alkyl optionally substituted with one or more fluoro; and each q, r and s independently represents 0, 1 or 2.

In some further particular embodiments of a compound of formula I:
each $R^1$ independently represents fluoro, methyl or hydroxy;
n represents 0, 1 or 2; preferably 0 or 1, more preferably 0;

$R^2$ represents
(i) phenyl optionally substituted by one or more groups independently selected from $A^4$,
(ii) 5- or 6-membered monocyclic heteroaryl optionally substituted by one or more groups selected from oxy and $A^5$, or
(iii) phenyl substituted with two adjacent groups which, together with the ring to which they are attached, form a bicyclic heteroaryl optionally substituted by one or more groups selected from oxy and $A^6$;

each $R^3$ independently represents
(i) halo, $-CN$, $-R^{2a}$, $-OR^{2}b$, $-S(O)_qR^{2c}$, $-N(R^{2h})(R^{2i})$, $-C(O)OR^{2j}$, or $-C(O)NR^{2k}R^{2l}$,
(ii) aryl optionally substituted by one or more groups independently selected from $A^7$,
(iii) heteroaryl optionally substituted by one or more groups selected from $A^8$, or
(iv) heterocyclyl optionally substituted by one or more groups independently selected from $A^9$;

each $R^{2a}$ independently represents
(i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $B^1$;

each $R^{2b}$ to $R^{2l}$ independently represents H or (i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $B^1$;

(iii) heteroaryl optionally substituted by one or more groups selected from oxy and $B^3$, or (iv) heterocyclyl optionally substituted by one or more groups independently selected from oxy and $B^4$;

each $A^4$ to $A^9$ independently represents (i) halo, —CN, —$R^{3a}$, —$OR^{3b}$, —$S(O)_r N(R^{3d})(R^{3e})$, —$N(R^{3h})(R^{3i})$, —$C(O)OR^{3j}$, or —$C(O)NR^{3k}R^{3l}$, each $B^1$ independently represents (i) halo, —$OR^{4b}$, —$N(R^{4f})S(O)_s R^{4g}$, —$N(R^{4h})(R^{4i})$, —$C(O)OR^{4j}$, or —$C(O)NR^{4k}R^{4l}$, (ii) aryl optionally substituted by one or more groups independently selected from $D^4$, (iii) heteroaryl optionally substituted by one or more groups selected from $D^5$, or (iv) heterocyclyl optionally substituted by one or more groups independently selected from $D^6$;

each $B^3$ and $B^4$ independently represents —$R^{4a}$;

each $R^{3a}$ and $R^{4a}$ independently represents (i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $E^1$;

each $R^{3b}$ to $R^{3l}$, and $R^{4b}$ to $R^{4l}$ independently represents H or (i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $E^1$;

each $D^4$ to $D^6$ independently represents (i) —$R^{5a}$, —$OR^{5b}$, —$N(R^{5h})(R^{5i})$, or —$C(O)NR^{5k}R^{5l}$, each $E^1$ independently represents (i) halo, —$OR^{6b}$, —$N(R^{6h})(R^{6i})$, —$C(O)NR^{6k}R^{6l}$, or (iv) heterocyclyl;

each $R^{5a}$ represents (i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $J^1$;

each $R^{5b}$ to $R^{5l}$, and $R^{6b}$ to $R^{6l}$ independently represents H or (i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $J^1$;

each $J^1$ independently represents (i) halo, or —$N(R^{8h})(R^{8i})$, or (iv) heterocyclyl, each $R^{8h}$ and $R^{8i}$ independently represents H or $C_{1-3}$ alkyl optionally substituted with one or more fluoro;

each q, r and s independently represents 0, 1 or 2.

In some further particular embodiments of a compound of formula I:

each $R^1$ independently represents fluoro, methyl or hydroxy;

n represents 0, 1 or 2; preferably 0 or 1, more preferably 0;

$R^2$ represents (i) phenyl optionally substituted by one or more groups independently selected from $A^4$, (ii) 5- or 6-membered monocyclic heteroaryl optionally substituted by one or more groups selected from oxy and $A^5$, or (iii) phenyl substituted with two adjacent groups which, together with the ring to which they are attached, form a bicyclic heteroaryl optionally substituted by one or more groups selected from oxy and $A^1$;

each $R^3$ independently represents (i) halo, —CN, —$R^{2a}$, —$OR^{2b}$, —$S(O)_q R^{2c}$, —$N(R^{2h})(R^{2i})$, —$C(O)OR^{2j}$, or —$C(O)NR^{2k}R^{2l}$, (ii) aryl optionally substituted by one or more groups independently selected from $A^7$, (iii) heteroaryl optionally substituted by one or more groups selected from $A^8$, or (iv) heterocyclyl optionally substituted by one or more groups independently selected from $A^9$;

each $R^{2a}$ independently represents (i) $C_{1-6}$ alkyl, optionally substituted by one or more groups independently selected from oxy and $B^1$;

each $R^{2b}$ to $R^{2l}$ independently represents H or (i) $C_{1-6}$ alkyl, $C_{2-6}$ alkenyl or $C_{2-6}$ alkynyl, optionally substituted by one or more groups independently selected from oxy and $B^1$;

(iii) heteroaryl optionally substituted by one or more groups selected from oxy and $B^3$, or (iv) heterocyclyl optionally substituted by one or more groups independently selected from oxy and $B^4$;

each $A^4$ to $A^9$ independently represents (ii) halo, —CN, —$R^{3a}$, —$OR^{3b}$, —$S(O)_r N(R^{3d})(R^{3e})$, —$N(R^{3h})(R^{3i})$, —$C(O)OR^{3j}$, or —$C(O)NR^{3k}R^{3l}$, each $B^1$ independently represents (i) halo, —$OR^{4b}$, —$N(R^{4f})S(O)_s R^{4g}$, —$N(R^{4h})(R^{4i})$, —$C(O)OR^{4j}$, or —$C(O)NR^{4k}R^{4l}$, (ii) aryl optionally substituted by one or more groups independently selected from $D^4$, (iii) heteroaryl optionally substituted by one or more groups selected from $D^5$, or (iv) heterocyclyl optionally substituted by one or more groups independently selected from $D^6$;

each $B^3$ and $B^4$ independently represents —$R^{4a}$;

each $R^{3a}$ and $R^{4a}$ independently represents (i) $C_{1-6}$ alkyl, optionally substituted by one or more groups independently selected from oxy and $E^1$;

each $R^{3b}$ to $R^{3l}$, and $R^{4b}$ to $R^{4l}$ independently represents H or (i) $C_{1-6}$ alkyl, optionally substituted by one or more groups independently selected from oxy and $E^1$;

each $D^4$ to $D^6$ independently represents (i) —$R^{5a}$, —$OR^{5b}$, —$N(R^{5h})(R^{5i})$, or —$C(O)NR^{5k}R^{5l}$, each $E^1$ independently represents (i) halo, —$OR^{6b}$, —$N(R^{6h})(R^{6i})$, —$C(O)NR^{6k}R^{6l}$, or (iv) heterocyclyl;

each $R^{5a}$ represents (i) $C_{1-6}$ alkyl, optionally substituted by one or more groups independently selected from oxy and $J^1$;

each $R^{5b}$ to $R^{5l}$, and $R^{6b}$ to $R^{6l}$ independently represents H or (i) $C_{1-6}$ alkyl, optionally substituted by one or more groups independently selected from oxy and $J^1$;

each $J^1$ independently represents (i) halo, or —$N(R^{8h})(R^{8i})$, or (iv) heterocyclyl, each $R^{8h}$ and $R^{8i}$ independently represents H or $C_{1-3}$ alkyl optionally substituted with one or more fluoro;

each q, r and s independently represents 0, 1 or 2.

In some further particular embodiments of a compound of formula I:

each $R^1$ independently represents fluoro, methyl or hydroxy;

n represents 0, 1 or 2; preferably 0 or 1, more preferably 0;

$R^2$ represents
(i) phenyl optionally substituted by one or more groups independently selected from $A^4$,
(ii) 5- or 6-membered monocyclic heteroaryl optionally substituted by one or more groups selected from oxy and $A^5$, or
(iii) phenyl substituted with two adjacent groups which, together with the ring to which they are attached, form a bicyclic heteroaryl optionally substituted by one or more groups selected from oxy and $A^6$;

each $R^3$ independently represents
(i) halo, —CN, —$R^{2a}$, —$OR^{2b}$, —$S(O)_qR^{2c}$, —$N(R^{2h})(R^{2i})$, —$C(O)OR^{2j}$, or —$C(O)NR^{2k}R^{2l}$, each $R^{2a}$ independently represents
(i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $B^1$;

each $R^{2b}$ to $R^{2l}$ independently represents H or
(i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $B^1$;

each $A^4$ to $A^6$ independently represents
(i) halo, —CN, —$R^{3a}$, —$OR^{3b}$, —$N(R^{3h})(R^{3i})$, —$C(O)OR^{3j}$, or —$C(O)NR^{3k}R^{3l}$, each $B^1$ independently represents
(i) halo, —$OR^{4b}$, —$N(R^{4f})S(O)_sR^{4g}$, —$N(R^{4h})(R^{4i})$, —$C(O)OR^{4j}$, or —$C(O)NR^{4k}R^{4l}$,
(ii) aryl optionally substituted by one or more groups independently selected from $D^4$,
(iii) heteroaryl optionally substituted by one or more groups selected from $D^5$, or
(iv) heterocyclyl optionally substituted by one or more groups independently selected from $D^6$;

each $R^{3a}$ and $R^{4a}$ represent
(i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $E^1$;

each $R^{3b}$ to $R^{3l}$, and $R^{4b}$ to $R^{4l}$ independently represents H or
(i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $E^1$;

each $D^4$ to $D^6$ independently represents
(i) halo, —$R^{5a}$, —$OR^{5b}$, —$N(R^{5h})(R^{5i})$, or —$C(O)NR^{5k}R^{5l}$,
each $E^1$ independently represents
(i) halo, —$OR^{6b}$, —$N(R^{6h})(R^{6i})$, —$C(O)NR^{6k}R^{6l}$, or
(iv) heterocyclyl;

each $R^{5a}$ represents
(i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $J^1$;

each $R^{5b}$ to $R^{5l}$, and $R^{6b}$ to $R^{6l}$ independently represents H or
(i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $J^1$;

each $J^1$ independently represents
(i) halo, —$N(R^{8h})(R^{8i})$, or
(iv) heterocyclyl;
each $R^{8h}$ and $R^{8i}$ independently represents H or $C_{1-3}$ alkyl optionally substituted with one or more fluoro;
each q and s independently represents 0, 1 or 2.

In some further particular embodiments of a compound of formula I:
each $R^1$ independently represents fluoro, methyl or hydroxy;
n represents 0, 1 or 2; preferably 0 or 1, more preferably 0;

$R^2$ represents
(i) phenyl optionally substituted by one or more groups independently selected from $A^4$, each $R^3$ independently represents
(i) halo, —CN, —$R^{2a}$, —$OR^{2b}$, —$S(O)_qR^{2c}$, —$N(R^{2h})(R^{2i})$, —$C(O)OR^{2j}$, or —$C(O)NR^{2k}R^{2l}$, each $R^{2a}$ independently represents
(i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $B^1$;

each $R^{2b}$ to $R^{2l}$ independently represents H or
(i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $B^1$;

each $A^4$ independently represents
(i) halo, —CN, —$R^{3a}$, —$OR^{3b}$, —$N(R^{3h})(R^{3i})$, —$C(O)OR^{3j}$, or —$C(O)NR^{3k}R^{3l}$, each $B^1$ independently represents
(i) halo, —$OR^{4b}$, —$N(R^{4f})S(O)_sR^{4g}$, —$N(R^{4h})(R^{4i})$, —$C(O)OR^{4j}$, or —$C(O)NR^{4k}R^{4l}$,
(ii) aryl optionally substituted by one or more groups independently selected from $D^4$,
(iii) heteroaryl optionally substituted by one or more groups selected from $D^5$, or
(iv) heterocyclyl optionally substituted by one or more groups independently selected from $D^6$;

each $R^{3a}$ and $R^{4a}$ represent
(i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $E^1$;

each $R^{3b}$ to $R^{3l}$, and $R^{4b}$ to $R^{4l}$ independently represents H or
(i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $E^1$;

each $D^4$ to $D^6$ independently represents
(i) halo, —$R^{5a}$, —$OR^{5b}$, —$N(R^{5h})(R^{5i})$, or —$C(O)NR^{5k}R^{5l}$, each $E^1$ independently represents
(i) halo, —$OR^{6b}$, —$N(R^{6h})(R^{6i})$, —$C(O)NR^{6k}R^{6l}$, or
(iv) heterocyclyl;

each $R^{5a}$ represents
(i) $C_6$ alkyl, $C_{2-6}$ alkenyl or $C_{2-6}$ alkynyl, wherein each such alkyl, alkenyl or alkynyl group is optionally substituted by one or more groups independently selected from oxy and $J^1$;

each $R^{5b}$ to $R^{5l}$, and $R^{6b}$ to $R^{6l}$ independently represents H or
(i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $J^1$;

each $J^1$ independently represents
(i) halo, —N($R^{8h}$)($R^{8i}$), or
(iv) heterocyclyl;
each $R^{8h}$ and $R^{8i}$ independently represents H or $C_{1-3}$ alkyl optionally substituted with one or more fluoro;
each q and s independently represents 0, 1 or 2.

In some further particular embodiments of a compound of formula I:
each $R^1$ independently represents fluoro, methyl or hydroxy;
n represents 0, 1 or 2; preferably 0 or 1, more preferably 0;
$R^2$ represents
(i) phenyl optionally substituted by one or more groups independently selected from $A^4$,
(ii) 5- or 6-membered monocyclic heteroaryl optionally substituted by one or more groups selected from oxy and $A^5$, or
(iii) phenyl substituted with two adjacent groups which, together with the ring to which they are attached, form a bicyclic heteroaryl optionally substituted by one or more groups selected from oxy and $A^6$;
each $R^3$ independently represents
(i) halo, —CN, —$R^{2a}$, —$OR^{2b}$, —S(O)$_q R^{2c}$, —N($R^{2h}$)($R^{2i}$), —C(O)$OR^{2j}$, or —C(O)$NR^{2k}R^{2l}$, each $R^{2a}$ independently represents
(i) $C_{1-6}$ alkyl, wherein each such alkyl is optionally substituted by one or more groups independently selected from oxy and $B^1$;
each $R^{2b}$ to $R^{2l}$ independently represents H or
(i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $B^1$;
each $A^4$ to $A^6$ independently represents
(i) halo, —CN, —$R^{3a}$, —$OR^{3b}$, —N($R^{3h}$)($R^{3i}$), —C(O)$OR^{3j}$, or —C(O)$NR^{3k}R^{3l}$,
each $B^1$ independently represents
(i) halo, —$OR^{4b}$, —N($R^{4f}$)S(O)$_s R^{4g}$, —N($R^{4h}$)($R^{4i}$), —C(O)$OR^{4j}$, or —C(O)$NR^{4k}R^{4l}$,
(ii) aryl optionally substituted by one or more groups independently selected from $D^4$,
(iii) heteroaryl optionally substituted by one or more groups selected from $D^5$, or
(iv) heterocyclyl optionally substituted by one or more groups independently selected from $D^6$;
each $R^{3a}$ and $R^{4a}$ independently represents
(i) $C_{1-6}$ alkyl, optionally substituted by one or more groups independently selected from oxy and $E^1$;
each $R^{3b}$ to $R^{3l}$, and $R^{4b}$ to $R^{4l}$ independently represents H or
(i) $C_{1-6}$ alkyl, optionally substituted by one or more groups independently selected from oxy and $E^1$;
each $D^4$ to $D^6$ independently represents
(i) halo, —$R^{5a}$, —$OR^{5b}$, —N($R^{5h}$)($R^{5i}$), or —C(O)$NR^{5k}R^{5l}$,
each $E^1$ independently represents
(i) halo, —$OR^{6b}$, —N($R^{6h}$)($R^{6i}$), —C(O)$NR^{6k}R^{6l}$, or
(iv) heterocyclyl;
each $R^{5a}$ represents
(i) $C_{1-6}$ alkyl, optionally substituted by one or more groups independently selected from oxy and J;
each $R^{5b}$ to $R^{5l}$, and $R^{6b}$ to $R^{6l}$ independently represents H or
(i) $C_{1-6}$ alkyl, optionally substituted by one or more groups independently selected from oxy and $J^1$;
each $J^1$ independently represents
(i) halo, —N($R^{8h}$)($R^{8i}$), or
(iv) heterocyclyl;
each $R^{8h}$ and $R^{8i}$ independently represents H or $C_{1-3}$ alkyl optionally substituted with one or more fluoro;
each q and s independently represents 0, 1 or 2.

In some further particular embodiments of a compound of formula I:
each $R^1$ independently represents fluoro, methyl or hydroxy;
n represents 0, 1 or 2; preferably 0 or 1, more preferably 0;
$R^2$ represents
(i) phenyl optionally substituted by one or more groups independently selected from $A^4$,
each $R^3$ independently represents
(i) halo, —CN, —$R^{2a}$, —$OR^{2b}$, —S(O)$_q R^{2c}$, —N($R^{2h}$)($R^{2i}$), —C(O)$OR^{2j}$, or —C(O)$NR^{2k}R^{2l}$, each $R^{2a}$ independently represents
(i) $C_{1-6}$ alkyl, wherein each such alkyl is optionally substituted by one or more groups independently selected from oxy and $B^1$;
each $R^{2b}$ to $R^{2l}$ independently represents H or
(i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $B^1$;
each $A^4$ independently represents
(i) halo, —CN, —$R^{3a}$, —$OR^{3b}$, —N($R^{3h}$)($R^{3i}$), —C(O)$OR^{3j}$, or —C(O)$NR^{3k}R^{3l}$,
each $B^1$ independently represents
(i) halo, —$OR^{4b}$, —N($R^{4f}$)S(O)$_s R^{4g}$, —N($R^{4h}$)($R^{4i}$), —C(O)$OR^{4j}$, or —C(O)$NR^{4k}R^{4l}$,
(ii) aryl optionally substituted by one or more groups independently selected from $D^4$,
(iii) heteroaryl optionally substituted by one or more groups selected from $D^5$, or
(iv) heterocyclyl optionally substituted by one or more groups independently selected from $D^6$;
each $R^{3a}$ and $R^{4a}$ independently represents
(i) $C_{1-6}$ alkyl, optionally substituted by one or more groups independently selected from oxy and $E^1$;
each $R^{3b}$ to $R^{3l}$, and $R^{4b}$ to $R^{4l}$ independently represents H or
(i) $C_{1-6}$ alkyl, optionally substituted by one or more groups independently selected from oxy and $E^1$;
each $D^4$ to $D^6$ independently represents
(i) halo, —$R^{5a}$, —$OR^{5b}$, —N($R^{5h}$)($R^{5i}$), or —C(O)$NR^{5k}R^{5l}$,
each $E^1$ independently represents
(i) halo, —$OR^{6b}$, —N($R^{6h}$)($R^{6i}$), —C(O)$NR^{6k}R^{6l}$, or
(iv) heterocyclyl;
each $R^{5a}$ represents
(i) $C_{1-6}$ alkyl, optionally substituted by one or more groups independently selected from oxy and $J^1$;
each $R^{5b}$ to $R^{5l}$, and $R^{6b}$ to $R^{6l}$ independently represents H or
(i) $C_{1-6}$ alkyl, optionally substituted by one or more groups independently selected from oxy and $J^1$;
each $J^1$ independently represents
(i) halo, —N($R^{8h}$)($R^{8i}$), or
(iv) heterocyclyl;
each $R^{8h}$ and $R^{8i}$ independently represents H or $C_{1-3}$ alkyl optionally substituted with one or more fluoro;
each q and s independently represents 0, 1 or 2.

In the above mentioned embodiments, any aryl preferably is phenyl; any heteroaryl preferably is monocyclic, 5- or 6-membered and contains 1, 2 or 3 heteroatoms selected from N, O and S; any heterocyclyl preferably is 4- to 6-membered and contains 1, 2 or 3 heteroatoms selected from N, O and S.

In the above mentioned embodiments, when $R^2$ is an optionally substituted phenyl, such phenyl more preferably is substituted by at least one group $A^4$.

It should be realized that, unless otherwise indicated or apparent from the context, any reference made herein to a compound of formula I also should be construed as a reference to a compound of any one of the formulas Ia-In.

Particular compounds of the invention that may be mentioned include those compounds as described in the examples provided herein, and pharmaceutically acceptable salts thereof. For the avoidance of doubt, where such compounds of the invention include compounds in a particular salt form, compounds of the invention include those compounds in non-salt form and in the form of any pharmaceutically acceptable salt thereof (which may include the salt form present in such examples).

In some embodiments, the compound of formula I is not 4-(2-oxo-2,3-dihydro-1H-1,3-benzodiazol-1-yl)-N-phenylpiperidine-1-carboxamide, or 4-(5-methylsulfonyl-2-oxo-2,3-dihydro-1H-1,3-benzodiazol-1-yl)-N-(4-iodophenyl)piperidine-1-carboxamide.

Medical Uses

As indicated herein, the compounds of the invention, and therefore compositions and kits comprising the same, are useful as pharmaceuticals.

Thus, according to a second aspect of the invention there is provided a compound of the invention, as hereinbefore defined (i.e. a compound as defined in the first aspect of the invention, including all embodiments and particular features thereof), for use as a pharmaceutical (or for use in medicine).

For the avoidance of doubt, references to compounds as defined in the first aspect of the invention will include references to compounds of formula I (including all embodiments thereof, such as compounds of formula Ia, Ib and Ic) and pharmaceutically acceptable salts thereof.

Although compounds of the invention may possess pharmacological activity as such, certain pharmaceutically acceptable (e.g. "protected") derivatives of compounds of the invention may exist or be prepared which may not possess such activity, but may be administered parenterally or orally and thereafter be metabolized in the body to form compounds of the invention. Such compounds (which may possess some pharmacological activity, provided that such activity is appreciably lower than that of the active compounds to which they are metabolized) may therefore be described as "prodrugs" of compounds of the invention.

As used herein, references to prodrugs will include compounds that form a compound of the invention, in an experimentally-detectable amount, within a predetermined time, following enteral or parenteral administration (e.g. oral or parenteral administration). All prodrugs of the compounds of the invention are included within the scope of the invention.

Furthermore, certain compounds of the invention may possess no or minimal pharmacological activity as such, but may be administered parenterally or orally, and thereafter be metabolized in the body to form compounds of the invention that possess pharmacological activity as such. Such compounds (which also includes compounds that may possess some pharmacological activity, but that activity is appreciably lower than that of the active compounds of the invention to which they are metabolized), may also be described as "prodrugs".

For the avoidance of doubt, compounds of the invention are therefore useful because they possess pharmacological activity, and/or are metabolized in the body following oral or parenteral administration to form compounds that possess pharmacological activity.

As described herein, compounds of the invention may be particularly useful in treating cell proliferation disorders, which the skilled person will understand as being diseases and disorders characterized by abnormal cell proliferation.

Thus, in a third aspect of the invention, there is provided a compound of the invention, as hereinbefore defined, for use in the treatment of a cell proliferation disorder.

In an alternative third aspect of the invention, there is provided a method of treating a cell proliferation disorder comprising administering to a patient in need thereof a therapeutically effective amount of a compound of the invention, as hereinbefore defined.

In a further alternative third aspect of the invention, there is provided the use of a compound of the invention, as hereinbefore defined, for the manufacture of a medicament for the treatment a cell proliferation disorder.

The skilled person will understand that references to the treatment of a particular condition (or, similarly, to treating that condition) will take their normal meanings in the field of medicine. In particular, the terms may refer to achieving a reduction in the severity and/or frequency of occurrence of one or more clinical symptom associated with the condition, as adjudged by a physician attending a patient having or being susceptible to such symptoms.

As used herein, references to a patient (or to patients) will refer to a living subject being treated, including mammalian (e.g. human) patients. In particular, references to a patient will refer to human patients.

For the avoidance of doubt, the skilled person will understand that such treatment will be performed in a patient (or subject) in need thereof. The need of a patient (or subject) for such treatment may be assessed by those skilled the art using routine techniques.

As used herein, the terms disease and disorder (and, similarly, the terms condition, illness, medical problem, and the like) may be used interchangeably.

As used herein, the term effective amount will refer to an amount of a compound that confers a therapeutic effect on the treated patient. The effect may be observed in a manner that is objective (i.e. measurable by some test or marker) or subjective (i.e. the subject gives an indication of and/or feels an effect). In particular, the effect may be observed (e.g. measured) in a manner that is objective, using appropriate tests as known to those skilled in the art.

The skilled person will be able to identify various diseases and disorders characterized by abnormal cell proliferation.

In particular embodiments (i.e. particular embodiments of the third aspect of the invention), the cell proliferation disorder is a selected from the group consisting of: (a) cancer; and (b) inflammation.

As described herein, the compounds of the first aspect of the invention may find particular utility in the treatment of inflammation. Thus, 'in certain embodiments, the cell proliferation disorder is inflammation.

In particular embodiments, the inflammation is an acute and/or systemic inflammation.

In more particular embodiments, the inflammation is an inflammation of the:
  lungs (such as asthma, chronic obstructive pulmonary disease (COPD), acute lung injury/acute respiratory distress and/or interstitial lung disease);
  joints (such as rheumatoid arthritis);

digestive system, e.g. the intestine (such as ulcerative colitis and/or Chron's disease);
skin (such as eczema and/or psoriasis); and/or
liver (such as inflammation resulting from chronic hepatitis).

Particular types of inflammation that may be mentioned include inflammation of the lungs (such as asthma, chronic obstructive pulmonary disease (COPD), acute lung injury/acute respiratory distress and/or interstitial lung disease).

In further embodiments, the inflammation may also be systemic inflammation triggered by an autoimmune response, as may occur in conditions such as sepsis.

As also described herein, the compounds of the first aspect of the invention may find particular utility in the treatment of cancers. Thus, in certain embodiments, the cell proliferation disorder is cancer (i.e. a cancer). In particular embodiments, the cancer is a solid tumour cancer. In further embodiments, the cancer is a blood cell cancer, such as leukaemia. In more particular embodiments, the cancer is selected from the group consisting of:
leukemia (such as acute lymphoblastic leukemia, acute monocytic leukemia, acute myelogenous leukemia, chronic myelogenous leukemia, acute myeloid leukemia, acute Promyelocytic leukemia, and/or acute promyelocytic leukemia);
lymphomas (such as Burkitt's lymphoma);
carcinomas, including adenocarcinomas (such as lung carcinoma, e.g. large cell lung carcinoma and/or small cell lung carcinoma, cervical adenocarcinoma, colorectal adenocarcinoma, colorectal carcinoma, prostate carcinoma, e.g. prostate adenocarcinoma, renal carcinoma, e.g. renal cell adenocarcinoma and/or endometrioid adenocarcinoma);
lymphoblastoma;
glioblastomas (such as glioblastoma multiforme and/or malignant glioblastoma); lymphomas (such as mantle cell lymphoma); and/or sarcomas (such as osteosarcoma).

Specific cancers that may be mentioned include lung cancer (e.g. large cell lung cancer and small cell lung cancer), breast cancer, renal cancer, colorectal cancer, prostate cancer, brain cancer (e.g. glioblastoma) and leukaemia. More particular cancers that may be mentioned include lung cancer (e.g. large cell lung cancer and small cell lung cancer). Further cancers that may be mentioned include those cancers expressing a relevant oncogene (i.e. an oncogene specific to that cancer types), as known to those skilled in the art (such as Ras).

Pharmaceutical Compositions

As described herein, compounds of the invention are useful as pharmaceuticals. Such compounds may be administered alone or may be administered by way of known pharmaceutical compositions/formulations.

In a fourth aspect of the invention, there is provided a pharmaceutical composition comprising a compound of the invention as defined herein, and optionally one or more pharmaceutically acceptable excipient.

As used herein, the term pharmaceutically acceptable excipients includes references to vehicles, adjuvants, carriers, diluents, pH adjusting and buffering agents, tonicity adjusting agents, stabilizers, wetting agents and the like. In particular, such excipients may include adjuvants, diluents or carriers.

For the avoidance of doubt, references herein to compounds of invention being for particular uses (and, similarly, to uses and methods of use relating to compounds of the invention) may also apply to pharmaceutical compositions comprising compounds of the invention, as described herein.

Thus, in a fifth aspect of the invention, there is provided a pharmaceutical composition as defined in the fourth aspect of the invention for use in the treatment a cell proliferation disorder (as defined herein, with reference to the third aspect of the invention and all embodiments thereof).

The skilled person will understand that compounds of the invention may act systemically and/or locally (i.e. at a particular site), and may therefore be administered accordingly using suitable techniques known to those skilled in the art.

The skilled person will understand that compounds and compositions as described herein will normally be administered orally, intravenously, subcutaneously, buccally, rectally, dermally, nasally, tracheally, bronchially, sublingually, intranasally, topically, by any other parenteral route or via inhalation, in a pharmaceutically acceptable dosage form.

Pharmaceutical compositions as described herein will include compositions in the form of tablets, capsules or elixirs for oral administration, suppositories for rectal administration, sterile solutions or suspensions for parenteral or intramuscular administration, and the like. Alternatively, particularly where such compounds of the invention act locally, pharmaceutical compositions may be formulated for topical administration.

Thus, in particular embodiments, the pharmaceutical formulation is provided in a pharmaceutically acceptable dosage form, including tablets or capsules, liquid forms to be taken orally or by injection, suppositories, creams, gels, foams, inhalants (e.g. to be applied intranasally), or forms suitable for topical administration. For the avoidance of doubt, in such embodiments, compounds of the invention may be present as a solid (e.g. a solid dispersion), liquid (e.g. in solution) or in other forms, such as in the form of micelles.

For example, in the preparation of pharmaceutical formulations for oral administration, the compound may be mixed with solid, powdered ingredients such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture may then be processed into granules or compressed into tablets.

Soft gelatin capsules may be prepared with capsules containing one or more active compounds (e.g. compounds of the first and, therefore, second and third aspects of the invention, and optionally additional therapeutic agents), together with, for example, vegetable oil, fat, or other suitable vehicle for soft gelatin capsules. Similarly, hard gelatine capsules may contain such compound(s) in combination with solid powdered ingredients such as lactose, saccharose, sorbitol, mannitol, potato starch, corn starch, amylopectin, cellulose derivatives or gelatin.

Dosage units for rectal administration may be prepared (i) in the form of suppositories which contain the compound(s) mixed with a neutral fat base; (ii) in the form of a gelatin rectal capsule which contains the active substance in a mixture with a vegetable oil, paraffin oil, or other suitable vehicle for gelatin rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions, containing the compound(s) and the remainder of the formulation consisting of sugar or sugar alcohols, and a mixture of ethanol, water, glycerol, propylene glycol and polyethylene glycol. If desired, such liquid preparations may contain colouring agents, flavouring agents, saccharine and carboxymethyl cellulose or other thickening agent. Liquid preparations for oral administration may also be prepared in the form of a dry powder to be reconstituted with a suitable solvent prior to use.

Solutions for parenteral administration may be prepared as a solution of the compound(s) in a pharmaceutically acceptable solvent. These solutions may also contain stabilizing ingredients and/or buffering ingredients and are dispensed into unit doses in the form of ampoules or vials. Solutions for parenteral administration may also be prepared as a dry preparation to be reconstituted with a suitable solvent extemporaneously before use.

Depending on e.g. potency and physical characteristics of the compound of the invention (i.e. active ingredient), pharmaceutical formulations that may be mentioned include those in which the active ingredient is present in an amount that is at least 1% (or at least 10%, at least 30% or at least 50%) by weight. That is, the ratio of active ingredient to the other components (i.e. the addition of adjuvant, diluent and carrier) of the pharmaceutical composition is at least 1:99 (or at least 10:90, at least 30:70 or at least 50:50) by weight.

The skilled person will understand that compounds of the invention may be administered (for example, as formulations as described hereinabove) at varying doses, with suitable doses being readily determined by one of skill in the art. Oral, pulmonary and topical dosages (and subcutaneous dosages, although these dosages may be relatively lower) may range from between about 1 mg/kg of body weight per day (mg/kg/day) to about 200 mg/kg/day. For example, treatment with such compounds may comprise administration of a formulations typically containing between about 100 mg to about 10,000 mg, such as a dose of about 6,000 mg, of the active ingredient(s). Advantageously, treatment may comprise administration of such compounds and compositions in a single daily dose, or the total daily dosage may be administered in divided doses of two, three or four times daily.

When used herein in relation to a specific value (such as an amount), the term "about" (or similar terms, such as "approximately") will be understood as indicating that such values may vary by up to 10% (particularly, up to 5%, such as up to 1%) of the value defined. It is contemplated that, at each instance, such terms may be replaced with the notation "±10%", or the like (or by indicating a variance of a specific amount calculated based on the relevant value). It is also contemplated that, at each instance, such terms may be deleted.

For the avoidance of doubt, the skilled person (e.g. the physician) will be able to determine the actual dosage which will be most suitable for an individual patient, which is likely to vary with the route of administration, the type and severity of the condition that is to be treated, as well as the species, age, weight, sex, renal function, hepatic function and response of the particular patient to be treated. Although the above-mentioned dosages are exemplary of the average case, there can, of course, be individual instances where higher or lower dosage ranges are merited, and such doses are within the scope of the invention.

Combinations and Kits-of-Parts

The skilled person will understand that treatment with compounds of the invention may further comprise (i.e. be combined with) further treatment(s) for the same condition. In particular, treatment with compounds of the invention may be combined with means for the treatment of a cell proliferation disorder as described herein (such as inflammation and/or cancer, as described herein), such as treatment with one or more other therapeutic agent that is useful in the in the treatment of a cell proliferation disorder and/or one or more physical method used in the treatment of a cell proliferation disorder (such as, particularly in the treatment of cancer, treatment through surgery), as known to those skilled in the art.

As described herein, compounds of the invention may also be combined with one or more other (i.e. different) therapeutic agents (i.e. agents that are not compounds of the invention) that are useful in the treatment of a cell proliferation disorder. Such combination products that provide for the administration of a compound of the invention in conjunction with one or more other therapeutic agent may be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the one or more other therapeutic agent).

Thus, according to a sixth aspect of the invention, there is provided a combination product comprising:
(I) a compound of the invention, as hereinbefore defined (i.e. in the first aspect of the invention, including all embodiments and particular features thereof); and
(II) one or more other therapeutic agent that is useful in the treatment of a cell proliferation disorder (such as inflammation and/or cancer, as described herein), wherein each of components (I) and (II) is formulated in admixture, optionally with one or more a pharmaceutically acceptable excipient.

In a seventh aspect of the invention, there is provided a kit-of-parts comprising:
(a) a pharmaceutical formulation as hereinbefore defined (i.e. in the fifth aspect of the invention); and
(b) one or more other therapeutic agent that is useful in the treatment of a cell proliferation disorder (such as cancer or inflammation, as described herein), optionally in admixture with one or more pharmaceutically acceptable excipient, which components (a) and (b) are each provided in a form that is suitable for administration in conjunction (i.e. concomitantly or sequentially) with the other.

With respect to the kits-of-parts as described herein, by "administration in conjunction with" (and similarly "administered in conjunction with") we include that respective formulations are administered, sequentially, separately or simultaneously, as part of a medical intervention directed towards treatment of the relevant condition. Thus, in relation to the present invention, the term "administration in conjunction with" (and similarly "administered in conjunction with") includes that the two active ingredients (i.e. a compound of the invention and a further agent for the treatment of a cell proliferation disorder, or compositions comprising the same) are administered (optionally repeatedly) either together, or sufficiently closely in time, to enable a beneficial effect for the patient, that is greater, over the course of the treatment of the relevant condition, than if either agent is administered (optionally repeatedly) alone, in the absence of the other component, over the same course of treatment. Determination of whether a combination provides a greater beneficial effect in respect of, and over the course of, treatment of a particular condition will depend upon the condition to be treated but may be achieved routinely by the skilled person.

Further, in the context of the present invention, the term "in conjunction with" includes that one or other of the two formulations may be administered (optionally repeatedly) prior to, after, and/or at the same time as, administration of the other component. When used in this context, the terms "administered simultaneously" and "administered at the same time as" includes instances where the individual doses of the compound of the invention and the additional compound for the treatment of cancer, or pharmaceutically acceptable salts thereof, are administered within 48 hours (e.g. within 24 hours, 12 hours, 6 hours, 3 hours, 2 hours, 1 hour, 45 minutes, 30 minutes, 20 minutes or 10 minutes) of each other.

Other therapeutic agents useful in the treatment of a cell proliferation disorder (such as those known for use in the treatment of cancer or inflammation as described herein) will be well-known to those skilled in the art. For example, therapeutic agents that may be mentioned (particularly, when for use in the treatment of cancer) include MTH1 inhibitors (such as karonudib, and MTH1 inhibitors as described in WO 2014/084778 A1, WO 2015/187088 A1 and WO 2015/187089 A1) and tubulin inhibitors (i.e. poisons) (such as paclitaxel).

Other examples of therapeutic agents that may be mentioned are anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors; kinase inhibitors; angiogenesis inhibitors; immunotherapeutic agents; pro-apoptotic agents; and cell cycle signaling inhibitors.

Preparation of Compounds/Compositions

Pharmaceutical compositions/formulations, combination products and kits as described herein may be prepared in accordance with standard and/or accepted pharmaceutical practice. Thus, in a further aspect of the invention there is provided a process for the preparation of a pharmaceutical composition/formulation, as hereinbefore defined, which process comprises bringing into association a compound of the invention, as hereinbefore defined, with one or more pharmaceutically acceptable excipient.

In further aspects of the invention, there is provided a process for the preparation of a combination product or kit-of-parts as hereinbefore defined, which process comprises bringing into association a compound of the invention, as hereinbefore defined, with the other therapeutic agent that is useful in the treatment of the relevant disease or disorder, and at least one pharmaceutically acceptable excipient.

As used herein, references to bringing into association will mean that the two components are rendered suitable for administration in conjunction with each other.

Thus, in relation to the process for the preparation of a kit-of-parts as hereinbefore defined, by bringing the two components "into association with" each other, we include that the two components of the kit-of-parts may be:
(i) provided as separate formulations (i.e. independently of one another), which are subsequently brought together for use in conjunction with each other in combination therapy; or
(ii) packaged and presented together as separate components of a "combination pack" for use in conjunction with each other in combination therapy.

Compounds of the invention as described herein may be prepared in accordance with techniques that are well known to those skilled in the art, such as those described in the examples provided hereinafter.

According to an eighth aspect of the invention a process is provided, for the preparation of a compound of the invention as hereinbefore defined, comprising:
(i) for compounds of formula I wherein $X^i$ represents 0, reacting a compound of formula II

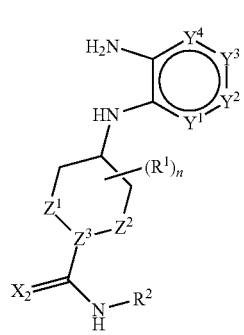

II wherein $R^1$, $R^2$, $X^2$, $Y^1$ to $Y^4$, $Z^1$ to $Z^3$, and n are as defined herein (i.e. in the first aspect of the invention, including all embodiments thereof), with phosgene or a suitable equivalent thereof (e.g. a source of phosgene, such as diphosgene or triphosgene, or a functional equivalent. such as carbonyl diimidazole), in the presence of a suitable solvent (such as DCM) and a suitable base (such as an amine base, e.g. N,N-diisopropylethylamine);

(ii) for compounds of formula I wherein $Z^3$ represents N, reaction of a compound of formula III

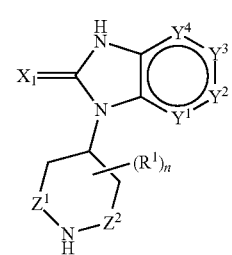

III wherein $R^1$, $X^1$, $Y^1$ to Y, $Z^1$, $Z^2$, and n are as defined herein, with a compound of formula IV

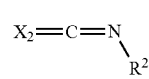

IV or a suitable salt thereof (e.g. a trifluoroacetate salt), wherein $X^2$ and $R^2$ are as defined herein, in the presence of a suitable solvent (sucas DCM) and a suitable base (such as an amine base, e.g. N,N-diisopropylethylamine);

(iii) reaction of a compound of formula III as defined herein with a compound of formula V

V wherein R² is as defined herein, and with phosgene or a suitable equivalent thereof (such as diphosgene or triphosgene), in the presence of a suitable solvent (such as DCM) and a suitable base (such as an amine base, e.g. N,N-diisopropylethylamine);

(iv) where Z³ represents CH or CR¹ (e.g. CH), reaction of a compound of formula VI

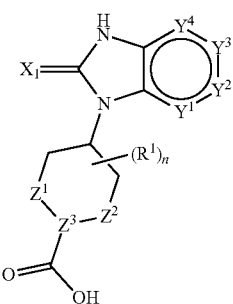

VI wherein R¹, X¹, Y¹ to Y⁴, Z¹, Z², and n are as defined herein, with a compound of formula V as defined herein, in presence of a suitable coupling agent (such as propylphosphonic anhydride) and in the presence of a suitable solvent (such as THF) and a suitable base (such as an amine base, e.g. N,N-diisopropylethylamine); or (v) for compounds of formula I wherein at least one R³ group is present and represents an alkyl, aryl, heteroaryl or heterocycloalkyl group, reaction of a corresponding compound of formula I but wherein the relevant R³ group instead represents LG¹, wherein LG¹ represents a suitable leaving group (such as halo, e.g. Br), with a compound of formula VII

VII wherein R³ is as defined herein and LG² represents a suitable leaving group (such as a suitable boronic ester), in the presence of a suitable catalyst (such as a Pd catalyst, e.g. Pd(PPh₃)₄), and in the presence of a suitable solvent (such as a mixture of 1,4-dioxane and water) and a suitable base (such an inorganic base, e.g. K₂CO₃).

Compounds of formulas II, III, IV, V, VI and VII are either commercially available, are known in the literature, or may be obtained either by analogy with the processes described herein, or by conventional synthetic procedures, in accordance with standard techniques, from available starting materials using appropriate reagents and reaction conditions. In this respect, the skilled person may refer to inter alia "*Comprehensive Organic Synthesis*" by B. M. Trost and I. Fleming, Pergamon Press, 1991. Further references that may be employed include "*Heterocyclic Chemistry*" by J. A. Joule, K. Mills and G. F. Smith, 3$^{rd}$ edition, published by Chapman & Hall, "*Comprehensive Heterocyclic Chemistry II*" by A. R. Katritzky, C. W. Rees and E. F. V. Scriven, Pergamon Press, 1996 and "*Science of Synthesis*", Volumes 9-17 (Hetarenes and Related Ring Systems), Georg Thieme Verlag, 2006.

The skilled person will understand that the substituents as defined herein, and substituents thereon, may be modified one or more times, after or during the processes described above for the preparation of compounds of the invention by way of methods that are well known to those skilled in the art. Examples of such methods include substitutions, reductions, oxidations, dehydrogenations, alkylations, dealkylations, acylations, hydrolyses, esterifications, etherifications, halogenations and nitrations. The precursor groups can be changed to a different such group, or to the groups defined in formula I, at any time during the reaction sequence. The skilled person may also refer to "*Comprehensive Organic Functional Group Transformations*" by A. R. Katritzky, O. Meth-Cohn and C. W. Rees, Pergamon Press, 1995 and/or "*Comprehensive Organic Transformations*" by R. C. Larock, Wiley-VCH, 1999.

Compounds of the invention may be isolated from their reaction mixtures and, if necessary, purified using conventional techniques as known to those skilled in the art. Thus, processes for preparation of compounds of the invention as described herein may include, as a final step, isolation and optionally purification of the compound of the invention.

It will be appreciated by those skilled in the art that, in the processes described above and hereinafter, the functional groups of intermediate compounds may need to be protected by protecting groups. The protection and deprotection of functional groups may take place before or after a reaction in the above-mentioned schemes.

Protecting groups may be applied and removed in accordance with techniques that are well-known to those skilled in the art and as described hereinafter. For example, protected compounds/intermediates described herein may be converted chemically to unprotected compounds using standard deprotection techniques. The type of chemistry involved will dictate the need, and type, of protecting groups as well as the sequence for accomplishing the synthesis. The use of protecting groups is fully described in "*Protective Groups in Organic Synthesis*", 3rd edition, T. W. Greene & P. G. M. Wutz, Wiley-Interscience (1999), the contents of which are incorporated herein by reference.

Compounds of the invention may have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise. In particular, compounds of the invention may have the advantage that they are more efficacious and/or exhibit advantageous properties in vivo.

EXAMPLES

The present invention will be further described by reference to the following examples, which are not intended to limit the scope of the invention.

In the event that there is a discrepancy between nomenclature and any compounds depicted graphically, then it is the latter that presides (unless contradicted by any experimental details that may be given or unless it is clear from the context).

Experimental Procedures

Starting materials and intermediates used in the synthesis of compounds described herein are commercially available or can be prepared by the methods described herein or by methods known in the art.

Where necessary, experiments were carried out in dry conditions and/or under inert atmosphere (nitrogen or argon), particularly in cases where oxygen- or moisture-sensitive reagents or intermediates were used.

Mass spectrometry data are reported from liquid chromatography-mass spectrometry (LC-MS) using electrospray ionization. Chemical shifts for NMR data are expressed in parts per million (ppm, δ) referenced to residual peaks from the deuterated solvent used.

For syntheses referencing general procedures, reaction conditions (such as length of reaction or temperature) may vary. In general, reactions were followed by thin layer chromatography or LC-MS, and subjected to work-up when appropriate. Purifications may vary between experiments: in general, solvents and the solvent ratios used for eluents/gradients were chosen to provide an appropriate $R_f$ and/or retention time.

General Procedures

Processes used in the synthesis of compounds as described in the following examples may be represented by the following general procedures, wherein variable groups indicated (such as $R^1$, $R^2$, X, and the like) may have meanings distinct from those indicated in the first aspect of the invention.

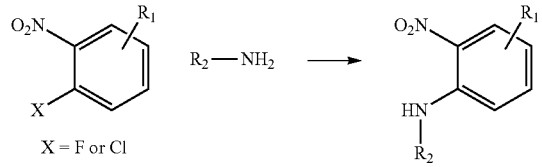

General procedure A: A mixture of the corresponding nitrobenzene compound (1.0 equiv.), a suitable amine (1.1 equiv.), and N,N-diisopropylethylamine (1.2 equiv.) was stirred in 2-propanol at 120° C. for 12-72 h. Thereafter, the mixture was poured into NaHCO$_3$ and extracted with DCM× 3. The combined organics were dried (using MgSO$_4$), filtered, concentrated, and purified by silica gel chromatography.

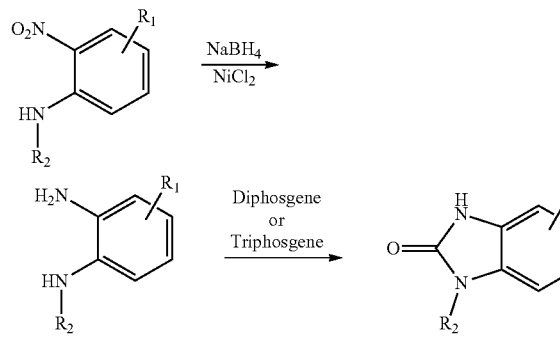

General procedure B: To a mixture of a substituted 2-amino-1-nitrobenzene compound (1.0 equiv.) and NiCl$_2$ (0.20 equiv.) in acetonitrile/water (9:1 v/v) was added NaBH$_4$ (4.0 equiv.) portion wise. After complete reaction, DCM was added and the liquids were poured into NaHCO$_3$ by means of decantation. The aqueous phase was extracted with DCM×3 and the combined extracts were dried (using MgSO$_4$) and filtered. To the filtrate was then added N,N-diisopropylethylamine (2.2 equiv.) and diphosgene (0.50 equiv.) or triphosgene (0.34 equiv.). After complete reaction, the mixture was concentrated and purified by silica gel chromatography.

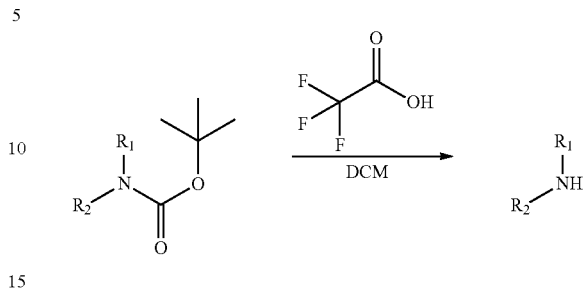

General procedure C: The corresponding tert-butyl carbamate compound was dissolved in DCM, then trifluoroacetic acid (5-15 equiv.) was added and the mixture was stirred at 20° C. for 10-60 min. After complete reaction, the solvents were removed by co-evaporation with 2-propanol. Unless otherwise stated, no further purification was done.

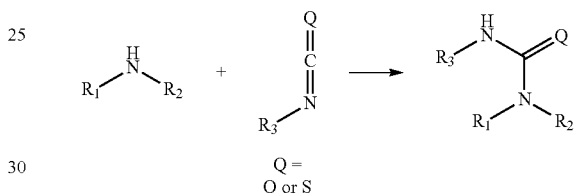

Q = O or S

General procedure D: A mixture of the corresponding amine or trifluoroacetate salt thereof (1.0 equiv.) and N,N-diisopropylethylamine (2.0 equiv.) was stirred in DCM, then a suitable isocyanate or isothiocyanate (1.0 equiv.) was added and the resulting mixture was stirred at 50° C. for 3-16 h. After complete reaction the mixture was purified by silica gel chromatography or by preparative liquid chromatography.

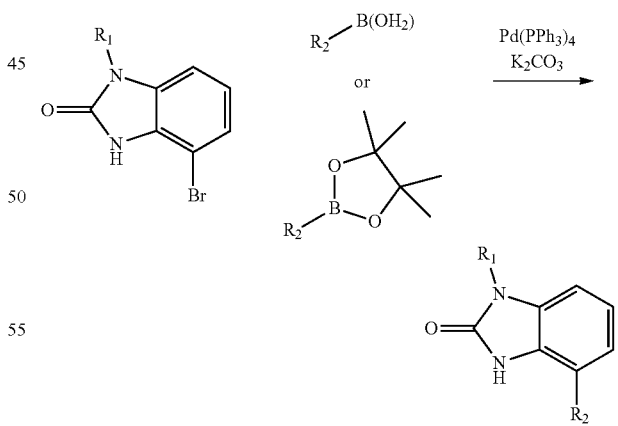

General procedure E: A mixture of the corresponding 4-bromobenzimidazolone (1.0 equiv.), a suitable organoboronic acid or pinacol boronic acid ester (1.2 equiv.), K$_2$CO$_3$ (2.5 equiv.), and Pd(PPh$_3$)$_4$ (0.030 equiv.) in 1,4-dioxane and water (5:1 v/v mixture) was stirred at 100° C. for 2-72 h. After complete reaction, the mixture was poured into NaHCO$_3$ (sat.) and extracted with DCM×3. The combined organics were concentrated and the crude material was purified by silica gel chromatography or by preparative liquid chromatography.

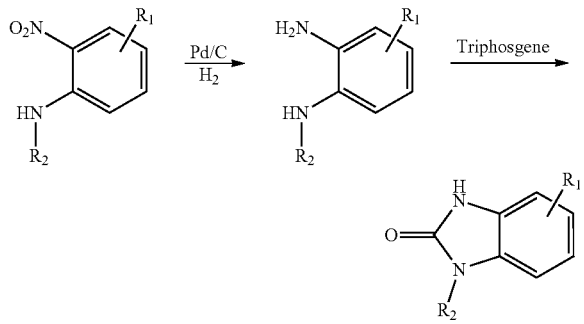

General procedure F: A mixture of the corresponding nitrobenzene compound (1.0 equiv.) and Pd/C (0.05 equiv.) was stirred in THF at 20° C. for 12-24 h under an $H_2$ atmosphere provided by a balloon. After complete reaction the balloon was removed and N,N-diisopropylethylamine (2.0 equiv.) and triphosgene (0.35 equiv.) were added. The resulting mixture was stirred for 20-60 min at 20° C. and was then filtered, concentrated, and purified by silica gel chromatography.

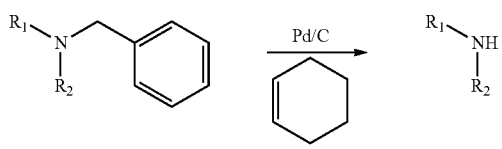

General procedure G: A mixture of the corresponding benzyl protected compound (1 equiv.) and Pd/C (0.1 equiv.) was stirred in 1,4-dioxane and cyclohexene (10:1 v/v) in a sealed vial at 120° C. for 2-16 h. Upon complete reaction the mixture was filtered, concentrated, and purified by silica gel chromatography.

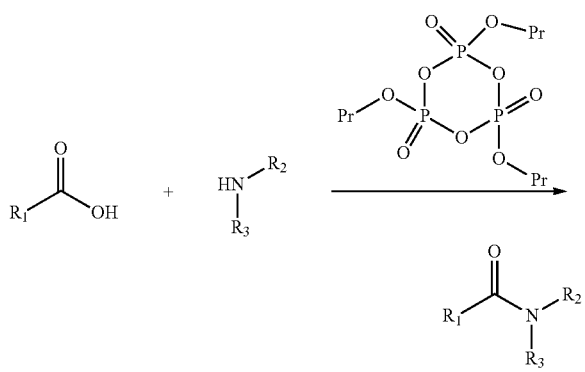

General procedure H: A mixture of the corresponding carboxylic acid (1.0 equiv.), an appropriate amine (2 equiv.), propylphosphonic anhydride (4 equiv.) and N,N-diisopropylethylamine (3.0 equiv.) was stirred in THF or acetonitrile at an elevated temperature for 3-16 h. After complete reaction the mixture was purified by silica gel chromatography or by preparative liquid chromatography.

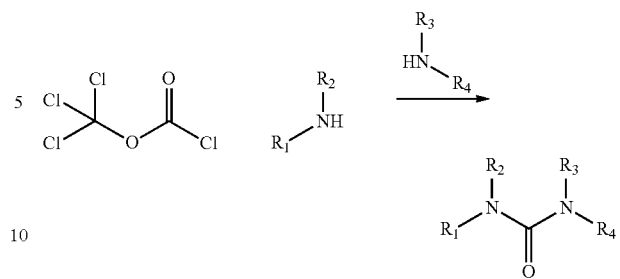

General procedure I: To a mixture of a suitable amine or a salt thereof (1.0 equiv.) and N,N-diisopropylethylamine (2.0 equiv.) in DCM was added diphosgene (0.50 equiv.) under vigorous stirring. The mixture was stirred at 20° C. for 5-15 min after which it was added to a separate mixture of the corresponding amine or a salt thereof (1.0 equiv.) and N,N-diisopropylethylamine (2.0 equiv.) in DCM. The resulting mixture was stirred at 50° C. for 3-16 h. After complete reaction the mixture was purified by silica gel chromatography or by preparative liquid chromatography.

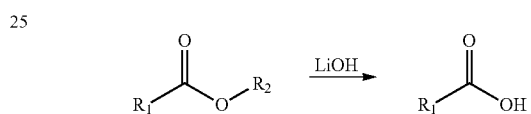

General procedure J: A mixture of the corresponding ester (1.0 equiv.) and LiOH (5.0 equiv.) was stirred in MeOH and water (3:1 v/v) at 20° C. for 5-24 h. After complete reaction the mixture poured into aqueous HCl (2 M) and extracted with DCM×3. The combined organics were concentrated and purified by silica gel chromatography.

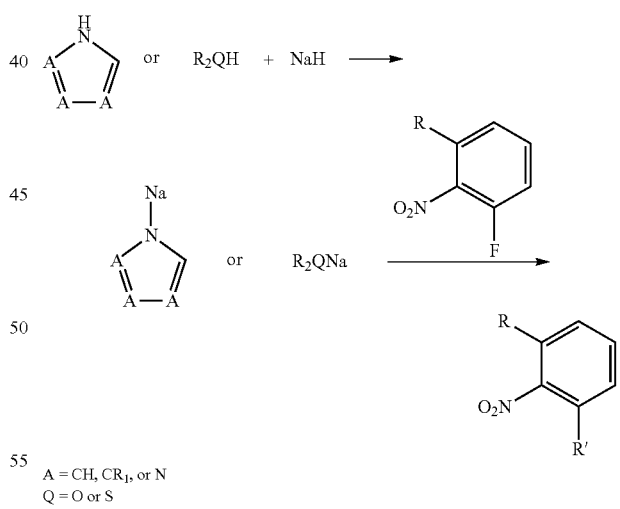

A = CH, $CR_1$, or N
Q = O or S

General procedure K: A mixture of the corresponding reactant (1.0 equiv.) and NaH (1.1 equiv.) was stirred in THF at 20° C. for 20 min. Then a substituted 1-fluoro-2-nitrobenzene compound (1.0 equiv.) was added and the resulting mixture was stirred at elevated temperatures. Upon completion of the reaction, the mixture was poured into $NaHCO_3$ and extracted with DCM×3. The combined organics were dried (using $MgSO_4$), filtered, concentrated, and purified by silica gel chromatography.

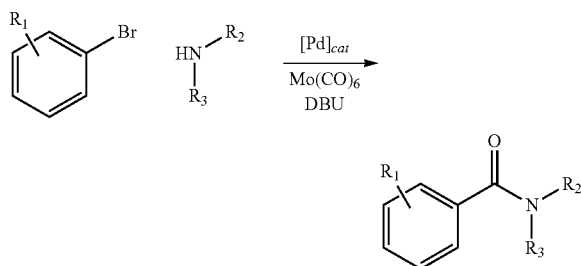

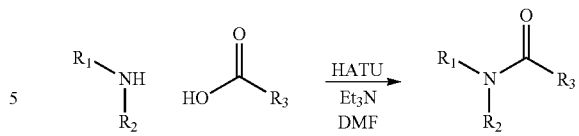

General procedure L: A sealable, two-chamber reaction vessel that allows for gas exchange between the two chambers was used. Chamber 1 was charged with a magnetic stirring bar, the appropriate aryl bromide (1.0 equiv.), the appropriate amine (1.5 equiv.), Pd(PPh$_3$)$_4$ or Pd(dppf)Cl$_2$ (0.050 equiv.), diisopropylethylamine (3 equiv.), and dioxane. Chamber 2 was charged with a magnetic stirring bar, Mo(CO)$_6$ (2.0 equiv.) and dioxane. The two-chamber reaction vial was then sealed and flushed with nitrogen for 3-5 min. Thereafter DBU (2.1 equiv.) was injected into chamber 2. Both chambers were then heated to 70° C. and the reaction mixtures were stirred 16-48 h. After cooling the reaction mixture, the seal was punctured with a needle to release excess carbon monoxide before opening the seal. The reaction mixture was then poured into HCl (2M) and extracted with DCM×3, the combined organics were then dried (MgSO$_4$) and concentrated. The crude mixture was purified by preparative HPLC or by silica gel chromatography.

General procedure M: A mixture of the appropriate 2-fluoronitrobenzene compound (1.0 equiv.) and the appropriate amine (3-5 equiv.) was stirred at 120° C. for 16-72 h. The mixture was then poured into HCl (2 M) and extracted with DCM×3. The combined organics were concentrated and purified by silica gel chromatography.

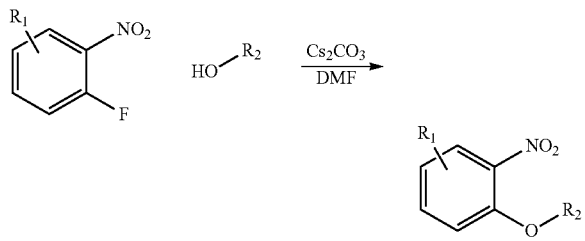

General procedure N: A mixture of the appropriate 2-fluoronitrobenzene compound (1.0 equiv.), the appropriate alcohol, and Cs$_2$CO$_3$ in DMF was stirred at 60° C. overnight. The mixture was then diluted with methanol, filtered, and purified by preparative HPLC.

General procedure O: A mixture of an appropriate amine (1.0 equiv.), an appropriate carboxylic acid (1.3 equiv.), HATU (1.5 equiv.) and triethylamine (3 equiv.) in DMF was stirred at r.t. for 16-24 h. The mixture was then diluted with methanol, filtered and purified by preparative HPLC.

Synthesis of Intermediates

Intermediate 1: 4-Bromo-1-(piperidin-4-yl)-2,3-dihydro-1H-1,3-benzodiazol-2-one;2,2,2-trifluoroacetic acid Step 1: tert-butyl 4-(3-bromo-2-nitro-anilino)piperidine-1-carboxylate was synthesized according to General procedure A from 1-bromo-3-fluoro-2-nitrobenzene and tert-butyl 4-aminopiperidine-1-carboxylate. LCMS [M-isobutene+H]$^+$ 344.

Step 2: tert-butyl 4-(4-bromo-2-oxo-2,3-dihydro-1H-1,3-benzodiazol-1-yl)piperidine-1-carboxylate was synthesized according to General procedure B from tert-butyl 4-(3-bromo-2-nitro-anilino)piperidine-1-carboxylate. LCMS [M-isobutene+H]$^+$ 340. $^1$H-NMR (400 MHz, CHLOROFORM-d) δ ppm 7.76 (s, 1H), 7.18-7.21 (m, 1H), 7.05-7.09 (m, 1H), 6.94-6.99 (m, 1H), 4.45 (tt, J=12.5, 3.9 Hz, 1H), 4.27-4.37 (m, 2H), 2.86 (m, 2H), 2.28 (m, 2H), 1.83 (m, 2H), 1.51 (s, 9H).

Step 3: 4-bromo-1-(piperidin-4-yl)-2,3-dihydro-1H-1,3-benzodiazol-2-one;2,2,2-trifluoroacetic acid was synthesized according to General procedure C from tert-butyl 4-(4-bromo-2-oxo-2,3-dihydro-1H-1,3-benzodiazol-1-yl)piperidine-1-carboxylate. LCMS [M+H]$^+$ 296. $^1$H-NMR (400 MHz, DMSO-d$_6$) δ ppm 11.38 (s, 1H), 8.57-8.70 (m, 1H), 8.31-8.47 (m, 1H), 7.32 (d, J=8.1 Hz, 1H), 7.21 (dd, J=8.1, 0.9 Hz, 1H), 7.01 (t, J=8.1 Hz, 1H), 4.53 (tt, J=12.2, 4.5 Hz, 1H), 3.45 (br. s., 2H), 3.02-3.16 (m, 2H), 2.52-2.61 (m, 2H), 1.84-1.93 (m, 2H).

Intermediate 2: 4-Chloro-1-(piperidin-4-yl)-2,3-dihydro-1H-1,3-benzodiazol-2-one;2,2,2-trifluoroacetic acid Step 1: tert-butyl 4-(3-chloro-2-nitro-anilino)piperidine-1-carboxylate was synthesized according to General procedure A from 1-chloro-3-fluoro-2-nitrobenzene and tert-butyl 4-aminopiperidine-1-carboxylate. LCMS [M-isobutene+H]$^+$ 300.

Step 2: tert-butyl 4-(4-chloro-2-oxo-2,3-dihydro-1H-1,3-benzodiazol-1-yl)piperidine-1-carboxylate was synthesized according to General procedure B from tert-butyl 4-(3-chloro-2-nitro-anilino)piperidine-1-carboxylate. $^1$H-NMR (400 MHz, CHLOROFORM-d) δ ppm 7.80 (br. s., 1H), 6.97-7.09 (m, 3H), 4.45 (tt, J=12.5, 4.1 Hz, 1H), 4.32 (m, 2H), 2.82-2.91 (m, 2H), 2.28 (m, 2H), 1.83 (m, 2H), 1.51 (s, 9H).

Step 3: 4-chloro-1-(piperidin-4-yl)-2,3-dihydro-1H-1,3-benzodiazol-2-one;2,2,2-trifluoroacetic acid was synthesized according to General procedure C from tert-butyl 4-(4-chloro-2-oxo-2,3-dihydro-1H-1,3-benzodiazol-1-yl)piperidine-1-carboxylate. LCMS [M+H]$^+$ 232.

Intermediate 3: 4-Fluoro-1-(piperidin-4-yl)-2,3-dihydro-1H-1,3-benzodiazol-2-one;2,2,2-trifluoroacetic acid Step 1: tert-butyl 4-(3-fluoro-2-nitro-anilino)piperidine-1-carboxylate was synthesized according to General procedure A from 1,3-difluoro-2-nitrobenzene and tert-butyl 4-aminopiperidine-1-carboxylate. LCMS [M-isobutene+H]$^+$ 284.

Step 2: tert-butyl 4-(4-fluoro-2-oxo-2,3-dihydro-1H-1,3-benzodiazol-1-yl)piperidine-1-carboxylate was synthesized according to General procedure B from tert-butyl 4-(3-fluoro-2-nitro-anilino)piperidine-1-carboxylate. LCMS [M-isobutene+H]$^+$ 280. $^1$H-NMR (400 MHz, CHLOROFORM-d) δ ppm 8.19 (s, 1H), 6.97-7.04 (m, 1H), 6.91-6.94 (m, 1H), 6.82-6.87 (m, 1H), 4.47 (tt, J=12.5, 4.2 Hz, 1H), 4.33 (m, 2H), 2.82-2.92 (m, 2H), 2.29 (m, 2H), 1.84 (m, 2H), 1.51 (s, 9H).

Step 3: 4-fluoro-1-(piperidin-4-yl)-2,3-dihydro-1H-1,3-benzodiazol-2-one;2,2,2-trifluoroacetic acid was synthesized according to General procedure C from tert-butyl 4-(4-fluoro-2-oxo-2,3-dihydro-1H-1,3-benzodiazol-1-yl)piperidine-1-carboxylate. LCMS [M+H]$^+$ 236. $^1$H-NMR (400 MHz, DMSO-d$_6$) δ ppm 11.52 (s, 1H), 8.89 (br. s., 1H), 8.65 (br. s., 1H), 7.19 (d, J=7.9 Hz, 1H), 7.02 (td, J=8.1, 5.4 Hz, 1H), 6.88-6.96 (m, 1H), 4.54 (m, 1H), 3.04-3.17 (m, 2H), 2.53-2.61 (m, 2H), 1.88 (m, 2H).

Intermediate 4: 4-Methyl-1-(piperidin-4-yl)-2,3-dihydro-1H-1,3-benzodiazol-2-one;2,2,2-trifluoroacetic acid Step 1: tert-butyl 4-(3-methyl-2-nitro-anilino)piperidine-1-carboxylate was synthesized according to General procedure A from 1-fluoro-3-methyl-2-nitrobenzene and tert-butyl 4-aminopiperidine-1-carboxylate. LCMS [M+H]$^+$ 336.

Step 2: (tert-butyl 4-(4-methyl-2-oxo-2,3-dihydro-1H-1,3-benzodiazol-1-yl)piperidine-1-carboxylate was synthesized according to General procedure F from tert-butyl 4-(3-methyl-2-nitro-anilino)piperidine-1-carboxylate. LCMS [M-isobutene+H]$^+$ 276.

Step 3: 4-methyl-1-(piperidin-4-yl)-2,3-dihydro-1H-1,3-benzodiazol-2-one;2,2,2-trifluoroacetic acid was synthesized according to General procedure C from tert-butyl 4-(4-methyl-2-oxo-2,3-dihydro-1H-1,3-benzodiazol-1-yl)piperidine-1-carboxylate. LCMS [M+H]$^+$ 232. $^1$H-NMR (400 MHz, DMSO-d$_6$) δ ppm 11.00 (br. s., 1H), 8.71 (br. s, 1H), 8.47 (br. s, 1H), 7.11-7.18 (m, 1H), 6.90-6.97 (m, 1H), 6.80-6.86 (m, 1H), 4.46-4.57 (m, 1H), 3.38-3.49 (m, 2H), 3.03-3.18 (m, 2H), 2.53-2.63 (m, 2H), 2.28 (s, 3H), 1.80-1.91 (m, 2H).

Intermediate 5: 4-Methoxy-1-(piperidin-4-yl)-2,3-dihydro-1H-1,3-benzodiazol-2-one;2,2,2-trifluoroacetic acid Step 1: tert-butyl 4-(3-methoxy-2-nitro-anilino)piperidine-1-carboxylate was synthesized according to General procedure A from 1-fluoro-3-methoxy-2-nitrobenzene and tert-butyl 4-aminopiperidine-1-carboxylate.

Step 2: tert-butyl 4-(4-methoxy-2-oxo-2,3-dihydro-1H-1,3-benzodiazol-1-yl)piperidine-1-carboxylate was synthesized according to General procedure F from tert-butyl 4-(3-methoxy-2-nitro-anilino)piperidine-1-carboxylate. LCMS [M-isobutene+H]$^+$ 292.

Step 3: 4-methoxy-1-(piperidin-4-yl)-2,3-dihydro-1H-1,3-benzodiazol-2-one;2,2,2-trifluoroacetic acid was synthesized according to General procedure C from tert-butyl 4-(4-methoxy-2-oxo-2,3-dihydro-1H-1,3-benzodiazol-1-yl)piperidine-1-carboxylate. LCMS [M+H]$^+$ 248. $^1$H-NMR (400 MHz, DMSO-d$_6$) δ ppm 11.03 (s, 1H), 8.66 (br. s., 1H), 8.43 (br. s, 1H), 6.94-7.03 (m, 2H), 6.68-6.77 (m, 1H), 4.50 (br. t, J=11.7, 11.7 Hz, 1H), 3.85 (s, 3H), 3.45 (br. s., 2H), 3.03-3.17 (m, 2H), 2.53-2.61 (m, 2H), 1.79-1.89 (m, 2H).

Intermediate 6: 4-Hydroxy-1-(piperidin-4-yl)-2,3-dihydro-1H-1,3-benzodiazol-2-one;2,2,2-trifluoroacetic acid Step 1: A mixture of 3-fluoro-2-nitro-phenol (1.0 equiv.), tert-butyl-chloro-dimethyl-silane (1.1 equiv.), and imidazole (2.0 equiv.) in DMF was stirred at 20° C. for 16 h. The mixture was then poured into water and extracted with Et$_2$O×3. The combined organics were dried and concentrated. The crude tert-butyl-(3-fluoro-2-nitro-phenoxy)-dimethyl-silane was used without further purification in step 2. LCMS [M+H]$^+$ 272.

Step 2: tert-butyl 4-[3-[tert-butyl(dimethyl)silyl]oxy-2-nitro-anilino]piperidine-1-carboxylate was synthesized according to General procedure A from tert-butyl-(3-fluoro-2-nitro-phenoxy)-dimethyl-silane and tert-butyl 4-aminopiperidine-1-carboxylate. LCMS [M-(TBDMS)-isobutene+H]$^+$ 282.

Step 3: tert-butyl 4-{4-[(tert-butyldimethylsilyl)oxy]-2-oxo-2,3-dihydro-1H-1,3-benzodiazol-1-yl}piperidine-1-carboxylate was synthesized according to General procedure F from tert-butyl 4-[3-[tert-butyl(dimethyl)silyl]oxy-2-nitro-anilino]piperidine-1-carboxylate. LCMS [M–H]$^-$ 446.

Step 4: Synthesis of tert-butyl 4-(4-hydroxy-2-oxo-2,3-dihydro-1H-1,3-benzodiazol-1-yl)piperidine-1-carboxylate. A mixture of tert-butyl 4-[4-[tert-butyl(dimethyl)silyl]oxy-2-oxo-3H-benzimidazol-1-yl]piperidine-1-carboxylate (1.0 equiv.) and LiOH (6.0 equiv.) was stirred in DMF at 80° C. for 4 h. The mixture was then poured into NaHCO$_3$ and extracted with DCM×3. The combined organics were dried, concentrated, and purified by silica gel chromatography. LCMS [M-isobutene+H]$^+$ 278. $^1$H-NMR (400 MHz, DMSO-d$_6$) δ ppm 10.64 (br. s., 1H), 9.62 (br. s., 1H), 6.75-6.81 (m, 1H), 6.65 (dd, J=8.1, 0.8 Hz, 1H), 6.48 (dd, J=8.1, 0.8 Hz, 1H), 4.23-4.33 (m, 1H), 4.01-4.14 (m, 2H), 2.85 (br. s., 2H), 2.16 (m, 2H), 1.60-1.69 (m, 2H), 1.43 (s, 9H).

Step 5: 4-hydroxy-1-(piperidin-4-yl)-2,3-dihydro-1H-1,3-benzodiazol-2-one;2,2,2-trifluoroacetic acid was synthesized according to General procedure C from tert-butyl 4-(4-hydroxy-2-oxo-2,3-dihydro-1H-1,3-benzodiazol-1-yl)piperidine-1-carboxylate. LCMS [M+H]$^+$ 234.

Intermediate 7: 5-Fluoro-1-(piperidin-4-yl)-2,3-dihydro-1H-1,3-benzodiazol-2-one;2,2,2-trifluoroacetic acid Step 1: tert-butyl 4-(4-fluoro-2-nitro-anilino)piperidine-1-carboxylate was synthesized according to General procedure A from 1,4-difluoro-2-nitrobenzene and tert-butyl 4-aminopiperidine-1-carboxylate. LCMS [M-isobutene+H]$^+$ 284.

Step 2: tert-butyl 4-(5-fluoro-2-oxo-2,3-dihydro-1H-1,3-benzodiazol-1-yl)piperidine-1-carboxylate was synthesized according to General procedure B from tert-butyl 4-(4-fluoro-2-nitro-anilino)piperidine-1-carboxylate. LCMS [M-isobutene+H]$^+$ 280. $^1$H-NMR (400 MHz, CHLOROFORM-d) δ ppm 8.32 (s, 1H), 7.03 (dt, J=8.4, 4.0 Hz, 1H), 6.75-6.86 (m, 2H), 4.45 (tt, J=12.6, 4.0 Hz, 1H), 4.33 (m, 2H), 2.82-2.92 (m, 2H), 2.28 (m, 2H), 1.79-1.88 (m, 2H), 1.51 (s, 9H).

Step 3: 5-fluoro-1-(piperidin-4-yl)-2,3-dihydro-1H-1,3-benzodiazol-2-one;2,2,2-trifluoroacetic acid was synthesized according to General procedure C from tert-butyl 4-(5-fluoro-2-oxo-2,3-dihydro-1H-1,3-benzodiazol-1-yl)piperidine-1-carboxylate. LCMS [M+H]$^+$ 236. $^1$H-NMR (400 MHz, DMSO-d$_6$) δ ppm 8.56 (br. s., 1H), 8.35 (br. s., 1H), 7.27 (dd, J=8.5, 4.4 Hz, 1H), 6.86-6.94 (m, 2H), 4.46-4.55 (m, 1H), 3.44 (m, 2H), 3.03-3.14 (m, 2H), 2.45-2.58 (overlapping m, 2H), 1.83-1.90 (m, 2H).

Intermediate 8: 5-Methoxy-1-(piperidin-4-yl)-2,3-dihydro-1H-1,3-benzodiazol-2-one;2,2,2-trifluoroacetic acid Step 1: tert-butyl 4-(4-methoxy-2-nitro-anilino)piperidine-1-carboxylate was synthesized according to General procedure A from 1-fluoro-4-methoxy-2-nitrobenzene and tert-butyl 4-aminopiperidine-1-carboxylate.

Step 2: tert-butyl 4-(5-methoxy-2-oxo-2,3-dihydro-1H-1,3-benzodiazol-1-yl)piperidine-1-carboxylate was synthesized according to General procedure F from tert-butyl 4-(4-methoxy-2-nitro-anilino)piperidine-1-carboxylate. LCMS [M-isobutene+H]$^+$ 292.

Step 3: 5-methoxy-1-(piperidin-4-yl)-2,3-dihydro-1H-1,3-benzodiazol-2-one;2,2,2-trifluoroacetic acid was synthesized according to General procedure C from tert-butyl 4-(5-methoxy-2-oxo-2,3-dihydro-1H-1,3-benzodiazol-1-yl)piperidine-1-carboxylate. LCMS [M+H]$^+$ 248. $^1$H-NMR (400 MHz, DMSO-d$_6$) δ ppm 10.85 (s, 1H), 8.57-8.69 (m, 1H), 8.33-8.48 (m, 1H), 7.19 (d, J=8.5 Hz, 1H), 6.63 (dd, J=8.5, 2.4 Hz, 1H), 6.60 (d, J=2.4 Hz, 1H), 4.47 (tt, J=12.3, 4.5 Hz, 1H), 3.73 (s, 3H), 3.38-3.48 (m, 2H), 3.02-3.16 (m, 2H), 2.45-2.58 (overlapping m, 2H), 1.79-1.89 (m, 2H).

Intermediate 9: 2-Oxo-1-(piperidin-4-yl)-2,3-dihydro-1H-1,3-benzodiazole-5-carbonitrile;2,2,2-trifluoroacetic acid Step 1: tert-butyl 4-(4-cyano-2-nitro-anilino)piperidine-1-carboxylate was synthesized according to General procedure A from 4-fluoro-3-nitro-benzonitrile and tert-butyl 4-aminopiperidine-1-carboxylate. LCMS [M-isobutene+H]$^+$ 291.

Step 2: tert-butyl 4-(5-cyano-2-oxo-2,3-dihydro-1H-1,3-benzodiazol-1-yl)piperidine-1-carboxylate was synthesized according to General procedure F from tert-butyl 4-(4-cyano-2-nitro-anilino)piperidine-1-carboxylate. LCMS [M+H]$^+$ 343. $^1$H-NMR (400 MHz, CHLOROFORM-d) δ ppm 9.36 (br. s., 1H), 7.41 (dd, J=8.5, 1.6 Hz, 1H), 7.36-7.38 (m, 1H), 7.20 (d, J=8.2 Hz, 1H), 4.48 (tt, J=12.5, 4.1 Hz, 1H), 4.35 (m, 2H), 2.88 (m, 2H), 2.30 (m, 2H), 1.85 (m, 2H), 1.52 (s, 9H).

Step 3: 2-oxo-1-(piperidin-4-yl)-2,3-dihydro-1H-1,3-benzodiazole-5-carbonitrile;2,2,2-trifluoroacetic acid was synthesized according to General procedure C from tert-butyl 4-(5-cyano-2-oxo-2,3-dihydro-1H-1,3-benzodiazol-1-yl)piperidine-1-carboxylate. LCMS [M+H]$^+$ 243. $^1$H-NMR (400 MHz, DMSO-d$_6$) δ ppm 11.45 (s, 1H), 8.79 (br. s., 1H), 8.40-8.58 (m, 1H), 7.54-7.58 (m, 1H), 7.46-7.51 (m, 1H), 7.43 (d, J=1.6 Hz, 1H), 4.52-4.63 (m, 1H), 3.44 (m, 2H), 3.09 (m, 2H), 2.47-2.60 (m, 2H), 1.89 (m, 2H).

Intermediate 10: 4-(Methylsulfanyl)-1-(piperidin-4-yl-2,3-dihydro-1H-1,3-benzodiazol-2-one;2,2,2-trifluoroacetic acid Step 1: tert-butyl 4-(3-methylsulfanyl-2-nitro-anilino)piperidine-1-carboxylate was synthesized according to General procedure K from tert-butyl 4-(3-fluoro-2-nitro-anilino)piperidine-1-carboxylate and sodium methylthiolate. LCMS [M+H]$^+$ 368.

Step 2: tert-butyl 4-(4-methylsulfanyl-2-oxo-3H-benzimidazol-1-yl)piperidine-1-carboxylate was synthesized according to General procedure B from tert-butyl 4-(3-methylsulfanyl-2-nitro-anilino)piperidine-1-carboxylate. LCMS [M+H]$^+$ 364. $^1$H-NMR (400 MHz, CHLOROFORM-d) δ ppm 7.89 (s, 1H), 7.09-7.13 (m, 1H), 7.02-7.08 (m, 2H), 4.46 (tt, J=12.5, 4.1 Hz, 1H), 4.28-4.37 (m, 2H), 2.82-2.90 (m, 2H), 2.48 (s, 3H), 2.23-2.36 (m, 2H), 1.83 (m, 2H), 1.51 (s, 9H).

Step 3: 4-(methylsulfanyl)-1-(piperidin-4-yl)-2,3-dihydro-1H-1,3-benzodiazol-2-one;2,2,2-trifluoroacetic acid was synthesized according to General procedure C from tert-butyl 4-(4-methylsulfanyl-2-oxo-3H-benzimidazol-1-yl)piperidine-1-carboxylate. LCMS [M+H]$^+$ 264. $^1$H-NMR (400 MHz, DMSO-d$_6$) δ ppm 11.12 (s, 1H), 8.59 (br. s., 1H), 8.38 (br. s., 1H), 7.20 (dd, J=7.3, 0.9 Hz, 1H), 7.05 (t, J=7.7 Hz, 1H), 7.00-7.03 (m, 1H), 4.51 (ddt, J=12.4, 8.3, 4.1, 4.1 Hz, 1H), 3.40-3.48 (m, 2H), 3.03-3.16 (m, 2H), 2.45-2.62 (overlapping m, 2H), 1.82-1.91 (m, 2H).

Intermediate 11: 4-amino-1-(piperidin-4-yl)-2,3-dihydro-1H-1,3-benzodiazol-2-one;2,2,2-trifluoroacetic acid Step 1: N,N-dibenzyl-3-fluoro-2-nitro-aniline was synthesized according to General procedure A from 1,3-difluoro-2-nitrobenzene and N-benzyl-1-phenylmethanamine. LCMS [M+H]$^+$ 337. $^1$H-NMR (400 MHz, Chloroform-d) δ ppm 7.22-7.36 (m, 11H), 6.83-6.90 (m, 2H), 4.20 (s, 4H).

Step 2: tert-butyl 4-{[3-(dibenzylamino)-2-nitrophenyl]amino}piperidine-1-carboxylate was synthesized according to General procedure A from N,N-dibenzyl-3-fluoro-2-nitro-aniline and tert-butyl 4-aminopiperidine-1-carboxylate. LCMS [M+H]$^+$ 517. $^1$H-NMR (400 MHz, DMSO-d6) δ ppm 7.18-7.32 (m, 10H), 7.13 (t, J=8.2 Hz, 1H), 6.61 (d, J=8.2 Hz, 1H), 6.55 (d, J=7.3 Hz, 1H), 5.51 (d, J=7.9 Hz, 1H), 4.04 (s, 4H), 3.82-3.93 (m, 2H), 3.42-3.53 (m, 1H), 2.82 (br. s., 2H), 1.75-1.84 (m, 2H), 1.39 (s, 9H), 1.27-1.36 (m, 2H).

Step 3: tert-butyl 4-[4-(dibenzylamino)-2-oxo-2,3-dihydro-1H-1,3-benzodiazol-1-yl]piperidine-1-carboxylate was synthesized according to General procedure B from tert-butyl 4-{[3-(dibenzylamino)-2-nitrophenyl]amino}piperidine-1-carboxylate. LCMS [M+H]$^+$ 513. $^1$H-NMR (400 MHz, Chloroform-d) δ ppm 7.24-7.39 (overlapping m, 10H), 6.93 (s, 1H), 6.80-6.86 (m, 1H), 6.71-6.76 (m, 1H), 4.17-4.46 (m, 7H), 2.74-2.90 (m, 2H), 2.16-2.33 (m, 2H), 1.70-1.82 (m, 2H), 1.50 (s, 9H).

Step 4: tert-butyl 4-(4-amino-2-oxo-2,3-dihydro-1H-1,3-benzodiazol-1-yl)piperidine-1-carboxylate was synthesized according to General procedure G from tert-butyl 4-[4-(dibenzylamino)-2-oxo-2,3-dihydro-1H-1,3-benzodiazol-1-yl]piperidine-1-carboxylate. LCMS [M+H]$^+$ 333. $^1$H-NMR (400 MHz, DMSO-d6) δ ppm 10.24 (br. s., 1H), 6.72 (t, J=7.9 Hz, 1H), 6.55 (d, J=7.9 Hz, 1H), 6.30 (dd, J=7.9, 0.6 Hz, 1H), 4.86-4.93 (m, 2 H), 4.15 (tt, J=12.3, 4.3 Hz, 1H), 2.98-3.08 (m, 2H), 2.49-2.58 (overlapping m, 2H), 2.09-2.21 (m, 2H), 1.50-1.58 (m, 2H).

Step 5: The title compound was synthesized according to General procedure C from tert-butyl 4-(4-amino-2-oxo-2,3-dihydro-1H-1,3-benzodiazol-1-yl)piperidine-1-carboxylate. LCMS [M+H]$^+$ 233. $^1$H-NMR (400 MHz, DMSO-d$_6$) δ ppm 10.35 (s, 1H), 8.56-8.66 (m, 1H), 8.38 (br. s., 1H), 6.78 (t, J=8.1 Hz, 1H), 6.63 (d, J=8.1 Hz, 1H), 6.34-6.38 (m, 1H), 4.40-4.50 (m, 1H), 3.39-3.45 (m, 2H), 3.17 (s, 2H), 3.04-3.15 (m, 3H), 2.47-2.60 (overlapping m, 2H), 1.79-1.87 (m, 2H).

Intermediate 12: 4-(Methylamino)-1-(piperidin-4-yl)-2,3-dihydro-1H-1,3-benzodiazol-2-one;2,2,2-trifluoroacetic acid Step 1: N-benzyl-3-fluoro-N-methyl-2-nitroaniline was synthesized according to General procedure A from 1,3-difluoro-2-nitrobenzene and N-methyl-1-phenylmethanamine. LCMS [M+H]$^+$ 261.
Step 2: tert-butyl 4-[3-[benzyl(methyl)amino]-2-nitro-anilino]piperidine-1-carboxylate was synthesized according to General procedure A from N-benzyl-3-fluoro-N-methyl-2-nitroaniline and tert-butyl 4-aminopiperidine-1-carboxylate.
Step 3: tert-butyl 4-{4-[benzyl(methyl)amino]-2-oxo-2,3-dihydro-1H-1,3-benzodiazol-1-yl}piperidine-1-carboxylate was synthesized according to General procedure B from tert-butyl 4-[3-[benzyl(methyl)amino]-2-nitro-anilino]piperidine-1-carboxylate. LCMS [M+H]$^+$ 437.
Step 4: tert-butyl 4-[4-(methylamino)-2-oxo-2,3-dihydro-1H-1,3-benzodiazol-1-yl]piperidine-1-carboxylate was synthesized according to General procedure G from tert-butyl 4-{4-[benzyl(methyl)amino]-2-oxo-2,3-dihydro-1H-1,3-benzodiazol-1-yl}piperidine-1-carboxylate.
LCMS [M+H]$^+$ 347. $^1$H-NMR (400 MHz, CHLOROFORM-d) δ ppm 10.51-10.65 (m, 1H), 7.02 (td, J=8.1, 0.9 Hz, 1H), 6.69 (dd, J=7.9, 3.8 Hz, 1H), 6.50-6.56 (m, 1H), 4.45 (tt, J=12.4, 4.0 Hz, 1H), 4.32 (br. s., 2H), 3.00 (d, J=1.6 Hz, 3H), 2.88 (br. s., 2H), 2.34 (m, 2H), 1.79-1.86 (m, 2H), 1.51 (s, 9H).
Step 5: The title compound was synthesized according to General procedure C from tert-butyl 4-[4-(methylamino)-2-oxo-2,3-dihydro-1H-1,3-benzodiazol-1-yl]piperidine-1-carboxylate. LCMS [M+H]$^+$ 247. $^1$H-NMR (400 MHz, DMSO-d$_6$) δ ppm 8.57-8.67 (m, 1H), 8.33-8.44 (m, 1H), 6.90 (t, J=7.9 Hz, 1H), 6.68 (d, J=7.9 Hz, 1H), 6.30 (d, J=7.9 Hz, 1H), 4.46 (tt, J=12.4, 3.9 Hz, 1H), 3.38-3.47 (m, 2H), 3.04-3.16 (m, 2H), 2.80 (s, 3H), 2.47-2.60 (overlapping m, 2H), 1.79-1.87 (m, 2H).

Intermediate 13: 4-(Dimethylamino)-1-(piperidin-4-yl)-2,3-dihydro-1H-1,3-benzodiazol-2-one;2,2,2-trifluoroacetic acid Step 1: 3-fluoro-N,N-dimethyl-2-nitro-aniline was synthesized according to General procedure A from 1,3-difluoro-2-nitrobenzene and dimethylammonium chloride. LCMS [M+H]$^+$ 185.
Step 2: tert-butyl 4-[3-(dimethylamino)-2-nitro-anilino]piperidine-1-carboxylate was synthesized according to General procedure A from 3-fluoro-N,N-dimethyl-2-nitro-aniline and tert-butyl 4-aminopiperidine-1-carboxylate. LCMS [M+H]$^+$ 365.
Step 3: tert-butyl 4-[4-(dimethylamino)-2-oxo-2,3-dihydro-1H-1,3-benzodiazol-1-yl]piperidine-1-carboxylate was synthesized according to General procedure B from tert-butyl 4-[3-(dimethylamino)-2-nitro-anilino]piperidine-1-carboxylate. LCMS [M+H]$^+$ 361.
$^1$H-NMR (400 MHz, CHLOROFORM-d) δ ppm 7.01-7.06 (m, 1H), 6.89 (br. s., 1H), 6.77 (br. d, J=9.2 Hz, 1H), 4.46 (tt, J=12.6, 4.0 Hz, 1H), 4.32 (br. s., 2H), 2.81-2.94 (m, 6H), 2.31 (m, 2H), 1.79-1.87 (m, 2H), 1.55-1.63 (m, 2H), 1.51 (s, 9H).
Step 4: The title compound was synthesized according to General procedure C from tert-butyl 4-[4-(dimethylamino)-2-oxo-2,3-dihydro-1H-1,3-benzodiazol-1-yl]piperidine-1-carboxylate. LCMS [M+H]$^+$ 261.

Intermediate 14: 4-Ethoxy-1-(piperidin-4-yl)-2,3-dihydro-1H-1,3-benzodiazol-2-one;2,2,2-trifluoroacetic acid Step 1: In a flask, sodium (3.6 equiv.) was added to ethanol and the resulting mixture was stirred until all sodium had reacted. Then, tert-butyl 4-(3-fluoro-2-nitro-anilino)piperidine-1-carboxylate (1.0 equiv.) was added, and the resulting mixture was stirred at 120° C. for 16 h. Thereafter the mixture was poured into NaHCO$_3$ and extracted with DCM×3. The combined organics were dried (MgSO$_4$), concentrated, and purified by silica gel chromatography which afforded tert-butyl 4-(3-ethoxy-2-nitro-anilino)piperidine-1-carboxylate. LCMS [M-isobutene+H]$^+$ 310.
Step 2: tert-butyl 4-(4-ethoxy-2-oxo-2,3-dihydro-1H-1,3-benzodiazol-1-yl)piperidine-1-carboxylate was synthesized according to General procedure B from tert-butyl 4-(3-ethoxy-2-nitro-anilino)piperidine-1-carboxylate. LCMS [M+H]$^+$ 362.
Step 3: The title compound was synthesized according to General procedure C from tert-butyl 4-(4-ethoxy-2-oxo-2,3-dihydro-1H-1,3-benzodiazol-1-yl)piperidine-1-carboxylate. LCMS [M+H]$^+$ 262. $^1$H-NMR (400 MHz, DMSO-d$_6$) δ ppm 10.98 (s, 1H), 8.67 (br. s., 1H), 8.45 (br. s., 1H), 6.94-6.98 (m, 2H), 6.69-6.74 (m, 1H), 4.50 (tt, J=12.3, 4.3 Hz, 1H), 4.13 (q, J=7.0 Hz, 2H), 3.40-3.47 (m, 2H), 3.03-3.17 (m, 2H), 2.45-2.61 (overlapping m, 2H), 1.80-1.89 (m, 2H), 1.35 (t, J=7.0 Hz, 3H).

Intermediate 15: Methyl 2-[2-oxo-1-(piperidin-4-yl)-2,3-dihydro-1H-1,3-benzodiazol-4-yl]acetate;2,2,2-trifluoroacetic acid Step 1: tert-butyl 4-[3-(2-methoxy-2-oxo-ethyl)-2-nitro-anilino]piperidine-1-carboxylate was synthesized according to General procedure A from methyl 2-(3-fluoro-2-nitro-phenyl)acetate and tert-butyl 4-aminopiperidine-1-carboxylate. LCMS [M+H]$^+$ 394.
Step 2: tert-butyl 4-[4-(2-methoxy-2-oxoethyl)-2-oxo-2,3-dihydro-1H-1,3-benzodiazol-1-yl]piperidine-1-carboxylate was synthesized according to General procedure B from tert-butyl 4-[3-(2-methoxy-2-oxo-ethyl)-2-nitro-anilino]piperidine-1-carboxylate. LCMS [M-isobutene+H]+334. $^1$H-NMR (400 MHz, CHLOROFORM-d) δ ppm 8.56 (br. s., 1H), 6.98-7.09 (m, 2H), 6.92 (d, J=7.6 Hz, 1H), 4.47 (tt, J=12.4, 4.0 Hz, 1H), 4.32 (m, 2H), 3.73 (s, 3H), 3.70 (s, 2H), 2.87 (m, 2H), 2.31 (m, 2H), 1.83 (m, 2H), 1.51 (s, 9H).
Step 3: The title compound was synthesized according to General procedure C from tert-butyl 4-[4-(2-methoxy-2-oxoethyl)-2-oxo-2,3-dihydro-1H-1,3-benzodiazol-1-yl]piperidine-1-carboxylate. LCMS [M+H]$^+$ 290.

Intermediate 16: 5-Methyl-1-(piperidin-4-yl)-2,3-dihydro-1H-1,3-benzodiazol-2-one;2,2,2-trifluoroacetic acid Step 1: tert-butyl 4-[(4-methyl-2-nitrophenyl)amino]piperidine-1-carboxylate was synthesized according to General procedure A from 1-fluoro-4-methyl-2-nitrobenzene and tert-butyl 4-aminopiperidine-1-carboxylate. LCMS [M+H]$^+$ 336.
Step 2: tert-butyl 4-(5-methyl-2-oxo-2,3-dihydro-1H-1,3-benzodiazol-1-yl)piperidine-1-carboxylate was synthesized according to General procedure B from tert-butyl 4-[(4- methyl-2-nitrophenyl)amino]piperidine-1-carboxylate. LCMS [M+H]+ 332. ¹H-NMR (400 MHz, CHLOROFORM-d) δ ppm 8.47 (s, 1H), 7.02 (d, J=8.2 Hz, 1H), 6.85-6.93 (m, 2H), 4.46 (tt, J=12.5, 3.9 Hz, 1H), 4.32 (m, 2H), 2.81-2.93 (m, 2H), 2.38 (s, 3H), 2.31 (m, 2H), 1.83 (m, 2H), 1.51 (s, 9H).

Step 3: The title compound was synthesized according to General procedure C from tert-butyl 4-(5-methyl-2-oxo-2,3-dihydro-1H-1,3-benzodiazol-1-yl)piperidine-1-carboxylate. LCMS [M+H]*232.

¹H-NMR (400 MHz, DMSO-d₆) δ ppm 10.83 (s, 1H), 8.75 (br. s., 1H), 8.44-8.60 (m, 1H), 7.19 (d, J=8.5 Hz, 1H), 6.79-6.86 (m, 2H), 4.45-4.55 (m overlap w water, 1H), 3.43 (m, 2H), 3.10 (m, 2H), 2.46-2.59 (m overlap w DMSO, 2H), 2.30 (s, 3H), 1.84 (m, 2H).

Intermediate 17: 7-fluoro-1-(piperidin-4-yl)-2,3-dihydro-1H-1,3-benzodiazol-2-one;2,2,2-trifluoroacetic acid Step 1: tert-butyl 4-(2-fluoro-6-nitro-anilino)piperidine-1-carboxylate was synthesized according to General procedure A from 1,2-difluoro-3-nitrobenzene and tert-butyl 4-aminopiperidine-1-carboxylate. LCMS [M-isobutene+H]+ 284.

Step 2: tert-butyl 4-(7-fluoro-2-oxo-2,3-dihydro-1H-1,3-benzodiazol-1-yl)piperidine-1-carboxylate was synthesized according to General procedure B from tert-butyl 4-(2-fluoro-6-nitro-anilino)piperidine-1-carboxylate. LCMS [M-isobutene+H]+ 280.

Step 3: 7-fluoro-1-(piperidin-4-yl)-2,3-dihydro-1H-1,3-benzodiazol-2-one;2,2,2-trifluoroacetic acid was synthesized according to General procedure C from tert-butyl 4-(7-fluoro-2-oxo-2,3-dihydro-1H-1,3-benzodiazol-1-yl)piperidine-1-carboxylate. LCMS [M+H]+ 236.

Intermediate 18: 7-chloro-1-(piperidin-4-yl)-2,3-dihydro-1H-1,3-benzodiazol-2-one;2,2,2-trifluoroacetic acid Step 1: tert-butyl 4-(2-chloro-6-nitro-anilino)piperidine-1-carboxylate was synthesized according to General procedure A from 1-chloro-2-fluoro-3-nitrobenzene and tert-butyl 4-aminopiperidine-1-carboxylate. LCMS [M-isobutene+H]+ 300.

Step 2: tert-butyl 4-(7-chloro-2-oxo-2,3-dihydro-1H-1,3-benzodiazol-1-yl)piperidine-1-carboxylate was synthesized according to General procedure B from tert-butyl 4-(2-chloro-6-nitro-anilino)piperidine-1-carboxylate. LCMS [M-isobutene+H]+ 296.

Step 3: 7-chloro-1-(piperidin-4-yl)-2,3-dihydro-1H-1,3-benzodiazol-2-one;2,2,2-trifluoroacetic acid was synthesized according to General procedure C from tert-butyl 4-(7-chloro-2-oxo-2,3-dihydro-1H-1,3-benzodiazol-1-yl)piperidine-1-carboxylate. LCMS [M+H]+ 252.

Intermediate 19: 7-bromo-1-(piperidin-4-yl)-2,3-dihydro-1H-1,3-benzodiazol-2-one;2,2,2-trifluoroacetic acid Step 1: tert-butyl 4-(2-bromo-6-nitro-anilino)piperidine-1-carboxylate was synthesized according to General procedure A from 1-bromo-2-fluoro-3-nitrobenzene and tert-butyl 4-aminopiperidine-1-carboxylate. LCMS [M-isobutene+H]+ 344.

Step 2: tert-butyl 4-(7-bromo-2-oxo-2,3-dihydro-1H-1,3-benzodiazol-1-yl)piperidine-1-carboxylate was synthesized according to General procedure B from tert-butyl 4-(2-bromo-6-nitro-anilino)piperidine-1-carboxylate. LCMS [M-isobutene+H]+ 340.

Step 3: 7-bromo-1-(piperidin-4-yl)-2,3-dihydro-1H-1,3-benzodiazol-2-one;2,2,2-trifluoroacetic acid was synthesized according to General procedure C from tert-butyl 4-(7-bromo-2-oxo-2,3-dihydro-1H-1,3-benzodiazol-1-yl)piperidine-1-carboxylate. LCMS [M+H]+ 296.

Intermediate 20: 1-(Piperidin-4-yl)-4-(H-1,2,4-triazol-1-yl)-2,3-dihydro-1H-1,3-benzodiazol-2-one;2,2,2-trifluoroacetic acid Step 1: 1-(3-fluoro-2-nitro-phenyl)-1,2,4-triazole was synthesized according to General procedure K from 1,3-difluoro-2-nitrobenzene and 1,2,4-triazole. LCMS [M+H]+ 209. ¹H-NMR (400 MHz, METHANOL-d₄) δ ppm 9.01 (s, 1H), 8.19 (s, 1H), 7.79-7.86 (m, 1H), 7.69 (dt, J=8.2, 1.3 Hz, 1H), 7.63 (ddd, J=9.6, 8.7, 1.3 Hz, 1H).

Step 2: tert-butyl 4-[2-nitro-3-(1,2,4-triazol-1-yl)anilino]piperidine-1-carboxylate was synthesized according to General procedure A from 1-(3-fluoro-2-nitro-phenyl)-1,2,4-triazole and tert-butyl 4-aminopiperidine-1-carboxylate. LCMS [M+H]+ 389.

Step 3: tert-butyl 4-[2-oxo-4-(1H-1,2,4-triazol-1-yl)-2,3-dihydro-1H-1,3-benzodiazol-1-yl]piperidine-1-carboxylate was synthesized according to General procedure B from tert-butyl 4-[2-nitro-3-(1,2,4-triazol-1-yl)anilino]piperidine-1-carboxylate. LCMS [M+H]+ 385. ¹H-NMR (400 MHz, CHLOROFORM-d) δ ppm 9.29 (br. s., 1H), 8.78 (s, 1H), 8.19 (s, 1H), 7.07-7.26 (m, 3H), 4.51 (tt, J=12.5, 4.1 Hz, 1H), 4.35 (m, 2H), 2.88 (m, 2H), 2.33 (m, 2H), 1.86 (m, 2H), 1.52 (s, 9H).

Step 4: The title compound was synthesized according to General procedure C from tert-butyl 4-[2-oxo-4-(1H-1,2,4-triazol-1-yl)-2,3-dihydro-1H-1,3-benzodiazol-1-yl]piperidine-1-carboxylate. LCMS [M+H]+ 285.

Intermediate 21: 1-(Piperidin-4-yl)-4-(1H-pyrazol-1-yl)-2,3-dihydro-1H-1,3-benzodiazol-2-one;2,2,2-trifluoroacetic acid Step 1: 1-(3-fluoro-2-nitro-phenyl)pyrazole was synthesized according to General procedure K from 1,3-difluoro-2-nitrobenzene and pyrazole. LCMS [M+H]+ 208.

Step 2: tert-butyl 4-(2-nitro-3-pyrazol-1-yl-anilino)piperidine-1-carboxylate was synthesized according to General procedure A from 1-(3-fluoro-2-nitro-phenyl)pyrazole and tert-butyl 4-aminopiperidine-1-carboxylate. LCMS [M+H]+ 388. ¹H-NMR (400 MHz, CHLOROFORM-d) δ ppm 7.68-7.73 (m, 1H), 7.40 (dd, J=8.7, 7.7 Hz, 1H), 6.85-6.89 (m, 1H), 6.74 (dd, J=7.7, 1.1 Hz, 1H), 6.47 (dd, J=2.5, 1.9 Hz, 1H), 4.03 (m, 2H), 3.55-3.65 (m, 1H), 3.02 (m, 2H), 2.00-2.09 (m, 2H), 1.48 (s, 9H).

Step 3: tert-butyl 4-[2-oxo-4-(1H-pyrazol-1-yl)-2,3-dihydro-1H-1,3-benzodiazol-1-yl]piperidine-1-carboxylate was synthesized according to General procedure B from tert-butyl 4-(2-nitro-3-pyrazol-1-yl-anilino)piperidine-1-carboxylate. LCMS [M-isobutene+H]+328.

Step 4: The title compound was synthesized according to General procedure C from tert-butyl 4-[2-oxo-4-(1H-pyrazol-1-yl)-2,3-dihydro-1H-1,3-benzodiazol-1-yl]piperidine-1-carboxylate. LCMS [M+H]$^+$ 284.

Intermediate 22: 4-(4-Bromo-1H-pyrazol-1-yl)-1-(piperidin-4-yl)-2,3-dihydro-1H-1,3-benzodiazol-2-one;2,2,2-trifluoroacetic acid Step 1: 4-bromo-1-(3-fluoro-2-nitro-phenyl)pyrazole was synthesized according to General procedure K from 1,3-difluoro-2-nitrobenzene and 4-bromo-1H-pyrazol.

Step 2: tert-butyl 4-[3-(4-bromopyrazol-1-yl)-2-nitro-anilino]piperidine-1-carboxylate was synthesized according to General procedure A from 4-bromo-1-(3-fluoro-2-nitro-phenyl)pyrazole and tert-butyl 4-aminopiperidine-1-carboxylate. LCMS [M+H]$^+$ 466.

Step 3: tert-butyl 4-[4-(4-bromo-1H-pyrazol-1-yl)-2-oxo-2,3-dihydro-1H-1,3-benzodiazol-1-yl]piperidine-1-carboxylate was synthesized according to General procedure B from tert-butyl 4-[3-(4-bromopyrazol-1-yl)-2-nitro-anilino]piperidine-1-carboxylate. LCMS [M+H]$^+$ 462.

Step 4: The title compound was synthesized according to General procedure C from tert-butyl 4-[4-(4-bromo-1H-pyrazol-1-yl)-2-oxo-2,3-dihydro-1H-1,3-benzodiazol-1-yl]piperidine-1-carboxylate. LCMS [M+H]$^+$ 362. $^1$H-NMR (400 MHz, DMSO-d$_6$) δ ppm 10.88 (s, 1H), 8.66 (d, J=0.6 Hz, 1H), 8.60 (br. s., 1H), 8.37 (br. s, 1H), 7.90 (d, J=0.6 Hz, 1H), 7.35 (m, 2H), 7.19 (dd, J=8.5, 7.6 Hz, 1H), 4.52-4.63 (m, 2H), 3.03-3.17 (m, 2H), 2.59 (m, 2H), 1.87-1.95 (m, 2H).

Intermediate 23: 1-(1-(1-((4-Iodophenyl)carbamoyl)piperidin-4-yl)-2-oxo-2,3-dihydro-1H-benzo[d]imidazol-4-yl)-1H-pyrazole-4-carboxylic acid Step 1: ethyl 1-(3-fluoro-2-nitro-phenyl)pyrazole-4-carboxylate was synthesized according to General procedure K from 1,3-difluoro-2-nitrobenzene and ethyl 1H-pyrazole-4-carboxylate. LCMS [M+H]$^+$ 280. $^1$H-NMR (400 MHz, CHLOROFORM-d) δ ppm 8.27 (d, J=0.6 Hz, 1H), 8.11 (d, J=0.6 Hz, 1H), 7.64 (td, J=8.5, 5.4 Hz, 1H), 7.34-7.42 (m, 2H), 4.35 (q, J=7.1 Hz, 2H), 1.38 (t, J=7.1 Hz, 3H).

Step 2: tert-butyl 4-[3-(4-ethoxycarbonylpyrazol-1-yl)-2-nitro-anilino]piperidine-1-carboxylate was synthesized according to General procedure A from ethyl 1-(3-fluoro-2-nitro-phenyl)pyrazole-4-carboxylate and tert-butyl 4-aminopiperidine-1-carboxylate. LCMS [M-isobutene+H]$^+$ 404. $^1$H-NMR (400 MHz, CHLOROFORM-d) δ ppm 8.17 (d, J=0.6 Hz, 1H), 8.07 (d, J=0.6 Hz, 1H), 7.42 (dd, J=8.7, 7.7 Hz, 1H), 6.93 (dd, J=9.3, 1.1 Hz, 1H), 6.72 (dd, J=7.6, 1.3 Hz, 1H), 4.34 (q, J=7.2 Hz, 2H), 4.04 (m, 2H), 3.56-3.67 (m, 1H), 3.02 (m, 2H), 2.00-2.09 (m, 2H), 1.48 (m, 11H), 1.37 (t, J=7.2 Hz, 3H).

Step 3: tert-butyl 4-{4-[4-(ethoxycarbonyl)-1H-pyrazol-1-yl]-2-oxo-2,3-dihydro-1H-1,3-benzodiazol-1-yl}piperidine-1-carboxylate was synthesized according to General procedure B from tert-butyl 4-[3-(4-ethoxycarbonylpyrazol-1-yl)-2-nitro-anilino]piperidine-1-carboxylate. LCMS [M+H]$^+$ 456. $^1$H-NMR (400 MHz, CHLOROFORM-d) δ ppm 9.47 (br. s, 1H), 8.53 (s, 1H), 8.13 (s, 1H), 7.19 (dd, J=7.9, 1.3 Hz, 1H), 7.13 (t, J=8.1 Hz, 1H), 7.07-7.10 (m, 1H), 4.51 (tt, J=12.5, 4.1 Hz, 1H), 4.29-4.40 (m, 4H), 2.88 (m, 2H), 2.33 (m, 2H), 1.82-1.89 (m, 2H), 1.52 (s, 9H), 1.40 (t, J=7.1 Hz, 3H).

Step 4: Ethyl 1-[2-oxo-1-(piperidin-4-yl)-2,3-dihydro-1H-1,3-benzodiazol-4-yl]-1H-pyrazole-4-carboxylate was synthesized according to General procedure C from tert-butyl 4-{4-[4-(ethoxycarbonyl)-1H-pyrazol-1-yl]-2-oxo-2,3-dihydro-1H-1,3-benzodiazol-1-yl}piperidine-1-carboxylate. LCMS [M+H]$^+$ 356. $^1$H-NMR (400 MHz, DMSO-d$_6$) δ ppm 10.95 (s, 1H), 8.94 (s, 1H), 8.69 (br. s., 1H), 8.46 (br. s., 1H), 8.15 (s, 1H), 7.46 (d, J=7.9 Hz, 1H), 7.39 (d, J=7.6 Hz, 1H), 7.16-7.23 (m, 1H), 4.54-4.64 (m, 1H), 4.29 (q, J=7.0 Hz, 2H), 3.42-3.51 (m, 2H), 3.04-3.18 (m, 2H), 2.54-2.69 (m, 2H), 1.86-1.97 (m, 2H), 1.32 (t, J=7.0 Hz, 3H).

Step 5: Ethyl 1-[1-[1-[(4-iodophenyl)carbamoyl]-4-piperidyl]-2-oxo-3H-benzimidazol-4-yl]pyrazole-4-carboxylate was synthesized according to general procedure D from ethyl 1-[2-oxo-1-(piperidin-4-yl)-2,3-dihydro-1H-1,3-benzodiazol-4-yl]-1H-pyrazole-4-carboxylate. LCMS [M+H]$^+$ 601.

Step 6: The title compound was synthesized according to general procedure J from ethyl 1-[1-[1-[(4-iodophenyl)carbamoyl]-4-piperidyl]-2-oxo-3H-benzimidazol-4-yl]pyrazole-4-carboxylate. LCMS [M+H]$^+$ 573.

Intermediate 24: 1-(Piperidin-4-yl)-4-(pyridin-3-yl)-2,3-dihydro-1H-1,3-benzodiazol-2-one;2,2,2-trifluoroacetic acid Step 1: tert-butyl 4-[2-oxo-4-(pyridin-3-yl)-2,3-dihydro-1H-1,3-benzodiazol-1-yl]piperidine-1-carboxylate was synthesized according to General procedure E from tert-butyl 4-(4-bromo-2-oxo-2,3-dihydro-1H-1,3-benzodiazol-1-yl)piperidine-1-carboxylate and 3-pyridylboronic acid. LCMS [M+H]$^+$ 395. $^1$H-NMR (400 MHz, CHLOROFORM-d) δ ppm 9.51 (br. s., 1H), 8.89 (s, 1H), 8.73 (d, J=3.8 Hz, 1H), 8.05 (d, J=7.6 Hz, 1H), 7.57-7.63 (m, 1H), 7.22 (s, 1H), 7.21 (s, 1H), 7.10-7.14 (m, 1H), 4.48 (tt, J=12.4, 4.1 Hz, 1H), 4.35 (br. s., 2H), 2.90 (br. s., 2H), 2.27-2.42 (m, 2H), 1.86 (m, 2H), 1.53 (s, 9H).

Step 2: The title compound was synthesized according to General procedure C from tert-butyl 4-[2-oxo-4-(pyridin-3-yl)-2,3-dihydro-1H-1,3-benzodiazol-1-yl]piperidine-1-carboxylate. LCMS [M+H]$^+$ 295. $^1$H-NMR (400 MHz, DMSO-d$_6$) δ ppm 11.24 (br. s., 1H), 8.85 (br. s., 1H), 8.71 (br. s., 1H), 8.64 (br. s, 1H), 8.32-8.49 (m, 1H), 8.13-8.21 (m, 1H), 7.67-7.73 (m, 1H), 7.39-7.44 (m, 1H), 7.18-7.24 (m, 1H), 7.11-7.17 (m, 1H), 4.53-4.63 (m, 2H), 3.42-3.51 (m, 2H), 3.06-3.19 (m, 2H), 2.54-2.70 (m, 2H), 1.86-1.96 (m, 2H).

Intermediate 25: 1-{(endo)-8-Azabicyclo[3.2.1]octan-3-yl}-4-bromo-2,3-dihydro-1H-1,3-benzodiazol-2-one;2,2,2-trifluoroacetic acid Step 1: tert-butyl 3-[(3-bromo-2-nitrophenyl)amino]-(endo)-8-azabicyclo[3.2.1]octane-8-carboxylate was synthesized according to General procedure A from 1-bromo-3-fluoro-2-nitrobenzene and tert-butyl (endo)-3-amino-8-azabicyclo[3.2.1]octane-8-carboxylate.

Step 2: tert-butyl 3-(4-bromo-2-oxo-2,3-dihydro-1H-1,3-benzodiazol-1-yl)-(endo)-8-azabicyclo[3.2.1]octane-8-carboxylate was synthesized according to General procedure B from tert-butyl 3-[(3-bromo-2-nitrophenyl)amino]-(endo)-8-azabicyclo[3.2.1]octane-8-carboxylate. LCMS [M-isobutene+H]$^+$ 366.

Step 3: 1-{(endo)-8-azabicyclo[3.2.1]octan-3-yl}-4-bromo-2,3-dihydro-1H-1,3-benzodiazol-2-one;2,2,2-trifluoroacetic acid was synthesized according to General procedure C from tert-butyl 3-(4-bromo-2-oxo-2,3-dihydro-1H-1,3-benzodiazol-1-yl)-(endo)-8-azabicyclo[3.2.1]octane-8-carboxylate. LCMS [M+H]$^+$ 322. $^1$H-NMR (400 MHz, DMSO-d$_6$) δ ppm 11.42 (s, 1H), 8.71 (br. s., 2H), 7.22 (dd, J=8.1, 0.8 Hz, 1H), 7.11 (d, J=8.1 Hz, 1H), 7.01 (t, J=8.1 Hz, 1H), 4.63-4.77 (m, 1H), 4.06-4.15 (m, 2H), 2.42-2.47 (m, 1H), 2.37-2.42 (m, 1H), 2.13-2.22 (m, 2H), 2.09 (br. s, 4H).

Intermediate 26: (Cis)-4-(4-bromo-2-oxo-2,3-dihydro-1H-1,3-benzodiazol-1-yl)cyclohexane-1-carboxylic acid Step 1: A mixture of (cis)-4-aminocyclohexanecarboxylic acid (1.5 equiv.), N,N-diisopropylethylamine (3.2 equiv.), and 1-bromo-3-fluoro-2-nitro-benzene (1.0 equiv.) was stirred in MeOH at 120° C. for 6 days. The mixture was poured into HCl (2 M) and extracted with DCM×3. The combined organics were dried and concentrated. The crude material was then suspended in MeOH, after which $H_2SO_4$ (conc., 2.2 equiv.) was added carefully. The mixture was stirred at reflux for 20 h and was then poured into $NaHCO_3$ and extracted with DCM×3. The combined organics were dried, concentrated, and purified by silica gel chromatography which afforded methyl (cis)-4-(3-bromo-2-nitro-anilino)cyclohexanecarboxylate. LCMS [M+H]$^+$ 357.

Step 2: methyl (cis)-4-(4-bromo-2-oxo-2,3-dihydro-1H-1,3-benzodiazol-1-yl)cyclohexane-1-carboxylate was synthesized according to General procedure B from methyl (cis)-4-(3-bromo-2-nitro-anilino)cyclohexanecarboxylate. LCMS [M+H]$^+$ 353. $^1$H-NMR (400 MHz, CHLOROFORM-d) δ ppm 8.89 (br. s., 1H), 7.17 (dd, J=8.2, 0.6 Hz, 1H), 7.12-7.15 (m, 1H), 6.95 (t, J=8.1 Hz, 1H), 4.39 (tt, J=12.6, 4.1 Hz, 1H), 3.79 (s, 3H), 2.74-2.80 (m, 1H), 2.25-2.45 (m, 4H), 1.66-1.82 (m, 4H).

Step 3: (cis)-4-(4-bromo-2-oxo-2,3-dihydro-1H-1,3-benzodiazol-1-yl)cyclohexane-1-carboxylic acid was synthesized according to General procedure J from methyl (cis)-4-(4-bromo-2-oxo-2,3-dihydro-1H-1,3-benzodiazol-1-yl)cyclohexane-1-carboxylate. LCMS [M+H]$^+$ 339. $^1$H-NMR (400 MHz, DMSO-d$_6$) δ ppm 12.34 (br. s., 1H), 11.28 (s, 1H), 7.16 (d, J=7.9 Hz, 1H), 7.10 (d, J=7.9 Hz, 1H), 6.95 (t, J=7.9 Hz, 1H), 4.13-4.25 (m, 1H), 2.67 (br. s., 1H), 2.09-2.32 (m, 4H), 1.55-1.70 (m, 4H).

Intermediate 27: (Cis)-4-(4-chloro-2-oxo-2,3-dihydro-1H-1,3-benzodiazol-1-yl)cyclohexane-1-carboxylic acid Step 1: A mixture of cis-4-aminocyclohexanecarboxylic acid (1.5 equiv.), N,N-diisopropylethylamine (3.2 equiv.), and 1-chloro-3-fluoro-2-nitro-benzene (1.0 equiv.) was stirred in MeOH at 120° C. for 6 days. The mixture was poured into HCl (2 M) and extracted with DCM×3. The combined organics were dried and concentrated. The crude material was suspended in MeOH, then $H_2SO_4$ (conc., 2.2 equiv.) was added carefully. The mixture was stirred at reflux for 20 h and was then poured into $NaHCO_3$ and extracted with DCM×3. The combined organics were dried, concentrated, and purified by silica gel chromatography which afforded methyl (cis)-4-(3-chloro-2-nitro-anilino)cyclohexanecarboxylate. LCMS [M+H]$^+$ 313.

Step 2: methyl (cis)-4-(4-chloro-2-oxo-2,3-dihydro-1H-1,3-benzodiazol-1-yl)cyclohexane-1-carboxylate was synthesized according to General procedure B from methyl (cis)-4-(3-chloro-2-nitro-anilino)cyclohexanecarboxylate. LCMS [M+H]$^+$ 309. $^1$H-NMR (400 MHz, CHLOROFORM-d) δ ppm 8.27 (br. s., 1H), 7.08-7.13 (m, 1H), 6.97-7.06 (m, 2H), 4.33-4.46 (m, 1H), 3.79 (s, 3H), 2.78 (br. s., 1H), 2.23-2.44 (m, 4H), 1.66-1.82 (m, 4H).

Step 3: (cis)-4-(4-chloro-2-oxo-2,3-dihydro-1H-1,3-benzodiazol-1-yl)cyclohexane-1-carboxylic acid was synthesized according to General procedure J from methyl (cis)-4-(4-chloro-2-oxo-2,3-dihydro-1H-1,3-benzodiazol-1-yl)cyclohexane-1-carboxylate. LCMS [M+H]$^+$ 295. $^1$H-NMR (400 MHz, DMSO-d$_6$) δ ppm 12.35 (br. s., 1H), 11.39 (s, 1H), 7.05-7.08 (m, 1H), 6.98-7.05 (m, 2H), 4.20 (tt, J=12.4, 4.0 Hz, 1H), 2.63-2.70 (m, 1H), 2.11-2.32 (m, 4H), 1.55-1.70 (m, 4H).

Intermediate 28: 1-(Azepan-4-yl)-4-bromo-2,3-dihydro-1H-1,3-benzodiazol-2-one;2,2,2-trifluoroacetic acid Step 1: tert-butyl 4-(3-bromo-2-nitro-anilino)azepane-1-carboxylate was synthesized according to General procedure A from racemic tert-butyl 4-aminoazepane-1-carboxylate and 1-bromo-3-fluoro-2-nitro-benzene. LCMS [M-isobutene+H]$^+$ 358.

Step 2: tert-butyl 4-(4-bromo-2-oxo-3H-benzimidazol-1-yl)azepane-1-carboxylate was synthesized according to General procedure B from tert-butyl 4-(3-bromo-2-nitro-anilino)azepane-1-carboxylate. LCMS [M+H]$^+$ 410.

Step 3: 1-(azepan-4-yl)-4-bromo-2,3-dihydro-1H-1,3-benzodiazol-2-one;2,2,2-trifluoroacetic acid was synthesized according to General procedure C from tert-butyl 4-(4-bromo-2-oxo-3H-benzimidazol-1-yl)azepane-1-carboxylate. LCMS [M+H]$^+$ 310.

Intermediate 29: 1-{(endo)-8-Azabicyclo[3.2.1]octan-3-yl)-4-[6-(hydroxymethyl)pyridin-3-yl]-2,3-dihydro-1H-1,3-benzodiazol-2-one;2,2,2-trifluoroacetic acid Step 1: tert-butyl 3-{4-[6-(hydroxymethyl)pyridin-3-yl]-2-oxo-2,3-dihydro-1H-1,3-benzodiazol-1-yl}-(endo)-8-azabicyclo[3.2.1]octane-8-carboxylate was synthesized according to General procedure E from tert-butyl 3-(4-bromo-2-oxo-2,3-dihydro-1H-1,3-benzodiazol-1-yl)-(endo)-8-azabicyclo[3.2.1]octane-8-carboxylate and [6-(hydroxymethyl)-3-pyridyl]boronic acid. LCMS [M+H]$^+$ 451.

Step 2: 1-{(endo)-8-azabicyclo[3.2.1]octan-3-yl}-4-[6-(hydroxymethyl)pyridin-3-yl]-2,3-dihydro-1H-1,3-benzodiazol-2-one;2,2,2-trifluoroacetic acid was synthesized according to General procedure C from tert-butyl 3-{4-[6-(hydroxymethyl)pyridin-3-yl]-2-oxo-2,3-dihydro-1H-1,3-benzodiazol-1-yl}-(endo)-8-azabicyclo[3.2.1]octane-8-carboxylate. LCMS [M+H]$^+$ 351. $^1$H-NMR (400 MHz, DMSO-d$_6$) δ ppm 11.22 (s, 1H), 8.65-8.81 (m, 3H), 8.10 (d, J=7.9 Hz, 1H), 7.68 (d, J=7.6 Hz, 1H), 7.07-7.24 (m, 3H), 4.73-4.83 (m, 1H), 4.71 (br. s., 2H), 4.08-4.17 (m, 2H), 2.38-2.49 (m, 2H), 2.19-2.29 (m, 2H), 2.11 (br. s., 4H).

Intermediate 30: 4-[6-(Hydroxymethyl)pyridin-3-yl]-1-(piperidin-4-yl)-2,3-dihydro-1H-1,3-benzodiazol-2-one;2,2,2-trifluoroacetic acid Step 1: tert-butyl 4-[4-[6-(hydroxymethyl)-3-pyridyl]-2-oxo-3H-benzimidazol-1-yl]piperidine-1-carboxylate was synthesized according to General procedure E from tert-butyl 4-(4-bromo-2-oxo-3H-benzimidazol-1-yl)piperidine-1-carboxylate and [6-(hydroxymethyl)-3-pyridyl]boronic acid. LCMS [M-isobutene+H]$^+$ 325.

Step 2: 4-[6-(hydroxymethyl)pyridin-3-yl]-1-(piperidin-4-yl)-2,3-dihydro-1H-1,3-benzodiazol-2-one;2,2,2-trifluoroacetic acid was synthesized according to General procedure C from tert-butyl 4-{4-[6-(hydroxymethyl)pyridin-3-yl]-2-oxo-2,3-dihydro-1H-1,3-benzodiazol-1-yl}piperidine-1-carboxylate. LCMS [M+H]$^+$ 325. $^1$H-NMR (400 MHz, DMSO-d$_6$) δ ppm 11.19 (s, 1H), 8.63-8.71 (m, 2H), 8.37-

8.48 (m, 1H), 8.10 (dd, J=8.1, 2.1 Hz, 1H), 7.67 (d, J=8.1 Hz, 1H), 7.39 (d, J=7.9 Hz, 1H), 7.19 (t, J=7.9 Hz, 1H), 7.11 (dd, J=7.9, 0.9 Hz, 1H), 4.70 (s, 2H), 4.58 (m, 2H), 3.42-3.51 (m, 2H), 3.06-3.19 (m, 2H), 2.61-2.67 (m, 1H), 2.55-2.61 (m, 1H), 1.87-1.94 (m, 2H).

Intermediate 31: 4-bromo-1-(3-hydroxypiperidin-4-yl)-2,3-dihydro-1H-1,3-benzodiazol-2-one; 2,2,2-trifluoroacetic acid Step 1: tert-butyl 4-(3-bromo-2-nitro-anilino)-3-hydroxy-piperidine-1-carboxylate was synthesized according to General procedure A from tert-butyl 4-amino-3-hydroxy-piperidine-1-carboxylate (produced as described in WO 2011/103091 A1) and 1-bromo-3-fluoro-2-nitrobenzene. LCMS [M+H]$^+$ 362.

Step 2: tert-butyl 4-(4-bromo-2-oxo-2,3-dihydro-1H-1,3-benzodiazol-1-yl)-3-hydroxypiperidine-1-carboxylate was synthesized according to General procedure B from tert-butyl 4-(3-bromo-2-nitro-anilino)-3-hydroxy-piperidine-1-carboxylate. LCMS [M-isobutene+H]$^+$ 356.

$^1$H-NMR (400 MHz, CHLOROFORM-d) δ ppm 8.70 (br. s., 1H), 7.19 (d, J=8.2 Hz, 1H), 7.02-7.06 (m, 1H), 6.93-6.98 (m, 1H), 4.33-4.52 (m, 2H), 4.07-4.17 (m, 1H), 2.83 (br. s., 1H), 2.69 (br. s., 1H), 2.32 (m, 1H), 1.89 (m, 1H), 1.48-1.51 (m, 9H).

Step 3: 4-bromo-1-(3-hydroxypiperidin-4-yl)-2,3-dihydro-1H-1,3-benzodiazol-2-one; 2,2,2-trifluoroacetic acid was synthesized according to General procedure C from tert-butyl 4-(4-bromo-2-oxo-2,3-dihydro-1H-1,3-benzodiazol-1-yl)-3-hydroxypiperidine-1-carboxylate.

LCMS [M+H]$^+$ 312. $^1$H-NMR (400 MHz, DMSO-d$_6$) δ ppm 11.33 (s, 1H), 8.89 (br. s., 1H), 8.71 (br. s., 1H), 7.26 (br. d, J=8.1 Hz, 1H), 7.19 (dd, J=8.1, 0.9 Hz, 1H), 6.99 (t, J=8.1 Hz, 1H), 5.65 (br. s, 1H), 4.41-4.52 (m, 1H), 4.20-4.31 (m, 1H), 3.34-3.45 (m, 2H), 3.02-3.15 (m, 1H), 2.75-2.87 (m, 1H), 2.53-2.63 (m, 1H), 1.88-1.98 (m, 1H).

Intermediate 32: 4-Bromo-1-(2-methylpiperidin-4-yl)-1H-benzo[d]imidazol-2(3H)-one 2,2,2-trifluoro-acetate Step 1: tert-butyl 4-((3-bromo-2-nitrophenyl)amino)-2-methylpiperidine-1-carboxylate was synthesized according to General procedure A from 1-bromo-3-fluoro-2-nitrobenzene and tert-butyl 4-amino-2-methylpiperidine-1-carboxylate.

Step 2: tert-butyl 4-(4-bromo-2-oxo-2,3-dihydro-1H-benzo[d]imidazol-1-yl)-2-methylpiperidine-1-carboxylate was synthesized according to General procedure B from tert-butyl 4-((3-bromo-2-nitrophenyl)amino)-2-methylpiperidine-1-carboxylate. LCMS [M+H]$^+$ 410.

Step 3: 4-bromo-1-(2-methylpiperidin-4-yl)-1H-benzo[d]imidazol-2(3H)-one 2,2,2-trifluoroacetate was synthesized according to General procedure C from tert-butyl 4-(4-bromo-2-oxo-2,3-dihydro-1H-benzo[d]imidazol-1-yl)-2-methylpiperidine-1-carboxylate. LCMS [M+H]$^+$ 310.

Intermediate 33: 4-Bromo-1-(3-methylpiperidin-4-yl)-1H-benzo[d]imidazol-2(3H)-one 2,2,2-trifluoro-acetate Step 1: tert-butyl 4-((3-bromo-2-nitrophenyl)amino)-3-methylpiperidine-1-carboxylate was synthesized according to General procedure A from 1-bromo-3-fluoro-2-nitrobenzene and tert-butyl 4-amino-3-methylpiperidine-1-carboxylate.

Step 2: tert-butyl 4-(4-bromo-2-oxo-2,3-dihydro-1H-benzo[d]imidazol-1-yl)-3-methylpiperidine-1-carboxylate was synthesized according to General procedure B from tert-butyl 4-((3-bromo-2-nitrophenyl)amino)-3-methylpiperidine-1-carboxylate. LCMS [M+H]$^+$ 410.

Step 3: 4-bromo-1-(3-methylpiperidin-4-yl)-1H-benzo[d]imidazol-2(3H)-one 2,2,2-trifluoroacetate was synthesized according to General procedure C from tert-butyl 4-(4-bromo-2-oxo-2,3-dihydro-1H-benzo[d]imidazol-1-yl)-3-methylpiperidine-1-carboxylate. LCMS [M+H]$^+$ 310.

Intermediate 34: Cis-4-(4-methoxy-2-oxo-2,3-dihydro-1H-1,3-benzodiazol-1-yl)cyclohexane-1-carboxylic acid Step 1: methyl 4-(3-methoxy-2-nitro-anilino)cyclohexanecarboxylate was synthesized according to General procedure A from 1-fluoro-3-methoxy-2-nitrobenzene and methyl cis-4-aminocyclohexanecarboxylate. LCMS [M+H]$^+$ 309.

Step 2: methyl cis-4-[4-methoxy-2-oxo-3H-benzimidazol-1-yl]cyclohexanecarboxylate was synthesized according to General procedure F from methyl 4-(3-methoxy-2-nitro-anilino)cyclohexanecarboxylate. LCMS [M+H]$^+$ 305.

Step 3: the title compound was synthesized according to General procedure J from methyl cis-4-[4-methoxy-2-oxo-3H-benzimidazol-1-yl]cyclohexanecarboxylate. LCMS [M+H]$^+$ 291.

Intermediate 35: Cis-4-[(3-fluoro-2-nitrophenyl)amino]cyclohexane-1-carboxylate

The title compound was synthesized according to General procedure A from 1,3-difluoro-2-nitrobenzene and methyl cis-4-aminocyclohexanecarboxylate. LCMS [M+H]$^+$ 297.

Intermediate 36: Cis-4-(4-fluoro-2-oxo-2,3-dihydro-1H-1,3-benzodiazol-1-yl)cyclohexane-1-carboxylic acid Step 1: methyl cis-4-(4-fluoro-2-oxo-2,3-dihydro-1H-1,3-benzodiazol-1-yl)cyclohexane-1-carboxylate was synthesized according to General procedure B from cis-4-[(3-fluoro-2-nitrophenyl)amino]cyclohexane-1-carboxylate. LCMS [M+H]$^+$ 293.

Step 2: the title compound was synthesized according to General procedure J from methyl cis-4-(4-fluoro-2-oxo-2,3-dihydro-1H-1,3-benzodiazol-1-yl)cyclohexane-1-carboxylate. LCMS [M+H]$^+$ 279. $^1$H-NMR (400 MHz, DMSO-d6) δ ppm 12.35 (br. s., 1H), 11.41 (s, 1H), 6.92-7.02 (m, 2H), 6.84-6.92 (m, 1H), 4.15-4.25 (m, 1H), 2.64-2.70 (m, 1H), 2.19-2.31 (m, 2H), 2.11-2.19 (m, 2H), 1.55-1.70 (m, 4H).

Intermediate 37: Cis-4-(6-fluoro-2-oxo-2,3-dihydro-1H-1,3-benzodiazol-1-yl)cyclohexane-1-carboxylic acid Step 1: methyl cis-4-(5-fluoro-2-nitro-anilino)cyclohexanecarboxylate was synthesized according to General procedure A from 2,4-difluoro-1-nitrobenzene and methyl cis-4-aminocyclohexanecarboxylate. LCMS [M+H]$^+$ 297.

Step 2: methyl cis-4-(6-fluoro-2-oxo-3H-benzimidazol-1-yl)cyclohexanecarboxylate was synthesized according to General procedure B from methyl cis-4-(5-fluoro-2-nitro-anilino)cyclohexanecarboxylate. LCMS [M+H]$^+$ 293. $^1$H-NMR (400 MHz, Chloroform-d) δ ppm 9.61 (br. s., 1H), 6.94-7.04 (m, 2H), 6.78 (t, J=9.0 Hz, 1H), 4.34-4.45 (m, 1H), 3.81 (s, 3H), 2.79 (br. s., 1H), 2.26-2.43 (m, 4H), 1.66-1.83 (m, 4H).

Step 3: the title compound was synthesized according to General procedure J from methyl cis-4-(6-fluoro-2-oxo-3H-benzimidazol-1-yl)cyclohexanecarboxylate. LCMS [M+H]⁺ 279.

Intermediate 38: Cis-4-[4-(2-methoxyethoxy)-2-oxo-2,3-dihydro-1H-1,3-benzodiazol-1-yl]cyclohexane-1-carboxylic acid Step 1: 1-fluoro-3-(2-methoxyethoxy)-2-nitro-benzene was synthesized according to General procedure K from 1,3-difluoro-2-nitrobenzene and 2-methoxyethanol. LCMS [M+H]⁺ 216. ¹H-NMR (400 MHz, Chloroform-d) δ ppm 7.35-7.44 (m, 1H), 6.81-6.91 (m, 2H), 4.25 (t, J=4.6 Hz, 2H), 3.75 (t, J=4.6 Hz, 2H), 3.43 (s, 3H).

Step 2: methyl 4-[3-(2-methoxyethoxy)-2-nitro-anilino]cyclohexanecarboxylate was synthesized according to General procedure A from 1-fluoro-3-(2-methoxyethoxy)-2-nitro-benzene and methyl cis-4-aminocyclohexanecarboxylate. LCMS [M+H]⁺ 353.

Step 3: methyl cis-4-[4-(2-methoxyethoxy)-2-oxo-2,3-dihydro-1H-1,3-benzodiazol-1-yl]cyclohexane-1-carboxylate was synthesized according to General procedure B from methyl 4-[3-(2-methoxyethoxy)-2-nitro-anilino]cyclohexanecarboxylate. LCMS [M+H]⁺ 349.

Step 4: the title compound was synthesized according to General procedure J from methyl cis-4-[4-(2-methoxyethoxy)-2-oxo-2,3-dihydro-1H-1,3-benzodiazol-1-yl]cyclohexane-1-carboxylate. LCMS [M+H]⁺ 335.

Intermediate 39: Cis-4-amino-N-(3-methoxy-4-methylphenyl)cyclohexane-1-carboxamide hydrochloride Step 1: tert-butyl N-[cis-4-[(3-methoxy-4-methyl-phenyl)carbamoyl]cyclohexyl]carbamate was synthesized according to General procedure H from 4-(tert-butoxycarbonylamino)cyclohexanecarboxylic acid and 3-methoxy-4-methyl-aniline. LCMS [M-isobutene+H]⁺ 307. ¹H-NMR (400 MHz, DMSO-d6) δ ppm 9.66 (s, 1H), 7.33 (s, 1H), 7.04-7.09 (m, 1H), 6.98-7.03 (m, 1H), 6.74-6.81 (m, 1H), 3.74 (s, 3H), 3.46-3.54 (m, 1H), 2.31-2.40 (m, 1H), 2.08 (s, 3H), 1.83 (d, J=10.4 Hz, 2H), 1.70 (br. s., 2H), 1.47-1.57 (m, 4H), 1.39 (s, 9H).

Step 2: a mixture of tert-butyl N-[cis-4-[(3-methoxy-4-methyl-phenyl)carbamoyl]cyclohexyl]carbamate (1.0 equiv.) and HCl (4M in dioxane, 2 equiv.) was stirred in DCM for 16 h. The resulting precipitate was collected by filtration, washed with DCM and dried in vacuo. LCMS [M+H]⁺ 263.

Intermediate 40: Cis-4-[(3-fluoro-2-nitrophenyl)amino]-N-(3-methoxy-4-methylphenyl)cyclohexane-1-carboxamide The title compound was synthesized according to General procedure A from 1,3-difluoro-2-nitrobenzene and cis-4-amino-N-(3-methoxy-4-methylphenyl)cyclohexane-1-carboxamide hydrochloride. LCMS [M+H]⁺ 402.

Intermediate 41: Cis-4-{2-oxo-1H,2H,3H-imidazo[4,5-b]pyridin-1-yl}cyclohexane-1-carboxylic acid Step 1: methyl 4-[(2-nitro-3-pyridyl)amino]cyclohexanecarboxylate was synthesized according to General procedure A from 3-fluoro-2-nitro-pyridine and methyl cis-4-aminocyclohexanecarboxylate. LCMS [M+H]⁺ 280.

Step 2: methyl cis-4-{2-oxo-1H,2H,3H-imidazo[4,5-b]pyridin-1-yl}cyclohexane-1-carboxylate was synthesized according to General procedure B from methyl 4-[(2-nitro-3-pyridyl)amino]cyclohexanecarboxylate. LCMS [M+H]⁺ 276.

Step 3: the title compound was synthesized according to General procedure J from methyl cis-4-{2-oxo-1H,2H,3H-imidazo[4,5-b]pyridin-1-yl}cyclohexane-1-carboxylate. LCMS [M+H]⁺ 262.

Intermediate 42: 2-Oxo-1-[cis-4-[(3-methoxy-4-methylphenyl)carbamoyl]cyclohexyl]-2,3-dihydro-1H-1,3-benzodiazole-4-carboxylic acid Step 1: a mixture of 3-fluoro-2-nitro-benzoic acid, benzyl bromide, and K₂CO₃ was stirred in DMF at 20° C. for 16 h. The mixture was then poured into NaHCO₃ (aq.) and extracted with hexane ×5. The combined extracts were dried, concentrated, and purified by silica gel chromatography which afforded benzyl 3-fluoro-2-nitro-benzoate. LCMS [M+H30]+293. ¹H-NMR (400 MHz, Chloroform-d) δ ppm 7.57 (br. s, 1H), 7.30-7.42 (m, 7H), 7.01 (d, J=8.5 Hz, 1H), 6.93 (d, J=7.9 Hz, 1H), 6.73-6.78 (m, 2H), 5.32 (s, 2H), 3.81 (s, 3H), 3.77 (br. s., 1H), 2.38-2.47 (m, 1H), 2.16 (s, 3H), 1.75-1.99 (m, 8H).

Step 2: benzyl 3-[[4-[(3-methoxy-4-methyl-phenyl)carbamoyl]cyclohexyl]amino]-2-nitro-benzoate was synthesized according to General procedure A from cis-4-amino-N-(3-methoxy-4-methylphenyl)cyclohexane-1-carboxamide hydrochloride and benzyl 3-fluoro-2-nitro-benzoate. LCMS [M+H]⁺ 518.

Step 3: benzyl 1-[4-[(3-methoxy-4-methyl-phenyl)carbamoyl]cyclohexyl]-2-oxo-3H-benzimidazole-4-carboxylate was synthesized according to General procedure B from benzyl 3-[[4-[(3-methoxy-4-methyl-phenyl)carbamoyl]cyclohexyl]amino]-2-nitro-benzoate. LCMS [M+H]⁺ 514.

Step 4: the title compound was synthesized according to General procedure G from benzyl 1-[4-[(3-methoxy-4-methyl-phenyl)carbamoyl]cyclohexyl]-2-oxo-3H-benzimidazole-4-carboxylate.

Intermediate 43: Cis-4-(4-acetamido-2-oxo-2,3-dihydro-1H-1,3-benzodiazol-1-yl)cyclohexane-1-carboxylic acid Step 1: 4-[3-(dibenzylamino)-2-nitro-anilino]cyclohexanecarboxylic acid was synthesized according to general procedure M from cis-4-(4-fluoro-2-oxo-2,3-dihydro-1H-1,3-benzodiazol-1-yl)cyclohexane-1-carboxylic acid and dibenzylamine. LCMS [M+H]⁺ 460.

Step 2: 2-Trimethylsilylethyl 4-[3-(dibenzylamino)-2-nitro-anilino]cyclohexanecarboxylate was synthesized according to general procedure O from 4-[3-(dibenzylamino)-2-nitro-anilino]cyclohexanecarboxylic acid and 2-trimethylsilylethanol. LCMS [M+H]⁺ 560. ¹H-NMR (400 MHz, Chloroform-d) δ ppm 7.21-7.31 (m, 11H), 7.08-7.14 (m, 1H), 6.35-6.44 (m, 2H), 4.16-4.25 (m, 6H), 3.49-3.57 (m, 1H), 2.43-2.52 (m, 1H), 1.92-2.02 (m, 2H), 1.62-1.85 (m, 6H), 0.97-1.03 (m, 2H), 0.05-0.08 (m, 9H).

Step 3: 2-trimethylsilylethyl 4-[4-(dibenzylamino)-2-oxo-3H-benzimidazol-1-yl]cyclohexanecarboxylate was synthesized according to general procedure B from 2-trimethylsilylethyl 4-[3-(dibenzylamino)-2-nitro-anilino]cyclohexanecarboxylate. LCMS [M+H]⁺ 556.

Step 4: 2-Trimethylsilylethyl 4-(4-amino-2-oxo-3H-benzimidazol-1-yl)cyclohexanecarboxylate cyclohexanecarboxylate was synthesized according to general procedure G from 2-trimethylsilylethyl 4-[4-(dibenzylamino)-2-oxo-3H-benzimidazol-1-yl]cyclohexanecarboxylate. LCMS [M+H]$^+$ 376.

Step 5: A mixture of 2-trimethylsilylethyl 4-(4-amino-2-oxo-3H-benzimidazol-1-yl)cyclohexanecarboxylate cyclohexanecarboxylate (1.0 equiv.), N,N-diisopropylethylamine (2.0 equiv.), and acetyl chloride (1.0 equiv.) was stirred in DCM at 20° C. for 3 h. The mixture was then purified by silica gel chromatography which afforded 2-trimethylsilylethyl 4-(4-acetamido-2-oxo-3H-benzimidazol-1-yl)cyclohexanecarboxylate. LCMS [M+H]$^+$ 418. $^1$H-NMR (400 MHz, Chloroform-d) δ ppm 9.86-9.99 (m, 1H), 8.18-8.29 (m, 1H), 6.96-7.09 (m, 3H), 4.34-4.44 (m, 1H), 4.24-4.31 (m, 2H), 2.69-2.74 (m, 1H), 2.28-2.45 (m, 4H), 2.27 (s, 3H), 1.63-1.77 (m, 4H), 1.02-1.09 (m, 2H), 0.08 (s, 9H).

Step 6: A mixture of 2-trimethylsilylethyl 4-(4-acetamido-2-oxo-3H-benzimidazol-1-yl)cyclohexanecarboxylate (1.0 equiv.) and TBAF (1 M in THF, 4 equiv.) was stirred in DMF for 4 h. The mixture was then diluted to 5 times the volume using a mixture of THE and MeOH (1:1), thereafter Ca(OAc)$_2$ (25 equiv.) and DOWEX 50WX8 (1500 wt %) were added. The resulting mixture was stirred vigorously for 3 h and then filtered and concentrated. The mixture was then purified by silica gel chromatography. LCMS [M+H]$^+$ 318.

Example Compounds

Example compounds as described below were prepared in accordance with the general procedures indicated.

Example 1: 4-(5-Chloro-2-oxo-2,3-dihydro-1H-1,3-benzodiazol-1-yl)-N-(4-chlorophenyl) piperidine-1-carboxamide The title compound was synthesized using General procedure D from 5-chloro-1-(piperidin-4-yl)-2,3-dihydro-1H-1,3-benzodiazol-2-one and 4-chlorophenyl isocyanate. LCMS [M+H]$^+$ 405.

Example 2: 4-(5-Chloro-2-oxo-2,3-dihydro-1H-1,3-benzodiazol-1-yl)-N-(4-iodophenyl) piperidine-1-carboxamide The title compound was synthesized using General procedure D from 5-chloro-1-(piperidin-4-yl)-2,3-dihydro-1H-1,3-benzodiazol-2-one and 4-iodophenyl isocyanate. LCMS [M+H]$^+$ 497.

Example 3: 4-(5-Chloro-2-oxo-2,3-dihydro-1H-1,3-benzodiazol-1-yl)-N-(3,4-dichlorophenyl)piperidine-1-carboxamide The title compound was synthesized using General procedure D from 5-chloro-1-(piperidin-4-yl)-2,3-dihydro-1H-1,3-benzodiazol-2-one and 3,4-dichlorophenyl isocyanate. LCMS [M+H]$^+$ 439.

Example 4: N-(4-iodophenyl)-4-(4-methyl-2-oxo-2,3-dihydro-1H-1,3-benzodiazol-1-ylpiperidine-1-carboxamide The title compound was synthesized using General procedure D from 4-methyl-1-(piperidin-4-yl)-2,3-dihydro-1H-1,3-benzodiazol-2-one;2,2,2-trifluoroacetic acid and 4-iodophenyl isocyanate. LCMS [M+H]$^+$ 477.

Example 5: N-(4-iodophenyl)-4-(4-methoxy-2-oxo-2,3-dihydro-1H-1,3-benzodiazol-1-yl)piperidine-1-carboxamide The title compound was synthesized using General procedure D from 4-methoxy-1-(piperidin-4-yl)-2,3-dihydro-1H-1,3-benzodiazol-2-one;2,2,2-trifluoroacetic acid and 4-iodophenyl isocyanate. LCMS [M+H]$^+$ 493.

Example 6: 4-(4-Hydroxy-2-oxo-2,3-dihydro-1H-1,3-benzodiazol-1-yl)-N-(4-iodophenyl)piperidine-1-carboxamide The title compound was synthesized using General procedure D from 4-hydroxy-1-(piperidin-4-yl)-2,3-dihydro-1H-1,3-benzodiazol-2-one;2,2,2-trifluoroacetic acid and 4-iodophenyl isocyanate. LCMS [M+H]$^+$ 479.

Example 7: N-(4-chlorophenyl)-4-(4-methyl-2-oxo-2,3-dihydro-1H-1,3-benzodiazol-1-yl)piperidine-1-carboxamide The title compound was synthesized using General procedure D from 4-methyl-1-(piperidin-4-yl)-2,3-dihydro-1H-1,3-benzodiazol-2-one;2,2,2-trifluoroacetic acid and 4-chlorophenyl isocyanate. LCMS [M+H]$^+$ 385.

Example 8: N-(4-chlorophenyl)-4-(4-methoxy-2-oxo-2,3-dihydro-1H-1,3-benzodiazol-1-yl)piperidine-1-carboxamide The title compound was synthesized using General procedure D from 4-methoxy-1-(piperidin-4-yl)-2,3-dihydro-1H-1,3-benzodiazol-2-one;2,2,2-trifluoroacetic acid and 4-chlorophenyl isocyanate. LCMS [M+H]$^+$ 401.

Example 9: N-(3,4-dichlorophenyl)-4-(4-hydroxy-2-oxo-2,3-dihydro-1H-1,3-benzodiazol-1-yl)piperidine-1-carboxamide The title compound was synthesized using General procedure D from 4-hydroxy-1-(piperidin-4-yl)-2,3-dihydro-1H-1,3-benzodiazol-2-one;2,2,2-trifluoroacetic acid and 3,4-dichlorophenyl isocyanate. LCMS [M+H]$^+$ 421. $^1$H-NMR (400 MHz, DMSO-d$_6$) δ ppm 8.88 (br. s., 1H), 7.87 (dd, J=1.6, 0.9 Hz, 1H), 7.45-7.51 (m, 2H), 6.74-6.80 (m, 1H), 6.66 (d, J=7.9 Hz, 1H), 6.44-6.49 (m, 1H), 4.21-4.41 (m, 3H), 2.94 (m, 2H), 2.25 (m, 2H), 1.71 (m, 2H).

Example 10: 4-(5-Cyano-2-oxo-2,3-dihydro-1H-1,3-benzodiazol-1-yl)-N-(4-iodophenyl)piperidine-1-carboxamide The title compound was synthesized using General procedure D from 2-oxo-1-(4-piperidyl)-1H-benzimidazole-5-carbonitrile;2,2,2-trifluoroacetic acid and 4-iodophenyl isocyanate. LCMS [M+H]$^+$ 488.

Example 11: N-(4-iodophenyl)-4-(5-methyl-2-oxo-2,3-dihydro-1H-1,3-benzodiazol-1-yl)piperidine-1-carboxamide The title compound was synthesized using General procedure D from 5-methyl-1-(piperidin-4-yl)-2,3-dihydro-1H-

1,3-benzodiazol-2-one;2,2,2-trifluoroacetic acid and 4-iodophenyl isocyanate. LCMS [M+H]$^+$ 477. $^1$H-NMR (400 MHz, DMSO-d$_6$) δ ppm 8.70 (s, 1H), 7.56 (d, J=8.5 Hz, 2H), 7.35 (d, J=8.8 Hz, 2H), 7.07 (d, J=8.5 Hz, 1H), 6.75-6.81 (m, 2H), 4.22-4.41 (m, 3H), 2.92 (m, 2H), 2.16-2.30 (m, 5H), 1.70 (m, 2H).

Example 12: 4-(4-Fluoro-2-oxo-2,3-dihydro-1H-1,3-benzodiazol-1-yl)-N-(4-iodophenyl)piperidine-1-carboxamide The title compound was synthesized using General procedure D from 4-fluoro-1-(piperidin-4-yl)-2,3-dihydro-1H-1,3-benzodiazol-2-one;2,2,2-trifluoroacetic acid and 4-iodophenyl isocyanate. LCMS [M+H]$^+$ 481.

Example 13: 4-(4-Bromo-2-oxo-2,3-dihydro-1H-1,3-benzodiazol-1-yl)-N-(4-iodophenyl)piperidine-1-carboxamide The title compound was synthesized using General procedure D from 4-bromo-1-(piperidin-4-yl)-2,3-dihydro-1H-1,3-benzodiazol-2-one;2,2,2-trifluoroacetic acid and 4-iodophenyl isocyanate. LCMS [M+H]$^+$ 541. $^1$H-NMR (400 MHz, DMSO-d$_6$) δ ppm 11.31 (s, 1H), 8.69 (s, 1H), 7.53-7.59 (m, 2H), 7.33-7.39 (m, 2H), 7.25 (d, J=7.9 Hz, 1H), 7.16 (d, J=7.6 Hz, 1H), 6.95 (t, J=8.1 Hz, 1H), 4.34-4.45 (m, 1H), 4.28 (m, 2H), 2.93 (m, 2H), 2.26 (m, 2H), 1.74 (m, 2H).

Example 14: N-(4-iodophenyl)-4-(5-methoxy-2-oxo-2,3-dihydro-1H-1,3-benzodiazol-1-yl)piperidine-1-carboxamide The title compound was synthesized using General procedure D from 5-methoxy-1-(piperidin-4-yl)-2,3-dihydro-1H-1,3-benzodiazol-2-one;2,2,2-trifluoroacetic acid and 4-iodophenyl isocyanate. LCMS [M+H]$^+$ 493. $^1$H-NMR (400 MHz, DMSO-d$_6$) δ ppm 10.78 (s, 1H), 8.70 (s, 1H), 7.55-7.59 (m, 2H), 7.34-7.39 (m, 2H), 7.07-7.12 (m, 1H), 6.57 (m, 2H), 4.24-4.40 (m, 3H), 3.71 (s, 3H), 2.88-2.98 (m, 2H), 2.23 (m, 2H), 1.67-1.76 (m, 2H).

Example 15: N-(4-iodophenyl)-4-(5-fluoro-2-oxo-2,3-dihydro-1H-1,3-benzodiazol-1-yl)piperidine-1-carboxamide The title compound was synthesized using General procedure D from 5-fluoro-1-(piperidin-4-yl)-2,3-dihydro-1H-1,3-benzodiazol-2-one;2,2,2-trifluoroacetic acid and 4-Iodophenyl isocyanate. LCMS [M+H]$^+$ 481. $^1$H-NMR (400 MHz, DMSO-d$_6$) δ ppm 8.70 (s, 1H), 7.53-7.60 (m, 2H), 7.32-7.39 (m, 2H), 7.21 (dd, J=8.5, 4.4 Hz, 1H), 6.77-6.86 (m, 2H), 4.33-4.43 (m, 1H), 4.25-4.32 (m, 2H), 2.89-2.98 (m, 2H), 2.19-2.31 (m, 2H), 1.69-1.77 (m, 2H).

Example 16: Methyl 2-(1-{1-[(4-iodophenyl)carbamoyl]piperidin-4-yl}-2-oxo-2,3-dihydro-1H-1,3-benzodiazol-4-yl)acetate The title compound was synthesized using General procedure D from methyl 2-[2-oxo-1-(piperidin-4-yl)-2,3-dihydro-1H-1,3-benzodiazol-4-yl]acetate;2,2,2-trifluoroacetic acid and 4-iodophenyl isocyanate. LCMS [M+H]$^+$ 535. $^1$H-NMR (400 MHz, DMSO-d$_6$) δ ppm 10.98 (br. s., 1H), 8.71 (s, 1H), 7.54-7.60 (m, 2H), 7.34-7.39 (m, 2H), 7.14 (dd, J=7.9, 0.9 Hz, 1H), 6.95 (t, J=7.9 Hz, 1H), 6.83-6.87 (m, 1H), 4.40 (tt, J=12.3, 4.1 Hz, 1H), 4.25-4.33 (m, 2H), 3.76 (s, 2H), 3.62 (s, 3H), 2.89-3.00 (m, 2H), 2.22-2.35 (m, 2H), 1.69-1.78 (m, 2H).

Example 17: 4-(5-Chloro-2-oxo-2,3-dihydro-1H-1,3-benzodiazol-1-yl)-N-(3-chloro-4-iodophenyl)piperidine-1-carboxamide The title compound was synthesized using General procedure D from 5-chloro-1-(piperidin-4-yl)-2,3-dihydro-1H-1,3-benzodiazol-2-one and 3-chloro-4-iodophenyl isocyanate. LCMS [M+H]$^+$ 531.

Example 18: 4-(4-Ethoxy-2-oxo-2,3-dihydro-1H-1,3-benzodiazol-1-yl)-N-(4-iodophenyl)piperidine-1-carboxamide The title compound was synthesized using General procedure D from 4-ethoxy-1-(piperidin-4-yl)-2,3-dihydro-1H-1,3-benzodiazol-2-one;2,2,2-trifluoroacetic acid and 4-iodophenyl isocyanate. LCMS [M+H]$^+$ 507. $^1$H-NMR (400 MHz, DMSO-d$_6$) δ ppm 10.92 (br. s., 1H), 8.71 (br. s., 1H), 7.54-7.60 (m, 2H), 7.34-7.39 (m, 2H), 6.89-6.96 (m, 1H), 6.82-6.87 (m, 1H), 6.66-6.71 (m, 1H), 4.33-4.43 (m, 1H), 4.24-4.33 (m, 2H), 4.08-4.16 (m, 2H), 2.87-3.00 (m, 2H), 2.18-2.35 (m, 2H), 1.67-1.76 (m, 2H), 1.34 (br. t, J=6.5, 6.5 Hz, 3H).

Example 19: N-(4-iodophenyl)-4-[4-(methylamino)-2-oxo-2,3-dihydro-1H-1,3-benzodiazol-1-yl]piperidine-1-carboxamide The title compound was synthesized using General procedure D from 4-methylamino-1-(piperidin-4-yl)-2,3-dihydro-1H-1,3-benzodiazol-2-one;2,2,2-trifluoroacetic acid and 4-iodophenyl isocyanate. LCMS [M+H]$^+$ 492. $^1$H-NMR (400 MHz, DMSO-d6) δ ppm 10.21 (s, 1H), 8.70 (s, 1H), 7.55-7.59 (m, 2H), 7.34-7.38 (m, 2H), 6.85 (t, J=8.1 Hz, 1H), 6.55 (d, J=8.1 Hz, 1H), 6.27 (d, J=8.1 Hz, 1H), 4.99 (q, J=5.2 Hz, 1H), 4.31-4.38 (m, 1H), 4.27 (m, 2H), 2.88-2.98 (m, 2H), 2.79 (d, J=5.2 Hz, 3H), 2.20-2.32 (m, 2H), 1.66-1.74 (m, 2H).

Example 20: 4-(4-Amino-2-oxo-2,3-dihydro-1H-1,3-benzodiazol-1-yl)-N-(4-iodophenyl)piperidine-1-carboxamide The title compound was synthesized using General procedure D from 4-amino-1-(piperidin-4-yl)-2,3-dihydro-1H-1,3-benzodiazol-2-one;2,2,2-trifluoroacetic acid and 4-iodophenyl isocyanate. LCMS [M+H]$^+$ 478. $^1$H-NMR (400 MHz, DMSO-d6) δ ppm 10.27 (s, 1H), 8.69 (s, 1H), 7.54-7.59 (m, 2H), 7.32-7.38 (m, 2H), 6.72 (t, J=8.0 Hz, 1H), 6.46 (d, J=8.0 Hz, 1H), 6.30 (dd, J=8.1, 0.8 Hz, 1H), 4.91 (s, 2H), 4.22-4.37 (m, 3H), 2.86-2.97 (m, 2H), 2.18-2.31 (m, 2H), 1.65-1.73 (m, 2H).

Example 21: 4-(4-Dimethylamino-2-oxo-2,3-dihydro-1H-1,3-benzodiazol-1-yl)-N-(4-iodophenyl)piperidine-1-carboxamide The title compound was synthesized using General procedure D from 4-dimethylamino-1-(piperidin-4-yl)-2,3-dihydro-1H-1,3-benzodiazol-2-one;2,2,2-trifluoroacetic acid and 4-iodophenyl isocyanate. LCMS [M+H]$^+$ 506. $^1$H-NMR (400 MHz, DMSO-d$_6$) δ ppm 10.77 (s, 1H), 8.71 (s, 1H), 7.54-7.60 (m, 2H), 7.34-7.39 (m, 2H), 6.92 (t, J=7.9 Hz, 1H), 6.84-6.87 (m, 1H), 6.60 (dd, J=7.9, 0.9 Hz, 1H), 4.33-4.42 (m, 1H), 4.25-4.32 (m, 2H), 2.89-2.98 (m, 2H), 2.69 (s, 6H), 2.22-2.35 (m, 2H), 1.68-1.76 (m, 2H).

Example 22: N-(4-iodophenyl)-4-[2-oxo-4-(1H-pyrazol-1-yl)-2,3-dihydro-1H-1,3-benzodiazol-1-yl]piperidine-1-carboxamide The title compound was synthesized using General procedure D from 1-(piperidin-4-yl)-4-(1H-pyrazol-1-yl)-2,3-dihydro-1H-1,3-benzodiazol-2-one;2,2,2-trifluoroacetic acid and 4-iodophenyl isocyanate. LCMS [M+H]$^+$ 529.

Example 23: N-(4-iodophenyl)-4-[2-oxo-4-(1H-1,2,4-triazol-1-yl)-2,3-dihydro-1H-1,3-benzodiazol-1-yl]piperidine-1-carboxamide The title compound was synthesized using General procedure D from 1-(piperidin-4-yl)-4-(1H-1,2,4-triazol-1-yl)-2,3-dihydro-1H-1,3-benzodiazol-2-one;2,2,2-trifluoroacetic acid and 4-iodophenyl isocyanate. LCMS [M+H]$^+$ 530. $^1$H-NMR (400 MHz, DMSO-d6) δ ppm 11.02 (br. s., 1H), 9.11 (s, 1H), 8.72 (s, 1H), 8.27 (s, 1H), 7.55-7.60 (m, 2H), 7.34-7.40 (m, 3H), 7.32 (dd, J=8.1, 0.9 Hz, 1H), 7.16 (t, J=8.2 Hz, 1H), 4.41-4.53 (m, 1H), 4.26-4.35 (m, 2H), 2.92-3.02 (m, 2H), 2.25-2.38 (m, 2H), 1.73-1.82 (m, 2H).

Example 24: N-(4-iodophenyl)-4-[4-(methylsulfanyl)-2-oxo-2,3-dihydro-1H-1,3-benzodiazol-1-yl]piperidine-1-carboxamide The title compound was synthesized using General procedure D from 4-methylsulfanyl-1-(piperidin-4-yl)-2,3-dihydro-1H-1,3-benzodiazol-2-one;2,2,2-trifluoroacetic acid and 4-iodophenyl isocyanate. LCMS [M+H]$^+$ 509. $^1$H-NMR (400 MHz, DMSO-d6) δ ppm 11.06 (br. s., 1H), 8.71 (br. s., 1H), 7.54-7.61 (m, 2H), 7.34-7.40 (m, 2H), 7.12 (dd, J=3.0, 2.4 Hz, 1H), 6.96-7.04 (m, 2H), 4.34-4.46 (m, 1H), 4.24-4.33 (m, 2H), 2.88-3.00 (m, 2H), 2.45 (s, 3H), 2.21-2.36 (m, 2H), 1.68-1.78 (m, 2H).

Example 25: N-(4-iodophenyl)-4-[2-oxo-4-(1H-pyrrol-2-yl)-2,3-dihydro-1H-1,3-benzodiazol-1-yl]piperidine-1-carboxamide Step 1: A mixture of tert-butyl 4-(4-bromo-2-oxo-2,3-dihydro-1H-1,3-benzodiazol-1-yl)piperidine-1-carboxylate (1.0 equiv.), potassium {1-[(tert-butoxy)carbonyl]-1H-pyrrol-2-yl}trifluoroboranuide (1.5 equiv.), Pd(OAc)$_2$ (0.10 equiv.), 2-Dicyclohexylphosphino-2',6'-dimethoxybiphenyl (0.20 equiv.), and Na$_2$CO$_3$ (2.0 equiv.) was stirred in ethanol at reflux for 5 h. The mixture was then concentrated and purified by silica gel chromatography which afforded tert-butyl 4-(4-{1-[(tert-butoxy)carbonyl]-1H-pyrrol-2-yl}-2-oxo-2,3-dihydro-1H-1,3-benzodiazol-1-yl)piperidine-1-carboxylate. LCMS [M-isobutene+H]$^+$ 383.

Step 2: 1-(piperidin-4-yl)-4-(1H-pyrrol-2-yl)-2,3-dihydro-1H-1,3-benzodiazol-2-one;2,2,2-trifluoroacetic acid was synthesized using General procedure C from tert-butyl 4-(4-{1-[(tert-butoxy)carbonyl]-1H-pyrrol-2-yl}-2-oxo-2,3-dihydro-1H-1,3-benzodiazol-1-yl)piperidine-1-carboxylate. LCMS [M+H]$^+$ 283.

Step 3: The title compound was synthesized using General procedure D from 1-(piperidin-4-yl)-4-(1H-pyrrol-2-yl)-2,3-dihydro-1H-1,3-benzodiazol-2-one;2,2,2-trifluoroacetic acid and 4-iodophenyl isocyanate. LCMS [M+H]$^+$ 528. $^1$H-NMR (400 MHz, DMSO-d6) δ ppm 11.19 (br. s., 1H), 10.62 (s, 1H), 8.72 (s, 1H), 7.55-7.60 (m, 2H), 7.35-7.40 (m, 2H), 7.21 (dd, J=7.9, 1.1 Hz, 1H), 7.08-7.12 (m, 1H), 7.04 (t, J=7.9 Hz, 1H), 6.88 (td, J=2.7, 1.3 Hz, 1H), 6.64 (td, J=3.0, 1.6 Hz, 1H), 6.16 (dt, J=3.5, 2.4 Hz, 1H), 4.38-4.49 (m, 1H), 4.27-4.35 (m, 2H), 2.91-3.01 (m, 2H), 2.27-2.39 (m, 2H), 1.71-1.80 (m, 2H).

Example 26: N-(4-iodophenyl)-4-[2-oxo-4-(pyridin-3-yl)-2,3-dihydro-1H-1,3-benzodiazol-1-yl]piperidine-1-carboxamide The title compound was synthesized using General procedure D from 1-(piperidin-4-yl)-4-(pyridin-3-yl)-2,3-dihydro-1H-1,3-benzodiazol-2-one;2,2,2-trifluoroacetic acid and 4-iodophenyl isocyanate. LCMS [M+H]$^+$ 540. $^1$H-NMR (400 MHz, DMSO-d6) δ ppm 11.10 (s, 1H), 8.71-8.74 (m, 2H), 8.59 (dd, J=4.9, 1.7 Hz, 1H), 7.94 (ddd, J=7.9, 2.2, 1.6 Hz, 1H), 7.55-7.60 (m, 2H), 7.49 (ddd, J=7.9, 4.9, 0.8 Hz, 1H), 7.35-7.40 (m, 2H), 7.31 (br. d, J=7.9 Hz, 1H), 7.14 (t, J=7.9 Hz, 1H), 7.06 (dd, J=7.9, 1.0 Hz, 1H), 4.41-4.51 (m, 1H), 4.27-4.35 (m, 2H), 2.92-3.02 (m, 2H), 2.27-2.40 (m, 2H), 1.73-1.81 (m, 2H).

Example 27: 4-(4-Bromo-2-oxo-2,3-dihydro-1H-1,3-benzodiazol-1-yl)-N-(3,4-dichlorophenyl)piperidine-1-carboxamide The title compound was synthesized using General procedure D from 4-bromo-1-(piperidin-4-yl)-2,3-dihydro-1H-1,3-benzodiazol-2-one;2,2,2-trifluoroacetic acid and 3,4-dichlorophenyl isocyanate. LCMS [M+H]$^+$ 483.

Example 28: N-(3,4-dichlorophenyl)-4-{4-[6-(hydroxymethyl)pyridin-3-yl]-2-oxo-2,3-dihydro-1H-1,3-benzodiazol-1-yl}piperidine-1-carboxamide The title compound was synthesized using General procedure E from 4-(4-bromo-2-oxo-2,3-dihydro-1H-1,3-benzodiazol-1-yl)-N-(3,4-dichlorophenyl)piperidine-1-carboxamide and [6-(hydroxymethyl)-3-pyridyl]boronic acid. LCMS [M+H]$^+$ 512. $^1$H-NMR (400 MHz, DMSO-d$_6$) δ ppm 11.22 (s, 1H), 8.90 (s, 1H), 8.79 (d, J=1.6 Hz, 1H), 8.30 (dd, J=8.2, 1.9 Hz, 1H), 7.89 (t, J=1.3 Hz, 1H), 7.81 (d, J=8.2 Hz, 1H), 7.49 (d, J=1.6 Hz, 2H), 7.36 (d, J=7.9 Hz, 1H), 7.16 (t, J=7.6 Hz, 1H), 7.11 (dd, J=7.9, 0.9 Hz, 1H), 4.78 (s, 2H), 4.47 (ddt, J=16.3, 8.1, 3.9, 3.9 Hz, 1H), 4.31 (m, 2H), 2.99 (m, 2H), 2.26-2.39 (m, 2H), 1.73-1.81 (m, 2H).

Example 29: 4-[4-(3-Aminophenyl)-2-oxo-2,3-dihydro-1H-1,3-benzodiazol-1-yl]-N-(3,4-dichlorophenyl)piperidine-1-carboxamide The title compound was synthesized using General procedure E from 4-(4-bromo-2-oxo-2,3-dihydro-1H-1,3-benzodiazol-1-yl)-N-(3,4-dichlorophenyl)piperidine-1-carboxamide and 3-aminophenylboronic acid. LCMS [M+H]$^+$ 496. $^1$H-NMR (400 MHz, DMSO-d6) δ ppm 10.71 (br. s., 1H), 8.90 (s, 1H), 7.90 (t, J=1.3 Hz, 1H), 7.50 (d, J=1.6 Hz, 2H), 7.19-7.23 (m, 1H), 7.11 (t, J=7.7 Hz, 1H), 7.06 (t, J=7.9 Hz, 1H), 6.96-6.99 (m, 1H), 6.73 (t, J=1.9 Hz, 1H), 6.65-6.69 (m, 1H), 6.58 (ddd, J=8.0, 2.1, 0.9 Hz, 1H), 5.11 (s, 2H), 4.40-4.50 (m, 1H), 4.28-4.35 (m, 2H), 2.94-3.03 (m, 2H), 2.27-2.40 (m, 2H), 1.73-1.82 (m, 2H).

Example 30: 4-[4-(2-Hydroxyethyl)-2-oxo-2,3-dihydro-1H-1,3-benzodiazol-1-yl]-N-(4-iodophenyl)piperidine-1-carboxamide Step 1: A mixture of tert-butyl 4-[4-(2-methoxy-2-oxoethyl)-2-oxo-3H-benzimidazol-1-yl]piperidine-1-carboxylate (1.0 equiv.) and NaBH$_4$ (4.0 equiv.) in THF was stirred at 20° C. for 16 h. The mixture was then poured into NaHCO$_3$ and extracted with DCM×3. The combined organics were concentrated and purified by silica gel chromatography which afforded tert-butyl 4-[4-(2-hydroxyethyl)-2-oxo-2,3-dihydro-1H-1,3-benzodiazol-1-yl]piperidine-1-carboxylate. LCMS [M+H]$^+$ 362. $^1$H-NMR (400 MHz, CHLOROFORM-d) δ ppm 10.36 (s, 1H), 6.99-7.06 (m, 2H), 6.91 (dd, J=7.0, 1.9 Hz, 1H), 4.45 (tt, J=12.4, 4.0 Hz, 1H), 4.32 (d, J=12.0 Hz, 2H), 3.96 (t, J=5.8 Hz, 2H), 3.00 (t, J=5.8 Hz, 2H), 2.87 (m, 2H), 2.33 (m, 2H), 1.79-1.86 (m, 2H), 1.52 (s, 9H).

Step 2: 4-(2-hydroxyethyl)-1-(4-piperidyl)-1H-benzimidazol-2-one;2,2,2-trifluoroacetic acid was synthesized using General procedure C from tert-butyl 4-[4-(2-hydroxyethyl)-2-oxo-2,3-dihydro-1H-1,3-benzodiazol-1-yl]piperidine-1-carboxylate. LCMS [M+H]$^+$ 262.

Step 3: The title compound was synthesized using General procedure D from 4-(2-hydroxyethyl)-1-(4-piperidyl)-1H-benzimidazol-2-one;2,2,2-trifluoroacetic acid and 4-iodophenyl isocyanate. LCMS [M+H]$^+$ 507. $^1$H-NMR (400 MHz, DMSO-d$_6$) δ ppm 8.71 (s, 1H), 7.54-7.60 (m, 2H), 7.34-7.39 (m, 2H), 7.05 (dd, J=7.9, 0.9 Hz, 1H), 6.91 (t, J=7.9 Hz, 1H), 6.83 (br. d, J=7.9 Hz, 1H), 4.34-4.44 (m, 1H), 4.25-4.33 (m, 2H), 3.61 (t, J=6.8 Hz, 2H), 2.89-2.99 (m, 2H), 2.79 (t, J=6.8 Hz, 2H), 2.21-2.35 (m, 2H), 1.68-1.76 (m, 2H).

Example 31: 4-(4-Cyclopropyl-2-oxo-2,3-dihydro-1H-1,3-benzodiazol-1-yl)-N-(4-iodophenyl)piperidine-1-carboxamide Step 1: tert-butyl 4-(4-cyclopropyl-2-oxo-2,3-dihydro-1H-1,3-benzodiazol-1-yl)piperidine-1-carboxylate was synthesized using General procedure E from tert-butyl 4-(4-bromo-2-oxo-2,3-dihydro-1H-1,3-benzodiazol-1-yl)piperidine-1-carboxylate and cyclopropylboronic acid.
LCMS [M-isobutene+H]$^+$ 302.

Step 2: 4-cyclopropyl-1-(piperidin-4-yl)-2,3-dihydro-1H-1,3-benzodiazol-2-one was synthesized using General procedure C from tert-butyl 4-(4-cyclopropyl-2-oxo-2,3-dihydro-1H-1,3-benzodiazol-1-yl)piperidine-1-carboxylate. LCMS [M+H]$^+$ 258.

Step 3: The title compound was synthesized using General procedure D from 4-cyclopropyl-1-(piperidin-4-yl)-2,3-dihydro-1H-1,3-benzodiazol-2-one and 4-iodophenyl isocyanate.
LCMS [M+H]$^+$ 503. $^1$H-NMR (400 MHz, DMSO-d$_6$) δ ppm 8.71 (s, 1H), 7.54-7.59 (m, 2H), 7.34-7.39 (m, 2H), 7.01 (d, J=7.9 Hz, 1H), 6.89 (t, J=7.9 Hz, 1H), 6.50 (d, J=7.9 Hz, 1H), 4.34-4.44 (m, 1H), 4.25-4.33 (m, 2H), 2.90-2.99 (m, 2H), 2.22-2.35 (m, 2H), 1.99-2.07 (m, 1H), 1.69-1.77 (m, 2H), 0.91-0.97 (m, 2H), 0.64-0.70 (m, 2H).

Example 32: N-(3,4-dichlorophenyl)-4-[2-oxo-4-(pyridin-4-yl)-2,3-dihydro-1H-1,3-benzodiazol-1-yl]piperidine-1-carboxamide The title compound was synthesized using General procedure E from 4-(4-bromo-2-oxo-2,3-dihydro-1H-1,3-benzodiazol-1-yl)-N-(3,4-dichlorophenyl)piperidine-1-carboxamide and 4-pyridineboronic acid pinacol ester.
LCMS [M+H]$^+$ 482.

Example 33: 4-{4-[4-(Aminomethyl)phenyl]-2-oxo-2,3-dihydro-1H-1,3-benzodiazol-1-yl}-N-(3,4-dichlorophenyl)piperidine-1-carboxamide The title compound was synthesized using General procedure E from 4-(4-bromo-2-oxo-2,3-dihydro-1H-1,3-benzodiazol-1-yl)-N-(3,4-dichlorophenyl)piperidine-1-carboxamide and 4-aminomethylphenylboronic acid; hydrochloride. LCMS [M+H]$^+$ 510.

Example 34: 4-(4-Bromo-2-oxo-2,3-dihydro-1H-1,3-benzodiazol-1-yl)-N-(4-iodophenyl)azepane-1-carboxamide The title compound was synthesized using General procedure D from 1-(azepan-4-yl)-4-bromo-2,3-dihydro-1H-1,3-benzodiazol-2-one;2,2,2-trifluoroacetic acid and 4-iodophenyl isocyanate. LCMS [M+H]$^+$ 555. $^1$H-NMR (400 MHz, DMSO-d$_6$) δ ppm 11.29 (s, 1H), 8.40 (s, 1H), 7.57 (d, J=8.5 Hz, 2H), 7.40 (d, J=8.8 Hz, 2H), 7.23 (d, J=8.0 Hz, 1H), 7.16 (d, J=8.0 Hz, 1H), 6.94 (t, J=8.0 Hz, 1H), 4.31 (br. s., 1H), 3.65-3.81 (m, 2H), 3.41-3.51 (m, 2H), 2.25-2.40 (m, 2H), 1.87-2.00 (m, 2H), 1.66-1.84 (m, 2H).

Example 35: 4-(1-{1-[(3,4-Dichlorophenyl)carbamoyl]piperidin-4-yl}-2-oxo-2,3-dihydro-1H-1,3-benzodiazol-4-yl)benzoic acid The title compound was synthesized using General procedure E from 4-(4-bromo-2-oxo-2,3-dihydro-1H-1,3-benzodiazol-1-yl)-N-(3,4-dichlorophenyl)piperidine-1-carboxamide and 4-carboxyphenylboronic acid. LCMS [M+H]$^+$ 525.

Example 36: N-(3,4-dichlorophenyl)-4-(4-{4-[2-(dimethylamino)ethoxy]phenyl}-2-oxo-2,3-dihydro-1H-1,3-benzodiazol-1-yl)piperidine-1-carboxamide The title compound was synthesized using General procedure E from 4-(4-bromo-2-oxo-2,3-dihydro-1H-1,3-benzodiazol-1-yl)-N-(3,4-dichlorophenyl)piperidine-1-carboxamide and (4-[2-(dimethylamino)ethoxy]phenyl)boronic acid. LCMS [M+H]$^+$ 568.

Example 37: N-(3,4-dichlorophenyl)-4-[2-oxo-4-(pyrimidin-5-yl)-2,3-dihydro-1H-1,3-benzodiazol-1-yl]piperidine-1-carboxamide The title compound was synthesized using General procedure E from 4-(4-bromo-2-oxo-2,3-dihydro-1H-1,3-benzodiazol-1-yl)-N-(3,4-dichlorophenyl)piperidine-1-carboxamide and (pyrimidin-5-yl)boronic acid.
LCMS [M+H]$^+$ 483.

Example 38: 4-{4-[3,5-Bis(trifluoromethyl)phenyl]-2-oxo-2,3-dihydro-1H-1,3-benzodiazol-1-yl}-N-(3,4-dichlorophenyl)piperidine-1-carboxamide The title compound was synthesized using General procedure E from 4-(4-bromo-2-oxo-2,3-dihydro-1H-1,3-benzodiazol-1-yl)-N-(3,4-dichlorophenyl)piperidine-1-carboxamide and [3,5-bis(trifluoromethyl)phenyl]boronic acid.
LCMS [M+H]$^+$ 617.

Example 39: 4-[4-(6-Aminopyridin-3-yl)-2-oxo-2,3-dihydro-1H-1,3-benzodiazol-1-yl]-N-(3,4-dichlorophenyl)piperidine-1-carboxamide The title compound was synthesized using General procedure E from 4-(4-bromo-2-oxo-2,3-dihydro-1H-1,3-benzodiazol-1-yl)-N-(3,4-dichlorophenyl)piperidine-1-carboxamide and (6-aminopyridin-3-yl)boronic acid.
LCMS [M+H]$^+$ 497.

Example 40: N-(3,4-dichlorophenyl)-4-{2-oxo-4-[4-(2,2,2-trifluoroacetyl)phenyl]-2,3-dihydro-1H-1,3-benzodiazol-1-yl}piperidine-1-carboxamide The title compound was synthesized according to General procedure E from 4-(4-bromo-2-oxo-2,3-dihydro-1H-1,3-benzodiazol-1-yl)-N-(3,4-dichlorophenyl)piperidine-1-carboxamide and [4-(2,2,2-trifluoroacetyl)phenyl]boronic acid. LCMS [M+H]$^+$ 577.

Example 41: 4-[4-(4-Bromo-1H-pyrazol-1-yl)-2-oxo-2,3-dihydro-1H-1,3-benzodiazol-1-yl]-N-(4-iodophenyl)piperidine-1-carboxamide The title compound was synthesized according to General procedure D from 4-(4-bromo-1H-pyrazol-1-yl)-1-(piperidin-4-yl)-2,3-dihydro-1H-1,3-benzodiazol-2-one; 2,2,2-trifluoroacetic acid and 4-iodophenyl isocyanate.
LCMS [M+H]$^+$ 607. $^1$H-NMR (400 MHz, DMSO-d$_6$) δ ppm 10.82 (br. s., 1H), 8.72 (s, 1H), 8.66 (s, 1H), 7.89 (s, 1H), 7.55-7.60 (m, 2H), 7.35-7.39 (m, 2H), 7.26-7.32 (m, 2H), 7.09-7.15 (m, 1H), 4.41-4.52 (m, 1H), 4.26-4.35 (m, 2H), 2.91-3.01 (m, 2H), 2.25-2.38 (m, 2H), 1.72-1.81 (m, 2H).

Example 42: 4-(4-Bromo-2-oxo-2,3-dihydro-1H-1,3-benzodiazol-1-yl)-N-(4-ethylphenyl)piperidine-1-carboxamide The title compound was synthesized according to General procedure D from 4-bromo-1-(piperidin-4-yl)-2,3-dihydro-1H-1,3-benzodiazol-2-one; 2,2,2-trifluoroacetic acid and 4-ethylphenyl isocyanate. LCMS [M+H]$^+$ 443. $^1$H-NMR (400 MHz, DMSO-d$_6$) δ ppm 11.31 (br. s., 1H), 8.51 (s, 1H), 7.36-7.41 (m, 2H), 7.25 (d, J=8.1 Hz, 1H), 7.17 (d, J=8.1 Hz, 1H), 7.08 (d, J=8.8 Hz, 2H), 6.96 (t, J=8.1 Hz, 1H), 4.40 (ddt, J=12.3, 8.2, 4.0, 4.0 Hz, 1H), 4.30 (m, 2H), 2.88-2.97 (m, 2H), 2.53-2.58 (m, 2H), 2.20-2.33 (m, 2H), 1.70-1.78 (m, 2H), 1.16 (t, J=7.6 Hz, 3H).

Example 43: 4-(4-Bromo-2-oxo-2,3-dihydro-1H-1,3-benzodiazol-1-yl)-N-(4-methylphenyl)piperidine-1-carboxamide The title compound was synthesized according to General procedure D from 4-bromo-1-(piperidin-4-yl)-2,3-dihydro-1H-1,3-benzodiazol-2-one; 2,2,2-trifluoroacetic acid and 4-methylphenyl isocyanate. LCMS [M+H]$^+$ 429. $^1$H-NMR (400 MHz, DMSO-d$_6$) δ ppm 11.31 (br. s., 1H), 8.49 (s, 1H), 7.35-7.39 (m, 2H), 7.25 (d, J=8.1 Hz, 1H), 7.17 (dd, J=8.1, 0.6 Hz, 1H), 7.05 (dd, J=8.8, 0.6 Hz, 2H), 6.96 (t, J=8.1 Hz, 1H), 4.34-4.45 (m, 1H), 4.26-4.33 (m, 2H), 2.87-2.97 (m, 2H), 2.20-2.33 (m, 5H), 1.70-1.78 (m, 2H).

Example 44: 4-(4-Bromo-2-oxo-2,3-dihydro-1H-1,3-benzodiazol-1-yl)-N-(4-methoxyphenyl)piperidine-1-carboxamide The title compound was synthesized according to General procedure D from 4-bromo-1-(piperidin-4-yl)-2,3-dihydro-1H-1,3-benzodiazol-2-one; 2,2,2-trifluoroacetic acid and 4-methoxyphenyl isocyanate. LCMS [M+H]$^+$ 445. $^1$H-NMR (400 MHz, DMSO-d$_6$) δ ppm 11.31 (br. s., 1H), 8.43 (s, 1H), 7.35-7.41 (m, 2H), 7.23-7.27 (m, 1H), 7.17 (dd, J=8.2, 0.9 Hz, 1H), 6.96 (t, J=8.1 Hz, 1H), 6.81-6.87 (m, 2H), 4.34-4.44 (m, 1H), 4.24-4.33 (m, 2H), 3.72 (s, 3H), 2.87-2.97 (m, 2H), 2.20-2.32 (m, 2H), 1.69-1.79 (m, 2H).

Example 45: 4-(4-Bromo-2-oxo-2,3-dihydro-1H-1,3-benzodiazol-1-yl)-N-(3,4-dimethoxyphenyl)piperidine-1-carboxamide The title compound was synthesized according to General procedure D from 4-bromo-1-(piperidin-4-yl)-2,3-dihydro-1H-1,3-benzodiazol-2-one; 2,2,2-trifluoroacetic acid and 3,4-dimethoxyphenyl isocyanate. LCMS [M+H]$^+$ 475. $^1$H-NMR (400 MHz, DMSO-d$_6$) δ ppm 11.31 (br. s., 1H), 8.43 (br. s., 1H), 7.23-7.29 (m, 1H), 7.14-7.22 (m, 2H), 6.99-7.04 (m, 1H), 6.93-6.99 (m, 1H), 6.82-6.86 (m, 1H), 4.35-4.45 (m, 1H), 4.25-4.33 (m, 2H), 3.72 (s, 3H), 3.71 (br. s., 3H), 2.86-2.98 (m, 2H), 2.19-2.36 (m, 2H), 1.75 (m, 2H).

Example 46: 4-(4-Bromo-2-oxo-2,3-dihydro-1H-1,3-benzodiazol-1-yl)-N-(3-chloro-4-methoxyphenyl)piperidine-1-carboxamide The title compound was synthesized according to General procedure D from 4-bromo-1-(piperidin-4-yl)-2,3-dihydro-1H-1,3-benzodiazol-2-one; 2,2,2-trifluoroacetic acid and 3-chloro-4-methoxyphenyl isocyanate. LCMS [M+H]$^+$ 479. $^1$H-NMR (400 MHz, DMSO-d$_6$) δ ppm 11.31 (br. s., 1H), 8.58 (s, 1H), 7.65 (d, J=2.5 Hz, 1H), 7.38 (dd, J=9.0, 2.5 Hz, 1H), 7.27 (br. d, J=8.1 Hz, 1H), 7.17 (dd, J=8.1, 0.6 Hz, 1H), 7.06 (d, J=9.0 Hz, 1H), 6.96 (t, J=8.1 Hz, 1H), 4.35-4.45 (m, 1H), 4.28 (m, 2H), 3.81 (s, 3H), 2.89-2.98 (m, 2H), 2.20-2.32 (m, 2H), 1.71-1.79 (m, 2H).

Example 47: N-(2H-1,3-benzodioxol-5-yl)-4-(4-bromo-2-oxo-2,3-dihydro-1H-1,3-benzodiazol-1-yl)piperidine-1-carboxamide The title compound was synthesized according to General procedure D from 4-bromo-1-(piperidin-4-yl)-2,3-dihydro-1H-1,3-benzodiazol-2-one; 2,2,2-trifluoroacetic acid and 5-isocyanato-2H-1,3-benzodioxole. LCMS [M+H]$^+$ 459. $^1$H-NMR (400 MHz, DMSO-d$_6$) δ ppm 11.31 (br. s., 1H), 8.48 (s, 1H), 7.26 (dd, J=8.1, 0.9 Hz, 1H), 7.18 (d, J=2.1 Hz, 1H), 7.17 (dd, J=8.1, 0.9 Hz, 1H), 6.96 (t, J=8.1 Hz, 1H), 6.87 (dd, J=8.3, 2.1 Hz, 1H), 6.80 (d, J=8.3 Hz, 1H), 5.96 (s, 2H), 4.34-4.44 (m, 1H), 4.23-4.32 (m, 2H), 2.86-2.97 (m, 2H), 2.19-2.32 (m, 2H), 1.69-1.79 (m, 2H).

Example 48: 4-(4-Bromo-2-oxo-2,3-dihydro-1H-1,3-benzodiazol-1-yl)-N-(4-bromo-3-methylphenyl)piperidine-1-carboxamide The title compound was synthesized according to General procedure D from 4-bromo-1-(piperidin-4-yl)-2,3-dihydro-1H-1,3-benzodiazol-2-one; 2,2,2-trifluoroacetic acid and 4-bromo-3-methylphenyl isocyanate. LCMS [M+H]$^+$ 507. $^1$H-NMR (400 MHz, DMSO-d$_6$) δ ppm 11.32 (s, 1H), 8.66 (s, 1H), 7.51 (d, J=2.7 Hz, 1H), 7.42 (d, J=8.7 Hz, 1H), 7.31 (dd, J=8.7, 2.7 Hz, 1H), 7.26 (dd, J=8.1, 0.6 Hz, 1H), 7.17 (dd, J=8.1, 0.7 Hz, 1H), 6.96 (t, J=8.1 Hz, 1H), 4.40 (tt, J=12.2, 3.9 Hz, 1H), 4.25-4.34 (m, 2H), 2.89-2.99 (m, 2H), 2.30 (s, 3H), 2.20-2.30 (m, 2H), 1.71-1.79 (m, 2H).

Example 49: 4-(4-Bromo-2-oxo-2,3-dihydro-1H-1,3-benzodiazol-1-yl)-N-(4-bromo-3-chlorophenyl)piperidine-1-carboxamide The title compound was synthesized according to General procedure I from 4-bromo-1-(piperidin-4-yl)-2,3-dihydro- 1H-1,3-benzodiazol-2-one; 2,2,2-trifluoroacetic acid and 4-bromo-3-chloroaniline. LCMS [M+H]+ 527.

Example 50: 4-(4-Bromo-2-oxo-2,3-dihydro-1H-1,3-benzodiazol-1-yl)-N-(4-iodo-3-methylphenyl)piperidine-1-carboxamide The title compound was synthesized according to General procedure I from 4-bromo-1-(piperidin-4-yl)-2,3-dihydro-1H-1,3-benzodiazol-2-one; 2,2,2-trifluoroacetic acid and 4-iodo-3-methylaniline. LCMS [M+H]+ 555. $^1$H-NMR (400 MHz, DMSO-d$_6$) δ ppm 11.31 (br. s., 1H), 8.64 (s, 1H), 7.65 (d, J=8.8 Hz, 1H), 7.51 (d, J=2.5 Hz, 1H), 7.26 (br. d, J=8.1 Hz, 1H), 7.13-7.19 (m, 3H), 6.96 (t, J=8.1 Hz, 1H), 4.35-4.45 (m, 1H), 4.24-4.33 (m, 2H), 2.89-2.99 (m, 2H), 2.32 (s, 3H), 2.20-2.31 (m, 2H), 1.70-1.79 (m, 2H).

Example 51: 4-(4-bromo-2-oxo-2,3-dihydro-1H-1,3-benzodiazol-1-yl)-N-(3,4-dichlorophenyl)-3-trans-hydroxypiperidine-1-carboxamide The title compound was synthesized according to General procedure D from 4-bromo-1-(3-hydroxypiperidin-4-yl)-2,3-dihydro-1H-1,3-benzodiazol-2-one; 2,2,2-trifluoroacetic acid and 3,4-dichlorophenyl isocyanate. LCMS [M+H]+ 501. $^1$H-NMR (400 MHz, DMSO-d$_6$) δ ppm 11.25 (br. s., 1H), 8.94 (s, 1H), 7.89 (dd, J=1.6, 0.9 Hz, 1H), 7.49-7.50 (m, 2H), 7.22 (br. d, J=8.1 Hz, 1H), 7.15 (br. d, J=8.1 Hz, 1H), 6.94 (t, J=8.1 Hz, 1H), 5.32 (d, J=5.1 Hz, 1H), 4.30-4.38 (m, 1H), 4.05-4.25 (m, 3H), 2.90-3.00 (m, 1H), 2.63-2.71 (m, 1H), 2.28-2.36 (m, 1H), 1.74-1.82 (m, 1H).

Example 52: 4-(5-Hydroxy-2-oxo-2,3-dihydro-1H-1,3-benzodiazol-1-yl)-N-(4-iodophenyl)piperidine-1-carboxamide Step 1: tert-butyl 4-(4-hydroxy-2-nitro-anilino)piperidine-1-carboxylate was synthesized according to General procedure A from tert-butyl 4-amino-piperidine-1-carboxylate and 4-fluoro-3-nitrophenol. LCMS [M-isobutene+H]+ 282.

Step 2: tert-butyl 4-(4-hydroxy-2-nitro-anilino)piperidine-1-carboxylate (1.0 equiv.) was dissolved in THF, then NaH (60 wt % in mineral oil, 1.1 equiv.) was added and the resulting mixture was stirred at 20° C. for 2 min under a stream of N$_2$. Thereafter acetic anhydride (1.2 equiv.) was added and the resulting mixture was stirred at 20° C. in a sealed tube. After complete reaction, the mixture was poured into NaHCO$_3$ (aq.) and extracted with DCM×3. The combined organics were concentrated and purified by silica gel chromatography which afforded tert-butyl 4-(4-acetoxy-2-nitro-anilino)piperidine-1-carboxylate. LCMS [M-isobutene+H]+ 324.

Step 3: tert-butyl 4-[5-(acetyloxy)-2-oxo-2,3-dihydro-1H-1,3-benzodiazol-1-yl]piperidine-1-carboxylate was synthesized according to General procedure B from tert-butyl 4-(4-acetoxy-2-nitro-anilino)piperidine-1-carboxylate. LCMS [M-isobutene+H]+ 320.

Step 4: A mixture of tert-butyl 4-[5-(acetyloxy)-2-oxo-2,3-dihydro-1H-1,3-benzodiazol-1-yl]piperidine-1-carboxylate and NaHCO$_3$ (aq.) was stirred in MeOH at 20° C. for 16 h.

After complete reaction, the mixture was poured into NaHCO$_3$ (aq.) and extracted with DCM×3. The combined organics were concentrated and purified by silica gel chromatography which afforded N-tert-butyl-4-(5-hydroxy-2-oxo-2,3-dihydro-1H-1,3-benzodiazol-1-yl)piperidine-1-carboxamide. LCMS [M-isobutene+H]+ 278.

Step 5: 5-hydroxy-1-(piperidin-4-yl)-2,3-dihydro-1H-1,3-benzodiazol-2-one; 2,2,2-trifluoroacetic acid was synthesized according to General procedure C from N-tert-butyl-4-(5-hydroxy-2-oxo-2,3-dihydro-1H-1,3-benzodiazol-1-yl)piperidine-1-carboxamide. LCMS [M+H]+ 234.

Step 6: The title compound was synthesized according to General procedure D from 5-hydroxy-1-(piperidin-4-yl)-2,3-dihydro-1H-1,3-benzodiazol-2-one;2,2,2-trifluoroacetic acid and 4-iodophenyl isocyanate. LCMS [M+H]+ 479. $^1$H-NMR (400 MHz, DMSO-d$_6$) δ ppm 10.60 (s, 1H), 9.00 (s, 1H), 8.69 (s, 1H), 7.54-7.59 (m, 2H), 7.34-7.38 (m, 2H), 6.97 (d, J=8.5 Hz, 1H), 6.43 (d, J=2.5 Hz, 1H), 6.39 (dd, J=8.5, 2.5 Hz, 1H), 4.21-4.37 (m, 3H), 2.86-2.97 (m, 2H), 2.14-2.28 (m, 2H), 1.64-1.74 (m, 2H).

Example 53: N-(3,4-dichlorophenyl)-4-{2-oxo-4-[2-(trifluoromethyl)pyridin-4-yl]-2,3-dihydro-1H-1,3-benzodiazol-1-yl}piperidine-1-carboxamide The title compound was synthesized according to General procedure E from 4-(4-bromo-2-oxo-2,3-dihydro-1H-1,3-benzodiazol-1-yl)-N-(3,4-dichlorophenyl)piperidine-1-carboxamide and 4-(4,4,5,5-tetramethyl-1,3,2-dioxaborolan-2-yl)-2-(trifluoromethyl)pyridine. LCMS [M+H]+ 550.

Example 54: 4-[4-(5-Aminopyridin-3-yl)-2-oxo-2,3-dihydro-1H-1,3-benzodiazol-1-yl]-N-(3,4-dichlorophenyl)piperidine-1-carboxamide The title compound was synthesized according to General procedure E from 4-(4-bromo-2-oxo-2,3-dihydro-1H-1,3-benzodiazol-1-yl)-N-(3,4-dichlorophenyl)piperidine-1-carboxamide and 5-(4,4,5,5-tetramethyl-1,3,2-dioxaborolan-2-yl)pyridin-3-amine. LCMS [M+H]+ 497.

Example 55: N-(3,4-dichlorophenyl)-4-[4-(2-ethoxypyridin-3-yl)-2-oxo-2,3-dihydro-1H-1,3-benzodiazol-1-yl]piperidine-1-carboxamide The title compound was synthesized according to General procedure E from 4-(4-bromo-2-oxo-2,3-dihydro-1H-1,3-benzodiazol-1-yl)-N-(3,4-dichlorophenyl)piperidine-1-carboxamide and (2-ethoxy-3-pyridyl)boronic acid. LCMS [M+H]+ 526.

Example 56: N-(3,4-dichlorophenyl)-4-[4-(6-methoxypyridin-3-yl)-2-oxo-2,3-dihydro-1H-1,3-benzodiazol-1-yl]piperidine-1-carboxamide The title compound was synthesized according to General procedure E from 4-(4-bromo-2-oxo-2,3-dihydro-1H-1,3-benzodiazol-1-yl)-N-(3,4-dichlorophenyl)piperidine-1-carboxamide and (6-methoxy-3-pyridyl)boronic acid. LCMS [M+H]+ 512.

Example 57: 4-{4-[3-(Carbamoylmethyl)phenyl]-2-oxo-2,3-dihydro-1H-1,3-benzodiazol-1-yl}-N-(3,4-dichlorophenyl)piperidine-1-carboxamide The title compound was synthesized according to General procedure E from 4-(4-bromo-2-oxo-2,3-dihydro-1H-1,3-benzodiazol-1-yl)-N-(3,4-dichlorophenyl)piperidine-1-carboxamide and 2-[3-(4,4,5,5-tetramethyl-1,3,2-dioxaborolan-2-yl)phenyl]acetamide. LCMS [M+H]+ 538.

Example 58: 3-(1-{1-[(3,4-Dichlorophenyl)carbamoyl]piperidin-4-yl}-2-oxo-2,3-dihydro-1H-1,3-benzodiazol-4-yl)benzoic acid The title compound was synthesized according to General procedure E from 4-(4-bromo-2-oxo-2,3-dihydro-1H-1,3-benzodiazol-1-yl)-N-(3,4-dichlorophenyl)piperidine-1-carboxamide and 3-carboxyphenylboronic acid. LCMS [M+H]$^+$ 525.

Example 59: Methyl 3-(1-{1-[(3,4-dichlorophenyl)carbamoyl]piperidin-4-yl}-2-oxo-2,3-dihydro-1H-1,3-benzodiazol-4-yl)benzoate The title compound was synthesized according to General procedure E from 4-(4-bromo-2-oxo-2,3-dihydro-1H-1,3-benzodiazol-1-yl)-N-(3,4-dichlorophenyl)piperidine-1-carboxamide and 3-(methoxycarbonyl)phenylboronic acid. LCMS [M+H]$^+$ 539.

Example 60: N-(3,4-dichlorophenyl)-4-(4-{3-[2-(dimethylamino)ethoxy]phenyl}-2-oxo-2,3-dihydro-1H-1,3-benzodiazol-1-yl)piperidine-1-carboxamide The title compound was synthesized according to General procedure E from 4-(4-bromo-2-oxo-2,3-dihydro-1H-1,3-benzodiazol-1-yl)-N-(3,4-dichlorophenyl)piperidine-1-carboxamide and N,N-dimethyl-2-[3-(4,4,5,5-tetramethyl-1,3,2-dioxaborolan-2-yl)phenoxy]ethanamine. LCMS [M+H]$^+$ 568.

Example 61: N-(3,4-dichlorophenyl)-4-{4-[3-(morpholine-4-carbonyl)phenyl]-2-oxo-2,3-dihydro-1H-1,3-benzodiazol-1-yl}piperidine-1-carboxamide The title compound was synthesized according to General procedure E from 4-(4-bromo-2-oxo-2,3-dihydro-1H-1,3-benzodiazol-1-yl)-N-(3,4-dichlorophenyl)piperidine-1-carboxamide and [3-(morpholine-4-carbonyl)phenyl]boronic acid.
LCMS [M+H]$^+$ 594.

Example 62: N-(3,4-dichlorophenyl)-4-(4-{3-[(2-methoxyethyl)carbamoyl]phenyl}-2-oxo-2,3-dihydro-1H-1,3-benzodiazol-1-yl)piperidine-1-carboxamide The title compound was synthesized according to General procedure E from 4-(4-bromo-2-oxo-2,3-dihydro-1H-1,3-benzodiazol-1-yl)-N-(3,4-dichlorophenyl)piperidine-1-carboxamide and [3-(2-methoxyethylcarbamoyl)phenyl]boronic acid. LCMS [M+H]$^+$ 582.

Example 63: N-(3,4-dichlorophenyl)-4-[2-oxo-4-(4-sulfamoylphenyl)-2,3-dihydro-1H-1,3-benzodiazol-1-yl]piperidine-1-carboxamide The title compound was synthesized according to General procedure E from 4-(4-bromo-2-oxo-2,3-dihydro-1H-1,3-benzodiazol-1-yl)-N-(3,4-dichlorophenyl)piperidine-1-carboxamide and (4-sulfamoylphenyl)boronic acid. LCMS [M+H]$^+$ 560.

Example 64: N-(3,4-dichlorophenyl)-4-[4-(3-fluorophenyl)-2-oxo-2,3-dihydro-1H-1,3-benzodiazol-1-yl]piperidine-1-carboxamide The title compound was synthesized according to General procedure E from 4-(4-bromo-2-oxo-2,3-dihydro-1H-1,3-benzodiazol-1-yl)-N-(3,4-dichlorophenyl)piperidine-1-carboxamide and 3-fluorophenylboronic acid. LCMS [M+H]$^+$ 499.

Example 65: 4-{4-[3-(Aminomethyl)phenyl]-2-oxo-2,3-dihydro-1H-1,3-benzodiazol-1-yl}-N-(3,4-dichlorophenyl)piperidine-1-carboxamide The title compound was synthesized according to General procedure E from 4-(4-bromo-2-oxo-2,3-dihydro-1H-1,3-benzodiazol-1-yl)-N-(3,4-dichlorophenyl)piperidine-1-carboxamide and [3-(aminomethyl)phenyl]boronic acid;hydrochloride. LCMS [M+H]$^+$ 510.

Example 66: 4-[4-(2-Aminophenyl)-2-oxo-2,3-dihydro-1H-1,3-benzodiazol-1-yl]-N-(3,4-dichlorophenyl)piperidine-1-carboxamide The title compound was synthesized according to General procedure E from 4-(4-bromo-2-oxo-2,3-dihydro-1H-1,3-benzodiazol-1-yl)-N-(3,4-dichlorophenyl)piperidine-1-carboxamide and 2-aminophenylboronic acid.
LCMS [M+H]$^+$ 496.

Example 67: N-(3,4-dichlorophenyl)-4-(4-{2-[(dimethylamino)methyl]phenyl}-2-oxo-2,3-dihydro-1H-1,3-benzodiazol-1-yl)piperidine-1-carboxamide The title compound was synthesized according to General procedure E from 4-(4-bromo-2-oxo-2,3-dihydro-1H-1,3-benzodiazol-1-yl)-N-(3,4-dichlorophenyl)piperidine-1-carboxamide and [2-[(dimethylamino)methyl]phenyl]boronic acid. LCMS [M+H]$^+$ 538.

Example 68: 4-(4-Bromo-2-sulfanylidene-2,3-dihydro-1H-1,3-benzodiazol-1-yl)-N-(3,4-dichlorophenyl)piperidine-1-carboxamide Step 1: To a stirred suspension of tert-butyl 4-[(2-amino-3-bromophenyl)amino]piperidine-1-carboxylate (1.0 equiv.) and K$_2$CO$_3$ (2.0 equiv.) in an ethanol-water (1:2 v/v) mixture was added CS$_2$ (2.0 equiv.). The reaction mixture was stirred at 80° C. for 16 h. At this time another 2 equivalents of CS$_2$ was added and the resulting mixture was stirred another 24 h at 100° C. The reaction mixture was then cooled to room temperature and pour into NaHCO$_3$ (sat.) and extracted with DCM×3.

The combined organics were dried (MgSO$_4$) and purified by silica gel chromatography which afforded tert-butyl 4-(4-bromo-2-sulfanylidene-2,3-dihydro-1H-1,3-benzodiazol-1-yl)piperidine-1-carboxylate. LCMS [M-isobutene+H]$^+$ 358.

Step 2: 4-bromo-1-(piperidin-4-yl)-2,3-dihydro-1H-1,3-benzodiazole-2-thione;2,2,2-trifluoroacetic acid was synthesized according to General procedure C from tert-butyl 4-(4-bromo-2-sulfanylidene-2,3-dihydro-1H-1,3-benzodiazol-1-yl)piperidine-1-carboxylate. LCMS [M+H]$^+$ 312.

Step 3: The title compound was synthesized according to General procedure D from 4-bromo-1-(piperidin-4-yl)-2,3-dihydro-1H-1,3-benzodiazole-2-thione;2,2,2-trifluoroacetic acid and 3,4-dichlorophenyl isocyanate. LCMS [M+H]$^+$ 499. $^1$H-NMR (400 MHz, DMSO-de) δ ppm 13.26 (br. s., 1H), 8.91 (s, 1H), 7.90 (t, J=1.3 Hz, 1H), 7.57 (d, J=8.1 Hz, 1H), 7.50 (s, 1H), 7.50 (s, 1H), 7.39 (d, J=8.2 Hz, 1H), 7.11 (t, J=8.1 Hz, 1H), 5.33 (br. s., 1H), 4.30-4.41 (m, 2H), 2.93-3.06 (m, 2H), 2.25-2.45 (m, 2H), 1.73-1.83 (m, 2H).

Example 69: N-(3,4-dichlorophenyl)-4-(7-fluoro-2-oxo-2,3-dihydro-1H-1,3-benzodiazol-1-yl)piperidine-1-carboxamide The title compound was synthesized according to General procedure D from 7-fluoro-1-(piperidin-4-yl)-2,3-dihydro-1H-1,3-benzodiazol-2-one;2,2,2-trifluoroacetic acid and 3,4-dichlorophenyl isocyanate. LCMS [M+H]$^+$ 423. $^1$H-NMR (400 MHz, DMSO-d$_6$) δ ppm 11.24 (br. s., 1H), 8.90 (s, 1H), 7.87 (dd, J=1.9, 0.9 Hz, 1H), 7.46-7.52 (m, 2H), 6.97-7.03 (m, 1H), 6.84-6.92 (m, 2H), 4.51-4.62 (m, 1H), 4.23-4.31 (m, 2H), 2.92-3.02 (m, 2H), 2.05-2.20 (m, 2H), 1.73-1.82 (m, 2H).

Example 70: 4-(7-Chloro-2-oxo-2,3-dihydro-1H-1,3-benzodiazol-1-yl)-N-(3,4-dichlorophenyl)piperidine-1-carboxamide The title compound was synthesized according to General procedure D from 7-chloro-1-(piperidin-4-yl)-2,3-dihydro-1H-1,3-benzodiazol-2-one;2,2,2-trifluoroacetic acid and 3,4-dichlorophenyl isocyanate. LCMS [M+H]$^+$ 439. $^1$H-NMR (400 MHz, DMSO-d$_6$) δ ppm 11.09-11.38 (m, 1H), 8.89 (s, 1H), 7.86-7.90 (m, 1H), 7.48-7.51 (m, 2H), 7.03 (dd, J=7.6, 2.0 Hz, 1H), 6.99 (t, J=7.6 Hz, 1H), 6.95 (dd, J=7.6, 2.0 Hz, 1H), 5.11 (br. s., 1H), 4.23-4.34 (m, 2H), 2.45-2.97 (overlapping m, 2H), 2.56 (br. s., 2H), 1.74-1.86 (m, 2H).

Example 71: 4-(7-Bromo-2-oxo-2,3-dihydro-1H-1,3-benzodiazol-1-yl)-N-(3,4-dichlorophenyl)piperidine-1-carboxamide The title compound was synthesized according to General procedure D from 7-bromo-1-(piperidin-4-yl)-2,3-dihydro-1H-1,3-benzodiazol-2-one;2,2,2-trifluoroacetic acid and 3,4-dichlorophenyl isocyanate. LCMS [M+H]$^+$ 483. $^1$H-NMR (400 MHz, DMSO-d$_6$) δ ppm 11.19 (br. s., 1H), 8.89 (s, 1H), 7.87-7.89 (m, 1H), 7.48-7.51 (m, 2H), 7.19 (dd, J=8.0, 1.3 Hz, 1H), 6.99 (dd, J=8.0, 1.3 Hz, 1H), 6.92 (t, J=8.0 Hz, 1H), 5.28 (br. s., 1H), 4.24-4.34 (m, 2H), 2.82-2.94 (m, 2H), 2.53-2.58 (m, 2H), 1.75-1.85 (m, 2H).

Example 72: 3-(4-Bromo-2-oxo-2,3-dihydro-1H-1,3-benzodiazol-1-yl)-N-(3,4-dichlorophenyl)-(endo)-8-azabicyclo[3.2.1]octane-8-carboxamide The title compound was synthesized according to General procedure D from 1-{(endo)-8-azabicyclo[3.2.1]octan-3-yl}-4-bromo-2,3-dihydro-1H-1,3-benzodiazol-2-one;2,2,2-trifluoroacetic acid and 3,4-dichlorophenyl isocyanate. LCMS [M+H]$^+$ 509.

Example 73: 4-(4-Bromo-2-oxo-2,3-dihydro-1H-1,3-benzodiazol-1-yl)-N-(1H-indol-6-yl)piperidine-1-carboxamide The title compound was synthesized according to General procedure I from 4-bromo-1-(piperidin-4-yl)-2,3-dihydro-1H-1,3-benzodiazol-2-one;2,2,2-trifluoroacetic acid and 6-aminoindol. LCMS [M+H]$^+$ 454.

Example 74: 4-(4-Bromo-2-oxo-2,3-dihydro-1H-1,3-benzodiazol-1-yl)-N-[4-methyl-3-(trifluoromethyl)phenyl]piperidine-1-carboxamide The title compound was synthesized according to General procedure D from 4-bromo-1-(piperidin-4-yl)-2,3-dihydro-1H-1,3-benzodiazol-2-one;2,2,2-trifluoroacetic acid and 4-isocyanato-1-methyl-2-(trifluoromethyl)benzene. LCMS [M+H]$^+$ 497. $^1$H-NMR (400 MHz, DMSO-d$_6$) δ ppm 11.32 (br. s., 1H), 8.82 (s, 1H), 7.90 (d, J=2.2 Hz, 1H), 7.68 (dd, J=8.4, 2.2 Hz, 1H), 7.31 (d, J=8.4 Hz, 1H), 7.27 (br. d, J=8.1 Hz, 1H), 7.17 (dd, J=8.1, 0.6 Hz, 1H), 6.96 (t, J=8.1 Hz, 1H), 4.36-4.46 (m, 1H), 4.27-4.35 (m, 2H), 2.90-3.01 (m, 2H), 2.37 (br. d, J=1.6 Hz, 3H), 2.21-2.33 (m, 2H), 1.72-1.80 (m, 2H).

Example 75: 4-(4-Bromo-2-oxo-2,3-dihydro-1H-1,3-benzodiazol-1-yl)-N-(3-methoxy-4-methylphenyl)piperidine-1-carboxamide The title compound was synthesized according to General procedure I from 4-bromo-1-(piperidin-4-yl)-2,3-dihydro-1H-1,3-benzodiazol-2-one;2,2,2-trifluoroacetic acid and 3-methoxy-4-methylaniline. LCMS [M+H]$^+$ 459. $^1$H-NMR (400 MHz, DMSO-d6) δ ppm 11.32 (br. s., 1H), 8.50 (s, 1H), 7.25 (dd, J=8.1, 0.8 Hz, 1H), 7.18 (d, J=1.9 Hz, 1H), 7.16 (dd, J=8.2, 0.9 Hz, 1H), 7.00 (dd, J=8.2, 1.9 Hz, 1H), 6.97 (s, 1H), 6.94 (d, J=8.2 Hz, 1H), 4.39 (tt, J=12.2, 4.0 Hz, 1H), 4.24-4.33 (m, 2H), 3.74 (s, 3H), 2.85-2.97 (m, 2H), 2.20-2.33 (m, 2H), 2.07 (s, 3H), 1.70-1.79 (m, 2H).

Example 76: 4-(4-Bromo-2-oxo-2,3-dihydro-1H-1,3-benzodiazol-1-yl)-N-(4-fluoro-3-methoxyphenyl)piperidine-1-carboxamide The title compound was synthesized according to General procedure I from 4-bromo-1-(piperidin-4-yl)-2,3-dihydro-1H-1,3-benzodiazol-2-one;2,2,2-trifluoroacetic acid and 4-fluoro-3-methoxyaniline. LCMS [M+H]$^+$ 463.

Example 77: 4-(4-Bromo-2-oxo-2,3-dihydro-1H-1,3-benzodiazol-1-yl)-N-(4-chloro-3-methoxyphenyl)piperidine-1-carboxamide The title compound was synthesized according to General procedure I from 4-bromo-1-(piperidin-4-yl)-2,3-dihydro-1H-1,3-benzodiazol-2-one;2,2,2-trifluoroacetic acid and 4-chloro-3-methoxyaniline. LCMS [M+H]$^+$ 479. $^1$H-NMR (400 MHz, DMSO-d$_6$) δ ppm 11.32 (br. s., 1H), 8.71 (s, 1H), 7.42 (d, J=2.2 Hz, 1H), 7.25 (s, 1H), 7.13-7.19 (m, 2H), 6.96 (t, J=8.1 Hz, 1H), 4.36-4.46 (m, 1H), 4.26-4.34 (m, 2H), 3.81 (s, 3H), 2.87-3.01 (m, 2H), 2.20-2.36 (m, 2H), 1.71-1.81 (m, 2H).

Example 78: 4-(4-Bromo-2-oxo-2,3-dihydro-1H-1,3-benzodiazol-1-yl)-N-(4-chloro-3-fluorophenyl)piperidine-1-carboxamide The title compound was synthesized according to General procedure I from 4-bromo-1-(piperidin-4-yl)-2,3-dihydro-1H-1,3-benzodiazol-2-one;2,2,2-trifluoroacetic acid and 4-chloro-3-fluoroaniline. LCMS [M+H]$^+$ 467.

Example 79: 4-(4-Bromo-2-oxo-2,3-dihydro-1H-1,3-benzodiazol-1-yl)-N-(4-fluoro-3-methylphenyl)piperidine-1-carboxamide The title compound was synthesized according to General procedure I from 4-bromo-1-(piperidin-4-yl)-2,3-dihydro-1H-1,3-benzodiazol-2-one;2,2,2-trifluoroacetic acid and 4-fluoro-3-methylaniline. LCMS [M+H]$^+$ 447. $^1$H-NMR (400 MHz, DMSO-d$_6$) δ ppm 11.31 (br. s., 1H), 8.55 (s, 1H), 7.39 (dd, J=7.3, 2.2 Hz, 1H), 7.27-7.32 (m, 1H), 7.26 (dd, J=8.1, 0.8 Hz, 1H), 7.17 (dd, J=8.1, 0.8 Hz, 1H), 7.01 (t, J=9.2 Hz, 1H), 6.96 (t, J=8.1 Hz, 1H), 4.35-4.45 (m, 1H), 4.24-4.33 (m, 2H), 2.87-2.98 (m, 2H), 2.21-2.32 (m, 2H), 2.20 (s, 3H), 1.70-1.79 (m, 2H).

Example 80: 4-(4-Bromo-2-oxo-2,3-dihydro-1H-1, 3-benzodiazol-1-yl)-N-[3-chloro-4-(trifluoromethoxy)phenyl]piperidine-1-carboxamide The title compound was synthesized according to General procedure I from 4-bromo-1-(piperidin-4-yl)-2,3-dihydro-1H-1,3-benzodiazol-2-one;2,2,2-trifluoroacetic acid and 3-chloro-4-(trifluoromethoxy)aniline.

LCMS [M+H]$^+$ 533. $^1$H-NMR (400 MHz, DMSO-d$_6$) δ ppm 11.31 (br. s., 1H), 8.95 (s, 1H), 7.90 (d, J=2.5 Hz, 1H), 7.55 (dd, J=9.0, 2.5 Hz, 1H), 7.43-7.48 (m, 1H), 7.27 (d, J=8.2 Hz, 1H), 7.17 (d, J=8.2 Hz, 1H), 6.96 (t, J=8.2 Hz, 1H), 4.37-4.47 (m, 1H), 4.26-4.33 (m, 2H), 2.92-3.03 (m, 2H), 2.22-2.32 (m, 2H), 1.73-1.80 (m, 2H).

Example 81: 4-{4-[6-(Hydroxymethyl)pyridin-3-yl]-2-oxo-2,3-dihydro-1H-1,3-benzodiazol-1-yl}-N-(4-iodo-3-methylphenyl)piperidine-1-carboxamide The title compound was synthesized according to General procedure I from 4-[6-(hydroxymethyl)pyridin-3-yl]-1-(piperidin-4-yl)-2,3-dihydro-1H-1,3-benzodiazol-2-one;2,2,2-trifluoroacetic acid and 4-iodo-3-methylaniline.
LCMS [M+H]$^+$ 584.

Example 82: 4-{4-[6-(Hydroxymethyl)pyridin-3-yl]-2-oxo-2,3-dihydro-1H-1,3-benzodiazol-1-yl}-N-(3-methoxy-4-methylphenyl)piperidine-1-carboxamide The title compound was synthesized according to General procedure I from 4-[6-(hydroxymethyl)pyridin-3-yl]-1-(piperidin-4-yl)-2,3-dihydro-1H-1,3-benzodiazol-2-one;2,2,2-trifluoroacetic acid and 3-methoxy-4-methylaniline.
LCMS [M+H]$^+$ 488.

Example 83: N-(4-Chloro-3-methoxyphenyl)-4-{4-[6-(hydroxymethyl)pyridin-3-yl]-2-oxo-2,3-dihydro-1H-1,3-benzodiazol-1-yl}piperidine-1-carboxamide The title compound was synthesized according to General procedure I from 4-[6-(hydroxymethyl)pyridin-3-yl]-1-(piperidin-4-yl)-2,3-dihydro-1H-1,3-benzodiazol-2-one;2,2,2-trifluoroacetic acid and 4-chloro-3-methoxyanilin.
LCMS [M+H]$^+$ 508.

Example 84: 3-(4-Bromo-2-oxo-2,3-dihydro-1H-1, 3-benzodiazol-1-yl)-N-(4-iodo-3-methylphenyl)-(endo)-8-azabicyclo[3.2.1]octane-8-carboxamide The title compound was synthesized according to General procedure I from 1-{(endo)-8-azabicyclo[3.2.1]octan-3-yl}-4-bromo-2,3-dihydro-1H-1,3-benzodiazol-2-one;2,2,2-trifluoroacetic acid and 4-iodo-3-methylaniline. LCMS [M+H]$^+$ 581.

Example 85: 3-(4-Bromo-2-oxo-2,3-dihydro-1H-1, 3-benzodiazol-1-yl)-N-(3-methoxy-4-methylphenyl)-(endo)-8-azabicyclo[3.2.1]octane-8-carboxamide The title compound was synthesized according to General procedure I from 1-{(endo)-8-azabicyclo[3.2.1]octan-3-yl}-4-bromo-2,3-dihydro-1H-1,3-benzodiazol-2-one;2,2,2-trifluoroacetic acid and 3-methoxy-4-methylaniline. LCMS [M+H]$^+$ 485.

Example 86: 3-(4-Bromo-2-oxo-2,3-dihydro-1H-1, 3-benzodiazol-1-yl)-N-(4-chloro-3-fluorophenyl)-(endo)-8-azabicyclo[3.2.1]octane-8-carboxamide The title compound was synthesized according to General procedure I from 1-{(endo)-8-azabicyclo[3.2.1]octan-3-yl}-4-bromo-2,3-dihydro-1H-1,3-benzodiazol-2-one;2,2,2-trifluoroacetic acid and 4-chloro-3-fluoroaniline. LCMS [M+H]$^+$ 493.

Example 87: 4-{4-[4-(Ethylcarbamoyl)-1H-pyrazol-1-yl]-2-oxo-2,3-dihydro-1H-1,3-benzodiazol-1-yl}-N-(4-iodophenyl)piperidine-1-carboxamide The title compound was synthesized according to General procedure H from 1-(1-(1-((4-iodophenyl)carbamoyl)piperidin-4-yl)-2-oxo-2,3-dihydro-1H-benzo[d]imidazol-4-yl)-1H-pyrazole-4-carboxylic acid and ethylamine. LCMS [M+H]$^+$ 600.

Example 88: 4-{4-[4-(Diethylcarbamoyl)-1H-pyrazol-1-yl]-2-oxo-2,3-dihydro-1H-1,3-benzodiazol-1-yl}-N-(4-iodophenyl)piperidine-1-carboxamide The title compound was synthesized according to General procedure H from 1-(1-(1-((4-iodophenyl)carbamoyl)piperidin-4-yl)-2-oxo-2,3-dihydro-1H-benzo[d]imidazol-4-yl)-1H-pyrazole-4-carboxylic acid and diethylamine. LCMS [M+H]$^+$ 628.

Example 89: 4-(4-(4-((2-(Dimethylamino)ethyl)carbamoyl)-1H-pyrazol-1-yl)-2-oxo-2,3-dihydro-1H-benzo[d]imidazol-1-yl)-N-(4-iodophenyl)piperidine-1-carboxamide 2,2,2-trifluoroacetate The title compound was synthesized according to General procedure H from 1-(1-(1-((4-iodophenyl)carbamoyl)piperidin-4-yl)-2-oxo-2,3-dihydro-1H-benzo[d]imidazol-4-yl)-1H-pyrazole-4-carboxylic acid and N,N-dimethylethylenediamine. LCMS [M+H]$^+$ 643.

Example 90: 4-(4-{4-[(2,3-Dihydroxypropyl)carbamoyl]-1H-pyrazol-1-yl}-2-oxo-2,3-dihydro-1H-1, 3-benzodiazol-1-yl)-N-(4-iodophenyl)piperidine-1-carboxamide The title compound was synthesized according to General procedure H from 1-(1-(1-((4-iodophenyl)carbamoyl)piperidin-4-yl)-2-oxo-2,3-dihydro-1H-benzo[d]imidazol-4-yl)-1H-pyrazole-4-carboxylic acid and (±)-amino-1,2-propanediol. LCMS [M+H]$^+$ 646.

Example 91: 3-{4-[6-(Hydroxymethyl)pyridin-3-yl]-2-oxo-2,3-dihydro-1H-1,3-benzodiazol-1-yl}-N-(4-iodo-3-methylphenyl)-(endo)-8-azabicyclo[3.2.1] octane-8-carboxamide The title compound was synthesized according to General procedure I from 1-{(endo)-8-azabicyclo[3.2.1]octan-3-yl}-4-[6-(hydroxymethyl)pyridin-3-yl]-2,3-dihydro-1H-1,3-benzodiazol-2-one;2,2,2-trifluoroacetic acid and 4-iodo-3-methylaniline. LCMS [M+H]$^+$ 610.

Example 92: 3-{4-[6-(Hydroxymethyl)pyridin-3-yl]-2-oxo-2,3-dihydro-1H-1,3-benzodiazol-1-yl}-N-(3-methoxy-4-methylphenyl)-(endo)-8-azabicyclo[3.2.1]octane-8-carboxamide The title compound was synthesized according to General procedure I from 1-{(endo)-8-azabicyclo[3.2.1]octan-3-yl}-4-[6-(hydroxymethyl)pyridin-3-yl]-2,3-dihydro-1H-1,3-benzodiazol-2-one;2,2,2-trifluoroacetic acid and 3-methoxy-4-methylaniline. LCMS [M+H]$^+$ 514.

Example 93: N-(4-chloro-3-methoxyphenyl)-3-{4-[6-(hydroxymethyl)pyridin-3-yl]-2-oxo-2,3-dihydro-1H-1,3-benzodiazol-1-yl}-(endo)-8-azabicyclo[3.2.1]octane-8-carboxamide The title compound was synthesized according to General procedure I from 1-{(endo)-8-azabicyclo[3.2.1]octan-3-yl}-4-[6-(hydroxymethyl)pyridin-3-yl]-2,3-dihydro-1H-1,3-benzodiazol-2-one;2,2,2-trifluoroacetic acid and 4-chloro-3-methoxyaniline. LCMS [M+H]$^+$ 534.

Example 94: N-(4-chloro-3-fluorophenyl)-3-{4-[6-(hydroxymethyl) pyridin-3-yl]-2-oxo-2,3-dihydro-1H-1,3-benzodiazol-1-yl}-(endo)-8-azabicyclo[3.2.1]octane-8-carboxamide The title compound was synthesized according to General procedure I from 1-{(endo)-8-azabicyclo[3.2.1]octan-3-yl}-4-[6-(hydroxymethyl)pyridin-3-yl]-2,3-dihydro-1H-1,3-benzodiazol-2-one;2,2,2-trifluoroacetic acid and 4-chloro-3-fluoroaniline. LCMS [M+H]$^+$ 522.

Example 95: N-(3-methoxy-4-methylphenyl)-4-[2-oxo-4-(pyridin-3-yl)-2,3-dihydro-1H-1,3-benzodiazol-1-yl]piperidine-1-carboxamide The title compound was synthesized according to General procedure E from 4-(4-bromo-2-oxo-2,3-dihydro-1H-1,3-benzodiazol-1-yl)-N-(3-methoxy-4-methylphenyl)piperidine-1-carboxamide and 3-pyridylboronic acid. LCMS [M+H]$^+$ 458.

Example 96: 4-[4-(6-Aminopyridin-3-yl)-2-oxo-2,3-dihydro-1H-1,3-benzodiazol-1-yl]-N-(3-methoxy-4-methylphenyl)piperidine-1-carboxamide The title compound was synthesized according to General procedure E from 4-(4-bromo-2-oxo-2,3-dihydro-1H-1,3-benzodiazol-1-yl)-N-(3-methoxy-4-methylphenyl)piperidine-1-carboxamide and 5-(4,4,5,5-tetramethyl-1,3,2-dioxaborolan-2-yl)pyridin-2-amine. LCMS [M+H]$^+$ 473.

Example 97: 4-[4-(5-Aminopyridin-3-yl)-2-oxo-2,3-dihydro-1H-1,3-benzodiazol-1-yl]-N-(3-methoxy-4-methylphenyl)piperidine-1-carboxamide The title compound was synthesized according to General procedure E from 4-(4-bromo-2-oxo-2,3-dihydro-1H-1,3-benzodiazol-1-yl)-N-(3-methoxy-4-methylphenyl)piperidine-1-carboxamide and 5-(4,4,5,5-tetramethyl-1,3,2-dioxaborolan-2-yl)pyridin-3-amine. LCMS [M+H]$^+$ 473.

Example 98: N-(3-chloro-4-methoxyphenyl)-4-[2-oxo-4-(pyridin-3-yl)-2,3-dihydro-1H-1,3-benzodiazol-1-yl]piperidine-1-carboxamide The title compound was synthesized according to General procedure E from 4-(4-bromo-2-oxo-2,3-dihydro-1H-1,3-benzodiazol-1-yl)-N-(3-chloro-4-methoxyphenyl)piperidine-1-carboxamide and 3-pyridylboronic acid. LCMS [M+H]$^+$ 478.

Example 99: 4-[4-(6-Aminopyridin-3-yl)-2-oxo-2,3-dihydro-1H-1,3-benzodiazol-1-yl]-N-(3-chloro-4-methoxyphenyl)piperidine-1-carboxamide The title compound was synthesized according to General procedure E from 4-(4-bromo-2-oxo-2,3-dihydro-1H-1,3-benzodiazol-1-yl)-N-(3-chloro-4-methoxyphenyl)piperidine-1-carboxamide and 5-(4,4,5,5-tetramethyl-1,3,2-dioxaborolan-2-yl)pyridin-2-amine. LCMS [M+H]$^+$ 493.

Example 100: 4-[4-(5-Aminopyridin-3-yl)-2-oxo-2,3-dihydro-1H-1,3-benzodiazol-1-yl]-N-(3-chloro-4-methoxyphenyl)piperidine-1-carboxamide The title compound was synthesized according to General procedure E from 4-(4-bromo-2-oxo-2,3-dihydro-1H-1,3-benzodiazol-1-yl)-N-(3-chloro-4-methoxyphenyl)piperidine-1-carboxamide and 5-(4,4,5,5-tetramethyl-1,3,2-dioxaborolan-2-yl)pyridin-3-amine. LCMS [M+H]$^+$ 493.

Example 101: N-(3-chloro-4-methoxyphenyl)-4-(2-oxo-4-{1H-pyrazolo[3,4-b]pyridin-5-yl}-2,3-dihydro-1H-1,3-benzodiazol-1-yl)piperidine-1-carboxamide The title compound was synthesized according to General procedure E from 4-(4-bromo-2-oxo-2,3-dihydro-1H-1,3-benzodiazol-1-yl)-N-(3-chloro-4-methoxyphenyl)piperidine-1-carboxamide and 1H-pyrazolo[3,4-b]pyridin-5-ylboronic acid. LCMS [M+H]$^+$ 518.

Example 102: N-(4-chloro-3-methoxyphenyl)-4-[2-oxo-4-(pyridin-3-yl)-2,3-dihydro-1H-1,3-benzodiazol-1-yl]piperidine-1-carboxamide The title compound was synthesized according to General procedure E from 4-(4-bromo-2-oxo-2,3-dihydro-1H-1,3-benzodiazol-1-yl)-N-(4-chloro-3-methoxyphenyl)piperidine-1-carboxamide and 3-pyridylboronic acid. LCMS [M+H]$^+$ 478.

Example 103: 4-[4-(6-Aminopyridin-3-yl)-2-oxo-2,3-dihydro-1H-1,3-benzodiazol-1-yl]-N-(4-chloro-3-methoxyphenyl)piperidine-1-carboxamide The title compound was synthesized according to General procedure E from 4-(4-bromo-2-oxo-2,3-dihydro-1H-1,3-benzodiazol-1-yl)-N-(4-chloro-3-methoxyphenyl)piperidine-1-carboxamide and 5-(4,4,5,5-tetramethyl-1,3,2-dioxaborolan-2-yl)pyridin-2-amine. LCMS [M+H]$^+$ 493.

Example 104: 4-[4-(5-Aminopyridin-3-yl)-2-oxo-2,3-dihydro-1H-1,3-benzodiazol-1-yl]-N-(4-chloro-3-methoxyphenyl)piperidine-1-carboxamide The title compound was synthesized according to General procedure E from 4-(4-bromo-2-oxo-2,3-dihydro-1H-1,3-benzodiazol-1-yl)-N-(4-chloro-3-methoxyphenyl)piperidine-1-carboxamide and 5-(4,4,5,5-tetramethyl-1,3,2-dioxaborolan-2-yl)pyridin-3-amine. LCMS [M+H]$^+$ 493.

Example 105: N-(4-chloro-3-methoxyphenyl)-4-[4-(6-methoxypyridin-3-yl)-2-oxo-2,3-dihydro-1H-1,3-benzodiazol-1-yl]piperidine-1-carboxamide The title compound was synthesized according to General procedure E from 4-(4-bromo-2-oxo-2,3-dihydro-1H-1,3-benzodiazol-1-yl)-N-(4-chloro-3-methoxyphenyl)piperidine-1-carboxamide and (6-methoxy-3-pyridyl)boronic acid.
LCMS [M+H]$^+$ 508.

Example 106: N-(3-chloro-4-methoxyphenyl)-4-(4-{[2-(dimethylamino)ethyl](methyl)amino}-2-oxo-2,3-dihydro-1H-1,3-benzodiazol-1-yl)piperidine-1-carboxamide Step 1: tert-butyl 4-[3-[2-(dimethylamino)ethyl-methyl-amino]-2-nitro-anilino]piperidine-1-carboxylate was synthesized according to General procedure A from tert-butyl 4-(3-fluoro-2-nitro-anilino)piperidine-1-carboxylate and N,N',N'-trimethylethane-1,2-diamine. LCMS [M+H]$^+$ 422.
Step 2: tert-butyl 4-(4-{[2-(dimethylamino)ethyl](methyl)amino}-2-oxo-2,3-dihydro-1H-1,3-benzodiazol-1-yl)piperidine-1-carboxylate was synthesized according to General procedure B from tert-butyl 4-[3-[2-(dimethylamino)ethyl-methyl-amino]-2-nitro-anilino]piperidine-1-carboxylate. LCMS [M+H]$^+$ 418.
Step 3: 4-{[2-(dimethylamino)ethyl](methyl)amino}-1-(piperidin-4-yl)-2,3-dihydro-1H-1,3-benzodiazol-2-one;2,2,2-trifluoroacetic acid was synthesized according to General procedure C from tert-butyl 4-(4-{[2-(dimethylamino)ethyl](methyl)amino}-2-oxo-2,3-dihydro-1H-1,3-benzodiazol-1-yl)piperidine-1-carboxylate. LCMS [M+H]$^+$ 318. The title compound was synthesized according to General procedure D from 4-{[2-(dimethylamino)ethyl](methyl)amino}-1-(piperidin-4-yl)-2,3-dihydro-1H-1,3-benzodiazol-2-one;2,2,2-trifluoroacetic acid and 3-chloro-4-methoxylphenyl isocyanate. LCMS [M+H]$^+$ 501.

Example 107: (Cis)-4-(4-bromo-2-oxo-2,3-dihydro-1H-1,3-benzodiazol-1-yl)-N-(3-methoxy-4-methylphenyl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 3-methoxy-4-methylaniline. LCMS [M+H]$^+$ 458.

Example 108: N-(3-chloro-4-methoxyphenyl)-4-(2-oxo-4-{1H,4H,5H,6H-pyrrolo[3,4-c]pyrazol-5-yl}-2,3-dihydro-1H-1,3-benzodiazol-1-yl)piperidine-1-carboxamide Step 1: tert-butyl 4-[3-(4,6-dihydro-1H-pyrrolo[3,4-c]pyrazol-5-yl)-2-nitro-anilino]piperidine-1-carboxylate was synthesized according to General procedure A from tert-butyl 4-(3-fluoro-2-nitro-anilino)piperidine-1-carboxylate and 1,4,5,6-tetrahydropyrrolo[3,4-c]pyrazole;dihydrochloride. LCMS [M+H]$^+$ 429.
Step 2: tert-butyl 4-(2-oxo-4-{1H,4H,5H,6H-pyrrolo[3,4-c]pyrazol-5-yl}-2,3-dihydro-1H-1,3-benzodiazol-1-yl)piperidine-1-carboxylate was synthesized according to General procedure B from tert-butyl 4-[3-(4,6-dihydro-1H-pyrrolo[3,4-c]pyrazol-5-yl)-2-nitro-anilino]piperidine-1-carboxylate. LCMS [M-isobutene+H]$^+$ 369.
Step 3: 1-(piperidin-4-yl)-4-{1H,4H,5H,6H-pyrrolo[3,4-c]pyrazol-5-yl}-2,3-dihydro-1H-1,3-benzodiazol-2-one;2,2,2-trifluoroacetic acid was synthesized according to General procedure C from tert-butyl 4-(2-oxo-4-{1H,4H,5H,6H-pyrrolo[3,4-c]pyrazol-5-yl}-2,3-dihydro-1H-1,3-benzodiazol-1-yl)piperidine-1-carboxylate. LCMS [M+H]$^+$ 325.
Step 4: The title compound was synthesized according to General procedure D from 1-(piperidin-4-yl)-4-{1H,4H,5H,6H-pyrrolo[3,4-c]pyrazol-5-yl}-2,3-dihydro-1H-1,3-benzodiazol-2-one;2,2,2-trifluoroacetic acid and 3-chloro-4-methoxylphenyl isocyanate. LCMS [M+H]$^+$ 508.

Example 109: 4-(4-Bromo-2-oxo-2,3-dihydro-1H-1,3-benzodiazol-1-yl)-N-(5,6-dichloropyridin-3-yl)piperidine-1-carboxamide The title compound was synthesized according to General procedure I from 4-bromo-1-(piperidin-4-yl)-2,3-dihydro-1H-1,3-benzodiazol-2-one;2,2,2-trifluoroacetic acid and 5,6-dichloropyridin-3-amine. LCMS [M+H]$^+$ 484.

Example 110: 4-(4-Bromo-2-oxo-2,3-dihydro-1H-1,3-benzodiazol-1-yl)-N-(6-methoxy-5-methylpyridin-3-yl)piperidine-1-carboxamide The title compound was synthesized according to General procedure I from 4-bromo-1-(piperidin-4-yl)-2,3-dihydro-1H-1,3-benzodiazol-2-one;2,2,2-trifluoroacetic acid and 6-methoxy-5-methyl-pyridin-3-amine. LCMS [M+H]$^+$ 460.

Example 111: 4-(4-Bromo-2-oxo-2,3-dihydro-1H-1,3-benzodiazol-1-yl)-N-(5-chloro-6-methylpyridin-2-yl)piperidine-1-carboxamide The title compound was synthesized according to General procedure I from 4-bromo-1-(piperidin-4-yl)-2,3-dihydro-1H-1,3-benzodiazol-2-one;2,2,2-trifluoroacetic acid and 5-chloro-6-methyl-pyridin-2-amine. LCMS [M+H]$^+$ 464.

Example 112: 4-(4-Bromo-2-oxo-2,3-dihydro-1H-benzo[d]imidazol-1-yl)-N-(3,4-dichlorophenyl)-2-methylpiperidine-1-carboxamide The title compound was synthesized according to General procedure D from 4-bromo-1-(2-methylpiperidin-4-yl)-1H-benzo[d]imidazol-2(3H)-one 2,2,2-trifluoroacetate and 3,4-dichlorophenyl isocyanate. LCMS [M+H]$^+$ 497.

Example 113: 4-(4-Bromo-2-oxo-2,3-dihydro-1H-benzo[d]imidazol-1-yl)-N-(3,4-dichlorophenyl)-3-methylpiperidine-1-carboxamide The title compound was synthesized according to General procedure D from 4-bromo-1-(3-methylpiperidin-4-yl)-1H-benzo[d]imidazol-2(3H)-one 2,2,2-trifluoroacetate and 3,4-dichlorophenyl isocyanate. LCMS [M+H]$^+$ 497.

Example 114: 4-(4-Chloro-2-oxo-2,3-dihydro-1H-1,3-benzodiazol-1-yl)-N-(3-methoxy-4-methylphenyl)piperidine-1-carboxamide The title compound was synthesized according to General procedure I from 4-chloro-1-(piperidin-4-yl)-2,3-dihydro-1H-1,3-benzodiazol-2-one;2,2,2-trifluoroacetic acid and 3-methoxy-4-methylaniline. LCMS [M+H]$^+$ 415.

Example 115: N-(3-methoxy-4-methylphenyl)-4-(4-methyl-2-oxo-2,3-dihydro-1H-1,3-benzodiazol-1-yl)piperidine-1-carboxamide The title compound was synthesized according to General procedure I from 4-methyl-1-(piperidin-4-yl)-2,3-dihydro- 1H-1,3-benzodiazol-2-;2,2,2-trifluoroacetic acid and 3-methoxy-4-methylaniline. LCMS [M+H]+ 395.

Example 116: 4-(4-Methoxy-2-oxo-2,3-dihydro-1H-1,3-benzodiazol-1-yl)-N-(3-methoxy-4-methylphenyl)piperidine-1-carboxamide The title compound was synthesized according to General procedure I from 4-methoxy-1-(piperidin-4-yl)-2,3-dihydro-1H-1,3-benzodiazol-2-one;2,2,2-trifluoroacetic acid and 3-methoxy-4-methylaniline. LCMS [M+H]+ 411.

Example 117: N-(3-methoxy-4-methylphenyl)-4-[2-oxo-4-(1H-pyrazol-1-yl)-2,3-dihydro-1H-1,3-benzodiazol-1-yl]piperidine-1-carboxamide The title compound was synthesized according to General procedure I from 1-(piperidin-4-yl)-4-(1H-pyrazol-1-yl)-2,3-dihydro-1H-1,3-benzodiazol-2-one;2,2,2-trifluoroacetic acid and 3-methoxy-4-methylaniline. LCMS [M+H]+ 447.

Example 118: (Cis)-4-(4-bromo-2-oxo-2,3-dihydro-1H-1,3-benzodiazol-1-yl)-N-(3,4-dichlorophenyl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 3,4-dichloroaniline. LCMS [M+H]+ 482. $^1$H-NMR (400 MHz, CHLOROFORM-d) δ ppm 8.83 (br. s., 1H), 7.86 (s, 1H), 7.40-7.45 (m, 2H), 7.35-7.40 (m, 1H), 7.23 (dd, J=8.2, 0.6 Hz, 1H), 7.05 (t, J=8.1 Hz, 1H), 4.39-4.52 (m, 1H), 2.59-2.75 (m, 3H), 2.25 (m, 2H), 1.70-1.93 (m, 4H).

Example 119: (Cis)-4-(4-bromo-2-oxo-2,3-dihydro-1H-1,3-benzodiazol-1-yl)-N-(4-chlorophenyl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 4-chloroaniline. LCMS [M+H]+ 448. $^1$H-NMR (400 MHz, CHLOROFORM-d) δ ppm 8.76 (br. s., 1H), 7.49-7.59 (m, 2H), 7.36-7.44 (m, 2H), 7.29-7.36 (m, 2H), 7.14-7.21 (m, 1H), 6.94-7.01 (m, 1H), 4.39-4.52 (m, 1H), 2.61-2.77 (m, 3H), 2.18-2.32 (m, 2H), 1.69-1.90 (m, 4H).

Example 120: (Cis)-4-(4-bromo-2-oxo-2,3-dihydro-1H-1,3-benzodiazol-1-yl)-N-[4-chloro-3-(trifluoromethyl)phenyl]cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 4-chloro-3-(trifluoromethyl)aniline.
LCMS [M+H]+ 516. $^1$H-NMR (400 MHz, CHLOROFORM-d) δ ppm 8.89 (s, 1H), 7.93 (d, J=2.5 Hz, 1H), 7.81 (dd, J=8.7, 2.4 Hz, 1H), 7.63 (s, 1H), 7.49 (d, J=8.8 Hz, 1H), 7.37 (d, J=7.9 Hz, 1H), 7.19 (dd, J=8.2, 0.9 Hz, 1H), 6.99 (t, J=8.1 Hz, 1H), 4.40-4.51 (m, 1H), 2.61-2.75 (m, 3H), 2.26 (d, J=14.2 Hz, 2H), 1.73-1.90 (m, 4H).

Example 121: (Cis)-4-(4-bromo-2-oxo-2,3-dihydro-1H-1,3-benzodiazol-1-yl)-N-(4-chloro-3-fluorophenyl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 4-chloro-3-fluoroaniline. LCMS [M+H]+ 466. $^1$H-NMR (400 MHz, CHLOROFORM-d) δ ppm 8.96 (s, 1H), 7.74 (dd, J=11.1, 2.2 Hz, 1H), 7.54 (br. s., 1H), 7.38 (d, J=7.9 Hz, 1H), 7.32-7.37 (m, 1H), 7.18-7.20 (m, 1H), 7.15-7.18 (m, 1H), 7.01 (t, J=8.1 Hz, 1H), 4.45 (tt, J=12.6, 4.1 Hz, 1H), 2.62-2.74 (m, 3H), 2.19-2.29 (m, 2H), 1.72-1.88 (m, 4H).

Example 122: (Cis)-4-(4-bromo-2-oxo-2,3-dihydro-1H-1,3-benzodiazol-1-yl)-N-(4-chloro-3-methoxyphenyl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 4-chloro-3-methoxyaniline. CMS [M+H]+ 478. $^1$H-NMR (400 MHz, CHLOROFORM-d) δ ppm 9.09 (s, 1H), 7.56 (d, J=2.2 Hz, 1H), 7.51 (br. s., 1H), 7.37 (d, J=8.2 Hz, 1H), 7.30 (d, J=8.5 Hz, 1H), 7.17 (dd, J=8.2, 0.6 Hz, 1H), 6.95 (dd, J=8.2 Hz, 1H), 6.90-6.93 (m, 1H), 4.45 (tt, J=12.5, 4.1 Hz, 1H), 3.95 (s, 3H), 2.60-2.74 (m, 3H), 2.22-2.31 (m, 2H), 1.72-1.88 (m, 4H).

Example 123: (Cis)-4-(4-bromo-2-oxo-2,3-dihydro-1H-1,3-benzodiazol-1-yl)-N-(3-chloro-4-methoxyphenyl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 3-chloro-4-methoxyaniline. LCMS [M+H]+ 478. $^1$H-NMR (400 MHz, CHLOROFORM-d) δ ppm 8.82 (s, 1H), 7.65 (d, J=2.5 Hz, 1H), 7.37-7.43 (m, 2H), 7.34 (br. s., 1H), 7.17 (dd, J=8.2, 0.6 Hz, 1H), 6.96-7.01 (m, 1H), 6.92 (d, J=8.8 Hz, 1H), 4.46 (tt, J=12.6, 4.3 Hz, 1H), 3.90 (s, 3H), 2.62-2.75 (m, 3H), 2.20-2.29 (m, 2H), 1.71-1.88 (m, 4H).

Example 124: (Cis)-4-(4-bromo-2-oxo-2,3-dihydro-1H-1,3-benzodiazol-1-yl)-N-(3,4-dimethylphenyl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 3,4-dimethylaniline. LCMS [M+H]+ 442.1H-NMR (400 MHz, CHLOROFORM-d) δ ppm 8.81 (br. s., 1H), 7.39-7.45 (m, 1H), 7.37 (br. s., 1H), 7.24-7.32 (m, 2H), 7.11-7.21 (m, 2H), 6.94-7.01 (m, 1H), 4.43-4.56 (m, 1H), 2.64-2.78 (m, 3H), 2.23-2.33 (m, 8H), 1.72-1.92 (m, 4H).

Example 125: (Cis)-4-(4-bromo-2-oxo-2,3-dihydro-1H-1,3-benzodiazol-1-yl)-N-(3-chloro-4-cyanophenyl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 4-amino-2-chlorobenzonitrile. LCMS [M+H]+ 473. $^1$H-NMR (400 MHz, CHLOROFORM-d) δ ppm 8.34 (br. s., 1H), 8.00 (br. s., 1H), 7.61-7.69 (m, 2H), 7.51-7.58 (m, 1H), 7.31-7.37 (m, 1H), 7.17-7.23 (m, 1H), 6.98-7.06 (m, 1H), 4.39-4.50 (m, 1H), 2.58-2.77 (m, 3H), 2.20-2.31 (m, 2H), 1.75-1.93 (m, 4H).

Example 126: (Cis)-4-(4-bromo-2-oxo-2,3-dihydro-1H-1,3-benzodiazol-1-yl)-N-(4-methoxy-3-methylphenyl)cyclohexane-1-carboxamide The title compound was synthesized according to General procedure H from (cis)-4-(4-bromo-2-oxo-2,3-dihydro-1H-

1,3-benzodiazol-1-yl)cyclohexane-1-carboxylic acid and 4-methoxy-3-methylaniline. LCMS [M+H]⁺ 458. ¹H-NMR (400 MHz, CHLOROFORM-d) δ ppm 8.96 (br. s., 1H), 7.40-7.46 (m, 1H), 7.33-7.39 (m, 1H), 7.22-7.32 (m, 2H), 7.15-7.21 (m, 1H), 6.94-7.01 (m, 1H), 6.80-6.85 (m, 1H), 4.43-4.55 (m, 1H), 3.85 (br. s., 3H), 2.63-2.79 (m, 3H), 2.22-2.32 (m, 5H), 1.72-1.90 (m, 4H).

Example 127: (Cis)-4-(4-bromo-2-oxo-2,3-dihydro-1H-1,3-benzodiazol-1-yl)-N-phenylcyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and aniline. LCMS [M+H]⁺ 414.

Example 128: (Cis)-4-(4-bromo-2-oxo-2,3-dihydro-1H-1,3-benzodiazol-1-yl)-N-(3,4-difluorophenyl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 3,4-difluoroaniline. LCMS [M+H]⁺ 450. ¹H-NMR (400 MHz, CHLOROFORM-d) δ ppm 8.23-8.29 (m, 1H), 7.67-7.76 (m, 1H), 7.39 (d, J=7.9 Hz, 1H), 7.19 (dd, J=8.2, 0.9 Hz, 1H), 7.10-7.17 (m, 2H), 6.98-7.04 (m, 1H), 4.46 (tt, J=12.8, 4.3 Hz, 1H), 2.62-2.75 (m, 3H), 2.20-2.28 (m, 2H), 1.82 (d, J=18.3 Hz, 4H).

Example 129: (Cis)-4-(4-bromo-2-oxo-2,3-dihydro-1H-1,3-benzodiazol-1-yl)-N-[4-methoxy-3-(trifluoromethyl)phenyl]cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 4-methoxy-3-(trifluoromethyl)aniline.
LCMS [M+H]⁺ 512. ¹H-NMR (400 MHz, CHLOROFORM-d) δ ppm 8.27 (br. s., 1H), 7.75-7.81 (m, 1H), 7.68 (br. s., 1H), 7.39 (d, J=7.9 Hz, 1H), 7.15-7.24 (m, 2H), 6.95-7.06 (m, 2H), 4.40-4.52 (m, 1H), 3.92 (s, 3H), 2.62-2.75 (m, 3H), 2.22-2.31 (m, 2H), 1.73-1.90 (m, 4H).

Example 130: (Cis)-4-(4-bromo-2-oxo-2,3-dihydro-1H-1,3-benzodiazol-1-yl)-N-(4-fluoro-3-methoxyphenyl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 4-fluoro-3-methoxyaniline. LCMS [M+H]⁺ 462. ¹H-NMR (400 MHz, CHLOROFORM-d) δ ppm 8.95 (br. s., 1H), 7.49-7.55 (m, 1H), 7.34-7.41 (m, 2H), 7.14-7.20 (m, 1H), 7.01-7.08 (m, 1H), 6.92-6.99 (m, 1H), 6.86-6.92 (m, 1H), 4.39-4.52 (m, 1H), 3.94 (br. s., 3H), 2.62-2.76 (m, 3H), 2.22-2.32 (m, 2H), 1.72-1.90 (m, 4H).

Example 131: (Cis)-4-(4-bromo-2-oxo-2,3-dihydro-1H-1,3-benzodiazol-1-yl)-N-(2,4-dichlorophenyl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 2,4-dichloroaniline. LCMS [M+H]⁺ 482

Example 132: (Cis)-4-(4-bromo-2-oxo-2,3-dihydro-1H-1,3-benzodiazol-1-yl)-N-(4-cyanophenyl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 4-aminobenzonitrile. LCMS [M+H]⁺ 439.

Example 133: (Cis)-4-(4-bromo-2-oxo-2,3-dihydro-1H-1,3-benzodiazol-1-yl)-N-[4-(trifluoromethyl)phenyl]cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 4-(trifluoromethyl)aniline. LCMS [M+H]⁺ 482. ¹H-NMR (400 MHz, CHLOROFORM-d) δ ppm 8.84 (s, 1H), 7.73 (d, J=8.5 Hz, 2H), 7.63 (d, J=8.5 Hz, 2H), 7.55 (s, 1H), 7.38 (d, J=7.9 Hz, 1H), 7.18 (dd, J=8.2, 0.9 Hz, 1H), 6.96-7.02 (m, 1H), 4.47 (tt, J=12.6, 4.3 Hz, 1H), 2.62-2.76 (m, 3H), 2.23-2.32 (m, 2H), 1.73-1.91 (m, 4H).

Example 134: (Cis)-4-(4-bromo-2-oxo-2,3-dihydro-1H-1,3-benzodiazol-1-yl)-N-[3-chloro-4-(trifluoromethoxy)phenyl]cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 3-chloro-4-(trifluoromethoxy)aniline. LCMS [M+H]⁺ 532. ¹H-NMR (400 MHz, CHLOROFORM-d) δ ppm 8.74-8.95 (m, 1H), 7.89 (br. s., 1H), 7.43-7.57 (m, 2H), 7.35-7.41 (m, 1H), 7.28-7.34 (m, 1H), 7.16-7.22 (m, 1H), 6.96-7.05 (m, 1H), 4.39-4.52 (m, 1H), 2.60-2.76 (m, 3H), 2.19-2.30 (m, 2H), 1.72-1.90 (m, 4H).

Example 135: (Cis)-4-(4-bromo-2-oxo-2,3-dihydro-1H-1,3-benzodiazol-1-yl)-N-(1H-indol-6-yl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 6-aminoindol. LCMS [M+H]⁺ 453.

Example 136: (Cis)-4-(4-bromo-2-oxo-2,3-dihydro-1H-1,3-benzodiazol-1-yl)-N-(4-fluorophenyl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 4-fluoroaniline. LCMS [M+H]⁺ 432.

Example 137: (Cis)-4-(4-bromo-2-oxo-2,3-dihydro-1H-1,3-benzodiazol-1-yl)-N-[3-fluoro-4-(trifluoromethyl)phenyl]cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 3-fluoro-4-(trifluoromethyl)aniline. LCMS [M+H]⁺ 500. ¹H-NMR (400 MHz, METHANOL-d₄) δ ppm 7.87 (d, J=13.3 Hz, 1H), 7.57-7.65 (m, 1H), 7.43-7.49 (m, 2H), 7.16-7.22 (m, 1H), 6.98-7.06 (m, 1H), 4.33-4.46 (m, 1H), 2.65-2.84 (m, 3H), 2.19-2.30 (m, 2H), 1.80-1.92 (m, 2H), 1.64-1.74 (m, 2H).

Example 138: (Cis)-4-(4-bromo-2-oxo-2,3-dihydro-1H-1,3-benzodiazol-1-yl)-N-(3-chlorophenyl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 3-chloroaniline. LCMS [M+H]$^+$ 448. $^1$H-NMR (400 MHz, METHANOL-d$_4$) δ ppm 7.80 (br. s., 1H), 7.42-7.49 (m, 2H), 7.26-7.33 (m, 1H), 7.14-7.20 (m, 1H), 7.05-7.11 (m, 1H), 6.96-7.03 (m, 1H), 4.32-4.45 (m, 1H), 2.63-2.81 (m, 3H), 2.19-2.29 (m, 2H), 1.77-1.90 (m, 2H), 1.62-1.72 (m, 2H).

Example 139: (Cis)-4-(4-bromo-2-oxo-2,3-dihydro-1H-1,3-benzodiazol-1-yl)-N-(4-methylphenyl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 4-methylaniline. LCMS [M+H]$^+$ 428. $^1$H-NMR (400 MHz, METHANOL-d$_4$) δ ppm 7.40-7.50 (m, 3H), 7.10-7.21 (m, 3H), 6.93-7.03 (m, 1H), 4.33-4.47 (m, 1H), 2.65-2.81 (m, 3H), 2.31 (br. s., 3H), 2.20-2.28 (m, 2H), 1.77-1.90 (m, 2H), 1.62-1.72 (m, 2H).

Example 140: (Cis)-4-(4-bromo-2-oxo-2,3-dihydro-1H-1,3-benzodiazol-1-yl)-N-(4-methoxyphenyl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 4-methoxyaniline. LCMS [M+H]$^+$ 444. $^1$H-NMR (400 MHz, METHANOL-d$_4$) δ ppm 7.43-7.48 (m, 2H), 7.17 (dd, J=8.2, 0.9 Hz, 1H), 6.95-7.00 (m, 1H), 6.88-6.93 (m, 2H), 4.40 (tt, J=12.8, 4.4 Hz, 1H), 3.78 (s, 3H), 2.65-2.78 (m, 3H), 2.20-2.28 (m, 2H), 1.83 (m, 2H), 1.62-1.71 (m, 2H).

Example 141: (Cis)-4-(4-bromo-2-oxo-2,3-dihydro-1H-1,3-benzodiazol-1-yl)-N-[3-(trifluoromethyl)phenyl]cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 3-(trifluoromethyl)aniline.
LCMS [M+H]$^+$ 482. $^1$H-NMR (400 MHz, METHANOL-d$_4$) δ ppm 8.03-8.07 (m, 1H), 7.80-7.85 (m, 1H), 7.49-7.54 (m, 1H), 7.45 (dd, J=7.9, 0.9 Hz, 1H), 7.35-7.40 (m, 1H), 7.18 (dd, J=8.2, 0.9 Hz, 1H), 6.98 (t, J=8.1 Hz, 1H), 4.40 (tt, J=12.8, 4.4 Hz, 1H), 2.80 (dt, J=4.8, 2.5 Hz, 1H), 2.72-2.78 (m, 1H), 2.65-2.72 (m, 1H), 2.26 (m, 2H), 1.85 (m, 2H), 1.64-1.73 (m, 2H).

Example 142: (Cis)-4-(4-bromo-2-oxo-2,3-dihydro-1H-1,3-benzodiazol-1-yl)-N-(4-fluoro-3-methylphenyl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 4-fluoro-3-methylaniline. LCMS [M+H]$^+$ 446. $^1$H-NMR (400 MHz, METHANOL-d$_4$) δ ppm 7.42-7.47 (m, 2H), 7.35-7.41 (m, 1H), 7.15-7.20 (m, 1H), 6.95-7.03 (m, 2H), 4.39 (tt, J=12.8, 4.5 Hz, 1H), 2.72-2.78 (m, 2H), 2.65-2.71 (m, 1H), 2.20-2.29 (m, 5H), 1.84 (m, 2H), 1.63-1.71 (m, 2H).

Example 143: (Cis)-4-(4-bromo-2-oxo-2,3-dihydro-1H-1,3-benzodiazol-1-yl)-N-(3-methylphenyl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 3-methylaniline. LCMS [M+H]$^+$ 428. $^1$H-NMR (400 MHz, METHANOL-d$_4$) δ ppm 7.43-7.48 (m, 1H), 7.34-7.42 (m, 2H), 7.15-7.24 (m, 2H), 6.90-7.02 (m, 2H), 4.34-4.46 (m, 1H), 2.65-2.81 (m, 3H), 2.34 (br. s., 3H), 2.20-2.29 (m, 2H), 1.78-1.90 (m, 2H), 1.63-1.72 (m, 2H).

Example 144: (Cis)-4-(4-bromo-2-oxo-2,3-dihydro-1H-1,3-benzodiazol-1-yl)-N-[4-methyl-3-(trifluoromethyl)phenyl]cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 4-methyl-3-(trifluoromethyl)aniline.
LCMS [M+H]$^+$ 496. $^1$H-NMR (400 MHz, DMSO-d$_6$) δ ppm 11.29 (s, 1H), 10.12 (s, 1H), 8.02 (d, J=2.2 Hz, 1H), 7.82 (dd, J=8.4, 2.2 Hz, 1H), 7.40 (d, J=8.2 Hz, 1H), 7.28 (dd, J=8.1, 0.6 Hz, 1H), 7.16 (dd, J=8.1, 0.6 Hz, 1H), 6.96 (t, J=8.1 Hz, 1H), 4.27 (tt, J=12.6, 4.4 Hz, 1H), 2.76 (br. s., 1H), 2.47-2.60 (overlapping m, 2H), 2.40 (br. s, 3H), 2.09-2.20 (m, 2H), 1.69-1.81 (m, 2H), 1.53-1.63 (m, 2H).

Example 145: (Cis)-4-(4-bromo-2-oxo-2,3-dihydro-1H-1,3-benzodiazol-1-yl)-N-(1H-indol-4-yl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 4-aminoindol. LCMS [M+H]$^+$ 453. $^1$H-NMR (400 MHz, DMSO-d$_6$) δ ppm 11.29 (s, 1H), 11.12 (br. s., 1H), 9.59 (s, 1H), 7.51 (d, J=7.3 Hz, 1H), 7.35 (d, J=7.9 Hz, 1H), 7.28-7.31 (m, 1H), 7.18 (d, J=7.9 Hz, 1H), 7.15 (dd, J=8.1, 0.6 Hz, 1H), 7.03-7.08 (m, 1H), 6.96 (t, J=8.1 Hz, 1H), 6.66 (br. t, J=2.2, 2.2 Hz, 1H), 4.31 (tt, J=12.7, 4.5 Hz, 1H), 2.96 (br. s., 1H), 2.57-2.71 (m, 2H), 2.12-2.23 (m, 2H), 1.72-1.85 (m, 2H), 1.53-1.65 (m, 2H).

Example 146: (Cis)-4-(4-chloro-2-oxo-2,3-dihydro-1H-1,3-benzodiazol-1-yl)-N-(3-methoxy-4-methylphenyl)cyclohexane-1-carboxamide The title compound was synthesized according to General procedure H from (cis)-4-(4-chloro-2-oxo-2,3-dihydro-1H-1,3-benzodiazol-1-yl)cyclohexane-1-carboxylic acid and 3-methoxy-4-methylaniline. LCMS [M+H]$^+$ 414. $^1$H-NMR (400 MHz, DMSO-d$_6$) δ ppm 11.40 (s, 1H), 9.82 (s, 1H), 7.27-7.32 (m, 2H), 7.17 (dd, J=7.9, 1.9 Hz, 1H), 7.06 (dd, J=7.9, 0.9 Hz, 1H), 7.01-7.04 (m, 2H), 4.22-4.34 (m, 1H), 3.79 (s, 3H), 2.74 (br. s., 1H), 2.52-2.62 (m, 2H), 2.14 (m, 2H), 2.10 (s, 3H), 1.68-1.80 (m, 2H), 1.53-1.61 (m, 2H).

Example 147: (Cis)-4-(4-chloro-2-oxo-2,3-dihydro-1H-1,3-benzodiazol-1-yl)-N-(4-methoxyphenyl)cyclohexane-1-carboxamide The title compound was synthesized according to General procedure H from (cis)-4-(4-chloro-2-oxo-2,3-dihydro-1H-1,3-benzodiazol-1-yl)cyclohexane-1-carboxylic acid and 4-methoxyaniline. LCMS [M+H]$^+$ 400. $^1$H-NMR (400 MHz, DMSO-d$_6$) δ ppm 11.40 (br. s., 1H), 9.75 (br. s., 1H), 7.55 (br. d, J=7.9 Hz, 2H), 7.25-7.32 (m, 1H), 7.04 (br. s., 2H), 6.91 (br. d, J=8.2 Hz, 2H), 4.22-4.35 (m, 1H), 3.74 (s, 3H), 2.72 (br. s., 1H), 2.53-2.64 (m, 2H), 2.07-2.18 (m, 2H), 1.67-1.80 (m, 2H), 1.51-1.61 (m, 2H).

Example 148: (Cis)-4-(4-chloro-2-oxo-2,3-dihydro-1H-1,3-benzodiazol-1-yl)-N-(1H-indol-6-yl)cyclohexane-1-carboxamide The title compound was synthesized according to General procedure H from (cis)-4-(4-chloro-2-oxo-2,3-dihydro-1H-1,3-benzodiazol-1-yl)cyclohexane-1-carboxylic acid and 6-aminoindol. LCMS [M+H]$^+$ 409. $^1$H-NMR (400 MHz, DMSO-d$_6$) δ ppm 11.41 (s, 1H), 11.01 (s, 1H), 9.78 (s, 1H), 8.00-8.03 (m, 1H), 7.45 (d, J=8.5 Hz, 1H), 7.29-7.34 (m, 1H), 7.27 (dd, J=3.0, 2.4 Hz, 1H), 7.06-7.09 (m, 1H), 7.03-7.05 (m, 2H), 6.36 (ddd, J=3.1, 2.0, 0.9 Hz, 1H), 4.30 (tt, J=12.6, 4.3 Hz, 1H), 2.77 (br. s., 1H), 2.62 (qd, J=12.7, 3.2 Hz, 2H), 2.12-2.20 (m, 2H), 1.70-1.82 (m, 2H), 1.58 (dd, J=9.2, 3.5 Hz, 2H).

Example 149: (Cis)-4-(4-chloro-2-oxo-2,3-dihydro-1H-1,3-benzodiazol-1-yl)-N-(4-methylphenyl)cyclohexane-1-carboxamide The title compound was synthesized according to General procedure H from (cis)-4-(4-chloro-2-oxo-2,3-dihydro-1H-1,3-benzodiazol-1-yl)cyclohexane-1-carboxylic acid and 4-methylaniline. LCMS [M+H]$^+$ 384. $^1$H-NMR (400 MHz, DMSO-d$_6$) δ ppm 11.40 (s, 1H), 9.80 (s, 1H), 7.51-7.56 (m, 2H), 7.25-7.31 (m, 1H), 7.13 (br. d, J=7.9 Hz, 2H), 7.02-7.07 (m, 2H), 4.28 (tt, J=12.6, 4.2 Hz, 1H), 2.74 (br. s., 1H), 2.53-2.63 (m, 2H), 2.27 (s, 3H), 2.08-2.17 (m, 2H), 1.68-1.80 (m, 2H), 1.52-1.60 (m, 2H).

Example 150: (Cis)-4-(4-chloro-2-oxo-2,3-dihydro-1H-1,3-benzodiazol-1-yl)-N-(4-chlorophenyl)cyclohexane-1-carboxamide The title compound was synthesized according to General procedure H from (cis)-4-(4-chloro-2-oxo-2,3-dihydro-1H-1,3-benzodiazol-1-yl)cyclohexane-1-carboxylic acid and 4-chloroaniline. LCMS [M+H]$^+$ 404. $^1$H-NMR (400 MHz, DMSO-d$_6$) δ ppm 11.40 (s, 1H), 10.04 (s, 1H), 7.66-7.72 (m, 2H), 7.36-7.41 (m, 2H), 7.23-7.29 (m, 1H), 7.01-7.07 (m, 2H), 4.28 (tt, J=12.5, 4.3 Hz, 1H), 2.76 (br. s., 1H), 2.53-2.62 (m, 2H), 2.10-2.18 (m, 2H), 1.69-1.81 (m, 2H), 1.52-1.63 (m, 2H).

Example 151: Methyl 2-methoxy-5-[(cis)-4-(4-bromo-2-oxo-2,3-dihydro-1H-1,3-benzodiazol-1-yl)cyclohexaneamido]benzoate The title compound was synthesized according to General procedure H from (cis)-4-(4-bromo-2-oxo-2,3-dihydro-1H-1,3-benzodiazol-1-yl)cyclohexane-1-carboxylic acid and methyl 5-amino-2-methoxybenzoate. LCMS [M+H]$^+$ 502. $^1$H-NMR (400 MHz, METHANOL-d$_4$) δ ppm 7.88 (d, J=2.8 Hz, 1H), 7.65 (dd, J=9.0, 2.8 Hz, 1H), 7.34 (dd, J=8.2, 0.9 Hz, 1H), 7.08 (dd, J=8.2, 0.9 Hz, 1H), 7.02 (d, J=9.0 Hz, 1H), 6.88 (t, J=8.2 Hz, 1H), 4.30 (tt, J=12.7, 4.4 Hz, 1H), 3.78 (s, 3H), 3.78 (s, 3H), 2.54-2.70 (m, 3H), 2.11-2.20 (m, 2H), 1.74 (m, 2H), 1.54-1.62 (m, 2H).

Example 152: (Cis)-4-(4-bromo-2-oxo-2,3-dihydro-1H-1,3-benzodiazol-1-yl)-N-(4-chloro-3-methylphenyl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 4-chloro-3-methylaniline. LCMS [M+H]$^+$ 462. $^1$H-NMR (400 MHz, DMSO-d$_6$) δ ppm 11.29 (s, 1H), 9.95 (s, 1H), 7.64 (d, J=2.2 Hz, 1H), 7.52 (dd, J=8.5, 2.2 Hz, 1H), 7.36 (d, J=8.5 Hz, 1H), 7.29 (dd, J=8.1, 0.9 Hz, 1H), 7.16 (dd, J=8.1, 0.9 Hz, 1H), 6.98 (t, J=8.1 Hz, 1H), 4.27 (tt, J=12.5, 4.3 Hz, 1H), 2.75 (br. s., 1H), 2.53-2.61 (m, 2H), 2.33 (s, 3H), 2.09-2.17 (m, 2H), 1.69-1.81 (m, 2H), 1.52-1.62 (m, 2H).

Example 153: (Cis)-4-(4-bromo-2-oxo-2,3-dihydro-1H-1,3-benzodiazol-1-yl)-N-(2-fluoro-4-methylphenyl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 2-fluoro-4-methylaniline. LCMS [M+H]$^+$ 446. $^1$H-NMR (400 MHz, DMSO-d$_6$) δ ppm 11.28 (s, 1H), 9.60 (s, 1H), 7.56 (t, J=8.2 Hz, 1H), 7.27 (dd, J=7.8, 0.8 Hz, 1H), 7.15 (dd, J=8.1, 0.8 Hz, 1H), 7.07-7.13 (m, 1H), 6.99-7.03 (m, 1H), 6.95 (t, J=8.1 Hz, 1H), 4.29 (tt, J=12.5, 4.1 Hz, 1H), 2.83 (br. s., 1H), 2.47-2.60 (overlapping m, 2H), 2.31 (s, 3H), 2.10-2.18 (m, 2H), 1.67-1.79 (m, 2H), 1.51-1.61 (m, 2H).

Example 154: (Cis)-4-(4-bromo-2-oxo-2,3-dihydro-1H-1,3-benzodiazol-1-yl)-N-(2,3-difluoro-4-methoxyphenyl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 2,3-difluoro-4-methoxyaniline. LCMS [M+H]$^+$ 480. $^1$H-NMR (400 MHz, DMSO-d$_6$) δ ppm 11.28 (s, 1H), 9.71 (s, 1H), 7.32 (td, J=8.8, 2.5 Hz, 1H), 7.25 (dd, J=8.1, 0.9 Hz, 1H), 7.15 (dd, J=8.1, 0.9 Hz, 1H), 7.03 (td, J=8.8, 2.1 Hz, 1H), 6.94 (t, J=8.1 Hz, 1H), 4.29 (tt, J=12.5, 4.1 Hz, 1H), 3.89 (s, 3H), 2.81 (br. s., 1H), 2.45-2.58 (overlapping m, 2H), 2.10-2.20 (m, 2H), 1.68-1.80 (m, 2H), 1.52-1.62 (m, 2H).

Example 155: (Cis)-4-(4-bromo-2-oxo-2,3-dihydro-1H-1,3-benzodiazol-1-yl)-N-(3-fluoro-5-methoxyphenyl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 3-fluoro-5-methoxyaniline. LCMS [M+H]$^+$ 462. $^1$H-NMR (400 MHz, DMSO-d$_6$) δ ppm 11.28 (s, 1H), 10.06 (s, 1H), 7.28 (dd, J=8.1, 0.6 Hz, 1H), 7.23 (dt, J=11.2, 2.1 Hz, 1H), 7.16 (dd, J=8.1, 0.6 Hz, 1H), 7.04-7.07 (m, 1H), 6.99 (t, J=8.1 Hz, 1H), 6.53 (dt, J=11.2, 2.3 Hz, 1H), 4.27 (tt, J=12.4, 4.2 Hz, 1H), 3.77 (s, 3H), 2.74 (br. s., 1H), 2.46-2.59 (overlapping m, 2H), 2.08-2.17 (m, 2H), 1.69-1.82 (m, 2H), 1.52-1.63 (m, 2H).

Example 156: (Cis)-4-(4-bromo-2-oxo-2,3-dihydro-1H-1,3-benzodiazol-1-yl)-N-(2-fluoro-4-methoxyphenyl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 2-fluoro-4-methoxyaniline. LCMS [M+H]$^+$ 462. $^1$H-NMR (400 MHz, DMSO-d$_6$) δ ppm 11.28 (s, 1H), 9.51 (s, 1H), 7.48 (t, J=9.0 Hz, 1H), 7.24-7.28 (m, 1H), 7.15 (dd, J=8.2, 0.6 Hz, 1H), 6.90-6.97 (m, 3H), 6.79 (ddd, J=8.9, 2.8, 0.9 Hz, 1H), 4.29 (tt, J=12.4, 4.2 Hz, 1H), 3.78 (s, 3H), 2.80 (br. s., 1H), 2.47-2.59 (overlapping m, 2H), 2.15 (m, 2H), 1.67-1.79 (m, 2H), 1.56 (m, 2H).

Example 157: (Cis)-4-(4-bromo-2-oxo-2,3-dihydro-1H-1,3-benzodiazol-1-yl)-N-(4-chloro-3-cyanophenyl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 5-amino-2-chlorobenzonitrile. LCMS [M+H]$^+$ 473. $^1$H-NMR (400 MHz, DMSO-d$_6$) δ ppm 11.29 (s, 1H), 10.36 (s, 1H), 8.26 (d, J=2.7 Hz, 1H), 7.91 (dd, J=9.0, 2.8 Hz, 1H), 7.72 (d, J=9.0 Hz, 1H), 7.26 (dd, J=8.0, 0.9 Hz, 1H), 7.16 (dd, J=8.1, 0.9 Hz, 1H), 6.99 (t, J=8.2 Hz, 1H), 4.27 (tt, J=12.6, 4.0 Hz, 1H), 2.78 (br. s., 1H), 2.45-2.58 (overlapping m, 2H), 2.11-2.20 (m, 2H), 1.77 (m, 2H), 1.55-1.63 (m, 2H).

Example 158: (Cis)-4-(4-bromo-2-oxo-2,3-dihydro-1H-1,3-benzodiazol-1-yl)-N-[3-methoxy-5-(trifluoromethyl)phenyl]cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 3-methoxy-5-(trifluoromethyl)aniline.

LCMS [M+H]$^+$ 512. $^1$H-NMR (400 MHz, DMSO-d$_6$) δ ppm 11.29 (s, 1H), 10.20 (s, 1H), 7.67 (br. s, 1H), 7.57 (t, J=1.9 Hz, 1H), 7.27 (dd, J=7.9, 0.6 Hz, 1H), 7.16 (dd, J=8.2, 0.9 Hz, 1H), 6.93-6.99 (m, 2H), 4.27 (tt, J=12.6, 4.0 Hz, 1H), 3.84 (s, 3H), 2.77 (br. s., 1H), 2.45-2.58 (overlapping m, 2H), 2.17 (m, 2H), 1.76 (m, 2H), 1.54-1.63 (m, 2H).

Example 159: (Cis)-4-(4-bromo-2-oxo-2,3-dihydro-1H-1,3-benzodiazol-1-yl)-N-(4-cyano-3-methoxyphenyl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 4-amino-2-methoxybenzonitrile. LCMS [M+H]$^+$ 469. $^1$H-NMR (400 MHz, DMSO-d$_6$) δ ppm 11.29 (s, 1H), 10.34 (s, 1H), 7.67 (d, J=8.5 Hz, 1H), 7.62 (d, J=1.9 Hz, 1H), 7.40 (dd, J=8.5, 1.9 Hz, 1H), 7.28 (dd, J=8.1, 0.8 Hz, 1H), 7.16 (dd, J=8.1, 0.8 Hz, 1H), 6.98 (t, J=8.1 Hz, 1H), 4.27 (tt, J=12.5, 4.2 Hz, 1H), 3.92 (s, 3H), 2.80 (br. s., 1H), 2.44-2.58 (overlapping m, 2H), 2.16 (m, 2H), 1.71-1.83 (m, 2H), 1.55-1.63 (m, 2H).

Example 160: (Cis)-4-(4-bromo-2-oxo-2,3-dihydro-1H-1,3-benzodiazol-1-yl)-N-(3,5-difluoro-4-methoxyphenyl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 3,5-difluoro-4-methoxyaniline. LCMS [M+H]$^+$ 480. $^1$H-NMR (400 MHz, DMSO-d$_6$) δ ppm 11.29 (br. s., 1H), 10.15 (br. s., 1H), 7.39-7.50 (m, 2H), 7.27 (d, J=7.3 Hz, 1H), 7.16 (d, J=7.6 Hz, 1H), 6.96-7.03 (m, 1H), 4.21-4.32 (m, 1H), 3.87 (s, 3H), 2.73 (br. s., 1H), 2.44-2.58 (overlapping m, 2H), 2.13 (m, 2H), 1.70-1.82 (m, 2H), 1.53-1.62 (m, 2H).

Example 161: (Cis)-4-(4-bromo-2-oxo-2,3-dihydro-1H-1,3-benzodiazol-1-yl)-N-(3-cyano-4-methoxyphenyl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 5-amino-2-methoxybenzonitrile. LCMS [M+H]$^+$ 469.

Example 162: (Cis)-4-(4-bromo-2-oxo-2,3-dihydro-1H-1,3-benzodiazol-1-yl)-N-(3-chloro-4-fluorophenyl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 3-chloro-4-fluoroaniline. LCMS [M+H]$^+$ 466.

Example 163: (Cis)-4-(4-bromo-2-oxo-2,3-dihydro-1H-1,3-benzodiazol-1-yl)-N-(3-chloro-5-methoxyphenyl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 3-chloro-5-methoxyaniline. LCMS [M+H]$^+$ 478.

Example 164: (Cis)-4-(4-bromo-2-oxo-2,3-dihydro-1H-1,3-benzodiazol-1-yl)-N-(3-fluoro-4-methoxyphenyl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 3-fluoro-4-methoxyaniline. LCMS [M+H]$^+$ 462.

Example 165: (Cis)-4-(4-bromo-2-oxo-2,3-dihydro-1H-1,3-benzodiazol-1-yl)-N-(3-methoxyphenyl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 3-methoxyaniline. LCMS [M+H]$^+$ 444. $^1$H-NMR (400 MHz, DMSO-d$_6$) δ ppm 11.29 (s, 1H), 9.88 (s, 1H), 7.33-7.35 (m, 1H), 7.31 (d, J=8.1 Hz, 1H), 7.20-7.26 (m, 2H), 7.16 (dd, J=8.1, 0.6 Hz, 1H), 6.98 (t, J=8.1 Hz, 1H), 6.61-6.67 (m, 1H), 4.28 (tt, J=12.6, 4.3 Hz, 1H), 3.76 (s, 3H), 2.75 (br. s., 1H), 2.53-2.62 (m, 2H), 2.14 (m, 2H), 1.68-1.80 (m, 2H), 1.52-1.61 (m, 2H).

Example 166: (Cis)-N-(2H-1,3-benzodioxol-5-yl)-4-(4-bromo-2-oxo-2,3-dihydro-1H-1,3-benzodiazol-1-yl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 2H-1,3-benzodioxol-5-amine. LCMS [M+H]$^+$ 458. $^1$H-NMR (400 MHz, DMSO-d$_6$) δ ppm 11.28 (s, 1H), 9.80 (s, 1H), 7.36 (d, J=2.2 Hz, 1H), 7.31 (d, J=7.9 Hz, 1H), 7.16 (dd, J=8.2, 0.6 Hz, 1H), 6.96-7.03 (m, 2H), 6.87 (d, J=8.2 Hz, 1H), 6.00 (s, 2H), 4.27 (tt, J=12.6, 4.2 Hz, 1H), 2.71 (br. s., 1H), 2.53-2.62 (m, 2H), 2.06-2.17 (m, 2H), 1.66-1.80 (m, 2H), 1.50-1.60 (m, 2H).

Example 167: (Cis)-4-(4-bromo-2-oxo-2,3-dihydro-1H-1,3-benzodiazol-1-yl)-N-(2,3-dimethylphenyl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 2,3-dimethylaniline. LCMS [M+H]$^+$ 442. $^1$H-NMR (400 MHz, DMSO-d$_6$) δ ppm 11.28 (s, 1H), 9.42 (s, 1H), 7.26 (d, J=8.1 Hz, 1H), 7.15 (dd, J-8.1, 0.6 Hz, 1H), 7.07-7.11 (m, 2H), 7.03-7.07 (m, 1H), 6.94 (t, J=8.1 Hz, 1H), 4.29 (tt, J=12.6, 4.1 Hz, 1H), 2.80 (br. s., 1H), 2.53-2.64 (m, 2H), 2.28 (s, 3H), 2.14-2.22 (m, 2H), 2.11 (s, 3H), 1.70-1.82 (m, 2H), 1.52-1.61 (m, 2H).

Example 168: (Cis)-4-(4-bromo-2-oxo-2,3-dihydro-1H-1,3-benzodiazol-1-yl)-N-(6-methoxy-5-methylpyridin-3-yl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 6-methoxy-5-methylpyridin-3-amine. LCMS [M+H]$^+$ 459. $^1$H-NMR (400. MHz, DMSO-d$_6$) δ ppm 11.28 (br. s., 1H), 9.84 (s, 1H), 8.22 (dd, J=2.5, 0.6 Hz, 1H), 7.79 (dd, J=2.5, 0.9 Hz, 1H), 7.29 (dd, J=8.1, 0.6 Hz, 1H), 7.16 (dd, J=8.1, 0.6 Hz, 1H), 6.98 (t, J=8.1 Hz, 1H), 4.28 (tt, J=12.5, 4.4 Hz, 1H), 3.86 (s, 3H), 2.74 (br. s., 1H), 2.45-2.61 (overlapping m, 2H), 2.17 (d, J=0.6 Hz, 3H), 2.12 (br. s., 2H), 1.69-1.81 (m, 2H), 1.52-1.61 (m, 2H).

Example 169: (Cis)-4-(4-bromo-2-oxo-2,3-dihydro-1H-1,3-benzodiazol-1-yl)-N-(5-methyl-1,2-oxazol-3-yl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 5-methyl-1,2-oxazol-3-amine. LCMS [M+H]$^+$ 419. $^1$H-NMR (400 MHz, DMSO-d$_6$) δ ppm 11.29 (s, 1H), 10.89 (s, 1H), 7.25 (d, J=8.1 Hz, 1H), 7.16 (dd, J=8.1, 0.9 Hz, 1H), 6.98 (t, J=8.1 Hz, 1H), 6.75 (s, 1H), 4.26 (tt, J=12.5, 4.1 Hz, 1H), 2.80 (br. s., 1H), 2.42-2.49 (m, 2H), 2.40 (d, J=0.9 Hz, 3H), 2.05-2.15 (m, 2H), 1.66-1.79 (m, 2H), 1.51-1.61 (m, 2H).

Example 170: (Cis)-4-(4-bromo-2-oxo-2,3-dihydro-1H-1,3-benzodiazol-1-yl)-N-(1-methyl-1H-pyrazol-4-yl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 1-methyl-1H-pyrazol-4-amine. LCMS [M+H]$^+$ 418. $^1$H-NMR (400 MHz, DMSO-d$_6$) δ ppm 11.28 (s, 1H), 9.90 (s, 1H), 7.96 (d, J=0.6 Hz, 1H), 7.42 (d, J=0.6 Hz, 1H), 7.30 (d, J=8.1 Hz, 1H), 7.16 (dd, J=8.1, 0.9 Hz, 1H), 6.98 (t, J=8.1 Hz, 1H), 4.21-4.31 (m, 1H), 3.81 (s, 3H), 2.65-2.71 (m, 1H), 2.45-2.59 (overlapping m, 2H), 2.06-2.15 (m, 2H), 1.66-1.77 (m, 2H), 1.51-1.60 (m, 2H).

Example 171: (Cis)-4-(4-bromo-2-oxo-2,3-dihydro-1H-1,3-benzodiazol-1-yl)-N-(1-methyl-1H-indazol-5-yl)cyclohexane-1-carboxamide The title compound was synthesized according to General procedure H from (cis)-4-(4-bromo-2-oxo-2,3-dihydro-1H-1,3-benzodiazol-1-yl)cyclohexane-1-carboxylic acid and 1-methyl-1H-indazol-5-amine. LCMS [M+H]$^+$ 468. $^1$H-NMR (400 MHz, DMSO-d$_6$) δ ppm 11.29 (s, 1H), 9.92 (s, 1H), 8.18 (dd, J=1.9, 0.6 Hz, 1H), 8.02 (d, J=0.9 Hz, 1H), 7.60 (dt, J=9.0, 0.9 Hz, 1H), 7.50 (dd, J=9.0, 1.9 Hz, 1H), 7.34 (dd, J=8.1, 0.6 Hz, 1H), 7.16 (dd, J=8.1, 0.6 Hz, 1H), 6.99 (t, J=8.1 Hz, 1H), 4.30 (tt, J=12.6, 4.3 Hz, 1H), 4.03 (s, 3H), 2.78 (br. s., 1H), 2.61 (m, 2H), 2.13-2.21 (m, 2H), 1.70-1.83 (m, 2H), 1.54-1.62 (m, 2H).

Example 172: N-(3-Chloro-4-methoxyphenyl)-4-(5-methoxy-2-oxo-2,3-dihydro-1H-1,3-benzodiazol-1-yl)piperidine-1-carboxamide The title compound was synthesized according to General procedure I from 5-methoxy-1-(piperidin-4-yl)-2,3-dihydro-1H-1,3-benzodiazol-2-one and 3-chloro-4-methoxyaniline. LCMS [M+H]$^+$ 431.

Example 173: N-(3-Chloro-4-methoxyphenyl)-4-(5-fluoro-2-oxo-2,3-dihydro-1H-1,3-benzodiazol-1-yl)piperidine-1-carboxamide The title compound was synthesized according to General procedure I from 5-fluoro-1-(piperidin-4-yl)-2,3-dihydro-1H-1,3-benzodiazol-2-one and 3-chloro-4-methoxyaniline. LCMS [M+H]$^+$ 419.

Example 174: 4-(4-Amino-2-oxo-2,3-dihydro-1H-1,3-benzodiazol-1-yl)-N-(3-chloro-4-methoxyphenyl)piperidine-1-carboxamide The title compound was synthesized according to General procedure I from 4-amino-1-(piperidin-4-yl)-2,3-dihydro-1H-1,3-benzodiazol-2-one and 3-chloro-4-methoxyaniline. LCMS [M+H]$^+$ 416.

Example 175: N-(3-Chloro-4-methoxyphenyl)-4-[2-oxo-4-(propylamino)-2,3-dihydro-1H-1,3-benzodiazol-1-yl]piperidine-1-carboxamide Step 1: N-benzyl-3-fluoro-2-nitro-N-propyl-aniline was synthesized according to General procedure A from 1,3-difluoro-2-nitrobenzene and N-benzylpropylamine. LCMS [M+H]$^+$ 289.

Step 2: tert-butyl 4-[3-[benzyl(propyl)amino]-2-nitro-anilino]piperidine-1-carboxylate was synthesized according to General procedure A from N-benzyl-3-fluoro-2-nitro-N-propyl-aniline and tert-butyl 4-aminopiperidine-1-carboxylate. LCMS [M+H]$^+$ 469.

Step 3: tert-butyl 4-[4-[benzyl(propyl)amino]-2-oxo-3H-benzimidazol-1-yl]piperidine-1-carboxylate was synthesized according to General procedure B from tert-butyl 4-[3-[benzyl(propyl)amino]-2-nitro-anilino]piperidine-1-carboxylate. LCMS [M+H]⁺ 465

Step 4: tert-butyl 4-[2-oxo-4-(propylamino)-3H-benzimidazol-1-yl]piperidine-1-carboxylate was synthesized according to General procedure G from tert-butyl 4-[4-[benzyl(propyl)amino]-2-oxo-3H-benzimidazol-1-yl]piperidine-1-carboxylate. LCMS [M+H]⁺ 375. ¹H-NMR (400 MHz, Chloroform-d) δ ppm 10.97 (br. s., 1H), 6.98 (t, J=8.1 Hz, 1H), 6.62 (d, J=8.2 Hz, 1H), 6.48 (d, J=7.9 Hz, 1H), 4.19-4.45 (m, 3H), 3.22 (t, J=7.0 Hz, 2H), 2.84 (br. s., 2H), 2.27-2.40 (m, 2H), 1.70-1.84 (m, 4H), 1.51 (s, 9H), 1.07 (t, J=7.4 Hz, 3H).

Step 5: 1-(piperidin-4-yl)-4-(propylamino)-2,3-dihydro-1H-1,3-benzodiazol-2-one was synthesized according to General procedure G from tert-butyl 4-[2-oxo-4-(propylamino)-2,3-dihydro-1H-1,3-benzodiazol-1-yl]piperidine-1-carboxylate. LCMS [M+H]⁺ 275.

Step 5: the title compound was synthesized according to General procedure C from 1-(piperidin-4-yl)-4-(propylamino)-2,3-dihydro-1H-1,3-benzodiazol-2-one and 3-chloro-4-methoxyaniline. LCMS [M+H]⁺ 458.

Example 176: N-(3-Chloro-4-methoxyphenyl)-4-[4-(methylsulfanyl)-2-oxo-2,3-dihydro-1H-1,3-benzodiazol-1-yl]piperidine-1-carboxamide The title compound was synthesized according to General procedure I from 4-(methylsulfanyl)-1-(piperidin-4-yl)-2,3-dihydro-1H-1,3-benzodiazol-2-one and 3-chloro-4-methoxyaniline. LCMS [M+H]⁺ 447.

Example 177: 4-(4-Bromo-2-oxo-2,3-dihydro-1H-1,3-benzodiazol-1-yl)-N-(3-chloro-4-methoxyphenyl)-3-hydroxypiperidine-1-carboxamide The title compound was synthesized according to General procedure I from 4-bromo-1-(3-hydroxypiperidin-4-yl)-2,3-dihydro-1H-1,3-benzodiazol-2-one and 3-chloro-4-methoxyaniline. LCMS [M+H]⁺ 495.

Example 178: N-(3-Chloro-4-methoxyphenyl)-4-(5-cyano-2-oxo-2,3-dihydro-1H-1,3-benzodiazol-1-yl)piperidine-1-carboxamide The title compound was synthesized according to General procedure I from 2-oxo-1-(piperidin-4-yl)-2,3-dihydro-1H-1,3-benzodiazole-5-carbonitrile and 3-chloro-4-methoxyaniline. LCMS [M+H]⁺ 426.

Example 179: N-(3-Chloro-4-methoxyphenyl)-4-(5-methyl-2-oxo-2,3-dihydro-1H-1,3-benzodiazol-1-yl)piperidine-1-carboxamide The title compound was synthesized according to General procedure I from 5-methyl-1-(piperidin-4-yl)-2,3-dihydro-1H-1,3-benzodiazol-2-one and 3-chloro-4-methoxyaniline. LCMS [M+H]⁺ 415.

Example 180: N-(3-Chloro-4-methoxyphenyl)-4-{7-methyl-2-oxo-1H,2H,3H-imidazo[4,5-b]pyridin-3-yl}piperidine-1-carboxamide Step 1: tert-butyl 4-[(4-methyl-3-nitro-2-pyridyl)amino]piperidine-1-carboxylate was synthesized according to General procedure A from 2-chloro-4-methyl-3-nitro-pyridine and tert-butyl 4-aminopiperidine-1-carboxylate. LCMS [M+H]⁺ 337.

Step 2: tert-butyl 4-(7-methyl-2-oxo-1H-imidazo[4,5-b]pyridin-3-yl)piperidine-1-carboxylate was synthesized according to General procedure B from tert-butyl 4-[(4-methyl-3-nitro-2-pyridyl)amino]piperidine-1-carboxylate. LCMS [M+H]⁺ 333. ¹H-NMR (400 MHz, Chloroform-d) δ ppm 10.10 (br. s., 1H), 7.94 (d, J=5.4 Hz, 1H), 6.84 (dd, J=5.2, 0.8 Hz, 1H), 4.58 (tt, J=12.1, 4.0 Hz, 1H), 4.31 (br. s., 2H), 2.87 (br. s., 2H), 2.59-2.72 (m, 2H), 2.41 (s, 3H), 1.75-1.85 (m, 2H), 1.50 (s, 9H).

Step 3: 7-methyl-3-(4-piperidyl)-1H-imidazo[4,5-b]pyridin-2-one was synthesized according to General procedure C from tert-butyl 4-(7-methyl-2-oxo-1H-imidazo[4,5-b]pyridin-3-yl)piperidine-1-carboxylate. LCMS [M+H]⁺ 233. ¹H-NMR (400 MHz, DMSO-d6) δ ppm 11.31 (s, 1H), 8.82-8.95 (m, 1H), 8.41-8.56 (m, 1H), 7.83 (d, J=5.4 Hz, 1H), 6.88 (dd, J=5.4, 0.6 Hz, 1H), 4.53-4.64 (m, 1H), 3.37-3.40 (m, 2H), 3.05-3.18 (m, 2H), 2.67-2.82 (m, 2H), 2.30 (s, 3H), 1.82-1.92 (m, 2H).

Step 4: the title compound was synthesized according to General procedure I from 7-methyl-3-(4-piperidyl)-1H-imidazo[4,5-b]pyridin-2-one and 3-chloro-4-methoxyaniline. LCMS [M+H]⁺ 416.

Example 181: N-(3-Chloro-4-methoxyphenyl)-4-{6-methyl-2-oxo-1H,2H,3H-imidazo[4,5-b]pyridin-3-yl}piperidine-1-carboxamide Step 1: tert-butyl 4-[(5-methyl-3-nitro-2-pyridyl)amino]piperidine-1-carboxylate was synthesized according to General procedure A from 2-chloro-5-methyl-3-nitro-pyridine and tert-butyl 4-aminopiperidine-1-carboxylate. LCMS [M+H]⁺ 337.

Step 2: tert-butyl 4-(6-methyl-2-oxo-1H-imidazo[4,5-b]pyridin-3-yl)piperidine-1-carboxylate was synthesized according to General procedure B from tert-butyl 4-[(5-methyl-3-nitro-2-pyridyl)amino]piperidine-1-carboxylate. LCMS [M+H]⁺ 333. ¹H-NMR (400 MHz, Chloroform-d) δ ppm 9.46 (br. s., 1H), 7.86 (dd, J=1.9, 0.9 Hz, 1H), 7.17 (d, J=1.3 Hz, 1H), 4.55 (tt, J=12.1, 4.0 Hz, 1H), 4.20-4.40 (m, 2H), 2.60-2.80 (m, 2H), 2.64-2.73 (m, 2H), 2.36 (s, 3H), 1.74-1-84 (m, 2H), 1.51 (s, 9H).

Step 3: 6-methyl-3-(4-piperidyl)-1H-imidazo[4,5-b]pyridin-2-one was synthesized according to General procedure C from tert-butyl 4-(6-methyl-2-oxo-1H-imidazo[4,5-b]pyridin-3-yl)piperidine-1-carboxylate. LCMS [M+H]⁺ 233. ¹H-NMR (400 MHz, DMSO-d6) δ ppm 11.14 (s, 1H), 8.91 (br. s., 1H), 8.42-8.56 (m, 1H), 7.77 (s, 1H), 7.17 (d, J=0.6 Hz, 1H), 4.51-4.62 (m, 1H), 3.40 (br. s., 2H), 3.05-3.18 (m, 2H), 2.67-2.80 (m, 2H), 2.29 (s, 3H), 1.82-1.92 (m, 2H).

Step 4: the title compound was synthesized according to General procedure I from and 3-chloro-4-methoxyaniline. LCMS [M+H]⁺ 416.

Example 182: N-(3-Chloro-4-methoxyphenyl)-4-(4-fluoro-2-oxo-2,3-dihydro-1H-1,3-benzodiazol-1-yl)piperidine-1-carboxamide The title compound was synthesized according to General procedure I from 4-fluoro-1-(piperidin-4-yl)-2,3-dihydro-1H-1,3-benzodiazol-2-one and 3-chloro-4-methoxyaniline. LCMS [M+H]⁺ 419.

Example 183: Cis-4-(4-bromo-2-oxo-2,3-dihydro-1H-1,3-benzodiazol-1-yl)-N-(6-methoxypyridin-3-yl)cyclohexane-1-carboxamide The title compound was synthesized according to General procedure H from cis-4-(4-bromo-2-oxo-2,3-dihydro-1H-1,3-benzodiazol-1-yl)cyclohexane-1-carboxylic acid and 5-amino-2-methoxypyridine. LCMS [M+H]$^+$ 445.

Example 184: Cis-4-(4-bromo-2-oxo-2,3-dihydro-1H-1,3-benzodiazol-1-yl)-N-(6-chloropyridin-3-yl)cyclohexane-1-carboxamide The title compound was synthesized according to General procedure H from cis-4-(4-bromo-2-oxo-2,3-dihydro-1H-1,3-benzodiazol-1-yl)cyclohexane-1-carboxylic acid and 5-amino-2-chloropyridine. LCMS [M+H]$^+$ 449.

Example 185: Cis-4-(4-bromo-2-oxo-2,3-dihydro-1H-1,3-benzodiazol-1-yl)-N-(5,6-dichloropyridin-3-yl)cyclohexane-1-carboxamide The title compound was synthesized according to General procedure H from cis-4-(4-bromo-2-oxo-2,3-dihydro-1H-1,3-benzodiazol-1-yl)cyclohexane-1-carboxylic acid and 5-amino-2,3-dichloropyridine. LCMS [M+H]$^+$ 483.

Example 186: Cis-4-(4-bromo-2-oxo-2,3-dihydro-1H-1,3-benzodiazol-1-yl)-N-(1H-indazol-7-yl)cyclohexane-1-carboxamide The title compound was synthesized according to General procedure H from cis-4-(4-bromo-2-oxo-2,3-dihydro-1H-1,3-benzodiazol-1-yl)cyclohexane-1-carboxylic acid and 7-amino-1H-indazole. LCMS [M+H]$^+$ 454.

Example 187: Cis-4-(4-bromo-2-oxo-2,3-dihydro-1H-1,3-benzodiazol-1-yl)-N-(6-chloro-5-methylpyridin-3-yl)cyclohexane-1-carboxamide The title compound was synthesized according to General procedure H from cis-4-(4-bromo-2-oxo-2,3-dihydro-1H-1,3-benzodiazol-1-yl)cyclohexane-1-carboxylic acid and 5-amino-2-chloro-3-methylpyridine. LCMS [M+H]$^+$ 463.

Example 188: Cis-4-(4-bromo-2-oxo-2,3-dihydro-1H-1,3-benzodiazol-1-yl)-N-(5-chloropyridin-3-yl)cyclohexane-1-carboxamide The title compound was synthesized according to General procedure H cis-4-(4-bromo-2-oxo-2,3-dihydro-1H-1,3-benzodiazol-1-yl)cyclohexane-1-carboxylic acid and 3-amino-5-chloropyridine. LCMS [M+H]$^+$ 449.

Example 189: Cis-4-(4-bromo-2-oxo-2,3-dihydro-1H-1,3-benzodiazol-1-yl)-N-(5-methylpyridin-2-yl)cyclohexane-1-carboxamide The title compound was synthesized according to General procedure H from cis-4-(4-bromo-2-oxo-2,3-dihydro-1H-1,3-benzodiazol-1-yl)cyclohexane-1-carboxylic acid and 2-amino-5-methylpyridine. LCMS [M+H]$^+$ 429.

Example 190: Cis-4-(4-bromo-2-oxo-2,3-dihydro-1H-1,3-benzodiazol-1-yl)-N-(6-methylpyridin-3-yl)cyclohexane-1-carboxamide The title compound was synthesized according to General procedure H from cis-4-(4-bromo-2-oxo-2,3-dihydro-1H-1,3-benzodiazol-1-yl)cyclohexane-1-carboxylic acid and 5-amino-2-methylpyridine. LCMS [M+H]$^+$ 429.

Example 191: Cis-4-(4-bromo-2-oxo-2,3-dihydro-1H-1,3-benzodiazol-1-yl)-N-(4-hydroxyphenyl)cyclohexane-1-carboxamide The title compound was synthesized according to General procedure H from cis-4-(4-bromo-2-oxo-2,3-dihydro-1H-1,3-benzodiazol-1-yl)cyclohexane-1-carboxylic acid and 4-aminophenol. LCMS [M+H]$^+$ 430.

Example 192: Cis-4-(4-bromo-2-oxo-2,3-dihydro-1H-1,3-benzodiazol-1-yl)-N-(3,4-dimethoxyphenyl)cyclohexane-1-carboxamide The title compound was synthesized according to General procedure H from cis-4-(4-bromo-2-oxo-2,3-dihydro-1H-1,3-benzodiazol-1-yl)cyclohexane-1-carboxylic acid and 3,4-dimethoxyaniline. LCMS [M+H]$^+$ 474.

Example 193: Cis-4-(4-bromo-2-oxo-2,3-dihydro-1H-1,3-benzodiazol-1-yl)-N-(3,4,5-trimethoxyphenyl)cyclohexane-1-carboxamide The title compound was synthesized according to General procedure H from cis-4-(4-bromo-2-oxo-2,3-dihydro-1H-1,3-benzodiazol-1-yl)cyclohexane-1-carboxylic acid and 3,4,5-trimethoxyaniline. LCMS [M+H]$^+$ 504.

Example 194: Cis-4-(4-bromo-2-oxo-2,3-dihydro-1H-1,3-benzodiazol-1-yl)-N-(4-hydroxy-3-methylphenyl)cyclohexane-1-carboxamide The title compound was synthesized according to General procedure H from cis-4-(4-bromo-2-oxo-2,3-dihydro-1H-1,3-benzodiazol-1-yl)cyclohexane-1-carboxylic acid and 4-amino-2-methylphenol. LCMS [M+H]$^+$ 444.

Example 195: Cis-N-(3-aminophenyl)-4-(4-bromo-2-oxo-2,3-dihydro-1H-1,3-benzodiazol-1-yl)cyclohexane-1-carboxamide The title compound was synthesized according to General procedure H from cis-4-(4-bromo-2-oxo-2,3-dihydro-1H-1,3-benzodiazol-1-yl)cyclohexane-1-carboxylic acid and m-phenylenediamine. LCMS [M+H]$^+$ 429.

Example 196: Cis-4-(4-bromo-2-oxo-2,3-dihydro-1H-1,3-benzodiazol-1-yl)-N-(3-hydroxyphenyl)cyclohexane-1-carboxamide The title compound was synthesized according to General procedure H from cis-4-(4-bromo-2-oxo-2,3-dihydro-1H-1,3-benzodiazol-1-yl)cyclohexane-1-carboxylic acid and 3-aminophenol. LCMS [M+H]$^+$ 430.

Example 197: Cis-4-(4-bromo-2-oxo-2,3-dihydro-1H-1,3-benzodiazol-1-yl)-N-(2,3-dihydro-1,4-benzodioxin-6-yl)cyclohexane-1-carboxamide The title compound was synthesized according to General procedure H from cis-4-(4-bromo-2-oxo-2,3-dihydro-1H-1,3-benzodiazol-1-yl)cyclohexane-1-carboxylic acid and 2,3-dihydro-1,4-benzodioxin-6-amine. LCMS [M+H]$^+$ 472.

Example 198: Cis-4-(4-bromo-2-oxo-2,3-dihydro-1H-1,3-benzodiazol-1-yl)-N-[3-(dimethylamino)phenyl]cyclohexane-1-carboxamide The title compound was synthesized according to General procedure H from cis-4-(4-bromo-2-oxo-2,3-dihydro-1H-1,3-benzodiazol-1-yl)cyclohexane-1-carboxylic acid and N,N-dimethyl-m-phenylenediamine. LCMS [M+H]$^+$ 457.

Example 199: Cis-4-(4-bromo-2-oxo-2,3-dihydro-1H-1,3-benzodiazol-1-yl)-N-(3-methyl-1H-indazol-5-yl)cyclohexane-1-carboxamide The title compound was synthesized according to General procedure H from cis-4-(4-bromo-2-oxo-2,3-dihydro-1H-1,3-benzodiazol-1-yl)cyclohexane-1-carboxylic acid and 5-amino-3-methyl-1H-indazole. LCMS [M+H]$^+$ 468.

Example 200: Cis-4-(4-bromo-2-oxo-2,3-dihydro-1H-1,3-benzodiazol-1-yl)-N-[4-(dimethylamino)phenyl]cyclohexane-1-carboxamide The title compound was synthesized according to General procedure H from cis-4-(4-bromo-2-oxo-2,3-dihydro-1H-1,3-benzodiazol-1-yl)cyclohexane-1-carboxylic acid and N,N-dimethyl-p-phenylenediamine. LCMS [M+H]$^+$ 457.

Example 201: Cis-4-(4-bromo-2-oxo-2,3-dihydro-1H-1,3-benzodiazol-1-yl)-N-(3-chloro-4-hydroxyphenyl)cyclohexane-1-carboxamide The title compound was synthesized according to General procedure H from cis-4-(4-bromo-2-oxo-2,3-dihydro-1H-1,3-benzodiazol-1-yl)cyclohexane-1-carboxylic acid and 4-amino-2-chlorophenol. LCMS [M+H]$^+$ 464.

Example 202: Cis-4-(4-bromo-2-oxo-2,3-dihydro-1H-1,3-benzodiazol-1-yl)-N-(5-chloro-6-methoxypyridin-3-yl)cyclohexane-1-carboxamide The title compound was synthesized according to General procedure H from cis-4-(4-bromo-2-oxo-2,3-dihydro-1H-1,3-benzodiazol-1-yl)cyclohexane-1-carboxylic acid and 5-amino-3-chloro-2-methoxypyridine. LCMS [M+H]$^+$ 479.

Example 203: Cis-4-(4-bromo-2-oxo-2,3-dihydro-1H-1,3-benzodiazol-1-yl)-N-(2-methyl-1,3-benzoxazol-6-yl)cyclohexane-1-carboxamide The title compound was synthesized according to General procedure H from cis-4-(4-bromo-2-oxo-2,3-dihydro-1H-1,3-benzodiazol-1-yl)cyclohexane-1-carboxylic acid and 6-amino-2-methyl-1,3-benzoxazole. LCMS [M+H]$^+$ 469.

Example 204: Cis-4-(4-bromo-2-oxo-2,3-dihydro-1H-1,3-benzodiazol-1-yl)-N-(quinolin-6-yl)cyclohexane-1-carboxamide The title compound was synthesized according to General procedure H from cis-4-(4-bromo-2-oxo-2,3-dihydro-1H-1,3-benzodiazol-1-yl)cyclohexane-1-carboxylic acid and 6-amino-quinoline. LCMS [M+H]$^+$ 465.

Example 205: Cis-4-(4-methoxy-2-oxo-2,3-dihydro-1H-1,3-benzodiazol-1-yl)-N-(4-methoxyphenyl)cyclohexane-1-carboxamide The title compound was synthesized according to General procedure H from cis-4-(4-methoxy-2-oxo-2,3-dihydro-1H-1,3-benzodiazol-1-yl)cyclohexane-1-carboxylic acid and 4-methoxyaniline. LCMS [M+H]$^+$ 396.

Example 206: Cis-4-(4-methoxy-2-oxo-2,3-dihydro-1H-1,3-benzodiazol-1-yl)-N-(4-methoxy-3-methylphenyl)cyclohexane-1-carboxamide The title compound was synthesized according to General procedure H from cis-4-(4-methoxy-2-oxo-2,3-dihydro-1H-1,3-benzodiazol-1-yl)cyclohexane-1-carboxylic acid and 4-methoxy-3-methylaniline. LCMS [M+H]$^+$ 410.

Example 207: Cis-N-(3-fluoro-4-methoxyphenyl)-4-(4-methoxy-2-oxo-2,3-dihydro-1H-1,3-benzodiazol-1-yl)cyclohexane-1-carboxamide The title compound was synthesized according to General procedure H from cis-4-(4-methoxy-2-oxo-2,3-dihydro-1H-1,3-benzodiazol-1-yl)cyclohexane-1-carboxylic acid and 3-fluoro-4-methoxyaniline. LCMS [M+H]$^+$ 414.

Example 208: Cis-4-(4-methoxy-2-oxo-2,3-dihydro-1H-1,3-benzodiazol-1-yl)-N-(6-methoxy-5-methylpyridin-3-yl)cyclohexane-1-carboxamide The title compound was synthesized according to General procedure H from cis-4-(4-methoxy-2-oxo-2,3-dihydro-1H-1,3-benzodiazol-1-yl)cyclohexane-1-carboxylic acid and 3-amino-2-methoxy-3-methylpyridine. LCMS [M+H]$^+$ 411.

Example 209: Cis-N-(1H-indol-6-yl)-4-(4-methoxy-2-oxo-2,3-dihydro-1H-1,3-benzodiazol-1-yl)cyclohexane-1-carboxamide The title compound was synthesized according to General procedure H from cis-4-(4-methoxy-2-oxo-2,3-dihydro-1H-1,3-benzodiazol-1-yl)cyclohexane-1-carboxylic acid and 6-amino-1H-indole. LCMS [M+H]$^+$ 405.

Example 210: N-(3-Methoxy-4-methylphenyl)-4-(2-oxo-2,3-dihydro-1H-1,3-benzodiazol-1-yl)piperidine-1-carboxamide The title compound was synthesized according to General procedure I from 1-(piperidin-4-yl)-2,3-dihydro-1H-1,3-benzodiazol-2-one and 3-methoxy-4-methylaniline. LCMS [M+H]$^+$ 381.

Example 211: Cis-4-(4-fluoro-2-oxo-2,3-dihydro-1H-1,3-benzodiazol-1-yl)-N-(4-methoxyphenyl)cyclohexane-1-carboxamide The title compound was synthesized according to General procedure H from cis-4-(4-fluoro-2-oxo-2,3-dihydro-1H-1,3-benzodiazol-1-yl)cyclohexane-1-carboxylic acid and 4-methoxyaniline. LCMS [M+H]$^+$ 384.

Example 212: Cis-4-(4-fluoro-2-oxo-2,3-dihydro-1H-1,3-benzodiazol-1-yl)-N-(4-methoxy-3-methylphenyl)cyclohexane-1-carboxamide The title compound was synthesized according to General procedure H from cis-4-(4-fluoro-2-oxo-2,3-dihydro-1H-1,3-benzodiazol-1-yl)cyclohexane-1-carboxylic acid and 4-methoxy-3-methylaniline. LCMS [M+H]$^+$ 398.

Example 213: Cis-4-(4-fluoro-2-oxo-2,3-dihydro-1H-1,3-benzodiazol-1-yl)-N-(3-fluoro-4-methoxyphenyl)cyclohexane-1-carboxamide The title compound was synthesized according to General procedure H from cis-4-(4-fluoro-2-oxo-2,3-dihydro-1H-1,3-benzodiazol-1-yl)cyclohexane-1-carboxylic acid and 3-fluoro-4-methoxyaniline. LCMS [M+H]+ 402.

Example 214: Cis-4-(4-fluoro-2-oxo-2,3-dihydro-1H-1,3-benzodiazol-1-yl)-N-(6-methoxy-5-methylpyridin-3-yl)cyclohexane-1-carboxamide The title compound was synthesized according to General procedure H from cis-4-(4-fluoro-2-oxo-2,3-dihydro-1H-1,3-benzodiazol-1-yl)cyclohexane-1-carboxylic acid and 5-amino-2-methoxy-3-methylpyridine. LCMS [M+H]+ 399.

Example 215: Cis-4-(4-fluoro-2-oxo-2,3-dihydro-1H-1,3-benzodiazol-1-yl)-N-(1H-indol-6-yl)cyclohexane-1-carboxamide The title compound was synthesized according to General procedure H from cis-4-(4-fluoro-2-oxo-2,3-dihydro-1H-1,3-benzodiazol-1-yl)cyclohexane-1-carboxylic acid and 6-amino-1H-indole. LCMS [M+H]+ 393.

Example 216: Cis-4-(6-fluoro-2-oxo-2,3-dihydro-1H-1,3-benzodiazol-1-yl)-N-(4-methoxyphenyl)cyclohexane-1-carboxamide The title compound was synthesized according to General procedure H from cis-4-(6-fluoro-2-oxo-2,3-dihydro-1H-1,3-benzodiazol-1-yl)cyclohexane-1-carboxylic acid and 4-methoxyaniline. LCMS [M+H]+ 384.

Example 217: Cis-4-(6-fluoro-2-oxo-2,3-dihydro-1H-1,3-benzodiazol-1-yl)-N-(4-methoxy-3-methylphenyl)cyclohexane-1-carboxamide The title compound was synthesized according to General procedure H from cis-4-(6-fluoro-2-oxo-2,3-dihydro-1H-1,3-benzodiazol-1-yl)cyclohexane-1-carboxylic acid and 4-methoxy-3-methylaniline. LCMS [M+H]+ 398.

Example 218: Cis-4-(6-fluoro-2-oxo-2,3-dihydro-1H-1,3-benzodiazol-1-yl)-N-(3-fluoro-4-methoxyphenyl)cyclohexane-1-carboxamide The title compound was synthesized according to General procedure H from cis-4-(6-fluoro-2-oxo-2,3-dihydro-1H-1,3-benzodiazol-1-yl)cyclohexane-1-carboxylic acid and 3-fluoro-4-methoxyaniline. LCMS [M+H]+ 402.

Example 219: Cis-4-(6-fluoro-2-oxo-2,3-dihydro-1H-1,3-benzodiazol-1-yl)-N-(3-methoxy-4-methylphenyl)cyclohexane-1-carboxamide The title compound was synthesized according to General procedure H from cis-4-(6-fluoro-2-oxo-2,3-dihydro-1H-1,3-benzodiazol-1-yl)cyclohexane-1-carboxylic acid and 3-methoxy-4-methylaniline. LCMS [M+H]+ 398.

Example 220: Cis-4-(6-fluoro-2-oxo-2,3-dihydro-1H-1,3-benzodiazol-1-yl)-N-(4-hydroxy-3-methylphenyl)cyclohexane-1-carboxamide The title compound was synthesized according to General procedure H from cis-4-(6-fluoro-2-oxo-2,3-dihydro-1H-1,3-benzodiazol-1-yl)cyclohexane-1-carboxylic acid and 4-amino-2-methylphenol. LCMS [M+H], 384.

Example 221: Cis-4-(4-bromo-2-oxo-2,3-dihydro-1H-1,3-benzodiazol-1-yl)-N-(3-hydroxy-4-methylphenyl)cyclohexane-1-carboxamide The title compound was synthesized according to General procedure H from cis-4-(4-bromo-2-oxo-2,3-dihydro-1H-1,3-benzodiazol-1-yl)cyclohexane-1-carboxylic acid and 5-amino-2-methylphenol. LCMS [M+H], 444.

Example 222: Cis-4-(4-bromo-2-oxo-2,3-dihydro-1H-1,3-benzodiazol-1-yl)-N-(2-hydroxy-4-methylphenyl)cyclohexane-1-carboxamide The title compound was synthesized according to General procedure H from cis-4-(4-bromo-2-oxo-2,3-dihydro-1H-1,3-benzodiazol-1-yl)cyclohexane-1-carboxylic acid and 2-amino-5-methylphenol. LCMS [M+H]444.

Example 223: Cis-N-(2-amino-4,5-dimethylphenyl)-4-(4-bromo-2-oxo-2,3-dihydro-1H-1,3-benzodiazol-1-yl)cyclohexane-1-carboxamide The title compound was synthesized according to General procedure H from cis-4-(4-bromo-2-oxo-2,3-dihydro-1H-1,3-benzodiazol-1-yl)cyclohexane-1-carboxylic acid and 3,4-dimethyl-o-phenylenediamine. LCMS [M+H]+ 457.

Example 224: 4-[cis-4-(4-bromo-2-oxo-2,3-dihydro-1H-1,3-benzodiazol-1-yl)cyclohexaneamido]benzamide The title compound was synthesized according to General procedure H from cis-4-(4-bromo-2-oxo-2,3-dihydro-1H-1,3-benzodiazol-1-yl)cyclohexane-1-carboxylic acid and 4-aminobenzamide. LCMS [M+H]+ 457.

Example 225: Cis-4-(4-{3-[2-(dimethylamino)ethoxy]phenyl}-2-oxo-2,3-dihydro-1H-1,3-benzodiazol-1-yl)-N-(3-methoxy-4-methylphenyl)cyclohexane-1-carboxamide The title compound was synthesized according to General procedure E from cis-4-(4-bromo-2-oxo-2,3-dihydro-1H-1,3-benzodiazol-1-yl)-N-(3-methoxy-4-methylphenyl)cyclohexane-1-carboxamide and dimethyl-(2-[3-(4,4,5,5-tetramethyl-[1,3,2]dioxaborolan-2-yl)-phenoxy]-ethyl)-amine. LCMS [M+H]+ 543.

Example 226: Cis-N-(3-methoxy-4-methylphenyl)-4-(2-oxo-2,3-dihydro-1H-1,3-benzodiazol-1-yl)cyclohexane-1-carboxamide A mixture of cis-4-(4-bromo-2-oxo-2,3-dihydro-1H-1,3-benzodiazol-1-yl)-N-(3-methoxy-4-methylphenyl)cyclohexane-1-carboxamide (1.0 equiv.) and Pd/C (0.20 equiv.) was stirred in a mixture of 1,4-dioxane and cyclohexene under nitrogen atmosphere at 100° C. for 20 h. The mixture was then purified by silica gel chromatography using EtOAc as eluent. LCMS [M+H]+ 380.

Example 227: Cis-4-(4-hydroxy-2-oxo-2,3-dihydro-1H-1,3-benzodiazol-1-yl)-N-(3-methoxy-4-methylphenyl)cyclohexane-1-carboxamide A mixture of cis-4-(4-bromo-2-oxo-2,3-dihydro-1H-1,3-benzodiazol-1-yl)-N-(3-methoxy-4-methylphenyl)cyclohexane-1-carboxamide (1.0 equiv.), 4,4,4',4',5,5,5',5'-Octamethyl-2,2'-bi-1,3,2-dioxaborolane (3.0 equiv.), KOAc (3.0 equiv.), and Pd(dppf) (0.15 equiv.) was stirred in 1,4-dioxane at 100° C. for 20 h. After cooling the reaction mixture to 20° C., $H_2O_2$ (30 wt % in $H_2O$, 6 equiv.) was added and the resulting mixture was stirred at 20° C. for 16 h. The mixture was then concentrated and purified by preparative HPLC. LCMS [M+H]$^+$ 396.

Example 228: N-[2-(Dimethylamino)ethyl]-2-oxo-1-[cis-4-[(3-methoxy-4-methylphenyl)carbamoyl]cyclohexyl]-2,3-dihydro-1H-1,3-benzodiazole-4-carboxamide The title compound was synthesized according to General procedure H from 2-oxo-1-[cis-4-[(3-methoxy-4-methylphenyl)carbamoyl]cyclohexyl]-2,3-dihydro-1H-1,3-benzodiazole-4-carboxylic acid and N,N-dimethyl-1,2-ethylenediamine. LCMS [M+H]$^+$ 494.

Example 229: Cis-4-(4-{[2-(dimethylamino)ethyl](methyl)amino}-2-oxo-2,3-dihydro-1H-1,3-benzodiazol-1-yl)-N-(3-methoxy-4-methylphenyl)cyclohexane-1-carboxamide Step 1: 4-[3-[2-(dimethylamino)ethyl-methyl-amino]-2-nitro-anilino]-N-(3-methoxy-4-methyl-phenyl)cyclohexanecarboxamide was synthesized according to General procedure M from cis-4-[(3-fluoro-2-nitrophenyl)amino]-N-(3-methoxy-4-methylphenyl)cyclohexane-1-carboxamide and N,N',N'-trimethylethylene-1,2-diamine. LCMS [M+H]$^+$ 484. $^1$H-NMR (400 MHz, Chloroform-d) δ ppm 7.43 (d, J=1.6 Hz, 1H), 7.36 (s, 1H), 7.20 (t, J=8.2 Hz, 1H), 7.03 (d, J=8.5 Hz, 1H), 6.77 (dd, J=7.9, 2.2 Hz, 1H), 6.34-6.41 (m, 2H), 6.23 (d, J=7.0 Hz, 1H), 3.84 (s, 3H), 3.63-3.72 (m, 1H), 3.47 (m, 2H), 2.92-2.97 (m, 2H), 2.79 (s, 3H), 2.58-2.67 (m, 6H), 2.39-2.47 (m, 1H), 2.17 (s, 3H), 1.71-1.99 (m, 8H).

Step 2: the title compound was synthesized according to General procedure B from 4-[3-[2-(dimethylamino)ethyl-methyl-amino]-2-nitro-anilino]-N-(3-methoxy-4-methyl-phenyl)cyclohexanecarboxamide. LCMS [M+H]$^+$ 480.

Example 230: Cis-N-(3-methoxy-4-methylphenyl)-4-(4-{[(4-methoxyphenyl)methyl]sulfanyl}-2-oxo-2,3-dihydro-1H-1,3-benzodiazol-1-yl)cyclohexane-1-carboxamide Step 1: a mixture of cis-4-[(3-fluoro-2-nitrophenyl)amino]cyclohexane-1-carboxylate (1.0 equiv.), 4-methoxybenzyl mercaptane (1.1 equiv.), and N,N-diisopropylethylamine (1.3 equiv.) in methanol was stirred at 70° C. for 16 h. The resulting mixture was concentrated and purified by silica gel chromatography which afforded methyl cis-4-[3-[(4-methoxyphenyl)methylsulfanyl]-2-nitro-anilino]cyclohexanecarboxylate. LCMS [M+H]$^+$ 297.

Step 2: methyl cis-4-[4-[(4-methoxyphenyl)methylsulfanyl]-2-oxo-3H-benzimidazol-1-yl]cyclohexanecarboxylate was synthesized according to General procedure B from methyl cis-4-[3-[(4-methoxyphenyl)methylsulfanyl]-2-nitro-anilino]cyclohexanecarboxylate. LCMS [M+H]$^+$ 427.

Step 3: cis-4-[4-[(4-methoxyphenyl)methylsulfanyl]-2-oxo-3H-benzimidazol-1-yl]cyclohexanecarboxylic acid was synthesized according to General procedure J from methyl cis-4-[4-[(4-methoxyphenyl)methylsulfanyl]-2-oxo-3H-benzimidazol-1-yl]cyclohexanecarboxylate. LCMS [M+H]$^+$ 413.

Step 4: the title compound was synthesized according to General procedure H from cis-4-[4-[(4-methoxyphenyl)methylsulfanyl]-2-oxo-3H-benzimidazol-1-yl]cyclohexanecarboxylic acid and 3-methoxy-4-methylaniline. LCMS [M+H]$^+$ 532.

Example 231: Cis-4-(4-bromo-2-oxo-2,3-dihydro-1H-1,3-benzodiazol-1-yl)-N-[3-(hydroxymethyl)phenyl]cyclohexane-1-carboxamide The title compound was synthesized according to General procedure H from cis-4-(4-bromo-2-oxo-2,3-dihydro-1H-1,3-benzodiazol-1-yl)cyclohexane-1-carboxylic acid and 3-aminobenzyl alcohol. LCMS [M+H]$^+$ 444.

Example 232: Cis-N-(3-methoxy-4-methylphenyl)-4-{2-oxo-1H,2H,3H-imidazo[4,5-b]pyridin-1-yl}cyclohexane-1-carboxamide The title compound was synthesized according to General procedure H from cis-4-{2-oxo-1H,2H,3H-imidazo[4,5-b]pyridin-1-yl}cyclohexane-1-carboxylic acid and 3-methoxy-4-methylaniline. LCMS [M+H]$^+$ 381. $^1$H-NMR (400 MHz, DMSO-d6) δ ppm 11.55 (br. s., 1H), 9.83 (s, 1H), 7.90 (d, J=5.4 Hz, 1H), 7.53-7.57 (m, 1H), 7.28 (s, 1H), 7.16-7.20 (m, 1H), 7.00-7.09 (m, 2H), 4.24-4.36 (m, 1H), 3.79 (s, 3H), 2.70-2.77 (m, 1H), 2.44-2.57 (m overlapping with solvent signal, 2H), 2.07-2.17 (m, 5H), 1.68-1.80 (m, 2H), 1.50-1.65 (m, 2H).

Example 233: Cis-N-(4-methoxy-3-methylphenyl)-4-{2-oxo-1H,2H,3H-imidazo[4,5-b]pyridin-1-yl}cyclohexane-1-carboxamide The title compound was synthesized according to General procedure H from cis-4-{2-oxo-1H,2H,3H-imidazo[4,5-b]pyridin-1-yl}cyclohexane-1-carboxylic acid and 4-methoxy-3-methylaniline. LCMS [M+H]$^+$ 381.

Example 234: Cis-N-(4-methoxyphenyl)-4-{2-oxo-1H,2H,3H-imidazo[4,5-b]pyridin-1-yl}cyclohexane-1-carboxamide The title compound was synthesized according to General procedure H from cis-4-{2-oxo-1H,2H,3H-imidazo[4,5-b]pyridin-1-yl}cyclohexane-1-carboxylic acid and 4-methoxyaniline. LCMS [M+H]$^+$ 367. $^1$H-NMR (400 MHz, DMSO-d6) δ ppm 11.51-11.58 (m, 1H), 9.76 (s, 1H), 7.89 (dd, J=5.2, 1.4 Hz, 1H), 7.51-7.56 (m, 3H), 7.04 (dd, J=7.7, 5.2 Hz, 1H), 6.87-6.92 (m, 2H), 4.24-4.35 (m, 1H), 3.73 (s, 3H), 2.71 (br. s., 1H), 2.45-2.58 (m overlapping with solvent signal, 2H), 2.07-2.15 (m, 2H), 1.67-1.78 (m, 2H), 1.52-1.62 (m, 2H).

Example 235: Cis-N-(6-methoxy-5-methylpyridin-3-yl)-4-{2-oxo-1H,2H,3H-imidazo[4,5-b]pyridin-1-yl}cyclohexane-1-carboxamide The title compound was synthesized according to General procedure H from cis-4-{2-oxo-1H,2H,3H-imidazo[4,5-b]pyridin-1-yl}cyclohexane-1-carboxylic acid and 5-amino-2-methoxy-3-methylpyridine. LCMS [M+H]$^+$ 382. $^1$H-NMR (400 MHz, DMSO-d6) δ ppm 11.56 (br. s., 1H), 9.85 (s, 1H), 8.23 (s, 1H), 7.90 (d, J=5.1 Hz, 1H), 7.79 (s, 1H), 7.50-7.55 (m, 1H), 7.02-7.08 (m, 1H), 4.24-4.36 (m, 1H), 3.86 (s, 3H), 2.71-2.77 (m, 2H), 2.43-2.56 (m overlapping with solvent signal, 2H), 2.08-2.19 (m, 5H), 1.69-1.81 (m, 2H), 1.54-1.64 (m, 2H).

Example 236: Cis-N-(3-methoxy-4-methylphenyl)-4-{2-oxo-1H,2H,3H-imidazo[4,5-c]pyridin-1-yl}cyclohexane-1-carboxamide Step 1: methyl cis-4-[(2-nitro-4-pyridyl)amino]cyclohexanecarboxylate was synthesized according to General procedure A from 4-chloro-3-nitro-pyridine and methyl cis-4-aminocyclohexanecarboxylate. LCMS [M+H]$^+$ 280.

Step 2: methyl cis-4-(2-oxo-3H-imidazo[4,5-c]pyridin-1-yl)cyclohexanecarboxylate was synthesized according to General procedure F from methyl cis-4-[(2-nitro-4-pyridyl)amino]cyclohexanecarboxylate. LCMS [M+H]$^+$ 276.

Step 3: cis-4-[-oxo-3H-imidazo[4,5-c]pyridin-1-yl]cyclohexanecarboxylic acid was synthesized according to General procedure J from methyl cis-4-(2-oxo-3H-imidazo[4,5-c]pyridin-1-yl)cyclohexanecarboxylate. LCMS [M+H]$^+$ 262.

Step 4: the title compound was synthesized according to General procedure H from cis-4-[2-oxo-3H-imidazo[4,5-c]pyridin-1-yl]cyclohexanecarboxylic acid. LCMS [M+H]$^+$ 382.

$^1$H-NMR (400 MHz, DMSO-d6) δ ppm 12.28 (s, 1H), 9.87 (s, 1H), 8.56-8.60 (m, 2H), 7.77 (d, J=6.3 Hz, 1H), 7.28 (d, J=1.9 Hz, 1H), 7.20 (dd, J=7.9, 1.9 Hz, 1H), 7.04-7.08 (m, 1H), 4.35-4.45 (m, 1H), 3.79 (s, 3H), 2.73-2.78 (m, 1H), 2.52-2.61 (m, 2H), 2.12-2.18 (m, 2H), 2.11 (s, 3H), 1.72-1.83 (m, 2H), 1.63-1.72 (m, 2H).

Example 237: Cis-N-(3-methoxy-4-methylphenyl)-4-(2-oxo-4-sulfanyl-2,3-dihydro-1H-1,3-benzodiazol-1-yl)cyclohexane-1-carboxamide A mixture of N-(4-methoxy-3-methyl-phenyl)-4-[4-[(4-methoxyphenyl)methylsulfanyl]-2-oxo-3H-benzimidazol-1-yl]cyclohexanecarboxamide (1.0 equiv.) and anisole (2.0 equiv.) was stirred in TFA at 80° C. The mixture was then poured into NaHCO$_3$ (aq.) and extracted with DCM×3. The combined organics were concentrated and purified using preparative HPLC. LCMS [M+H]$^+$ 412.

Example 238: Cis-4-(5-cyano-2-oxo-2,3-dihydro-1H-1,3-benzodiazol-1-yl)-N-(3-methoxy-4-methylphenyl)cyclohexane-1-carboxamide Step 1: methyl 4-(4-cyano-2-nitro-anilino)cyclohexanecarboxylate was synthesized according to General procedure A from 4-chloro-3-nitrobenzonitrile and methyl cis-4-aminocyclohexanecarboxylate. LCMS [M+H]$^+$ 304.

Step 2: methyl cis-4-(5-cyano-2-oxo-3H-benzimidazol-1-yl)cyclohexanecarboxylate was synthesized according to General procedure F from methyl 4-(4-cyano-2-nitro-anilino)cyclohexanecarboxylate. LCMS [M+H]$^+$ 300. $^1$H-NMR (400 MHz, Chloroform-d) δ ppm 10.28 (s, 1H), 7.37-7.43 (m, 2H), 7.28-7.33 (m, 1H), 4.38-4.50 (m, 1H), 3.80 (s, 3H), 2.81 (m, 1H), 2.25-2.47 (m, 4H), 1.69-1.83 (m, 4H).

Step 3: cis-4-(5-cyano-2-oxo-3H-benzimidazol-1-yl)cyclohexanecarboxylic acid was synthesized according to General procedure J from methyl cis-4-(5-cyano-2-oxo-3H-benzimidazol-1-yl)cyclohexanecarboxylate. LCMS [M+H]$^+$ 286. $^1$H-NMR (400 MHz, DMSO-d6) δ ppm 12.36 (s, 1H), 11.33 (s, 1H), 7.49 (dd, J=8.2, 1.6 Hz, 1H), 7.37 (d, J=1.3 Hz, 1H), 7.25 (d, J=8.2 Hz, 1H), 4.23 (tt, J=12.4, 3.8 Hz, 1H), 2.63-2.69 (m, 1H), 2.19-2.31 (m, 2H), 2.11-2.19 (m, 2H), 1.57-1.70 (m, 4H).

Step 4. The title compound was synthesized according to General procedure H from cis-4-(5-cyano-2-oxo-3H-benzimidazol-1-yl)cyclohexanecarboxylic acid and 3-methoxy-4-methylaniline. LCMS [M+H]$^+$ 405. $^1$H-NMR (400 MHz, DMSO-d6) δ ppm 11.34 (br. s., 1H), 9.83 (s, 1H), 7.50-7.55 (m, 1H), 7.43-7.47 (m, 1H), 7.38 (d, J=1.3 Hz, 1H), 7.31 (d, J=1.9 Hz, 1H), 7.16 (dd, J=8.1, 1.7 Hz, 1H), 7.06 (d, J=8.2 Hz, 1H), 4.25-4.36 (m, 1H), 3.79 (s, 3H), 2.70-2.76 (m, 1H), 2.53-2.62 (m, 2H), 2.11-2.17 (m, 2H), 2.11 (s, 3H), 1.69-1.81 (m, 2H), 1.53-1.63 (m, 2H).

Example 239: 2-({2-Oxo-1-[cis-4-[(3-methoxy-4-methylphenyl)carbamoyl]cyclohexyl]-2,3-dihydro-1H-1,3-benzodiazol-4-yl}sulfonyl)acetic acid Step 1: a mixture of cis-N-(3-methoxy-4-methylphenyl)-4-(2-oxo-4-sulfanyl-2,3-dihydro-1H-1,3-benzodiazol-1-yl)cyclohexane-1-carboxamide (1.0 equiv.), diisopropylethylamine (1.1 equiv.), and ethyl bromoacetate (1.0 equiv.) was stirred in THF at 40° C. for 16 h. The mixture was then poured into NaHCO$_3$ (aq.) and extracted with DCM×3. The combined extracts were dried, concentrated, and purified by silica gel chromatography. LCMS [M+H]$^+$ 526.

Step 2: a mixture of tert-butyl 2-[[1-[4-[(4-methoxy-3-methyl-phenyl)carbamoyl]cyclohexyl]-2-oxo-3H-benzimidazol-4-yl]sulfanyl]acetate (1.0 equiv.) and 3-chloroperbenzoic acid (2.1 equiv.) was stirred in DCM at 20° C. for 30 min. The mixture was then poured into NaHCO$_3$ (aq.) and extracted with DCM×3. The combined extracts were dried, concentrated, and purified by silica gel chromatography. LCMS [M+H]$^+$ 556.

Step 3: tert-butyl 2-[[1-[4-[(3-methoxy-4-methyl-phenyl)carbamoyl]cyclohexyl]-2-oxo-3H-benzimidazol-4-yl]sulfonyl]acetate (1.0 equiv.) was dissolved in DCM, then TFA (10 equiv.) was added. The resulting mixture was stirred at 20° C. for 16 h after which the mixture was purified by silica gel chromatography. LCMS [M+H]$^+$ 502. $^1$H-NMR (400 MHz, Methanol-d4) δ ppm 7.80 (d, J=7.9 Hz, 1H), 7.50 (d, J=7.9 Hz, 1H), 7.35 (dd, J=8.8, 2.5 Hz, 1H), 7.29 (d, J=2.2 Hz, 1H), 7.26 (t, J=8.0 Hz, 1H), 6.88 (d, J=8.5 Hz, 1H), 4.39-4.51 (m, 1H), 4.34 (br. s, 2H), 3.82 (s, 3H), 2.68-2.82 (m, 3H), 2.22-2.30 (m, 2H), 2.20 (s, 3H), 1.80-1.92 (m, 2H), 1.66-1.74 (m, 2H).

Example 240: Cis-N-(3-methoxy-4-methylphenyl)-4-[2-oxo-4-(piperazin-1-yl)-2,3-dihydro-1H-1,3-benzodiazol-1-yl]cyclohexane-1-carboxamide Step 1: tert-butyl 4-[cis-1-(4-methoxycarbonylcyclohexyl)-2-oxo-3H-benzimidazol-4-yl]piperazine-1-carboxylate was synthesized according to General procedure A from cis-4-[(3-fluoro-2-nitrophenyl)amino]cyclohexane-1-carboxylate and tert-butyl piperazine-1-carboxylate. LCMS [M+H]$^+$ 463.

Step 2: tert-butyl 4-[cis-1-(4-methoxycarbonylcyclohexyl)-2-oxo-3H-benzimidazol-4-yl]piperazine-1-carboxylate was synthesized according to General procedure B from tert-butyl 4-[1-(4-methoxycarbonylcyclohexyl)-2-oxo-3H-benzimidazol-4-yl]piperazine-1-carboxylate. LCMS [M+H]$^+$ 459.

Step 3: cis-4-[4-(4-tert-butoxycarbonylpiperazin-1-yl)-2-oxo-3H-benzimidazol-1-yl]cyclohexanecarboxylic acid was synthesized according to General procedure J from tert-butyl 4-[cis-1-(4-methoxycarbonylcyclohexyl)-2-oxo-3H-benzimidazol-4-yl]piperazine-1-carboxylate. LCMS [M+H]+ 445.

Step 4: tert-butyl 4-[1-[cis-4-[(3-methoxy-4-methyl-phenyl)carbamoyl]cyclohexyl]-2-oxo-3H-benzimidazol-4-yl]piperazine-1-carboxylate was synthesized according to General procedure H from cis-4-[4-(4-tert-butoxycarbonylpiperazin-1-yl)-2-oxo-3H-benzimidazol-1-yl]cyclohexanecarboxylic acid and 3-methoxy-4-methylaniline. LCMS [M+H]+ 564.

Step 5: the title compound was synthesized according to General procedure C from tert-butyl 4-[1-[cis-4-[(3-methoxy-4-methyl-phenyl)carbamoyl]cyclohexyl]-2-oxo-3H-benzimidazol-4-yl]piperazine-1-carboxylate. LCMS [M+H]+ 464

Example 241: Cis-N-(3-methoxy-4-methylphenyl)-4-[4-(morpholin-4-yl)-2-oxo-2,3-dihydro-1H-1,3-benzodiazol-1-yl]cyclohexane-1-carboxamide Step 1: methyl 4-(3-morpholino-2-nitro-anilino)cyclohexanecarboxylate was synthesized according to General procedure A from Cis-4-[(3-fluoro-2-nitrophenyl)amino]cyclohexane-1-carboxylate and morpholine. LCMS [M+H]+ 364.

Step 2: methyl cis-4-(4-morpholino-2-oxo-3H-benzimidazol-1-yl)cyclohexanecarboxylate was synthesized according to General procedure B from methyl cis-4-(3-morpholino-2-nitro-anilino)cyclohexanecarboxylate. LCMS [M+H]+ 360.

Step 3: cis-4-(4-morpholino-2-oxo-3H-benzimidazol-1-yl)cyclohexanecarboxylic acid was synthesized according to General procedure B from methyl cis-4-(4-morpholino-2-oxo-3H-benzimidazol-1-yl)cyclohexanecarboxylate. LCMS [M+H]+ 346.

Step 4: the title compound was synthesized according to General procedure H from cis-4-(4-morpholino-2-oxo-3H-benzimidazol-1-yl)cyclohexanecarboxylic acid and 3-methoxy-4-methylaniline. LCMS [M+H]+ 465.

Example 242: 2-({2-Oxo-1-[cis-4-[(3-methoxy-4-methylphenyl)carbamoyl]cyclohexyl]-2,3-dihydro-1H-1,3-benzodiazol-4-yl}oxy)acetic acid Step 1: to a mixture of cis-4-(4-hydroxy-2-oxo-2,3-dihydro-1H-1,3-benzodiazol-1-yl)-N-(3-methoxy-4-methylphenyl)cyclohexane-1-carboxamide (1.0 equiv.) and tert-butyl bromoacetate (1.1 equiv.) in THF was added NaH (1.0 equiv.). The resulting mixture was stirred for 4 days at 40° C. after which it was concentrated and purified by silica gel chromatography which afforded tert-butyl 2-[[1-[cis-4-[(3-methoxy-4-methyl-phenyl)carbamoyl]cyclohexyl]-2-oxo-3H-benzimidazol-4-yl]oxy]acetate. LCMS [M+H]+ 468.

Step 2: tert-butyl 2-[[1-[cis-4-[(3-methoxy-4-methyl-phenyl)carbamoyl]cyclohexyl]-2-oxo-3H-benzimidazol-4-yl]oxy]acetate (1.0 equiv.) was dissolved in DCM, then TFA (10 equiv.) was added and the resulting mixture was stirred for 6 h. The mixture was concentrated and purified by preparative HPLC. LCMS [M+H]+ 454.

Example 243: Cis-4-{4-[benzyl(methyl)amino]-2-oxo-2,3-dihydro-1H-1,3-benzodiazol-1-yl}-N-(3-methoxy-4-methylphenyl)cyclohexane-1-carboxamide Step 1: methyl cis-4-[4-[benzyl(methyl)amino]-2-oxo-3H-benzimidazol-1-yl]cyclohexanecarboxylate was synthesized according to general procedure A from cis-4-[(3-fluoro-2-nitrophenyl)amino]cyclohexane-1-carboxylate and N-methylbenzylamine. LCMS [M+H]+ 398.

Step 2: methyl 4-[4-[benzyl(methyl)amino]-2-oxo-3H-benzimidazol-1-yl]cyclohexanecarboxylate was synthesized according to general procedure B from methyl cis-4-[4-[benzyl(methyl)amino]-2-oxo-3H-benzimidazol-1-yl]cyclohexanecarboxylate. LCMS [M+H]+ 394.

Step 3: cis-4-[4-[benzyl(methyl)amino]-2-oxo-3H-benzimidazol-1-yl]cyclohexanecarboxylic acid was synthesized according to general procedure J from methyl 4-[4-[benzyl(methyl)amino]-2-oxo-3H-benzimidazol-1-yl]cyclohexanecarboxylate.

Step 4: the title compound was synthesized according to general procedure H from cis-4-[4-[benzyl(methyl)amino]-2-oxo-3H-benzimidazol-1-yl]cyclohexanecarboxylic acid. LCMS [M+H]+ 499. $^1$H-NMR (400 MHz, DMSO-d6) δ ppm 10.83 (s, 1H), 9.79 (s, 1H), 7.25-7.30 (m, 5H), 7.19-7.23 (m, 1H), 7.17 (dd, J=8.1, 1.7 Hz, 1H), 7.05 (d, J=7.9 Hz, 1H), 6.98 (d, J=7.9 Hz, 1H), 6.86 (t, J=8.1 Hz, 1H), 6.58 (d, J=8.2 Hz, 1H), 4.22-4.32 (m, 1H), 4.20 (s, 2H), 3.78 (s, 3H), 3.57 (s, 1H), 2.70-2.75 (m, 1H), 2.54-2.63 (m, 5H), 2.11-2.18 (m, 2H), 2.09 (s, 3H), 1.67-1.78 (m, 2H), 1.50-1.59 (m, 2H).

Example 244: Cis-N-(3-methoxy-4-methylphenyl)-4-[4-(methylamino)-2-oxo-2,3-dihydro-1H-1,3-benzodiazol-1-yl]cyclohexane-1-carboxamide The title compound was synthesized according to general procedure G from cis-4-{4-[benzyl(methyl)amino]-2-oxo-2,3-dihydro-1H-1,3-benzodiazol-1-yl}-N-(3-methoxy-4-methylphenyl)cyclohexane-1-carboxamide. LCMS [M+H]+ 409. $^1$H-NMR (400 MHz, DMSO-d6) δ ppm 10.25 (s, 1H), 9.78 (s, 1H), 7.28 (d, J=1.9 Hz, 1H), 7.16 (dd, J=7.9, 1.9 Hz, 1H), 7.05 (dd, J=8.1, 0.8 Hz, 1H), 6.82-6.88 (m, 1H), 6.73 (d, J=7.9 Hz, 1H), 6.31 (d, J=8.2 Hz, 1H), 4.16-4.27 (m, 1H), 2.79 (s, 3H), 2.69-2.74 (m, 1H), 2.52-2.61 (m, 2H), 2.10-2.17 (m, 2H), 2.09 (s, 3H), 1.65-1.77 (m, 2H), 1.46-1.55 (m, 2H).

Example 245: Cis-N-(3-methoxy-4-methylphenyl)-4-[4-(2-methoxyethoxy)-2-oxo-2,3-dihydro-1H-1,3-benzodiazol-1-yl]cyclohexane-1-carboxamide The title compound was synthesized according to general procedure H from cis-4-[4-(2-methoxyethoxy)-2-oxo-2,3-dihydro-1H-1,3-benzodiazol-1-yl]cyclohexane-1-carboxylic acid and 3-methoxy-4-methylaniline. LCMS [M+H]+ 454.

Example 246: Cis-N-(1H-indol-6-yl)-4-[4-(2-methoxyethoxy)-2-oxo-2,3-dihydro-1H-1,3-benzodiazol-1-yl]cyclohexane-1-carboxamide The title compound was synthesized according to general procedure H from cis-4-[4-(2-methoxyethoxy)-2-oxo-2,3-dihydro-1H-1,3-benzodiazol-1-yl]cyclohexane-1-carboxylic acid and 6-amino-1H-indole. LCMS [M+H]+ 449. $^1$H-NMR (400 MHz, DMSO-d6) δ ppm 10.97-11.01 (m, 1H), 10.91 (s, 1H), 9.77 (s, 1H), 7.99-8.01 (m, 1H), 7.42 (d, J=8.5 Hz, 1H), 7.25 (dd, J=3.0, 2.4 Hz, 1H), 7.06 (dd, J=8.5, 1.9 Hz, fH), 6.89-6.97 (m, 2H), 6.71 (d, J=1.6 Hz, 1H), 6.34 (s, 1H), 4.12-4.22 (m, 3H), 3.67-3.71 (m, 2H), 3.33 (s, 3H), 2.44-2.50 (m, 1H), 2.20-2.32 (m, 2H), 1.96-2.04 (m, 2H), 1.75-1.83 (m, 2H), 1.62-1.75 (m, 2H).

Example 247: N-(2-Aminoethyl)-2-oxo-1-[cis-4-[(3-methoxy-4-methylphenyl)carbamoyl]cyclohexyl]-2,3-dihydro-1H-1,3-benzodiazole-4-carboxamide The title compound was synthesized according to general procedure H from 2-oxo-1-[cis-4-[(3-methoxy-4-methylphenyl)carbamoyl]cyclohexyl]-2,3-dihydro-1H-1,3-benzodiazole-4-carboxylic acid and 1,2-ethylenediamine. LCMS [M+H]$^+$ 466.

Example 248: N-(2,3-Dihydroxypropyl)-2-oxo-1-[cis-4-[(3-methoxy-4-methylphenyl)carbamoyl]cyclohexyl]-2,3-dihydro-1H-1,3-benzodiazole-4-carboxamide The title compound was synthesized according to general procedure L from cis-4-(4-bromo-2-oxo-2,3-dihydro-1H-1,3-benzodiazol-1-yl)-N-(3-methoxy-4-methylphenyl)cyclohexane-1-carboxamide and (±)-3-amino-1,2-propanediol. LCMS [M+H]$^+$ 497.

Example 249: Cis-4-(4-amino-2-oxo-2,3-dihydro-1H-1,3-benzodiazol-1-yl)-N-(3-methoxy-4-methylphenyl)cyclohexane-1-carboxamide Step 1: cis-4-[3-(dibenzylamino)-2-nitro-anilino]-N-(3-methoxy-4-methyl-phenyl)cyclohexanecarboxamide was synthesized according to general procedure M from cis-4-[(3-fluoro-2-nitrophenyl)amino]-N-(3-methoxy-4-methylphenyl)cyclohexane-1-carboxamide and dibenzylamine. LCMS [M+H]$^+$ 579.

Step 2: cis-4-[4-(dibenzylamino)-2-oxo-3H-benzimidazol-1-yl]-N-(3-methoxy-4-methyl-phenyl)cyclohexanecarboxamide was synthesized according to general procedure B from cis-4-[3-(dibenzylamino)-2-nitro-anilino]-N-(3-methoxy-4-methyl-phenyl)cyclohexanecarboxamide. LCMS [M+H]$^+$ 575.

Step 3: The title compound was synthesized according to general procedure G from cis-4-[4-(dibenzylamino)-2-oxo-3H-benzimidazol-1-yl]-N-(3-methoxy-4-methyl-phenyl)cyclohexanecarboxamide. LCMS [M+H]$^+$ 395. $^1$H-NMR (400 MHz, DMSO-d6) δ ppm 10.25 (s, 1H), 9.77 (s, 1H), 7.28 (d, J=1.6 Hz, 1H), 7.15 (dd, J=8.2, 1.9 Hz, 1H), 7.05 (dd, J=8.2, 0.9 Hz, 1H), 6.71 (t, J=8.2 Hz, 1H), 6.61 (d, J=7.9 Hz, 1H), 6.30 (dd, J=8.1, 0.9 Hz, 1H), 4.20 (tt, J=12.4, 4.2 Hz, 1H), 3.77 (s, 3H), 2.71 (br. s., 1H), 2.52-2.60 (m, 2H), 2.08-2.14 (m, 2H), 2.09 (s, 3H), 1.64-1.76 (m, 2H), 1.45-1.55 (m, 2H).

Example 250: Cis-N-(3-methoxy-4-methylphenyl)-4-[4-(2-methoxyacetamido)-2-oxo-2,3-dihydro-1H-1,3-benzodiazol-1-yl]cyclohexane-1-carboxamide A mixture of cis-4-(4-amino-2-oxo-2,3-dihydro-1H-1,3-benzodiazol-1-yl)-N-(3-methoxy-4-methylphenyl)cyclohexane-1-carboxamide (1.0 equiv.), diisopropylethylamine (2.0 equiv.), and 2-methoxyacetyl chloride (1.0 equiv.) was stirred in 1,4-dioxane for 16 h.

The mixture was then concentrated and purified by preparative HPLC. LCMS [M+H]$^+$ 467. $^1$H-NMR (400 MHz, DMSO-d6) δ ppm 10.59 (s, 1H), 9.81 (s, 1H), 9.49 (s, 1H), 7.28-7.33 (m, 1H), 7.14-7.20 (m, 2H), 7.03-7.10 (m, 2H), 6.92-6.99 (m, 1H), 4.21-4.33 (m, 2H), 4.02 (s, 2H), 3.79 (s, 3H), 3.41 (s, 3H), 2.71-2.77 (m, 1H), 2.54-2.65 (m, 2H), 2.12-2.20 (m, 2H), 2.11 (s, 3H), 1.67-1.80 (m, 2H), 1.51-1.61 (m, 2H).

Example 251: N-(2-Methanesulfonamidoethyl)-2-oxo-1-[cis-4-[(3-methoxy-4-methylphenyl)carbamoyl]cyclohexyl]-2,3-dihydro-1H-1,3-benzodiazole-4-carboxamide The title compound was synthesized according to general procedure L from cis-4-(4-bromo-2-oxo-2,3-dihydro-1H-1,3-benzodiazol-1-yl)-N-(3-methoxy-4-methylphenyl)cyclohexane-1-carboxamide and N-(2-aminoethyl)methanesulfonamide. LCMS [M+H]$^+$ 544. $^1$H-NMR (400 MHz, DMSO-d6) δ ppm 10.51 (s, 1H), 9.83 (s, 1H), 8.51-8.56 (m, 1H), 7.46 (d, J=7.9 Hz, 1H), 7.39-7.43 (m, 1H), 7.31 (d, J=1.9 Hz, 1H), 7.16-7.20 (m, 2H), 7.05-7.11 (m, 2H), 4.25-4.37 (m, 1H), 3.79 (s, 3H), 3.36-3.42 (m, 2H), 3.10-3.17 (m, 2H), 2.92 (s, 3H), 2.71-2.77 (m, 1H), 2.53-2.65 (m, 2H), 2.12-2.18 (m, 2H), 2.11 (s, 3H), 1.69-1.81 (m, 2H), 1.51-1.60 (m, 2H).

Example 252: 2-Oxo-N-[2-(piperazin-1-yl)ethyl]-1-[cis-4-[(3-methoxy-4-methylphenyl)carbamoyl]cyclohexyl]-2,3-dihydro-1H-1,3-benzodiazole-4-carboxamide Step 1: tert-butyl cis-4-[2-[[1-[4-[(3-methoxy-4-methylphenyl)carbamoyl]cyclohexyl]-2-oxo-3H-benzimidazole-4-carbonyl]amino]ethyl]piperazine-1-carboxylate was synthesized according to General procedure H from cis-4-(4-bromo-2-oxo-2,3-dihydro-1H-1,3-benzodiazol-1-yl)-N-(3-methoxy-4-methylphenyl)cyclohexane-1-carboxamide and 1-tert-butoxycarbonyl-4-(2-aminoethyl)piperazine and was used in step 2 without purification.

Step 2: the title compound was synthesized according to General procedure C from tert-butyl cis-4-[2-[[1-[4-[(3-methoxy-4-methyl-phenyl)carbamoyl]cyclohexyl]-2-oxo-3H-benzimidazole-4-carbonyl]amino]ethyl]piperazine-1-carboxylate. LCMS [M+H]$^+$ 535. $^1$H-NMR (400 MHz, DMSO-d6) δ ppm 10.55 (s, 1H), 9.84 (s, 1H), 8.58-8.66 (m, 1H), 7.48 (d, J=7.9 Hz, 1H), 7.39 (d, J=7.9 Hz, 1H), 7.30 (d, J=1.9 Hz, 1H), 7.18 (dd, J=7.9, 1.9 Hz, 1H), 7.10 (t, J=7.9 Hz, 1H), 7.06 (dd, J=8.1, 0.8 Hz, 1H), 4.25-4.37 (m, 1H), 3.79 (s, 3H), 3.50-3.59 (m, 2H), 3.24-3.36 (m, 4H), 2.86-3.24 (m, 6H), 2.72-2.77 (m, 1H), 2.54-2.65 (m, 2H), 2.12-2.19 (m, 2H), 2.11 (s, 3H), 1.70-1.81 (m, 2H), 1.52-1.61 (m, 2H).

Example 253: Cis-4-{4-[(2-acetamidoethyl)carbamoyl]-2-oxo-2,3-dihydro-1H-1,3-benzodiazol-1-yl}-N-(3-methoxy-4-methylphenyl)cyclohexane-1-carboxamide The title compound was synthesized according to General procedure L from cis-4-(4-bromo-2-oxo-2,3-dihydro-1H-1,3-benzodiazol-1-yl)-N-(3-methoxy-4-methylphenyl)cyclohexane-1-carboxamide and N-(2-aminoethyl)acetamide. LCMS [M+H]$^+$ 508. $^1$H-NMR (400 MHz, Methanol-d4) δ ppm 7.65 (d, J=7.9 Hz, 1H), 7.43 (d, J=7.9 Hz, 1H), 7.25-7.29 (m, 1H), 7.13 (t, J=8.1 Hz, 1H), 7.06-7.10 (m, 1H), 7.01-7.05 (m, 1H), 4.39-4.51 (m, 1H), 3.87 (s, 3H), 3.48-3.55 (m, 2H), 3.39-3.46 (m, 2H), 2.69-2.83 (m, 3H), 2.23-2.32 (m, 2H), 2.17 (s, 3H), 1.96 (s, 2H), 1.80-1.93 (m, 2H), 1.65-1.75 (m, 2H).

Example 254: 2-Oxo-N-[(pyrrolidin-2-yl)methyl]-1-[cis-4-[(3-methoxy-4-methylphenyl)carbamoyl]cyclohexyl]-2,3-dihydro-1H-1,3-benzodiazole-4-carboxamide Step 1: tert-butyl cis-2-[[[1-[4-[(3-methoxy-4-methylphenyl)carbamoyl]cyclohexyl]-2-oxo-3H-benzimidazole-4- carbonyl]amino]methyl]pyrrolidine-1-carboxylate was synthesized according to General procedure L from cis-4-(4-bromo-2-oxo-2,3-dihydro-1H-1,3-benzodiazol-1-yl)-N-(3-methoxy-4-methylphenyl)cyclohexane-1-carboxamide and (±)-tert-butyl 2-(aminomethyl)pyrrolidine-1-carboxylate and was used in step 2 without purification.

Step 2: the title compound was synthesized according to General procedure C from tert-butyl cis-2-[[[1-[4-[(3-methoxy-4-methyl-phenyl)carbamoyl]cyclohexyl]-2-oxo-3H-benzimidazole-4-carbonyl]amino]methyl]pyrrolidine-1-carboxylate. LCMS [M+H]$^+$ 506.
$^1$H-NMR (400 MHz, Methanol-d4) δ ppm 7.68 (d, J=7.9 Hz, 1H), 7.49 (d, J=7.9 Hz, 1H), 7.23-7.30 (m, 1H), 7.16 (t, J=7.9 Hz, 1H), 7.06-7.12 (m, 1H), 7.02-7.06 (m, 1H), 4.36-4.49 (m, 1H), 3.87 (s, 3H), 3.65-3.85 (m, 3H), 3.27-3.43 (m, 2H), 2.66-2.83 (m, 3H), 2.20-2.33 (m, 3H), 2.17 (s, 3H), 1.99-2.15 (m, 2H), 1.80-1.93 (m, 3H), 1.58-1.74 (m, 2H).

Example 255: Cis-4-[4-(2-aminoacetamido)-2-oxo-2,3-dihydro-1H-1,3-benzodiazol-1-yl]-N-(3-methoxy-4-methylphenyl)cyclohexane-1-carboxamide Step 1: tert-butyl N-[2-[[1-cis-[4-[(3-methoxy-4-methylphenyl)carbamoyl]cyclohexyl]-2-oxo-3H-benzimidazol-4-yl]amino]-2-oxo-ethyl]carbamate was synthesized according to General procedure H from cis-4-(4-amino-2-oxo-2,3-dihydro-1H-1,3-benzodiazol-1-yl)-N-(3-methoxy-4-methylphenyl)cyclohexane-1-carboxamide and 2-[(tert-butoxy)carbonyl]aminoacetic acid and was used in step 2 without purification.

Step 2: the title compound was synthesized according to General procedure C from tert-butyl N-[2-[[1-cis-[4-[(3-methoxy-4-methyl-phenyl)carbamoyl]cyclohexyl]-2-oxo-3H-benzimidazol-4-yl]amino]-2-oxo-ethyl]carbamate LCMS [M+H]$^+$ 452. $^1$H-NMR (400 MHz, Methanol-d4) δ ppm 7.43 (d, J=7.9 Hz, 1H), 7.25-7.30 (m, 1H), 7.06-7.12 (m, 2H), 6.99-7.06 (m, 2H), 4.38-4.49 (m, 1H), 3.95 (s, 2H), 3.88 (s, 3H), 2.71-2.84 (m, 3H), 2.23-2.33 (m, 2H), 2.17 (s, 3H), 1.81-1.93 (m, 2H), 1.65-1.76 (m, 2H).

Example 256: Cis-4-[5-(aminomethyl)-2-oxo-2,3-dihydro-1H-1,3-benzodiazol-1-yl]-N-(3-methoxy-4-methylphenyl)cyclohexane-1-carboxamide A mixture of 4-(5-cyano-2-oxo-3H-benzimidazol-1-yl)-N-(3-methoxy-4-methyl-phenyl)cyclohexanecarboxamide (1.0 equiv.), triethylamine (10 equiv.), and Pd/C (0.25 equiv.) was stirred in THE and formic acid at 40° C. for 48 h. The product was isolated by preparative HPLC. LCMS [M+H]$^+$ 409.

Example 257: Cis-4-(4-bromo-2-oxo-2,3-dihydro-1H-1,3-benzodiazol-1-yl)-N-(1-methyl-1H-1,3-benzodiazol-2-yl)cyclohexane-1-carboxamide The title compound was synthesized according to General procedure H from cis-4-(4-bromo-2-oxo-2,3-dihydro-1H-1,3-benzodiazol-1-yl)cyclohexane-1-carboxylic acid and 2-amino-1-methylbenzimidazole. LCMS [M+H]$^+$ 468.

Example 258: Methyl 2-oxo-1-[cis-4-[(3-methoxy-4-methylphenyl)carbamoyl]cyclohexyl]-2,3-dihydro-1H-1,3-benzodiazole-4-carboxylate Step 1: methyl 3-[[cis-4-[(3-methoxy-4-methyl-phenyl)carbamoyl]cyclohexyl]amino]-2-nitro-benzoate was synthesized according to General procedure A from cis-4-amino-N-(3-methoxy-4-methylphenyl)cyclohexane-1-carboxamide hydrochloride and methyl 3-fluoro-2-nitro-benzoate. LCMS [M+H]$^+$ 442.

Step 2: the title compound was synthesized according to General procedure F from methyl 3-[[cis-4-[(3-methoxy-4-methyl-phenyl)carbamoyl]cyclohexyl]amino]-2-nitro-benzoate. LCMS [M+H]$^+$ 438.

Example 259: N-Methyl-2-oxo-1-[cis-4-[(3-methoxy-4-methylphenyl)carbamoyl]cyclohexyl]-2,3-dihydro-1H-1,3-benzodiazole-4-carboxamide The title compound was synthesized according to General procedure H from 2-oxo-1-[cis-4-[(3-methoxy-4-methylphenyl)carbamoyl]cyclohexyl]-2,3-dihydro-1H-1,3-benzodiazole-4-carboxylic acid and methylammonium chloride. LCMS [M+H]$^+$ 437.

Example 260: N,N-Dimethyl-2-oxo-1-[cis-4-[(3-methoxy-4-methylphenyl)carbamoyl]cyclohexyl]-2,3-dihydro-1H-1,3-benzodiazole-4-carboxamide The title compound was synthesized according to General procedure H from 2-oxo-1-[cis-4-[(3-methoxy-4-methylphenyl)carbamoyl]cyclohexyl]-2,3-dihydro-1H-1,3-benzodiazole-4-carboxylic acid and dimethylammonium chloride. LCMS [M+H]$^+$ 451.

Example 261: Cis-N-(3-methoxy-4-methylphenyl)-4-[2-oxo-4-(piperazine-1-carbonyl)-2,3-dihydro-1H-1,3-benzodiazol-1-yl]cyclohexane-1-carboxamide The title compound was synthesized according to General procedure H from 2-oxo-1-[cis-4-[(3-methoxy-4-methylphenyl)carbamoyl]cyclohexyl]-2,3-dihydro-1H-1,3-benzodiazole-4-carboxylic acid and piperazine. LCMS [M+H]$^+$ 492.

Example 262: Cis-N-(3-methoxy-4-methylphenyl)-4-[4-(morpholine-4-carbonyl)-2-oxo-2,3-dihydro-1H-1,3-benzodiazol-1-yl]cyclohexane-1-carboxamide The title compound was synthesized according to General procedure H from 2-oxo-1-[cis-4-[(3-methoxy-4-methylphenyl)carbamoyl]cyclohexyl]-2,3-dihydro-1H-1,3-benzodiazole-4-carboxylic acid and morpholine. LCMS [M+H]$^+$ 493.

Example 263: N-(2-Hydroxyethyl)-2-oxo-1-[cis-4-[(3-methoxy-4-methylphenyl)carbamoyl]cyclohexyl]-2,3-dihydro-1H-1,3-benzodiazole-4-carboxamide The title compound was synthesized according to General procedure H from 2-oxo-1-[cis-4-[(3-methoxy-4-methylphenyl)carbamoyl]cyclohexyl]-2,3-dihydro-1H-1,3-benzodiazole-4-carboxylic acid and ethanolamine. LCMS [M+H]$^+$ 467.

Example 264: Cis-4-{4-[(2-carbamoylethyl)carbamoyl]-2-oxo-2,3-dihydro-1H-1,3-benzodiazol-1-yl}-N-(3-methoxy-4-methylphenyl)cyclohexane-1-carboxamide The title compound was synthesized according to General procedure H from 2-oxo-1-[cis-4-[(3-methoxy-4-methylphenyl)carbamoyl]cyclohexyl]-2,3-dihydro-1H-1,3-benzodiazole-4-carboxylic acid and 3-aminopropanamide. LCMS [M+H]⁺ 494.

Example 265: N-(3-Aminopropyl)-2-oxo-1-[cis-4-[(3-methoxy-4-methylphenyl)carbamoyl]cyclohexyl]-2,3-dihydro-1H-1,3-benzodiazole-4-carboxamide The title compound was synthesized according to General procedure H from 2-oxo-1-[cis-4-[(3-methoxy-4-methylphenyl)carbamoyl]cyclohexyl]-2,3-dihydro-1H-1,3-benzodiazole-4-carboxylic acid and 1,3-diaminopropane. LCMS [M+H]⁺ 480.

Example 266: N-Methyl-N-[2-(methylamino)ethyl]-2-oxo-1-[cis-4-[(3-methoxy-4-methylphenyl)carbamoyl]cyclohexyl]-2,3-dihydro-1H-1,3-benzodiazole-4-carboxamide The title compound was synthesized according to General procedure H from 2-oxo-1-[cis-4-[(3-methoxy-4-methylphenyl)carbamoyl]cyclohexyl]-2,3-dihydro-1H-1,3-benzodiazole-4-carboxylic acid and N,N'-dimethylethylenediamine. LCMS [M+H]⁺ 494.

Example 267: Cis-4-{4-[(3R)-3-(dimethylamino)pyrrolidine-1-carbonyl]-2-oxo-2,3-dihydro-1H-1,3-benzodiazol-1-yl}-N-(3-methoxy-4-methylphenyl)cyclohexane-1-carboxamide The title compound was synthesized according to General procedure H from 2-oxo-1-[cis-4-[(3-methoxy-4-methylphenyl)carbamoyl]cyclohexyl]-2,3-dihydro-1H-1,3-benzodiazole-4-carboxylic acid and (R)-(+)-3-(dimethylamino)pyrrolidine. LCMS [M+H]⁺ 520.

Example 268: Cis-N-(3-methoxy-4-methylphenyl)-4-[4-(4-methylpiperazine-1-carbonyl)-2-oxo-2,3-dihydro-1H-1,3-benzodiazol-1-yl]cyclohexane-1-carboxamide The title compound was synthesized according to General procedure H from 2-oxo-1-[cis-4-[(3-methoxy-4-methylphenyl)carbamoyl]cyclohexyl]-2,3-dihydro-1H-1,3-benzodiazole-4-carboxylic acid and N-methylpiperazine. LCMS [M+H]⁺ 506. Example 269: Cis-4-{4-[4-(dimethylamino)piperidine-1-carbonyl]-2-oxo-2,3-dihydro-1H-1,3-benzodiazol-1-yl}-N-(3-methoxy-4-methylphenyl)cyclohexane-1-carboxamide The title compound was synthesized according to General procedure H from 2-oxo-1-[cis-4-[(3-methoxy-4-methylphenyl)carbamoyl]cyclohexyl]-2,3-dihydro-1H-1,3-benzodiazole-4-carboxylic acid and 4-dimethylaminopiperidine. LCMS [M+H]⁺ 534.

Example 270: N-[(1H-Imidazol-2-yl)methyl]-2-oxo-1-[cis-4-[(3-methoxy-4-methylphenyl)carbamoyl]cyclohexyl]-2,3-dihydro-1H-1,3-benzodiazole-4-carboxamide The title compound was synthesized according to General procedure H from 2-oxo-1-[cis-4-[(3-methoxy-4-methylphenyl)carbamoyl]cyclohexyl]-2,3-dihydro-1H-1,3-benzodiazole-4-carboxylic acid and 1H-imidazol-2-ylmethanamine. LCMS [M+H]⁺ 503.

Example 271: Cis-N-(3-methoxy-4-methylphenyl)-4-{2-oxo-4-[(2S)-2-[(pyrrolidin-1-yl)methyl]pyrrolidine-1-carbonyl]-2,3-dihydro-1H-1,3-benzodiazol-1-yl}cyclohexane-1-carboxamide The title compound was synthesized according to General procedure H from 2-oxo-1-[cis-4-[(3-methoxy-4-methylphenyl)carbamoyl]cyclohexyl]-2,3-dihydro-1H-1,3-benzodiazole-4-carboxylic acid and (S)-(+)-1-(2-pyrrolidinylmethyl)pyrrolidine. LCMS [M+H]⁺ 560.

Example 272: N-[2-(Morpholin-4-yl)ethyl]-2-oxo-1-[cis-4-[(3-methoxy-4-methylphenyl)carbamoyl]cyclohexyl]-2,3-dihydro-1H-1,3-benzodiazole-4-carboxamide The title compound was synthesized according to General procedure H from 2-oxo-1-[cis-4-[(3-methoxy-4-methylphenyl)carbamoyl]cyclohexyl]-2,3-dihydro-1H-1,3-benzodiazole-4-carboxylic acid and 4-(2-aminoethyl)morpholine. LCMS [M+H]⁺ 536.

Example 273: 2-Oxo-N-[(oxolan-2-yl)methyl]-1-[cis-4-[(3-methoxy-4-methylphenyl)carbamoyl]cyclohexyl]-2,3-dihydro-1H-1,3-benzodiazole-4-carboxamide The title compound was synthesized according to General procedure H from 2-oxo-1-[cis-4-[(3-methoxy-4-methylphenyl)carbamoyl]cyclohexyl]-2,3-dihydro-1H-1,3-benzodiazole-4-carboxylic acid and tetrahydrofuran-2-ylmethanamine. LCMS [M+H]⁺ 507.

Example 274: Cis-N-(3-methoxy-4-methylphenyl)-4-{2-oxo-4-[3-(trifluoromethyl)piperazine-1-carbonyl]-2,3-dihydro-1H-1,3-benzodiazol-1-yl}cyclohexane-1-carboxamide The title compound was synthesized according to General procedure H from 2-oxo-1-[cis-4-[(3-methoxy-4-methylphenyl)carbamoyl]cyclohexyl]-2,3-dihydro-1H-1,3-benzodiazole-4-carboxylic acid and (±)-2-trifluoromethylpiperazine. LCMS [M+H]⁺ 560.

Example 275: Cis-4-(4-{4-[2-(dimethylamino)ethyl]piperazine-1-carbonyl}-2-oxo-2,3-dihydro-1H-1,3-benzodiazol-1-yl)-N-(3-methoxy-4-methylphenyl)cyclohexane-1-carboxamide The title compound was synthesized according to General procedure H from 2-oxo-1-[cis-4-[(3-methoxy-4-methylphenyl)carbamoyl]cyclohexyl]-2,3-dihydro-1H-1,3-benzodiazole-4-carboxylic acid and 1-(2-dimethylamino-ethyl)-piperazine. LCMS [M+H]⁺ 563.

Example 276: 2-Oxo-N-[(pyrimidin-2-yl)methyl]-1-[cis-4-[(3-methoxy-4-methylphenyl)carbamoyl]cyclohexyl]-2,3-dihydro-1H-1,3-benzodiazole-4-carboxamide The title compound was synthesized according to General procedure H from 2-oxo-1-[cis-4-[(3-methoxy-4-methylphenyl)carbamoyl]cyclohexyl]-2,3-dihydro-1H-1,3-benzodiazole-4-carboxylic acid and 2-aminomethylpyrimidine hydrochloride. LCMS [M+H]⁺ 515.

Example 277: N-Methyl-N-(1-methylpyrrolidin-3-yl)-2-oxo-1-[cis-4-[(3-methoxy-4-methylphenyl)carbamoyl]cyclohexyl]-2,3-dihydro-1H-1,3-benzodiazole-4-carboxamide The title compound was synthesized according to General procedure H from 2-oxo-1-[cis-4-[(3-methoxy-4-methylphenyl)carbamoyl]cyclohexyl]-2,3-dihydro-1H-1,3-benzodiazole-4-carboxylic acid and (±)—N,N'-dimethyl-3-aminopyrrolidine. LCMS [M+H]$^+$ 520.

Example 278: 1-{2-Oxo-1-[cis-4-[(3-methoxy-4-methylphenyl)carbamoyl]cyclohexyl]-2,3-dihydro-1H-1,3-benzodiazole-4-carbonyl}pyrrolidine-2-carboxamide The title compound was synthesized according to General procedure H from 2-oxo-1-[cis-4-[(3-methoxy-4-methylphenyl)carbamoyl]cyclohexyl]-2,3-dihydro-1H-1,3-benzodiazole-4-carboxylic acid and (±)-2-pyrrolidinecarboxamide hydrochloride. LCMS [M+H]$^+$ 520.

Example 279: Cis-N-(3-methoxy-4-methylphenyl)-4-{2-oxo-4-[(pyrimidin-2-yl)amino]-2,3-dihydro-1H-1,3-benzodiazol-1-yl}cyclohexane-1-carboxamide Step 1: A mixture of pyrimidine-2-amine (1.0 equiv.) and NaH (1.1 equiv.) was stirred in THF for 10 min, then 1,3-difluoro-2-nitro-benzene (1.0 equiv.) was added and the resulting mixture was stirred for 16 h at 65° C. The reaction mixture was then concentrated and purified by silica gel chromatography which afforded N-(3-fluoro-2-nitro-phenyl)pyrimidin-2-amine. LCMS [M+H]$^+$ 235. $^1$H-NMR (400 MHz, CHLOROFORM-d) δ ppm 9.05 (br. s., 1H), 8.53 (d, J=4.7 Hz, 2H), 8.47 (dt, J=8.6, 1.3 Hz, 1H), 7.52 (td, J=8.6, 5.7 Hz, 1H), 6.93 (t, J=4.7 Hz, 1H), 6.88-6.94 (m, 1H).

Step 2: N-(3-methoxy-4-methyl-phenyl)-4-[2-nitro-3-(pyrimidin-2-ylamino)anilino]cyclohexanecarboxamide was synthesized according to general procedure A from N-(3-fluoro-2-nitro-phenyl)pyrimidin-2-amine and cis-4-amino-N-(3-methoxy-4-methylphenyl)cyclohexane-1-carboxamide hydrochloride. LCMS [M+H]$^+$ 477. $^1$H-NMR (400 MHz, CHLOROFORM-d) δ ppm 10.69 (s, 1H), 8.50 (d, J=5.1 Hz, 2H), 8.16-8.39 (m, 1H), 7.82 (d, J=8.5 Hz, 1H), 7.44 (d, J=1.9 Hz, 1H), 7.35 (t, J=8.4 Hz, 1H), 7.18 (s, 1H), 7.04 (d, J=7.9 Hz, 1H), 6.86 (t, J=4.9 Hz, 1H), 6.74 (dd, J=7.9, 1.9 Hz, 1H), 6.50 (d, J=8.5 Hz, 1H), 3.85 (s, 3H), 3.79-3.84 (m, 1H), 2.39-2.48 (m, 1H), 2.17 (s, 3H), 2.00-2.08 (m, 3H), 1.89-1.98 (m, 4H), 1.78-1.87 (m, 2H).

Step 3: The title compound was synthesized according to general procedure F. LCMS [M+H]$^+$ 473. $^1$H-NMR (400 MHz, DMSO-d6) δ ppm 10.55 (s, 1H), 9.81 (s, 1H), 9.12 (s, 1H), 8.44 (d, J=5.1 Hz, 2H), 7.44 (dd, J=8.2, 0.6 Hz, 1H), 7.29 (d, J=1.9 Hz, 1H), 7.18 (dd, J=7.9, 1.9 Hz, 1H), 7.09 (d, J=7.9 Hz, 1H), 7.06 (br. d, J=8.0 Hz, 1H), 6.95 (t, J=8.1 Hz, 1H), 6.84 (t, J=4.9 Hz, 1H), 4.22-4.32 (m, 1H), 3.78 (s, 3H), 2.70-2.76 (m, 1H), 2.53-2.65 (m, 2H), 2.11-2.19 (m, 2H), 2.10 (s, 3H), 1.67-1.80 (m, 2H), 1.50-1.60 (m, 2H).

Example 280: Cis-4-(4-{[2-(dimethylamino)ethyl]amino}-2-oxo-2,3-dihydro-1H-1,3-benzodiazol-1-yl)-N-(3-methoxy-4-methylphenyl)cyclohexane-1-carboxamide Step 1: cis-4-[3-[benzyl-[2-(dimethylamino)ethyl]amino]-2-nitro-anilino]-N-(3-methoxy-4-methyl-phenyl)cyclohexanecarboxamide was synthesized according to General procedure A from Cis-4-[(3-fluoro-2-nitrophenyl)amino]-N-(3-methoxy-4-methylphenyl)cyclohexane-1-carboxamide and N-benzyl-N',N'-dimethylethylenediamine. LCMS [M+H]$^+$ 560.

Step 2: cis-4-[4-[benzyl-[2-(dimethylamino)ethyl]amino]-2-oxo-3H-benzimidazol-1-yl]-N-(3-methoxy-4-methyl-phenyl)cyclohexanecarboxamide was synthesized according to General procedure B from 4-[3-[benzyl-[2-(dimethylamino)ethyl]amino]-2-nitro-anilino]-N-(3-methoxy-4-methyl-phenyl)cyclohexanecarboxamide. LCMS [M+H]$^+$ 556.

Step 3: the title compound was synthesized according to General procedure G from cis-4-[4-[benzyl-[2-(dimethylamino)ethyl]amino]-2-oxo-3H-benzimidazol-1-yl]-N-(3-methoxy-4-methyl-phenyl)cyclohexanecarboxamide. LCMS [M+H]$^+$ 466.

Example 281: tert-Butyl N-(1-{2-oxo-1-[cis-4-[(3-methoxy-4-methylphenyl)carbamoyl]cyclohexyl]-2,3-dihydro-1H-1,3-benzodiazol-4-yl}pyrrolidin-3-yl)carbamate Step 1: tert-butyl N-[1-[3-cis-[[4-[(3-methoxy-4-methylphenyl)carbamoyl]cyclohexyl]amino]-2-nitro-phenyl]pyrrolidin-3-yl]carbamate was synthesized according to General procedure A from cis-4-[(3-fluoro-2-nitrophenyl)amino]-N-(3-methoxy-4-methylphenyl)cyclohexane-1-carboxamide and (±)-tert-butyl N-pyrrolidin-3-ylcarbamate. LCMS [M+H]$^+$ 568.

Step 2: The title compound was synthesized according to General procedure B from tert-butyl N-[1-[3-cis-[[4-[(3-methoxy-4-methyl-phenyl)carbamoyl]cyclohexyl]amino]-2-nitro-phenyl]pyrrolidin-3-yl]carbamate. LCMS [M+H]$^+$ 564.

Example 282: Cis-4-[4-(3-aminopyrrolidin-1-yl)-2-oxo-2,3-dihydro-1H-1,3-benzodiazol-1-yl]-N-(3-methoxy-4-methylphenyl)cyclohexane-1-carboxamide The title compound was synthesized according to General procedure C from tert-butyl N-(1-{2-oxo-1-[cis-4-[(3-methoxy-4-methylphenyl)carbamoyl]cyclohexyl]-2,3-dihydro-1H-1,3-benzodiazol-4-yl}pyrrolidin-3-yl)carbamate. LCMS [M+H]$^+$ 464.

Example 283: Cis-4-{4-[2-(dimethylamino)acetamido]-2-oxo-2,3-dihydro-1H-1,3-benzodiazol-1-yl}-N-(3-methoxy-4-methylphenyl)cyclohexane-1-carboxamide The title compound was synthesized according to General procedure H from cis-4-(4-amino-2-oxo-2,3-dihydro-1H-1,3-benzodiazol-1-yl)-N-(3-methoxy-4-methylphenyl)cyclohexane-1-carboxamide and N,N-dimethylglycine. LCMS [M+H]$^+$ 480.

Example 284: Cis-4-[4-(3-aminopropanamido)-2-oxo-2,3-dihydro-1H-1,3-benzodiazol-1-yl]-N-(3-methoxy-4-methylphenyl)cyclohexane-1-carboxamide Step 1: tert-Butyl N-[3-[[1-cis-[4-[(3-methoxy-4-methylphenyl)carbamoyl]cyclohexyl]-2-oxo-3H-benzimidazol-4-yl]amino]-3-oxo-propyl]carbamate was synthesized according to General procedure H from cis-4-(4-amino-2-oxo-2,3- dihydro-1H-1,3-benzodiazol-1-yl)-N-(3-methoxy-4-methylphenyl)cyclohexane-1-carboxamide and N-(tert-butoxycarbonyl)-β-alanine and was used in step 2 without purification.

Step 2 The title compound was synthesized according to General procedure C from tert-butyl N-[3-[[1-cis-4-[(3-methoxy-4-methyl-phenyl)carbamoyl]cyclohexyl]-2-oxo-3H-benzimidazol-4-yl]amino]-3-oxo-propyl]carbamate. LCMS [M+H]$^+$ 466.

Example 285: Cis-N-(3-methoxy-4-methylphenyl)-4-{4-[2-(morpholin-4-yl)acetamido]-2-oxo-2,3-dihydro-1H-1,3-benzodiazol-1-yl}cyclohexane-1-carboxamide The title compound was synthesized according to General procedure H from cis-4-(4-amino-2-oxo-2,3-dihydro-1H-1,3-benzodiazol-1-yl)-N-(3-methoxy-4-methylphenyl)cyclohexane-1-carboxamide and morpholin-4-yl-acetic acid hydrochloride. LCMS [M+H]$^+$ 522.

Example 286: (2S,4R)-4-Hydroxy-N-{2-oxo-1-[cis-4-[(3-methoxy-4-methylphenyl)carbamoyl]cyclohexyl]-2,3-dihydro-1H-1,3-benzodiazol-4-yl}pyrrolidine-2-carboxamide Step 1: tert-Butyl (2S,4R)-4-hydroxy-2-[[1-cis-[4-[(3-methoxy-4-methyl-phenyl)carbamoyl]cyclohexyl]-2-oxo-3H-benzimidazol-4-yl]carbamoyl]pyrrolidine-1-carboxylate was synthesized according to General procedure H from cis-4-(4-amino-2-oxo-2,3-dihydro-1H-1,3-benzodiazol-1-yl)-N-(3-methoxy-4-methylphenyl)cyclohexane-1-carboxamide and (2S,4R)-1-(tert-Butoxycarbonyl)-4-hydroxypyrrolidine-2-carboxylic acid and was used in step 2 without purification.

Step 2: The title compound was synthesized according to General procedure C from tert-butyl (2S,4R)-4-hydroxy-2-[[1-cis-[4-[(3-methoxy-4-methyl-phenyl)carbamoyl]cyclohexyl]-2-oxo-3H-benzimidazol-4-yl]carbamoyl]pyrrolidine-1-carboxylate. LCMS [M+H]$^+$ 508.

Example 287: (2S)—N-{2-Oxo-1-[cis-4-[(3-methoxy-4-methylphenyl)carbamoyl]cyclohexyl]-2,3-dihydro-1H-1,3-benzodiazol-4-yl}azetidine-2-carboxamide Step 1: tert-butyl (2S)-2-[[1-cis-[4-[(3-methoxy-4-methyl-phenyl)carbamoyl]cyclohexyl]-2-oxo-3H-benzimidazol-4-yl]carbamoyl]azetidine-1-carboxylate was synthesized according to General procedure H from cis-4-(4-amino-2-oxo-2,3-dihydro-1H-1,3-benzodiazol-1-yl)-N-(3-methoxy-4-methylphenyl)cyclohexane-1-carboxamide and (2S)-1-tert-butoxycarbonylazetidine-2-carboxylic acid and was used in step 2 without purification.

Step 2: The title compound was synthesized according to General procedure C from tert-butyl (2S)-2-[[1-cis-[4-[(3-methoxy-4-methyl-phenyl)carbamoyl]cyclohexyl]-2-oxo-3H-benzimidazol-4-yl]carbamoyl]azetidine-1-carboxylate. LCMS [M+H]$^+$ 478.

Example 288: Cis-4-(4-acetamido-2-oxo-2,3-dihydro-1H-1,3-benzodiazol-1-yl)-N-(3-methoxy-4-methylphenyl)cyclohexane-1-carboxamide A mixture of cis-4-(4-amino-2-oxo-2,3-dihydro-1H-1,3-benzodiazol-1-yl)-N-(3-methoxy-4-methylphenyl)cyclohexane-1-carboxamide (1.0 equiv.), acetic anhydride (1.0 equiv.), and diisopropylethylamine (2.0 equiv.) was stirred in THF at 20° C. for 16 h. The crude reaction mixture was then purified by preparative HPLC followed by recrystallization from EtOH/water. LCMS [M+H]$^+$ 437.

Example 289: N-{2-Oxo-1-[cis-4-[(3-methoxy-4-methylphenyl)carbamoyl]cyclohexyl]-2,3-dihydro-1H-1,3-benzodiazol-4-yl}morpholine-2-carboxamide Step 1: 4-benzyl-N-[1-[4-[(3-methoxy-4-methyl-phenyl)carbamoyl]cyclohexyl]-2-oxo-3H-benzimidazol-4-yl]morpholine-2-carboxamide was synthesized according to General procedure H from cis-4-(4-amino-2-oxo-2,3-dihydro-1H-1,3-benzodiazol-1-yl)-N-(3-methoxy-4-methylphenyl)cyclohexane-1-carboxamide and 4-benzyl-2-morpholinecarboxylic acid hydrochloride and was used in step 2 without purification.

Step 2: The title compound was synthesized according to General procedure G from 4-benzyl-N-[1-[4-[(3-methoxy-4-methyl-phenyl)carbamoyl]cyclohexyl]-2-oxo-3H-benzimidazol-4-yl]morpholine-2-carboxamide. LCMS [M+H]$^+$ 508.

Example 290: Cis-4-(4-acetamido-2-oxo-2,3-dihydro-1H-1,3-benzodiazol-1-yl)-N-(1H-indol-6-yl)cyclohexane-1-carboxamide The title compound was synthesized according to general procedure H from cis-4-(4-acetamido-2-oxo-2,3-dihydro-1H-1,3-benzodiazol-1-yl)cyclohexane-1-carboxylic acid and 1H-indol-6-amine. LCMS [M+H]$^+$ 432. $^1$H-NMR (400 MHz, DMSO-d6) δ ppm 11.01 (s, 1H), 10.38 (s, 1H), 9.77 (s, 1H), 9.52 (s, 1H), 8.00-8.03 (m, 1H), 7.44 (d, J=8.2 Hz, 1H), 7.26 (dd, J=3.0, 2.4 Hz, 1H), 7.16 (d, J=7.9 Hz, 1H), 7.04-7.10 (m, 2H), 6.93-6.98 (m, 1H), 6.35 (ddd, J=3.1, 2.0, 0.9 Hz, 1H), 4.21-4.33 (m, 1H), 2.71-2.80 (m, 1H), 2.57-2.70 (m, 2H), 2.10-2.21 (m, 2H), 2.05 (s, 3H), 1.68-1.80 (m, 2H), 1.50-1.60 (m, 2H).

Example 291: 2-Oxo-1-[cis-4-[(3-methoxy-4-methylphenyl)carbamoyl]cyclohexyl]-2,3-dihydro-1H-1,3-benzodiazole-4-carboxamide Step 1: cis-1-[4-[(3-methoxy-4-methyl-phenyl)carbamoyl]cyclohexyl]-N-[(4-methoxyphenyl)methyl]-2-oxo-3H-benzimidazole-4-carboxamide was synthesized according to General procedure H from 2-oxo-1-[cis-4-[(3-methoxy-4-methylphenyl)carbamoyl]cyclohexyl]-2,3-dihydro-1H-1,3-benzodiazole-4-carboxylic acid and 4-methoxybenzylamine and was used in step 2 without purification.

Step 2: A mixture of 2-oxo-1-[cis-4-[(3-methoxy-4-methylphenyl)carbamoyl]cyclohexyl]-2,3-dihydro-1H-1,3-benzodiazole-4-carboxamide and TFA was stirred at 70° C. for 16 h.

The excess TFA was then evaporated and the crude material was purified by preparative HPLC which afforded the title compound. LCMS [M+H]$^+$ 423.

Example 292: N-[(Morpholin-3-yl)methyl]-2-oxo-1-[cis-4-[(3-methoxy-4-methylphenyl)carbamoyl]cyclohexyl]-2,3-dihydro-1H-1,3-benzodiazole-4-carboxamide Step 1: tert-butyl 3-[[[1-cis-[4-[(3-methoxy-4-methyl-phenyl)carbamoyl]cyclohexyl]-2-oxo-3H-benzimidazole-4-carbonyl]amino]methyl]morpholine-4-carboxylate was synthesized according to General procedure H from 2-oxo-1-

[cis-4-[(3-methoxy-4-methylphenyl)carbamoyl] cyclohexyl]-2,3-dihydro-1H-1,3-benzodiazole-4-carboxylic acid and (±) tert-butyl 3-(aminomethyl)morpholine-4-carboxylate and was used in step 2 without purification.

Step 2: The title compound was synthesized according to General procedure C from the crude tert-butyl 3-[[[1-cis-[4-[(3-methoxy-4-methyl-phenyl)carbamoyl]cyclohexyl]-2-oxo-3H-benzimidazole-4-carbonyl]amino]methyl]morpholine-4-carboxylate from step 1. LCMS [M+H]$^+$ 522.

Example 293: N-(Azetidin-3-yl)-2-oxo-1-[cis-4-[(3-methoxy-4-methylphenyl)carbamoyl]cyclohexyl]-2,3-dihydro-1H-1,3-benzodiazole-4-carboxamide Step 1: tert-butyl 3-[[1-cis-[4-[(3-methoxy-4-methyl-phenyl)carbamoyl]cyclohexyl]-2-oxo-3H-benzimidazole-4-carbonyl]amino]azetidine-1-carboxylate was synthesized according to General procedure H from 2-oxo-1-[cis-4-[(3-methoxy-4-methylphenyl)carbamoyl]cyclohexyl]-2,3-dihydro-1H-1,3-benzodiazole-4-carboxylic acid and tert-butyl 3-aminoazetidine-1-carboxylate and was used in step 2 without purification.

Step 2: The title compound was synthesized according to General procedure C from the crude tert-butyl 3-[[1-cis-[4-[(3-methoxy-4-methyl-phenyl)carbamoyl]cyclohexyl]-2-oxo-3H-benzimidazole-4-carbonyl]amino]azetidine-1-carboxylate from step 1. LCMS [M+H]$^+$ 478.

Example 294: 2-Oxo-N-(pyrrolidin-3-yl)-1-[cis-4-[(3-methoxy-4-methylphenyl)carbamoyl]cyclohexyl]-2,3-dihydro-1H-1,3-benzodiazole-4-carboxamide Step 1: tert-butyl 3-[[1-cis-[4-[(3-methoxy-4-methyl-phenyl)carbamoyl]cyclohexyl]-2-oxo-3H-benzimidazole-4-carbonyl]amino]pyrrolidine-1-carboxylate was synthesized according to General procedure H from 2-oxo-1-[cis-4-[(3-methoxy-4-methylphenyl)carbamoyl]cyclohexyl]-2,3-dihydro-1H-1,3-benzodiazole-4-carboxylic acid and (±) tert-butyl 3-aminopyrrolidine-1-carboxylate and was used in step 2 without purification.

Step 2: The title compound was synthesized according to General procedure C from the crude tert-butyl 3-[[1-cis-[4-[(3-methoxy-4-methyl-phenyl)carbamoyl]cyclohexyl]-2-oxo-3H-benzimidazole-4-carbonyl]amino]pyrrolidine-1-carboxylate from step 1. LCMS [M+H]$^+$ 492.

Example 295: Cis-4-{4-[(3S)-3-(dimethylamino) pyrrolidin-1-yl]-2-oxo-2,3-dihydro-1H-1,3-benzodiazol-1-yl}-N-(3-methoxy-4-methylphenyl)cyclohexane-1-carboxamide Step 1: cis-4-[3-[(3S)-3-(dimethylamino)pyrrolidin-1-yl]-2-nitro-anilino]-N-(3-methoxy-4-methyl-phenyl)cyclohexanecarboxamide was synthesized according to General procedure M from cis-4-[(3-fluoro-2-nitrophenyl)amino]-N-(3-methoxy-4-methylphenyl)cyclohexane-1-carboxamide and S-3-(dimethylamino)pyrrolidine. LCMS [M+H]$^+$ 496. $^1$H-NMR (400 MHz, Chloroform-d) δ ppm 7.44 (s, 1H), 7.38 (s, 1H), 7.15 (t, J=8.4 Hz, 1H), 7.03 (d, J=8.2 Hz, 1H), 6.95 (d, J=7.0 Hz, 1H), 6.78 (dd, J=8.1, 1.7 Hz, 1H), 6.16 (d, J=8.2 Hz, 1H), 6.08 (d, J=8.5 Hz, 1H), 3.84 (s, 3H), 3.71 (br. s., 1H), 3.45-3.54 (m, 1H), 3.28-3.42 (m, 2H), 3.15-3.24 (m, 2H), 2.52 (s, 6H), 2.37-2.47 (m, 1H), 2.25 (d, J=4.7 Hz, 1H), 2.16 (s, 3H), 2.07-2.15 (m, 1H), 1.69-2.04 (m, 8H).

Step 2: The title compound was synthesized according to General procedure F from cis-4-[3-[(3S)-3-(dimethylamino) pyrrolidin-1-yl]-2-nitro-anilino]-N-(3-methoxy-4-methylphenyl)cyclohexanecarboxamide. LCMS [M+H]$^+$ 492.

Example 296: Cis-N-(3-Methoxy-4-methylphenyl)-4-{4-[methyl(1-methylpyrrolidin-3-yl)amino]-2-oxo-2,3-dihydro-1H-1,3-benzodiazol-1-yl}cyclohexane-1-carboxamide Step 1: N-(3-methoxy-4-methyl-phenyl)-4-[3-[methyl-(1-methylpyrrolidin-3-yl)amino]-2-nitro-anilino]cyclohexanecarboxamide was synthesized according to General procedure M from cis-4-[(3-fluoro-2-nitrophenyl)amino]-N-(3-methoxy-4-methylphenyl)cyclohexane-1-carboxamide and (±)—N,N'-dimethyl-3-aminopyrrolidine. LCMS [M+H]$^+$ 496. $^1$H-NMR (400 MHz, Chloroform-d) δ ppm 7.44 (d, J=1.6 Hz, 1H), 7.39 (s, 1H), 7.24 (t, J=8.2 Hz, 1H), 7.03 (d, J=8.2 Hz, 1H), 6.76 (dd, J=7.9, 1.9 Hz, 1H), 6.52 (d, J=8.5 Hz, 1H), 6.44 (d, J=7.9 Hz, 1H), 5.44-5.62 (m, 1H), 3.94-4.01 (m, 1H), 3.82-3.86 (m, 3H), 3.60-3.70 (m, 1H), 3.40-3.52 (m, 1H), 3.22-3.34 (m, 1H), 3.00-3.10 (m, 1H), 2.90 (br. s., 1H), 2.73 (s, 3H), 2.69 (s, 3H), 2.40-2.48 (m, 1H), 2.18-2.29 (m, 1H), 2.17 (s, 3H), 1.73-1.98 (m, 9H).

Step 2: the title compound was synthesized according to General procedure F from N-(3-methoxy-4-methyl-phenyl)-4-[3-[methyl-(1-methylpyrrolidin-3-yl)amino]-2-nitro-anilino]cyclohexanecarboxamide. LCMS [M+H]$^+$ 492. $^1$H-NMR (400 MHz, DMSO-d6) δ ppm 10.79 (s, 1H), 9.88 (s, 1H), 7.37 (d, J=1.6 Hz, 1H), 7.26 (dd, J=8.1, 1.7 Hz, 1H), 7.14 (d, J=8.2 Hz, 1H), 7.07 (d, J=7.9 Hz, 1H), 6.97 (t, J=7.9 Hz, 1H), 6.74 (d, J=7.9 Hz, 1H), 4.28-4.39 (m, 1H), 3.90-3.98 (m, 1H), 3.87 (s, 3H), 2.78-2.84 (m, 1H), 2.68 (s, 3H), 2.60-2.67 (m, 4H), 2.52-2.57 (m, 1H), 2.37-2.46 (m, 1H), 2.29 (s, 3H), 2.20-2.26 (m, 2H), 2.19 (s, 3H), 1.98-2.09 (m, 1H), 1.73-1.87 (m, 3H), 1.57-1.68 (m, 2H).

Example 297: Cis-N-(3-methoxy-4-methylphenyl)-4-(4-{methyl[2-(methylamino)ethyl]amino}-2-oxo-2,3-dihydro-1H-1,3-benzodiazol-1-yl)cyclohexane-1-carboxamide Step 1: tert-butyl N-[2-[3-[[4-[(3-methoxy-4-methyl-phenyl)carbamoyl]cyclohexyl]amino]-N-methyl-2-nitro-anilino]ethyl]-N-methyl-carbamate was synthesized according to General procedure M from cis-4-[(3-fluoro-2-nitrophenyl)amino]-N-(3-methoxy-4-methylphenyl)cyclohexane-1-carboxamide and tert-butyl N-methyl-N-[2-(methylamino)ethyl]carbamate. LCMS [M+H]$^+$ 570.

Step 2: tert-butyl N-[2-[[1-[4-[(3-methoxy-4-methyl-phenyl)carbamoyl]cyclohexyl]-2-oxo-3H-benzimidazol-4-yl]-methyl-amino]ethyl]-N-methyl-carbamate was synthesized according to General procedure F from tert-butyl N-[2-[3-[[4-[(3-methoxy-4-methyl-phenyl)carbamoyl]cyclohexyl]amino]-N-methyl-2-nitro-anilino]ethyl]-N-methyl-carbamate. LCMS [M+H]$^+$ 566.

Step 3: the title compound was synthesized according to General procedure C from tert-butyl N-[2-[[1-[4-[(3-methoxy-4-methyl-phenyl)carbamoyl]cyclohexyl]-2-oxo-3H-benzimidazol-4-yl]-methyl-amino]ethyl]-N-methyl-carbamate. LCMS [M+H]$^+$ 466.

Example 298: Cis-4-{4-[(2-aminoethyl)(methyl) amino]-2-oxo-2,3-dihydro-1H-1,3-benzodiazol-1-yl}-N-(3-methoxy-4-methylphenyl)cyclohexane-1-carboxamide Step 1: tert-butyl N-[2-[3-[[4-[(3-methoxy-4-methyl-phenyl)carbamoyl]cyclohexyl]amino]-N-methyl-2-nitro-anilino]ethyl]carbamate was synthesized according to General procedure M from cis-4-[(3-fluoro-2-nitrophenyl)amino]-N-(3-methoxy-4-methylphenyl)cyclohexane-1-carboxamide and tert-butyl N-[2-(methylamino)ethyl]carbamate. LCMS [M+H]$^+$ 556. $^1$H-NMR (400 MHz, Chloroform-d) δ ppm 7.45 (s, 1H), 7.40 (s, 1H), 7.16 (t, J=8.2 Hz, 1H), 7.03 (d, J=7.9 Hz, 1H), 6.77 (d, J=7.9 Hz, 1H), 6.49-6.73 (m, 1H), 6.36 (d, J=8.2 Hz, 1H), 6.29 (d, J=8.2 Hz, 1H), 5.07-5.23 (m, 1H), 3.84 (s, 3H), 3.69 (br. s., 1H), 3.33 (br. s., 4H), 2.80 (s, 3H), 2.37-2.46 (m, 1H), 2.16 (s, 3H), 1.83-2.00 (m, 6H), 1.70-1.81 (m, 2H), 1.39-1.44 (m, 9H).

Step 2: tert-butyl N-[2-[[1-[4-[(3-methoxy-4-methyl-phenyl)carbamoyl]cyclohexyl]-2-oxo-3H-benzimidazol-4-yl]-methyl-amino]ethyl]carbamate was synthesized according to General procedure F from tert-butyl N-[2-[3-[[4-[(3-methoxy-4-methyl-phenyl)carbamoyl]cyclohexyl]amino]-N-methyl-2-nitro-anilino]ethyl]carbamate. LCMS [M+H]$^+$ 552. $^1$H-NMR (400 MHz, Chloroform-d) δ ppm 9.50 (br. s, 1H), 7.36 (br. s., 2H), 7.09 (d, J=8.2 Hz, 2H), 6.93-7.01 (m, 1H), 6.88 (d, J=6.6 Hz, 1H), 6.64-6.75 (m, 1H), 5.22-5.40 (m, 1H), 4.40-4.52 (m, 1H), 3.88 (s, 3H), 3.39 (br. s., 2H), 3.12 (br. s., 2H), 2.78 (br. s., 3H), 2.61-2.73 (m, 3H), 2.25-2.35 (m, 2H), 2.20 (s, 3H), 1.69-1.89 (m, 5H), 1.44 (s, 9H).

Step 3: the title compound was synthesized according to General procedure C from tert-butyl N-[2-[[1-[4-[(3-methoxy-4-methyl-phenyl)carbamoyl]cyclohexyl]-2-oxo-3H-benzimidazol-4-yl]-methyl-amino]ethyl]carbamate. LCMS [M+H]$^+$ 452. $^1$H-NMR (400 MHz, DMSO-d6) δ ppm 9.84 (s, 1H), 7.29 (d, J=1.9 Hz, 1H), 7.18 (dd, J=7.9, 1.9 Hz, 1H), 7.04-7.09 (m, 2H), 6.96 (t, J=7.9 Hz, 1H), 6.76 (d, J=7.6 Hz, 1H), 4.21-4.31 (m, 1H), 3.79 (s, 3H), 3.11-3.17 (m, 2H), 2.98-3.04 (m, 2H), 2.74 (br. s., 1H), 2.63 (s, 3H), 2.53-2.60 (m, 2H), 2.15 (d, J=13.3 Hz, 2H), 2.10 (s, 3H), 1.67-1.79 (m, 2H), 1.49-1.58 (m, 2H).

Example 299: N-{2-Oxo-1-[cis-4-[(3-methoxy-4-methylphenyl)carbamoyl]cyclohexyl]-2,3-dihydro-1H-1,3-benzodiazol-4-yl}-1H-pyrazole-3-carboxamide The title compound was synthesized according to General procedure O from cis-4-(4-amino-2-oxo-2,3-dihydro-1H-1,3-benzodiazol-1-yl)-N-(3-methoxy-4-methylphenyl)cyclohexane-1-carboxamide and 1H-pyrazole-3-carboxylic acid. LCMS [M+H]$^+$ 489.

Example 300: 5-Methyl-N-{2-oxo-1-[cis-4-[(3-methoxy-4-methylphenyl)carbamoyl]cyclohexyl]-2,3-dihydro-1H-1,3-benzodiazol-4-yl}-1,2-oxazole-3-carboxamide The title compound was synthesized according to General procedure O from cis-4-(4-amino-2-oxo-2,3-dihydro-1H-1,3-benzodiazol-1-yl)-N-(3-methoxy-4-methylphenyl)cyclohexane-1-carboxamide and 5-methylisoxazole-3-carboxylic acid. LCMS [M+H]$^+$ 504.

Example 301: N-{2-Oxo-1-[cis-4-[(3-methoxy-4-methylphenyl)carbamoyl]cyclohexyl]-2,3-dihydro-1H-1,3-benzodiazol-4-yl}-1,3-oxazole-5-carboxamide The title compound was synthesized according to General procedure O from cis-4-(4-amino-2-oxo-2,3-dihydro-1H-1,3-benzodiazol-1-yl)-N-(3-methoxy-4-methylphenyl)cyclohexane-1-carboxamide and oxazole-5-carboxylic acid. LCMS [M+H]$^+$ 490.

Example 302: Cis-4-{4-[(3-aminopropyl)(methyl)amino]-2-oxo-2,3-dihydro-1H-1,3-benzodiazol-1-yl}-N-(3-methoxy-4-methylphenyl)cyclohexane-1-carboxamide The title compound was synthesized according to General procedure C from tert-butyl N-[3-[[1-cis-[4-[(3-methoxy-4-methyl-phenyl)carbamoyl]cyclohexyl]-2-oxo-3H-benzimidazol-4-yl]-methyl-amino]propyl]carbamate. LCMS [M+H]$^+$ 466. $^1$H-NMR (400 MHz, DMSO-d6) δ ppm 10.77 (s, 1H), 9.83 (s, 1H), 7.61 (br. s., 2H), 7.28 (d, J=1.9 Hz, 1H), 7.18 (dd, J=7.9, 1.9 Hz, 1H), 7.05-7.08 (m, 1H), 7.03 (d, J=7.9 Hz, 1H), 6.94 (t, J=8.1 Hz, 1H), 6.70 (d, J=8.2 Hz, 1H), 4.21-4.32 (m, 1H), 3.79 (s, 3H), 3.07 (br. t, J=7.0, 7.0 Hz, 2H), 2.80-2.88 (m, 2H), 2.71-2.76 (m, 1H), 2.65 (s, 3H), 2.52-2.63 (m, 2H), 2.11-2.18 (m, 2H), 2.11 (s, 3H), 1.67-1.78 (m, 4H), 1.49-1.57 (m, 2H).

Example 303: Cis-4-[4-(4-aminopiperidin-1-yl)-2-oxo-2,3-dihydro-1H-1,3-benzodiazol-1-yl]-N-(3-methoxy-4-methylphenyl)cyclohexane-1-carboxamide Step 1: tert-butyl N-[1-[3-cis-[[4-[(3-methoxy-4-methyl-phenyl)carbamoyl]cyclohexyl]amino]-2-nitro-phenyl]-4-piperidyl]carbamate was synthesized according to General procedure M from cis-4-[(3-fluoro-2-nitrophenyl)amino]-N-(3-methoxy-4-methylphenyl)cyclohexane-1-carboxamide and tert-butyl N-(4-piperidyl)carbamate. LCMS [M+H]$^+$ 582.

Step 2: tert-butyl N-[1-cis-[1-[4-[(3-methoxy-4-methylphenyl)carbamoyl]cyclohexyl]-2-oxo-3H-benzimidazol-4-yl]-4-piperidyl]carbamate was synthesized according to General procedure F from tert-butyl N-[1-[3-cis-[[4-[(3-methoxy-4-methyl-phenyl)carbamoyl]cyclohexyl]amino]-2-nitro-phenyl]-4-piperidyl]carbamate. LCMS [M+H]$^+$ 578.

Step 3: the title compound was synthesized according to General procedure C from tert-butyl N-[1-cis-[1-[4-[(3-methoxy-4-methyl-phenyl)carbamoyl]cyclohexyl]-2-oxo-3H-benzimidazol-4-yl]-4-piperidyl]carbamate. LCMS [M+H]$^+$ 478. $^1$H-NMR (400 MHz, DMSO-d6) δ ppm 10.86 (s, 1H), 9.81 (s, 1H), 7.91 (br. d, J=4.4 Hz, 3H), 7.28 (d, J=1.9 Hz, 1H), 7.17 (dd, J=7.9, 1.9 Hz, 1H), 7.00-7.07 (m, 2H), 6.92 (t, J=8.1 Hz, 1H), 6.63 (d, J=7.9 Hz, 1H), 4.21-4.31 (m, 1H), 3.78 (s, 3H), 3.24-3.32 (m, 2H), 3.06-3.18 (m, 1H), 2.70-2.75 (m, 1H), 2.52-2.69 (m, 4H), 2.11-2.18 (m, 2H), 2.09 (s, 3H), 1.89-1.97 (m, 2H), 1.66-1.86 (m, 4H), 1.48-1.56 (m, 2H).

Example 304: Cis-4-{4-[2-(dimethylamino)ethoxy]-2-oxo-2,3-dihydro-1H-1,3-benzodiazol-1-yl}-N-(3-methoxy-4-methylphenyl)cyclohexane-1-carboxamide Step 1: cis-4-((3-(2-(dimethylamino)ethoxy)-2-nitrophenyl)amino)-N-(3-methoxy-4-methylphenyl)cyclohexanecarboxamide was synthesized according to General procedure N from cis-4-[(3-fluoro-2-nitrophenyl)amino]-N-(3-methoxy-4-methylphenyl)cyclohexane-1-carboxamide and 2-dimethylaminoethanol. LCMS [M+H]$^+$ 471.

Step 2: the title compound was synthesized from cis-4-((3-(2-(dimethylamino)ethoxy)-2-nitrophenyl)amino)-N-(3- methoxy-4-methylphenyl)cyclohexanecarboxamide according to General procedure B. LCMS [M+H]+ 467.

Example 305: tert-Butyl N-{3-[methyl({2-oxo-1-[cis-4-[(3-methoxy-4-methylphenyl)carbamoyl]cyclohexyl]-2,3-dihydro-1H-1,3-benzodiazol-4-yl})amino]propyl}carbamate Step 1: tert-butyl N-[3-[3-[[4-[(3-methoxy-4-methyl-phenyl)carbamoyl]cyclohexyl]amino]-N-methyl-2-nitro-anilino]propyl]carbamate was synthesized according to General procedure M from cis-4-[(3-fluoro-2-nitrophenyl)amino]-N-(3-methoxy-4-methylphenyl)cyclohexane-1-carboxamide and tert-butyl N-[3-(methylamino)propyl]carbamate. LCMS [M+H]+ 570.

Step 2: tert-butyl N-[3-[[1-[4-[(3-methoxy-4-methyl-phenyl)carbamoyl]cyclohexyl]-2-oxo-3H-benzimidazol-4-yl]-methyl-amino]propyl]carbamate was synthesized according to General procedure F from tert-butyl N-[3-[3-[[4-[(3-methoxy-4-methyl-phenyl)carbamoyl]cyclohexyl]amino]-N-methyl-2-nitro-anilino]propyl]carbamate. LCMS [M+H]+ 566.

Example 306: Cis-4-{4-[3-(dimethylamino)propoxyl-2-oxo-2,3-dihydro-1H-1,3-benzodiazol-1-yl}-N-(3-methoxy-4-methylphenyl)cyclohexane-1-carboxamide Step 1: cis-4-((3-(3-(dimethylamino)propoxy)-2-nitrophenyl)amino)-N-(3-methoxy-4-methylphenyl)cyclohexanecarboxamide was synthesized according to General procedure N from cis-4-[(3-fluoro-2-nitrophenyl)amino]-N-(3-methoxy-4-methylphenyl)cyclohexane-1-carboxamide and 3-dimethylamino-1-propanol. LCMS [M+H]+ 485.

Step 2: The title compound was synthesized from cis-4-((3-(3-(dimethylamino)propoxy)-2-nitrophenyl)amino)-N-(3-methoxy-4-methylphenyl)cyclohexanecarboxamide according to General procedure B. LCMS [M+H]+ 481.

Example 307: Cis-N-(3-methoxy-4-methylphenyl)-4-[2-oxo-4-(piperidin-4-yloxy)-2,3-dihydro-1H-1,3-benzodiazol-1-yl]cyclohexane-1-carboxamide Step 1: tert-butyl 4-(3-((cis-4-((3-methoxy-4-methylphenyl)carbamoyl)cyclohexyl)amino)-2-nitrophenoxy)piperidine-1-carboxylate was synthesized according to General procedure N from cis-4-[(3-fluoro-2-nitrophenyl)amino]-N-(3-methoxy-4-methylphenyl)cyclohexane-1-carboxamide and tert-butyl 4-hydroxypiperidine-1-carboxylate.

Step 2: the title compound was synthesized from tert-butyl 4-(3-((cis-4-((3-methoxy-4-methylphenyl)carbamoyl)cyclohexyl)amino)-2-nitrophenoxy)piperidine-1-carboxylate according to General procedure B followed by General procedure C. LCMS [M+H]+ 479.

Example 308: tert-Butyl N-methyl-N-[2-({2-oxo-1-[cis-4-[(3-methoxy-4-methylphenyl)carbamoyl]cyclohexyl]-2,3-dihydro-1H-1,3-benzodiazol-4-yl}oxy)ethyl]carbamate Step 1: tert-butyl (2-(3-((cis-4-((3-methoxy-4-methylphenyl)carbamoyl)cyclohexyl)amino)-2-nitrophenoxy)ethyl)(methyl)carbamate was synthesized according to General procedure N from cis-4-[(3-fluoro-2-nitrophenyl)amino]-N-(3-methoxy-4-methylphenyl)cyclohexane-1-carboxamide and tert-butyl (2-hydroxyethyl)(methyl)carbamate. LCMS [M+H]+ 557.

Step 2: the title compound was synthesized from tert-butyl (2-(3-((cis-4-((3-methoxy-4-methylphenyl)carbamoyl)cyclohexyl)amino)-2-nitrophenoxy)ethyl)(methyl)carbamate according to General procedure B. LCMS [M+H]+ 553.

Example 309: Cis-N-(3-methoxy-4-methylphenyl)-4-{4-[2-(methylamino)ethoxyl-2-oxo-2,3-dihydro-1H-1,3-benzodiazol-1-yl}cyclohexane-1-carboxamide The title compound was synthesized according to General procedure C from tert-butyl N-methyl-N-[2-({2-oxo-1-[cis-4-[(3-methoxy-4-methylphenyl)carbamoyl]cyclohexyl]-2,3-dihydro-1H-1,3-benzodiazol-4-yl}oxy)ethyl]carbamate. LCMS [M+H]+ 453.

Example 310: Cis-N-(3-methoxy-4-methylphenyl)-4-[2-oxo-4-(pyrrolidin-1-yl)-2,3-dihydro-1H-1,3-benzodiazol-1-yl]cyclohexane-1-carboxamide Step 1: cis-N-(3-methoxy-4-methylphenyl)-4-((2-nitro-3-(pyrrolidin-1-yl)phenyl)amino)cyclohexanecarboxamide was synthesized from cis-4-[(3-fluoro-2-nitrophenyl)amino]-N-(3-methoxy-4-methylphenyl)cyclohexane-1-carboxamide and pyrrolidine according to General procedure M. LCMS [M+H]+ 453.

Step 2: the title compound was synthesized from cis-N-(3-methoxy-4-methylphenyl)-4-((2-nitro-3-(pyrrolidin-1-yl)phenyl)amino)cyclohexanecarboxamide according to General procedure B. LCMS [M+H]+ 449.

Example 311: Cis-N-(3-methoxy-4-methylphenyl)-4-[2-oxo-4-(1,2,3,6-tetrahydropyridin-4-yl)-2,3-dihydro-1H-1,3-benzodiazol-1-yl]cyclohexane-1-carboxamide Step 1: A mixture of cis-4-(4-bromo-2-oxo-2,3-dihydro-1H-1,3-benzodiazol-1-yl)-N-(3-methoxy-4-methylphenyl)cyclohexane-1-carboxamide (1.0 equiv.), tert-butyl 4-(4,4,5,5-tetramethyl-1,3,2-dioxaborolan-2-yl)-3,6-dihydro-2H-pyridine-1-carboxylate (1.3 equiv.), Pd(dba)$_2$ (0.10 equiv.), S-Phos (0.10 equiv.), and triethylamine (5.3 equiv.) were dissolved in ethanol. The vial was flushed with nitrogen and sealed, thereafter the resulting reaction mixture was stirred at 120° C. for 24 h. After cooling, the reaction mixture was filtered through a short plug of silica. The material was concentrated and used in the next step without further purification.

Step 2: the filtrate from step 1 was dissolved in DCM, then trifluoroacetic acid was added. After complete reaction the mixture was purified by preparative HPLC which afforded the title compound.
LCMS [M+H]+ 461.

Example 312: Cis-N-(3-methoxy-4-methylphenyl)-4-[4-(1-methyl-1,2,3,6-tetrahydropyridin-4-yl)-2-oxo-2,3-dihydro-1H-1,3-benzodiazol-1-yl]cyclohexane-1-carboxamide A mixture of cis-4-(4-bromo-2-oxo-2,3-dihydro-1H-1,3-benzodiazol-1-yl)-N-(3-methoxy-4-methylphenyl)cyclohexane-1-carboxamide (1.0 equiv.), tert-butyl 4-(4,4,5,5-tetramethyl-1,3,2-dioxaborolan-2-yl)-3,6-dihydro-2H-pyridine-1-carboxylate (1.3 equiv.), Pd(dba)$_2$ (0.10 equiv.), S-Phos (0.10 equiv.), and triethylamine (5.3 equiv.) were dissolved in ethanol. The vial was flushed with nitrogen and sealed and the resulting reaction mixture was stirred at 120° C. for 24 h. After cooling, the material was concentrated and purified by preparative HPLC which afforded the title compound. LCMS [M+H]+ 475.

Example 313: Cis-4-[4-(3-acetamidopyrrolidin-1-yl)-2-oxo-2,3-dihydro-1H-1,3-benzodiazol-1-yl]-N-(3-methoxy-4-methylphenyl)cyclohexane-1-carboxamide A mixture of cis-4-[4-(3-aminopyrrolidin-1-yl)-2-oxo-2,3-dihydro-1H-1,3-benzodiazol-1-yl]-N-(3-methoxy-4-methylphenyl)cyclohexane-1-carboxamide, diisopropylethylamine, and acetic anhydride was stirred DCM for 16 h. The mixture was concentrated and purified by preparative HPLC which afforded the title compound. LCMS [M+H]+ 506.

Example 314: Cis-N-(3-methoxy-4-methylphenyl)-4-(2-oxo-4-{1H,4H,5H,6H-pyrrolo[3,4-c]pyrazol-5-yl}-2,3-dihydro-1H-1,3-benzodiazol-1-yl)cyclohexane-1-carboxamide Step 1: 4-[3-(4,6-dihydro-1H-pyrrolo[3,4-c]pyrazol-5-yl)-2-nitro-anilino]-N-(3-methoxy-4-methyl-phenyl)cyclohexanecarboxamide was synthesized according to General procedure A from cis-4-[(3-fluoro-2-nitrophenyl)amino]-N-(3-methoxy-4-methylphenyl)cyclohexane-1-carboxamide and 1,4,5,6-tetrahydropyrrolo[3,4-c]pyrazole dihydrochloride. LCMS [M+H]+ 491.

Step 2: The title compound was synthesized according to General procedure B from 4-[3-(4,6-dihydro-1H-pyrrolo[3,4-c]pyrazol-5-yl)-2-nitro-anilino]-N-(3-methoxy-4-methylphenyl)cyclohexanecarboxamide. LCMS [M+H]+ 487.

Example 315: Cis-4-(4-acetamido-2-oxo-2,3-dihydro-1H-1,3-benzodiazol-1-yl)-N-(1H-indazol-5-yl)cyclohexane-1-carboxamide The title compound was synthesized according to general procedure H from cis-4-(4-acetamido-2-oxo-2,3-dihydro-1H-1,3-benzodiazol-1-yl)cyclohexane-1-carboxylic acid and 1H-indazol-5-amine. LCMS [M+H]+ 433. $^1$H-NMR (400 MHz, DMSO-d6) δ ppm 10.39 (s, 1H), 9.89 (s, 1H), 9.53 (s, 1H), 8.18 (dd, J=1.7, 0.8 Hz, 1H), 8.06 (d, J=0.6 Hz, 1H), 7.49-7.52 (m, 1H), 7.46 (dd, J=9.0, 2.0 Hz, 1H), 7.16 (d, J=7.9 Hz, 1H), 7.08 (d, J=7.6 Hz, 1H), 6.94-7.00 (m, 1H), 4.23-4.34 (m, 1H), 2.73-2.82 (m, 1H), 2.57-2.70 (m, 2H), 2.12-2.22 (m, 2H), 2.06 (s, 3H), 1.71-1.81 (m, 2H), 1.57 (d, J=9.8 Hz, 2H).

Example 316: Methyl N-(1-{2-oxo-1-[cis-4-[(3-methoxy-4-methylphenyl)carbamoyl]cyclohexyl]-2,3-dihydro-1H-1,3-benzodiazol-4-yl}pyrrolidin-3-yl)carbamate A mixture of cis-4-[4-(3-aminopyrrolidin-1-yl)-2-oxo-2,3-dihydro-1H-1,3-benzodiazol-1-yl]-N-(3-methoxy-4-methylphenyl)cyclohexane-1-carboxamide (1.0 equiv.), N,N-diisopropylethylamine (2.0 equiv.), and methyl chloroformate (1.0 equiv.) was stirred in DCM at 20° C. for 3 h. The mixture was then purified by silica gel chromatography which afforded the title compound. LCMS [M+H]+ 522.

Example 317: Cis-4-{4-[3-(2-hydroxy-2-methylpropanamido)pyrrolidin-1-yl]-2-oxo-2,3-dihydro-1H-1,3-benzodiazol-1-yl}-N-(3-methoxy-4-methylphenyl)cyclohexane-1-carboxamide The title compound was synthesized according to general procedure O from cis-4-[4-(3-aminopyrrolidin-1-yl)-2-oxo-2,3-dihydro-1H-1,3-benzodiazol-1-yl]-N-(3-methoxy-4-methylphenyl)cyclohexane-1-carboxamide and α-hydroxyisobutyric acid. LCMS [M+H]+ 550. $^1$H-NMR (400 MHz, DMSO-d6) δ ppm 10.46 (s, 1H), 9.79 (s, 1H), 7.73 (d, J=7.6 Hz, 1H), 7.28 (d, J=1.9 Hz, 1H), 7.16 (dd, J=7.9, 1.9 Hz, 1H), 7.03-7.07 (m, 1H), 6.84-6.88 (m, 2H), 6.36-6.41 (m, 1H), 4.20-4.36 (m, 2H), 3.35-3.45 (m, 2H), 3.16-3.26 (m, 2H), 2.70-2.74 (m, 1H), 2.52-2.63 (m, 2H), 2.14 (d, J=14.5 Hz, 3H), 2.09 (s, 3H), 1.77-1.86 (m, 1H), 1.66-1.77 (m, 2H), 1.48-1.56 (m, 2H), 1.24 (d, J=4.4 Hz, 6H).

Example 318: 1-Methyl-N-{2-oxo-1-[cis-4-[(3-methoxy-4-methylphenyl)carbamoyl]cyclohexyl]-2,3-dihydro-1H-1,3-benzodiazol-4-yl}-1H-imidazole-2-carboxamide The title compound was synthesized according to general procedure O from cis-4-(4-amino-2-oxo-2,3-dihydro-1H-1,3-benzodiazol-1-yl)-N-(3-methoxy-4-methylphenyl)cyclohexane-1-carboxamide and 1-methylimidazole-2-carboxylic acid. LCMS [M+H]+ 503.

Example 319: 1-Methyl-N-{2-oxo-1-[cis-4-f(3-methoxy-4-methylphenyl)carbamoyl]cyclohexyl]-2,3-dihydro-1H-1,3-benzodiazol-4-yl}-1H-imidazole-4-carboxamide The title compound was synthesized according to general procedure O from cis-4-(4-amino-2-oxo-2,3-dihydro-1H-1,3-benzodiazol-1-yl)-N-(3-methoxy-4-methylphenyl)cyclohexane-1-carboxamide and 1-methylimidazole-4-carboxylic acid.
LCMS [M+H]+ 503. $^1$H-NMR (400 MHz, DMSO-d6) δ ppm 10.73 (s, 1H), 9.90 (s, 1H), 9.82 (s, 1H), 8.20-8.31 (m, 1H), 7.97 (s, 1H), 7.30 (d, J=1.9 Hz, 1H), 7.22 (d, J=7.9 Hz, 1H), 7.15-7.19 (m, 2H), 7.03-7.07 (m, 1H), 6.99 (t, J=8.1 Hz, 1H), 4.22-4.33 (m, 1H), 3.81 (s, 3H), 3.79 (s, 3H), 2.71-2.76 (m, 1H), 2.53-2.66 (m, 3H), 2.11-2.19 (m, 3H), 2.10 (s, 3H), 1.68-1.80 (m, 2H), 1.52-1.60 (m, 2H).

Example 320: 2-Amino-N-{2-oxo-1-[cis-4-[(3-methoxy-4-methylphenyl)carbamoyl]cyclohexyl]-2,3-dihydro-1H-1,3-benzodiazol-4-yl}-1,3-oxazole-4-carboxamide The title compound was synthesized according to general procedure O from cis-4-(4-amino-2-oxo-2,3-dihydro-1H-1,3-benzodiazol-1-yl)-N-(3-methoxy-4-methylphenyl)cyclohexane-1-carboxamide and 1-methylimidazole-4-carboxylic acid. LCMS [M+H]+ 505.

Example 321: 1-Methyl-N-{2-oxo-1-[cis-4-[(3-methoxy-4-methylphenyl)carbamoyl]cyclohexyl]-2,3-dihydro-1H-1,3-benzodiazol-4-yl}-1H-pyrazole-5-carboxamide The title compound was synthesized according to general procedure O from cis-4-(4-amino-2-oxo-2,3-dihydro-1H-1, 3-benzodiazol-1-yl)-N-(3-methoxy-4-methylphenyl)cyclohexane-1-carboxamide and 1-methylimidazole-4-carboxylic acid. LCMS [M+H]$^+$ 503. $^1$H-NMR (400 MHz, DMSO-d6) δ ppm 10.65-10.70 (m, 1H), 9.99 (s, 1H), 9.79-9.84 (m, 1H), 7.53 (d, J=1.9 Hz, 1H), 7.31 (d, J=2.0 Hz, 1H), 7.22 (br. d, J=7.4 Hz, 1H), 7.17 (dd, J=8.2, 1.9 Hz, 1H), 7.03-7.08 (m, 4H), 7.00 (t, J=7.8 Hz, 1H), 4.23-4.33 (m, 1H), 4.09 (s, 3H), 3.79 (s, 3H), 2.70-2.77 (m, 1H), 2.53-2.66 (m, 2H), 2.12-2.19 (m, 3H), 2.10 (s, 3H), 1.68-1.80 (m, 2H), 1.52-1.61 (m, 2H).

Example 322: Cis-N-(4-fluorophenyl)-4-(2-oxo-2,3-dihydro-1H-benzo[d]imidazol-1-yl)cyclohexanecarboxamide Step 1: cis-4-((2-nitrophenyl)amino)cyclohexanecarboxylic acid was synthesized according to general procedure A. LCMS [M+H]$^+$ 265.

Step 2: cis-4-(2-oxo-2,3-dihydro-1H-benzo[d]imidazol-1-yl)cyclohexanecarboxylic acid synthesized according to general procedure B from cis-4-((2-nitrophenyl)amino)cyclohexanecarboxylic acid and diphosgene. LCMS [M+H]$^+$ 261.

Step 3: The title compound was synthesized according to general procedure O from cis-4-(2-oxo-2,3-dihydro-1H-benzo[d]imidazol-1-yl)cyclohexanecarboxylic acid. LCMS [M+H]$^+$ 354.

Example 323: Cis-N-(3-methoxy-4-methylphenyl)-4-{2-oxo-4-[(2,2,2-trifluoroethyl)amino]-2,3-dihydro-1H-1,3-benzodiazol-1-yl}cyclohexane-1-carboxamide Step 1: 3-fluoro-2-nitro-N-(2,2,2-trifluoroethyl)aniline was synthesized according to general procedure A from 2,2,2-trifluoroethanamine hydrochloride and 1,3-difluoro-2-nitrobenzene. LCMS [M+H]$^+$ 239.

Step 2: cis-N-(3-methoxy-4-methyl-phenyl)-4-[2-nitro-3-(2,2,2-trifluoroethylamino)anilino]cyclohexanecarboxamide was synthesized according to general procedure A from cis-4-amino-N-(3-methoxy-4-methyl-phenyl)-cyclohexanecarboxamide hydrochloride and 3-fluoro-2-nitro-N-(2,2,2-trifluoroethyl)aniline. LCMS [M+H]$^+$ 481.

Step 3: The title compound was synthesized according to general procedure F. LCMS [M+H]$^+$ 477.

Example 324: Cis-4-{4-[(2,2-difluoroethyl)amino]-2-oxo-2,3-dihydro-1H-1,3-benzodiazol-1-yl}-N-(3-methoxy-4-methylphenyl)cyclohexane-1-carboxamide Step 1: N-(2,2-difluoroethyl)-3-fluoro-2-nitro-aniline was synthesized according to general procedure A from 2,2-difluoroethanamine and 1,3-difluoro-2-nitrobenzene. LCMS [M+H]$^+$ 221.

Step 2: N-(3-methoxy-4-methyl-phenyl)-cis-4-[2-nitro-3-(2,2,2-trifluoroethylamino)anilino]cyclohexanecarboxamide was synthesized according to general procedure A from N-(2,2-difluoroethyl)-3-fluoro-2-nitro-aniline and cis-4-amino-N-(3-methoxy-4-methyl-phenyl)-cyclohexanecarboxamide hydrochloride. LCMS [M+H]$^+$ 463.

Step 3: The title compound was synthesized according to general procedure F from N-(3-methoxy-4-methyl-phenyl)-cis-4-[2-nitro-3-(2,2,2-trifluoroethylamino)anilino]cyclohexanecarboxamide. LCMS [M+H]$^+$ 459.

Example 325: Cis-N-(3-methoxy-4-methylphenyl)-4-[4-(3-methylbutoxy)-2-oxo-2,3-dihydro-1H-1,3-benzodiazol-1-yl]cyclohexane-1-carboxamide Step 1: cis-4-((3-(isopentyloxy)-2-nitrophenyl)amino)-N-(3-methoxy-4-methylphenyl)cyclohexanecarboxamide was synthesized according to general procedure N from cis-4-[(3-fluoro-2-nitrophenyl)amino]-N-(3-methoxy-4-methylphenyl)cyclohexane-1-carboxamide and 3-methylbutan-1-ol. LCMS [M+H]$^+$ 470.

Step 2: The title compound was according to General procedure B from cis-4-((3-(isopentyloxy)-2-nitrophenyl)amino)-N-(3-methoxy-4-methylphenyl)cyclohexanecarboxamide. LCMS [M+H]$^+$ 466.

Example 326: Cis-4-(4-(2-(cyclohexyloxy)ethoxy)-2-oxo-2,3-dihydro-1H-benzo[d]imidazol-1-yl)-N-(3-methoxy-4-methylphenyl)cyclohexanecarboxamide Step 1: cis-4-((3-(2-(cyclohexyloxy)ethoxy)-2-nitrophenyl)amino)-N-(3-methoxy-4-methylphenyl)cyclohexanecarboxamide was synthesized according to general procedure N from cis-4-[(3-fluoro-2-nitrophenyl)amino]-N-(3-methoxy-4-methylphenyl)cyclohexane-1-carboxamide and 2-(cyclohexyloxy)ethanol. LCMS [M+H]$^+$ 526:

Step 2: The title compound was synthesized according to General procedure B from cis-4-((3-(2-(cyclohexyloxy)ethoxy)-2-nitrophenyl)amino)-N-(3-methoxy-4-methylphenyl)cyclohexanecarboxamide. LCMS [M+H]$^+$ 522.

The chemical names of the compounds described herein have been generated using as software Marvin Sketch version 18.22.3 and ACD Labs ChemSketch version 12.0.

For the avoidance of doubt, it is pointed out that in the event of a discrepancy between the chemical name and the structural formula of any particular compound, the structural formula prevails, unless contradicted by any experimental details or unless otherwise is clear from the context. The structural formulas of the Examples are shown in Table 1.

TABLE 1

| Example | Structural formula |
|---------|-------------------|
| 1 | |

TABLE 1-continued

| Example | Structural formula |
|---|---|
| 2 | 4-iodophenyl-NHC(O)-[piperidine-N]-4-(5-chloro-2-oxo-2,3-dihydro-1H-benzimidazol-1-yl) |
| 3 | 3,4-dichlorophenyl-NHC(O)-[piperidine-N]-4-(5-chloro-2-oxo-2,3-dihydro-1H-benzimidazol-1-yl) |
| 4 | 4-iodophenyl-NHC(O)-[piperidine-N]-4-(4-methyl-2-oxo-2,3-dihydro-1H-benzimidazol-1-yl) |
| 5 | 4-iodophenyl-NHC(O)-[piperidine-N]-4-(4-methoxy-2-oxo-2,3-dihydro-1H-benzimidazol-1-yl) |
| 6 | 4-iodophenyl-NHC(O)-[piperidine-N]-4-(4-hydroxy-2-oxo-2,3-dihydro-1H-benzimidazol-1-yl) |
| 7 | 4-chlorophenyl-NHC(O)-[piperidine-N]-4-(4-methyl-2-oxo-2,3-dihydro-1H-benzimidazol-1-yl) |
| 8 | 4-chlorophenyl-NHC(O)-[piperidine-N]-4-(4-methoxy-2-oxo-2,3-dihydro-1H-benzimidazol-1-yl) |
| 9 | 3,4-dichlorophenyl-NHC(O)-[piperidine-N]-4-(4-hydroxy-2-oxo-2,3-dihydro-1H-benzimidazol-1-yl) |

TABLE 1-continued

| Example | Structural formula |
|---|---|
| 10 | 4-iodophenyl urea-piperidine-benzimidazolone with 5-CN substituent |
| 11 | 4-iodophenyl urea-piperidine-benzimidazolone with 5-methyl substituent |
| 12 | 4-iodophenyl urea-piperidine-benzimidazolone with 4-F substituent |
| 13 | 4-iodophenyl urea-piperidine-benzimidazolone with 4-Br substituent |
| 14 | 4-iodophenyl urea-piperidine-benzimidazolone with 6-OMe substituent |
| 15 | 4-iodophenyl urea-piperidine-benzimidazolone with 6-F substituent |
| 16 | 4-iodophenyl urea-piperidine-benzimidazolone with 4-CH$_2$CO$_2$Me substituent |

TABLE 1-continued

| Example | Structural formula |
|---|---|
| 17 | |
| 18 | |
| 19 | |
| 20 | |
| 21 | |
| 22 | |
| 23 | |
| 24 | |

TABLE 1-continued

| Example | Structural formula |
|---|---|
| 25 | |
| 26 | |
| 27 | |
| 28 | |
| 29 | |
| 30 | |
| 31 | |
| 32 | |

TABLE 1-continued
| Example | Structural formula |
|---|---|
| 33 | 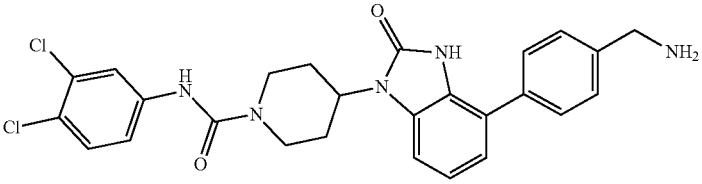 [SMILES: NCc1ccc(-c2cccc3c2[nH]c(=O)n3C2CCN(C(=O)Nc3ccc(Cl)c(Cl)c3)CC2)cc1] |
| 34 | 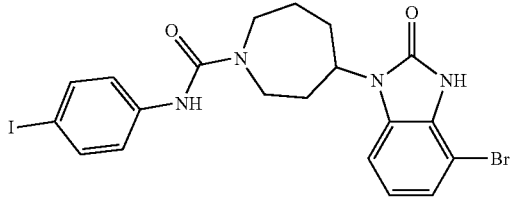 [SMILES: O=C(Nc1ccc(I)cc1)N1CCCC(n2c(=O)[nH]c3c(Br)cccc32)CC1] |
| 35 | 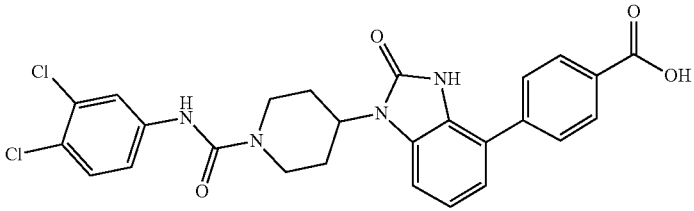 [SMILES: O=C(O)c1ccc(-c2cccc3c2[nH]c(=O)n3C2CCN(C(=O)Nc3ccc(Cl)c(Cl)c3)CC2)cc1] |
| 36 | 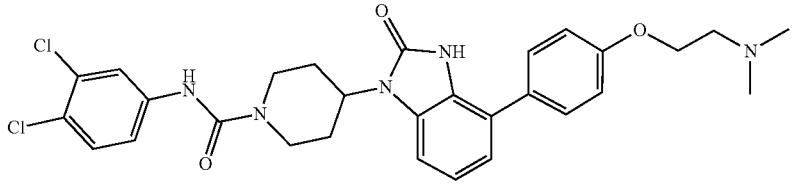 [SMILES: CN(C)CCOc1ccc(-c2cccc3c2[nH]c(=O)n3C2CCN(C(=O)Nc3ccc(Cl)c(Cl)c3)CC2)cc1] |
| 37 | 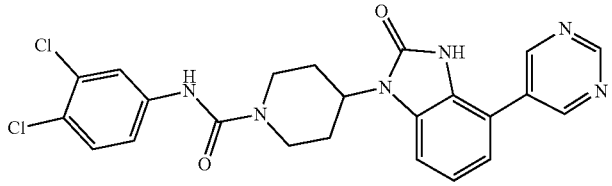 [SMILES: O=C(Nc1ccc(Cl)c(Cl)c1)N1CCC(n2c(=O)[nH]c3c(-c4cncnc4)cccc32)CC1] |
| 38 | 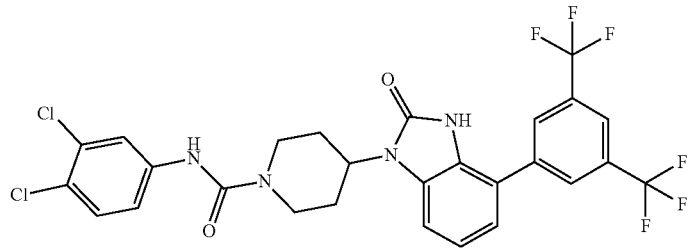 [SMILES: O=C(Nc1ccc(Cl)c(Cl)c1)N1CCC(n2c(=O)[nH]c3c(-c4cc(C(F)(F)F)cc(C(F)(F)F)c4)cccc32)CC1] |
| 39 | 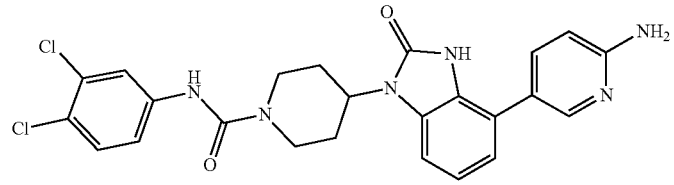 [SMILES: Nc1ccc(-c2cccc3c2[nH]c(=O)n3C2CCN(C(=O)Nc3ccc(Cl)c(Cl)c3)CC2)cn1] |

TABLE 1-continued
| Example | Structural formula |
|---|---|
| 40 | 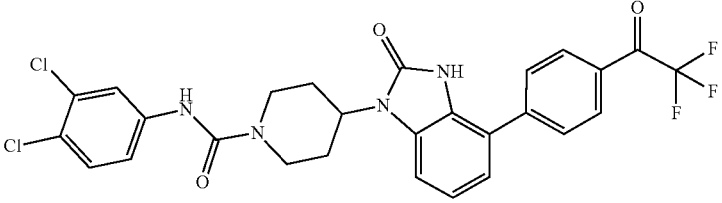 [SMILES: O=C(Nc1ccc(Cl)c(Cl)c1)N1CCC(n2c(=O)[nH]c3c(-c4ccc(C(=O)C(F)(F)F)cc4)cccc32)CC1] |
| 41 | 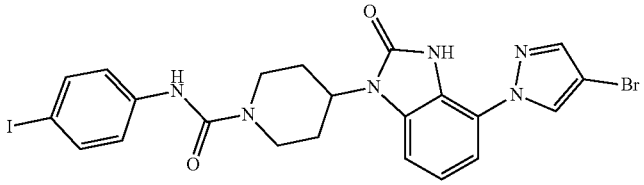 [SMILES: O=C(Nc1ccc(I)cc1)N1CCC(n2c(=O)[nH]c3c(-n4cc(Br)cn4)cccc32)CC1] |
| 42 | 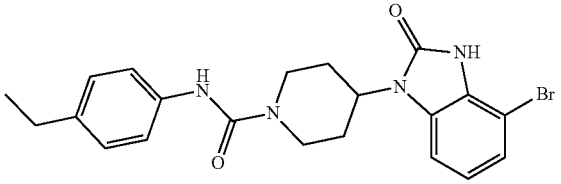 [SMILES: CCc1ccc(NC(=O)N2CCC(n3c(=O)[nH]c4c(Br)cccc43)CC2)cc1] |
| 43 | 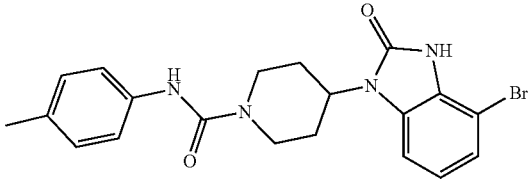 [SMILES: Cc1ccc(NC(=O)N2CCC(n3c(=O)[nH]c4c(Br)cccc43)CC2)cc1] |
| 44 | 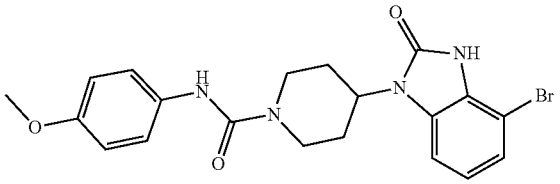 [SMILES: COc1ccc(NC(=O)N2CCC(n3c(=O)[nH]c4c(Br)cccc43)CC2)cc1] |
| 45 | 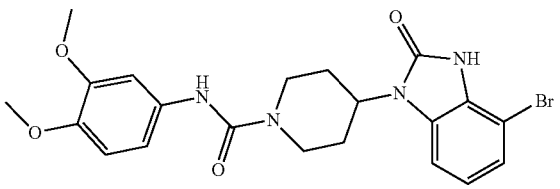 [SMILES: COc1ccc(NC(=O)N2CCC(n3c(=O)[nH]c4c(Br)cccc43)CC2)cc1OC] |
| 46 | 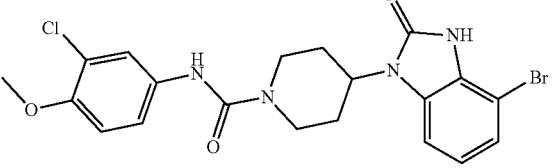 |
| 47 | 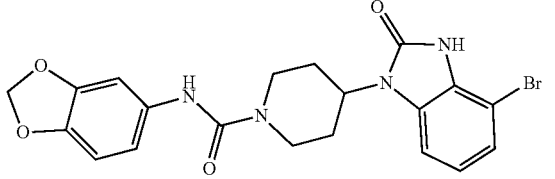 [SMILES: O=C(Nc1ccc2c(c1)OCO2)N1CCC(n2c(=O)[nH]c3c(Br)cccc32)CC1] |

TABLE 1-continued

| Example | Structural formula |
|---|---|
| 48 | |
| 49 | |
| 50 | |
| 51 | |
| 52 | |
| 53 | |
| 54 | |
| 55 | |

TABLE 1-continued

| Example | Structural formula |
|---|---|
| 56 | |
| 57 | |
| 58 | |
| 59 | |
| 60 | |
| 61 | |
| 62 | |

TABLE 1-continued

| Example | Structural formula |
|---|---|
| 63 | (3,4-dichlorophenyl)urea-piperidine-benzimidazolone with 4-sulfamoylphenyl substituent |
| 64 | (3,4-dichlorophenyl)urea-piperidine-benzimidazolone with 3-fluorophenyl substituent |
| 65 | (3,4-dichlorophenyl)urea-piperidine-benzimidazolone with 3-(aminomethyl)phenyl substituent |
| 66 | (3,4-dichlorophenyl)urea-piperidine-benzimidazolone with 2-aminophenyl substituent |
| 67 | (3,4-dichlorophenyl)urea-piperidine-benzimidazolone with 2-((dimethylamino)methyl)phenyl substituent |
| 68 | (3,4-dichlorophenyl)urea-piperidine-benzimidazolethione with bromo substituent |
| 69 | (3,4-dichlorophenyl)urea-piperidine-benzimidazolone with fluoro substituent |

TABLE 1-continued
| Example | Structural formula |
|---|---|
| 70 | 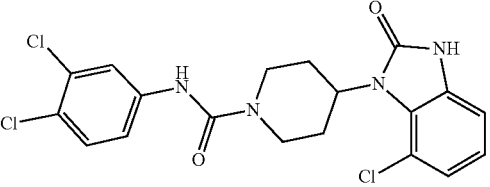 [SMILES: O=C(Nc1ccc(Cl)c(Cl)c1)N1CCC(n2c(=O)[nH]c3cccc(Cl)c32)CC1] |
| 71 | 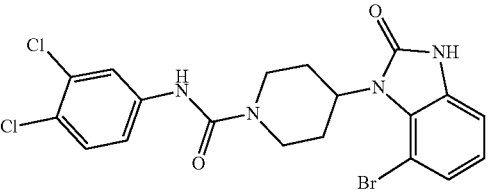 [SMILES: O=C(Nc1ccc(Cl)c(Cl)c1)N1CCC(n2c(=O)[nH]c3cccc(Br)c32)CC1] |
| 72 | 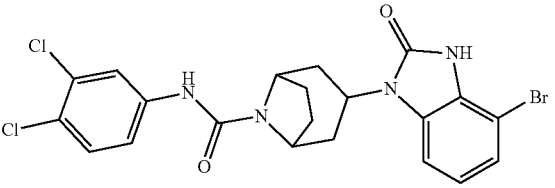 [SMILES: O=C(Nc1ccc(Cl)c(Cl)c1)N1C2CCC1CC(n1c(=O)[nH]c3c(Br)cccc31)C2] |
| 73 | 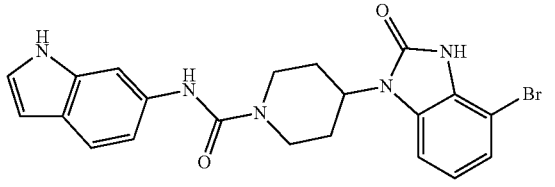 [SMILES: O=C(Nc1ccc2cc[nH]c2c1)N1CCC(n2c(=O)[nH]c3c(Br)cccc32)CC1] |
| 74 | 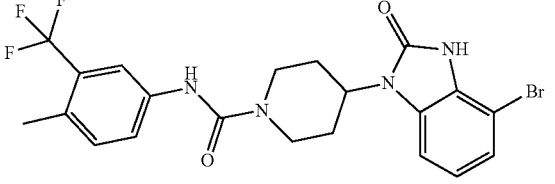 |
| 75 | 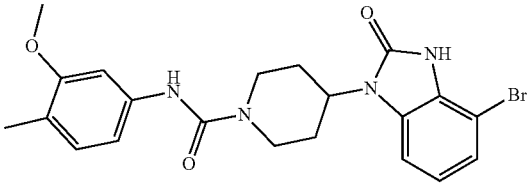 [SMILES: COc1cc(NC(=O)N2CCC(n3c(=O)[nH]c4c(Br)cccc43)CC2)ccc1C] |
| 76 | 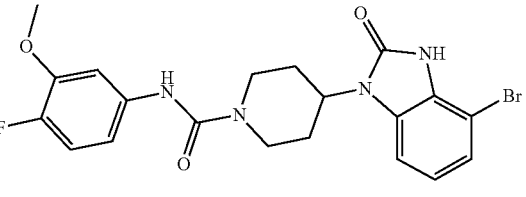 |
| 77 | 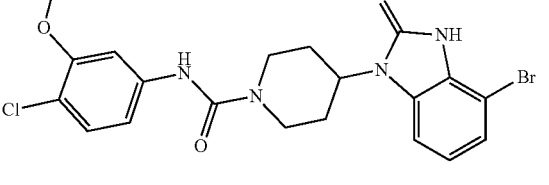 |

TABLE 1-continued
| Example | Structural formula |
|---|---|
| 78 | 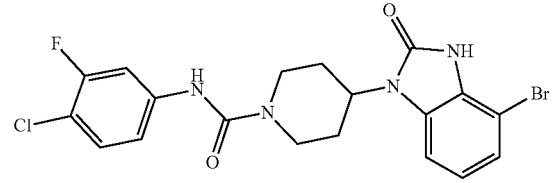 [SMILES: O=C(Nc1ccc(Cl)c(F)c1)N1CCC(n2c(=O)[nH]c3c(Br)cccc32)CC1] |
| 79 | 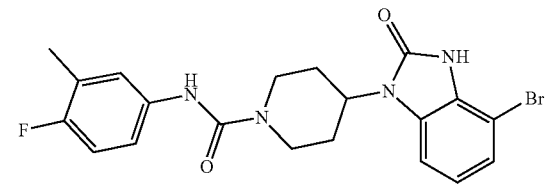 |
| 80 | 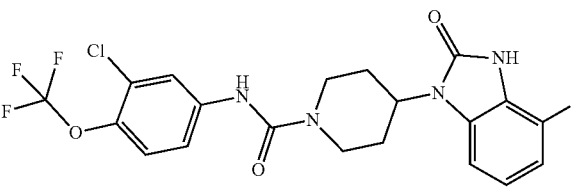 |
| 81 | 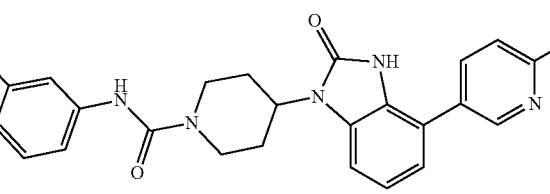 |
| 82 | 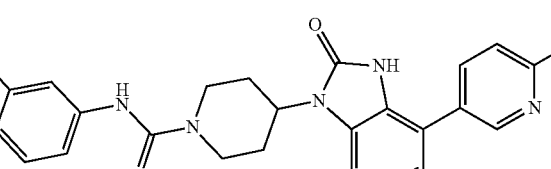 |
| 83 | 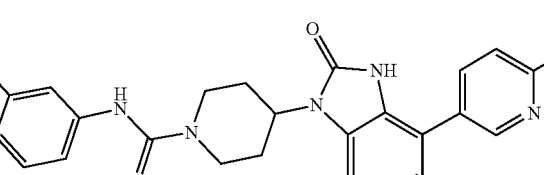 |
| 84 | 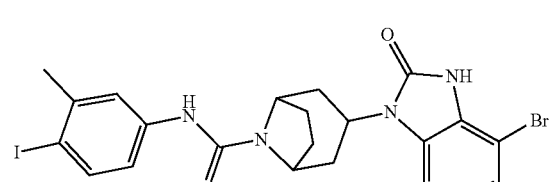 |
| 85 | 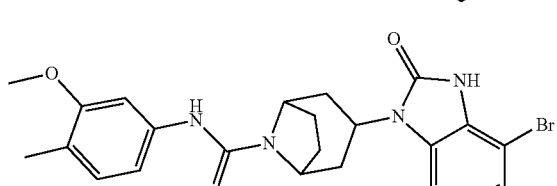 |

TABLE 1-continued

| Example | Structural formula |
|---------|-------------------|
| 86 | |
| 87 | |
| 88 | |
| 89 | |
| 90 | |
| 91 | |
| 92 | |

TABLE 1-continued

| Example | Structural formula |
|---------|-------------------|
| 93 | |
| 94 | |
| 95 | |
| 96 | |
| 97 | |
| 98 | |
| 99 | |

TABLE 1-continued

| Example | Structural formula |
|---|---|
| 100 | |
| 101 | |
| 102 | |
| 103 | |
| 104 | |
| 105 | |
| 106 | |

TABLE 1-continued

| Example | Structural formula |
|---------|--------------------|
| 107 | |
| 108 | |
| 109 | |
| 110 | |
| 111 | |
| 112 | |
| 113 | |
| 114 | |

TABLE 1-continued

| Example | Structural formula |
|---|---|
| 115 | |
| 116 | |
| 117 | |
| 118 | |
| 119 | |
| 120 | |
| 121 | |
| 122 | |

TABLE 1-continued

| Example | Structural formula |
|---|---|
| 123 | |
| 124 | |
| 125 | |
| 126 | |
| 127 | |
| 128 | |
| 129 | |
| 130 | |

TABLE 1-continued

| Example | Structural formula |
|---------|-------------------|
| 131 | |
| 132 | |
| 133 | |
| 134 | |
| 135 | |
| 136 | |
| 137 | |
| 138 | |

TABLE 1-continued

| Example | Structural formula |
|---|---|
| 139 | |
| 140 | |
| 141 | |
| 142 | |
| 143 | |
| 144 | |
| 145 | |
| 146 | |

TABLE 1-continued

| Example | Structural formula |
|---|---|
| 147 | (4-methoxyphenyl)-NHC(O)-cyclohexyl-N(4-Cl-benzimidazol-2(3H)-one) |
| 148 | (1H-indol-6-yl)-NHC(O)-cyclohexyl-N(4-Cl-benzimidazol-2(3H)-one) |
| 149 | (4-methylphenyl)-NHC(O)-cyclohexyl-N(4-Cl-benzimidazol-2(3H)-one) |
| 150 | (4-chlorophenyl)-NHC(O)-cyclohexyl-N(4-Cl-benzimidazol-2(3H)-one) |
| 151 | (methyl 4-methoxy-3-carboxylate-phenyl)-NHC(O)-cyclohexyl-N(4-Br-benzimidazol-2(3H)-one) |
| 152 | (4-chloro-3-methylphenyl)-NHC(O)-cyclohexyl-N(4-Br-benzimidazol-2(3H)-one) |
| 153 | (2-fluoro-4-methylphenyl)-NHC(O)-cyclohexyl-N(4-Br-benzimidazol-2(3H)-one) |
| 154 | (4-methoxy-2,3-difluorophenyl)-NHC(O)-cyclohexyl-N(4-Br-benzimidazol-2(3H)-one) |

TABLE 1-continued

| Example | Structural formula |
|---|---|
| 155 | 3-fluoro-5-methoxyphenyl amide of 4-(4-bromo-2-oxo-2,3-dihydro-1H-benzimidazol-1-yl)cyclohexane-1-carboxamide |
| 156 | 2-fluoro-4-methoxyphenyl amide of 4-(4-bromo-2-oxo-2,3-dihydro-1H-benzimidazol-1-yl)cyclohexane-1-carboxamide |
| 157 | 4-chloro-3-cyanophenyl amide of 4-(4-bromo-2-oxo-2,3-dihydro-1H-benzimidazol-1-yl)cyclohexane-1-carboxamide |
| 158 | 3-methoxy-5-(trifluoromethyl)phenyl amide of 4-(4-bromo-2-oxo-2,3-dihydro-1H-benzimidazol-1-yl)cyclohexane-1-carboxamide |
| 159 | 4-cyano-3-methoxyphenyl amide of 4-(4-bromo-2-oxo-2,3-dihydro-1H-benzimidazol-1-yl)cyclohexane-1-carboxamide |
| 160 | 3,5-difluoro-4-methoxyphenyl amide of 4-(4-bromo-2-oxo-2,3-dihydro-1H-benzimidazol-1-yl)cyclohexane-1-carboxamide |
| 161 | 3-cyano-4-methoxyphenyl amide of 4-(4-bromo-2-oxo-2,3-dihydro-1H-benzimidazol-1-yl)cyclohexane-1-carboxamide |

TABLE 1-continued

| Example | Structural formula |
|---|---|
| 162 | |
| 163 | |
| 164 | |
| 165 | |
| 166 | |
| 167 | |
| 168 | |
| 169 | |

TABLE 1-continued

| Example | Structural formula |
|---|---|
| 170 | |
| 171 | |
| 172 | |
| 173 | |
| 174 | |
| 175 | |
| 176 | |
| 177 | |

TABLE 1-continued
| Example | Structural formula |
|---|---|
| 178 | 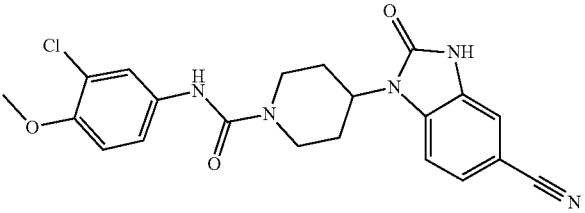 [SMILES: COc1ccc(NC(=O)N2CCC(n3c(=O)[nH]c4cc(C#N)ccc43)CC2)cc1Cl] |
| 179 | 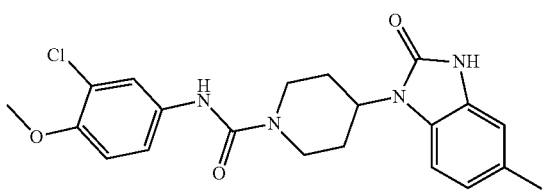 |
| 180 | 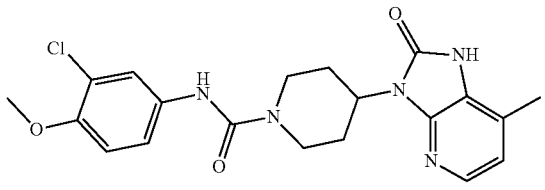 |
| 181 | 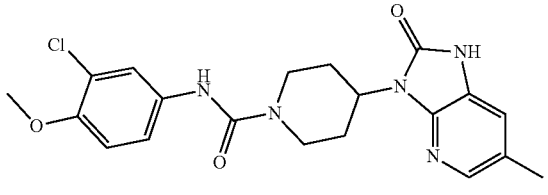 |
| 182 | 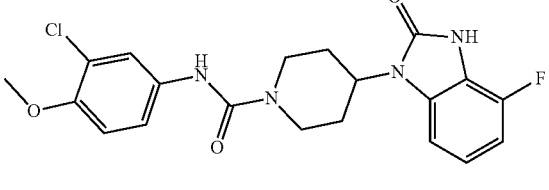 |
| 183 | 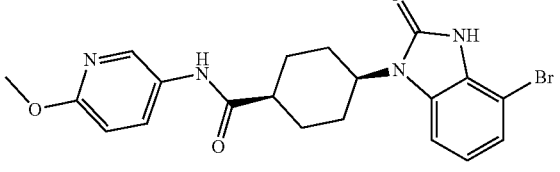 |
| 184 | 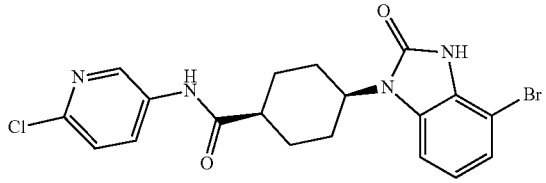 [SMILES: O=c1[nH]c2c(Br)cccc2n1[C@H]1CC[C@@H](C(=O)Nc2ccc(Cl)nc2)CC1] |
| 185 | 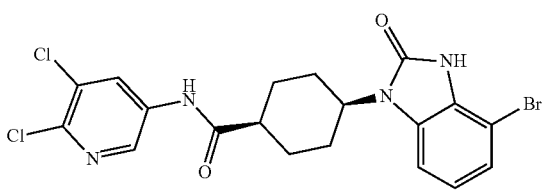 [SMILES: O=c1[nH]c2c(Br)cccc2n1[C@H]1CC[C@@H](C(=O)Nc2cnc(Cl)c(Cl)c2)CC1] |

TABLE 1-continued

| Example | Structural formula |
|---|---|
| 186 | |
| 187 | |
| 188 | |
| 189 | |
| 190 | |
| 191 | |
| 192 | |

TABLE 1-continued

| Example | Structural formula |
|---------|-------------------|
| 193 | |
| 194 | |
| 195 | |
| 196 | |
| 197 | |
| 198 | |
| 199 | |
| 200 | |

TABLE 1-continued

| Example | Structural formula |
|---|---|
| 201 | |
| 202 | |
| 203 | |
| 204 | |
| 205 | |
| 206 | |
| 207 | |
| 208 | |

TABLE 1-continued

| Example | Structural formula |
|---|---|
| 209 | (structure) |
| 210 | (structure) |
| 211 | (structure) |
| 212 | (structure) |
| 213 | (structure) |
| 214 | (structure) |
| 215 | (structure) |
| 216 | (structure) |

TABLE 1-continued

| Example | Structural formula |
|---|---|
| 217 | |
| 218 | |
| 219 | |
| 220 | |
| 221 | |
| 222 | |
| 223 | |

TABLE 1-continued
| Example | Structural formula |
|---|---|
| 224 | 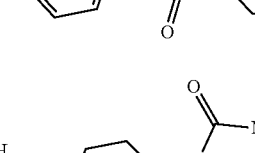 |
| 225 | 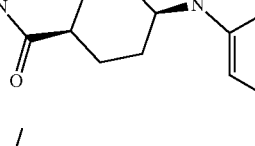 |
| 226 | 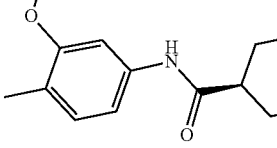 |
| 227 | 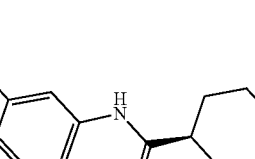 |
| 228 | 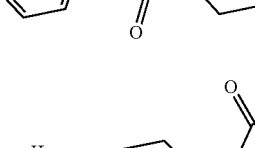 |
| 229 | 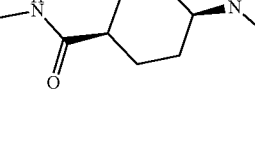 |
| 230 | 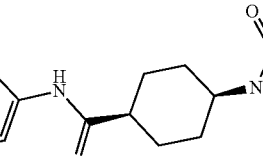 |
| 231 | 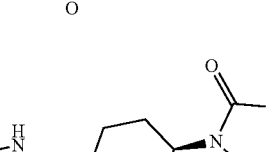 |

TABLE 1-continued
| Example | Structural formula |
|---|---|
| 232 | 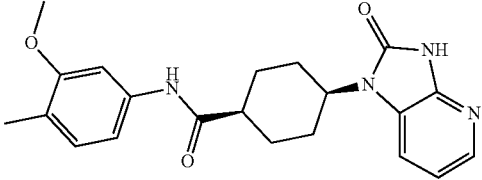 [SMILES: COc1cc(NC(=O)[C@H]2CC[C@@H](n3c(=O)[nH]c4ncccc43)CC2)ccc1C] |
| 233 | 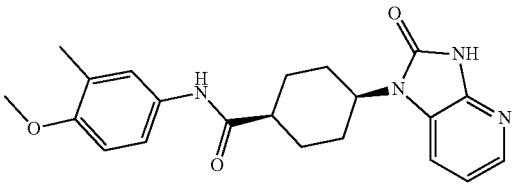 [SMILES: COc1ccc(NC(=O)[C@H]2CC[C@@H](n3c(=O)[nH]c4ncccc43)CC2)cc1C] |
| 234 | 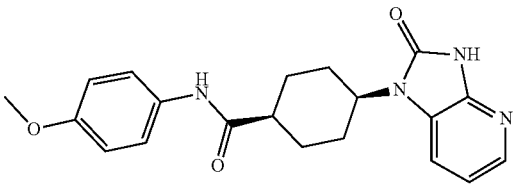 [SMILES: COc1ccc(NC(=O)[C@H]2CC[C@@H](n3c(=O)[nH]c4ncccc43)CC2)cc1] |
| 235 | 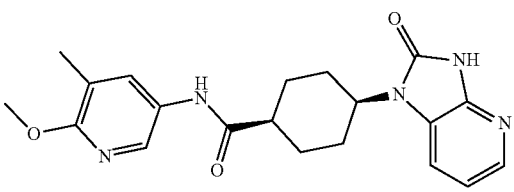 [SMILES: COc1ncc(NC(=O)[C@H]2CC[C@@H](n3c(=O)[nH]c4ncccc43)CC2)cc1C] |
| 236 | 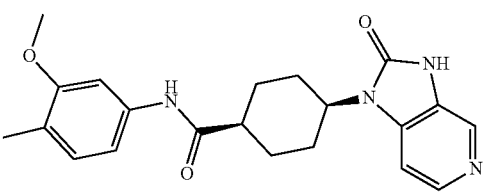 [SMILES: COc1cc(NC(=O)[C@H]2CC[C@@H](n3c(=O)[nH]c4cnccc43)CC2)ccc1C] |
| 237 | 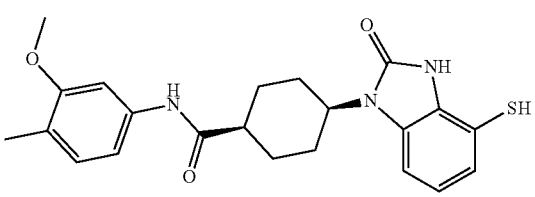 [SMILES: COc1cc(NC(=O)[C@H]2CC[C@@H](n3c(=O)[nH]c4c(S)cccc43)CC2)ccc1C] |
| 238 | 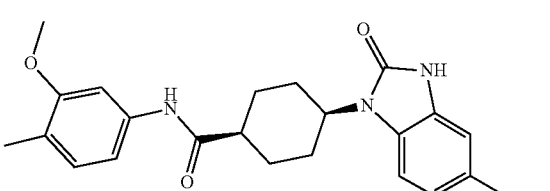 |
| 239 | 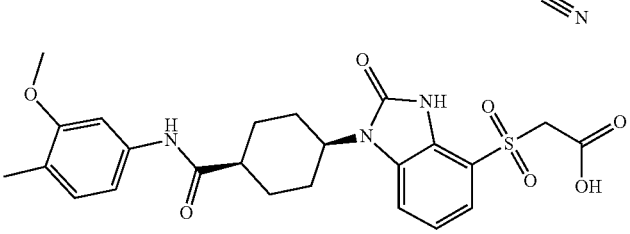 |

TABLE 1-continued
| Example | Structural formula |
|---|---|
| 240 | 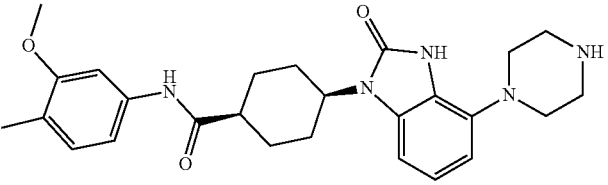 [SMILES: COc1cc(NC(=O)[C@H]2CC[C@@H](n3c(=O)[nH]c4c(N5CCNCC5)cccc43)CC2)ccc1C] |
| 241 | 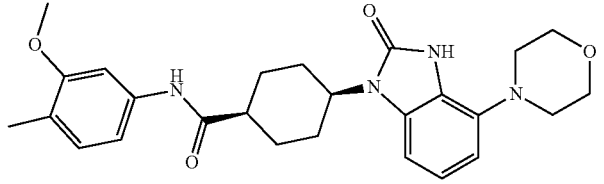 [SMILES: COc1cc(NC(=O)[C@H]2CC[C@@H](n3c(=O)[nH]c4c(N5CCOCC5)cccc43)CC2)ccc1C] |
| 242 | 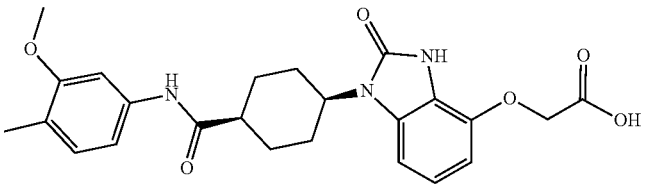 [SMILES: COc1cc(NC(=O)[C@H]2CC[C@@H](n3c(=O)[nH]c4c(OCC(=O)O)cccc43)CC2)ccc1C] |
| 243 | 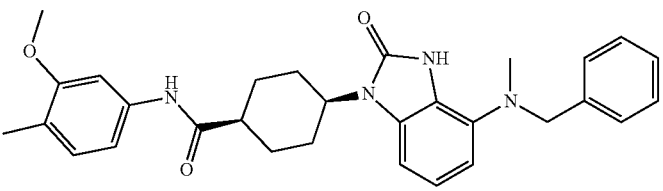 [SMILES: COc1cc(NC(=O)[C@H]2CC[C@@H](n3c(=O)[nH]c4c(N(C)Cc5ccccc5)cccc43)CC2)ccc1C] |
| 244 | 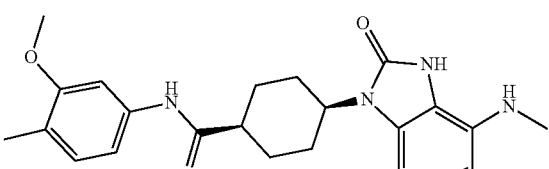 |
| 245 | 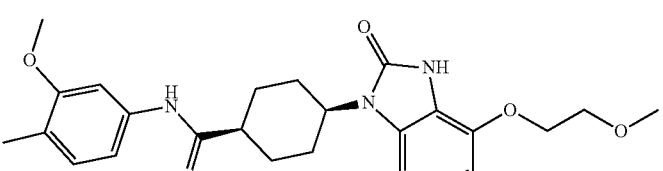 |
| 246 | 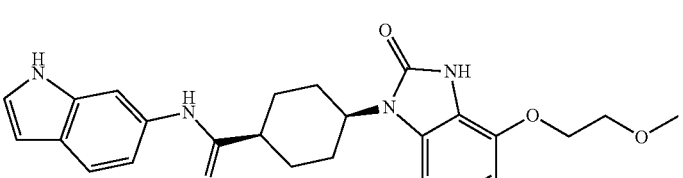 |
| 247 | 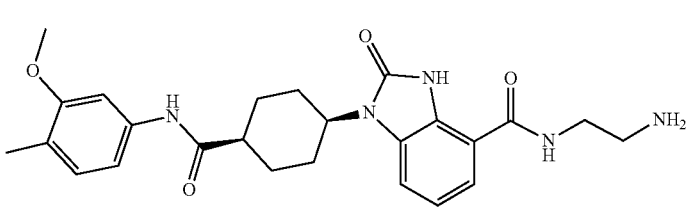 [SMILES: COc1cc(NC(=O)[C@H]2CC[C@@H](n3c(=O)[nH]c4c(C(=O)NCCN)cccc43)CC2)ccc1C] |

TABLE 1-continued

| Example | Structural formula |
|---|---|
| 248 | |
| 249 | |
| 250 | |
| 251 | |
| 252 | |
| 253 | |
| 254 | |

TABLE 1-continued
| Example | Structural formula |
|---|---|
| 255 | 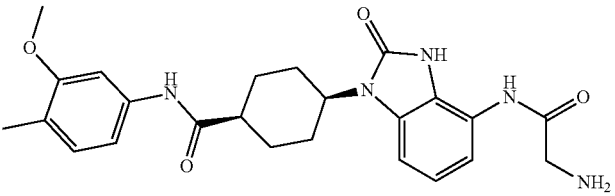 [SMILES: COc1cc(NC(=O)[C@H]2CC[C@@H](n3c(=O)[nH]c4c(NC(=O)CN)cccc43)CC2)ccc1C] |
| 256 | 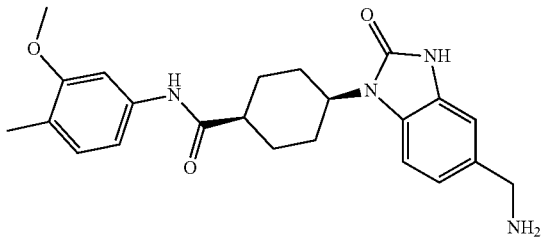 [SMILES: COc1cc(NC(=O)[C@H]2CC[C@@H](n3c(=O)[nH]c4cc(CN)ccc43)CC2)ccc1C] |
| 257 | 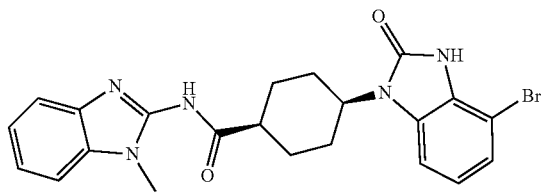 [SMILES: Cn1c(NC(=O)[C@H]2CC[C@@H](n3c(=O)[nH]c4c(Br)cccc43)CC2)nc2ccccc21] |
| 258 | 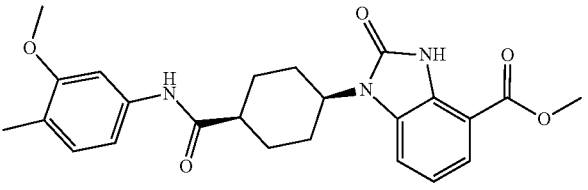 |
| 259 | 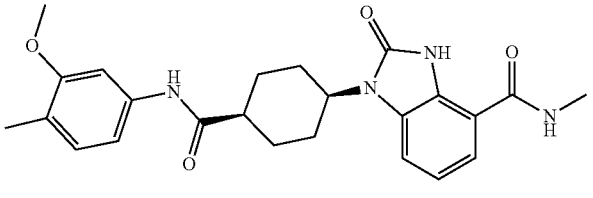 |
| 260 | 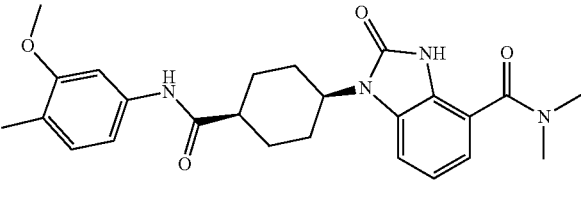 |
| 261 | 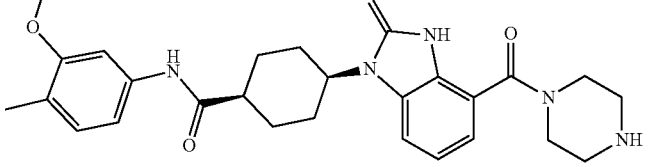 |

TABLE 1-continued

| Example | Structural formula |
|---|---|
| 262 | |
| 263 | |
| 264 | |
| 265 | |
| 266 | |
| 267 | |
| 268 | |

TABLE 1-continued

| Example | Structural formula |
|---------|-------------------|
| 269 | |
| 270 | |
| 271 | |
| 272 | |
| 273 | |
| 274 | |
| 275 | |

TABLE 1-continued

| Example | Structural formula |
|---|---|
| 276 | |
| 277 | |
| 278 | |
| 279 | |
| 280 | |
| 281 | |
| 282 | |

TABLE 1-continued

| Example | Structural formula |
|---|---|
| 283 | |
| 284 | |
| 285 | |
| 286 | |
| 287 | |
| 288 | |
| 289 | |

TABLE 1-continued

| Example | Structural formula |
|---|---|
| 290 | |
| 291 | |
| 292 | |
| 293 | |
| 294 | |
| 295 | |
| 296 | |
| 297 | |

TABLE 1-continued

| Example | Structural formula |
|---|---|
| 298 | |
| 299 | |
| 300 | |
| 301 | |
| 302 | |
| 303 | |
| 304 | |
| 305 | |

TABLE 1-continued

| Example | Structural formula |
|---|---|
| 306 | |
| 307 | |
| 308 | |
| 309 | |
| 310 | |
| 311 | |
| 312 | |
| 313 | |

TABLE 1-continued

| Example | Structural formula |
|---|---|
| 314 | |
| 315 | |
| 316 | |
| 317 | |
| 318 | |
| 319 | |
| 320 | |
| 321 | |

TABLE 1-continued

| Example | Structural formula |
|---|---|
| 322 | 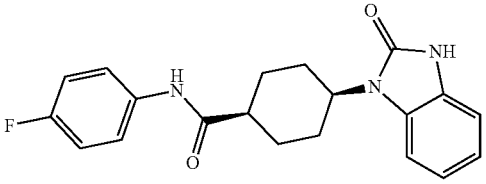 [SMILES: O=c1[nH]c2ccccc2n1[C@H]1CC[C@@H](C(=O)Nc2ccc(F)cc2)CC1] |
| 323 | 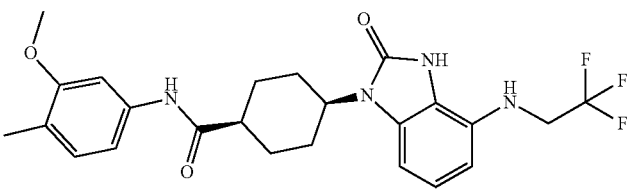 [SMILES: COc1cc(NC(=O)[C@H]2CC[C@@H](n3c(=O)[nH]c4c(NCC(F)(F)F)cccc43)CC2)ccc1C] |
| 324 | 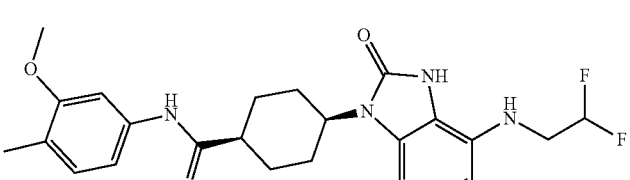 |
| 325 | 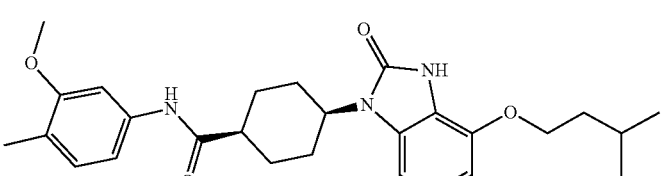 |
| 326 | 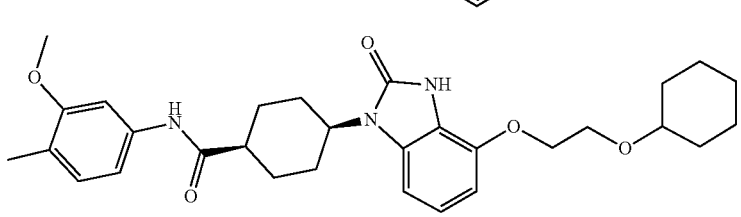 |

Biological Examples

The biological activity of example compounds as described herein above was assessed using the following biological assays.

Biological Example 1: OGG1 Inhibition

Method 1: In Vitro OGG1 Activity Assay

OGG1 activity is assayed by measuring the increase in fluorescence from a duplex oligonucleotide containing an OGG1 substrate and a fluorophore in close proximity that are quenched by a quencher on the complementary strand. One single-stranded DNA oligonucleotide with the sequence 5'-FAM-TCTG CCA 8CA CTG CGT CGA CCT G-3' (SEQ ID NO 1) is annealed to a 25% surplus of 5'-CAG GTC GAC GCA GTG CTG GCA GT-Dab-3' (SEQ ID NO 2), where "8" signifies 8-oxo-2'deoxyadenosine and "FAM" and "Dab" signify fluorescein and dabcyl, respectively. OGG1 activity releases the substrate base from DNA by cleaving the N-glycosidic bond between base and deoxyribose. The resulting apurinic site is cleaved by an excessive amount APEX1 activity which cause the duplex to melt, which in turn cause the fluorophore to become unquenched. Compounds to be tested are dissolved in DMSO and nano-dispensed directly into black 384-well plates, followed by transfer of enzyme and substrate solutions. Enzyme and DNA substrate solutions are added so that the assay mixture contains final concentrations of 25 mM Tris-HCl pH 8.0, 15 mM NaCl, 2 mM $MgCl_2$, 0.5 mM DTT and 0.0025% Tween-20, 800 µM OGG1 enzyme, 2 nM human APEX1 and 10 nM 8-oxoA:C substrate. The fluorescent signal is recorded in a plate reader equipped with suitable filters to register fluorescein fluorescence. The IC50 value is determined by fitting a dose response curve to the data points using nonlinear regression analysis and the equation Y=Bottom+(Top−Bottom)/(1+10^((Log IC50−X)*Hill-Slope)), where Y is the fluorescein signal read at 530 nm and X is log [compound]. Results obtained for the example compounds described herein are provided in Table 2.

TABLE 2

| Example | IC50 (nM) |
|---|---|
| 1 | 2796 |
| 2 | 1691 |
| 3 | 1293 |
| 4 | 660 |

TABLE 2-continued

| Example | IC50 (nM) |
|---|---|
| 5 | 1458 |
| 6 | 540 |
| 7 | 1084 |
| 8 | 1547 |
| 9 | 796 |
| 10 | 3956 |
| 11 | 1775 |
| 12 | 2354 |
| 13 | 359 |
| 14 | 6157 |
| 15 | 1912 |
| 16 | 3876 |
| 17 | 1423 |
| 18 | 1390 |
| 19 | 1870 |
| 20 | 1310 |
| 21 | 3070 |
| 22 | 848 |
| 23 | 728 |
| 24 | 1040 |
| 25 | 765 |
| 26 | 1020 |
| 27 | 488 |
| 28 | 766 |
| 29 | 2060 |
| 30 | 1710 |
| 31 | 1090 |
| 32 | 1190 |
| 33 | 2530 |
| 34 | 502 |
| 35 | 1970 |
| 36 | 3650 |
| 37 | 1590 |
| 38 | 1210 |
| 39 | 788 |
| 40 | 6320 |
| 41 | 1730 |
| 42 | 2410 |
| 43 | 2460 |
| 44 | 3140 |
| 45 | 5030 |
| 46 | 603 |
| 47 | 3800 |
| 48 | 551 |
| 49 | 379 |
| 50 | 149 |
| 51 | 2830 |
| 52 | 1340 |
| 53 | 2050 |
| 54 | 3120 |
| 55 | 4560 |
| 56 | 2120 |
| 57 | 3130 |
| 58 | 3870 |
| 59 | 3290 |
| 60 | 506 |
| 61 | 1865 |
| 62 | 1730 |
| 63 | 1860 |
| 64 | 2350 |
| 65 | 892 |
| 66 | 4510 |
| 67 | 4610 |
| 68 | 1210 |
| 69 | 3880 |
| 70 | 1330 |
| 71 | 9060 |
| 72 | 67 |
| 73 | 4360 |
| 74 | 803 |
| 75 | 223 |
| 76 | 5380 |
| 77 | 358 |
| 78 | 840 |
| 79 | 1900 |
| 80 | 4320 |
| 81 | 408 |
| 82 | 1000 |

TABLE 2-continued

| Example | IC50 (nM) |
|---|---|
| 83 | 958 |
| 84 | 30 |
| 85 | 33 |
| 86 | 59 |
| 87 | 471 |
| 88 | 1760 |
| 89 | 90 |
| 90 | 218 |
| 91 | 58 |
| 92 | 84 |
| 93 | 91 |
| 94 | 105 |
| 95 | 1808 |
| 96 | 1874 |
| 97 | 1725 |
| 98 | 2621 |
| 99 | 1165 |
| 100 | 1187 |
| 101 | 2264 |
| 102 | 2767 |
| 103 | 1455 |
| 104 | 2281 |
| 105 | 2940 |
| 106 | 1753 |
| 107 | 23 |
| 108 | 2531 |
| 109 | 6460 |
| 110 | 4360 |
| 111 | 5810 |
| 112 | 4940 |
| 113 | 3200 |
| 114 | 690 |
| 115 | 1430 |
| 116 | 2060 |
| 117 | 1360 |
| 118 | 234 |
| 119 | 72 |
| 120 | 1910 |
| 121 | 186 |
| 122 | 71 |
| 123 | 26 |
| 124 | 65 |
| 125 | 3620 |
| 126 | 12 |
| 127 | 1220 |
| 128 | 1310 |
| 129 | 116 |
| 130 | 551 |
| 131 | 676 |
| 132 | 6830 |
| 133 | 865 |
| 134 | 2740 |
| 135 | 94 |
| 136 | 501 |
| 137 | 2030 |
| 138 | 2010 |
| 139 | 58 |
| 140 | 25 |
| 141 | 5480 |
| 142 | 497 |
| 143 | 1200 |
| 144 | 983 |
| 145 | 1080 |
| 146 | 27 |
| 147 | 36 |
| 148 | 98 |
| 149 | 86 |
| 150 | 106 |
| 151 | 526 |
| 152 | 74 |
| 153 | 383 |
| 154 | 383 |
| 155 | 1820 |
| 156 | 173 |
| 157 | 152 |
| 158 | 6050 |
| 159 | 4940 |
| 160 | 81 |

TABLE 2-continued

| Example | IC50 (nM) |
|---|---|
| 161 | 175 |
| 162 | 1290 |
| 163 | 3160 |
| 164 | 43 |
| 165 | 1390 |
| 166 | 41 |
| 167 | 3890 |
| 168 | 44 |
| 169 | 9090 |
| 170 | 8800 |
| 171 | 211 |
| 172 | 7790 |
| 173 | 2420 |
| 174 | 2540 |
| 175 | 2620 |
| 176 | 1080 |
| 177 | 5020 |
| 178 | 6920 |
| 179 | 1570 |
| 180 | 8890 |
| 181 | 7090 |
| 182 | 4790 |
| 183 | 174 |
| 184 | 325 |
| 185 | 1390 |
| 186 | 2030 |
| 187 | 338 |
| 188 | 4630 |
| 189 | 1760 |
| 190 | 467 |
| 191 | 55.7 |
| 192 | 34.2 |
| 193 | 1380 |
| 194 | 17.2 |
| 195 | 3560 |
| 196 | 647 |
| 197 | 38.9 |
| 198 | 5370 |
| 199 | 494 |
| 200 | 631 |
| 201 | 35.1 |
| 202 | 52.8 |
| 203 | 6270 |
| 204 | 65.6 |
| 205 | 74.5 |
| 206 | 15.4 |
| 207 | 73.6 |
| 208 | 115 |
| 209 | 402 |
| 210 | 9490 |
| 211 | 153 |
| 212 | 9.43 |
| 213 | 155 |
| 214 | 556 |
| 215 | 580 |
| 216 | 8130 |
| 217 | 586 |
| 218 | 9010 |
| 219 | 2440 |
| 220 | 8630 |
| 221 | 27.2 |
| 222 | 350 |
| 223 | 1670 |
| 224 | 3660 |
| 225 | 33.5 |
| 226 | 77.9 |
| 227 | 17.9 |
| 228 | 0.15 |
| 229 | 29.8 |
| 230 | 606 |
| 231 | 8050 |
| 232 | 109 |
| 233 | 47.6 |
| 234 | 572 |
| 235 | 1450 |
| 236 | 196 |
| 237 | 67.1 |
| 238 | 40.9 |
| 239 | 50.6 |
| 240 | 15.3 |
| 241 | 960 |
| 242 | 126 |
| 243 | 1470 |
| 244 | 60.7 |
| 245 | 2760 |
| 246 | 3630 |
| 247 | 0.62 |
| 248 | 6.77 |
| 249 | 21.9 |
| 250 | 23.5 |
| 251 | 4.25 |
| 252 | 3.94 |
| 253 | 6.79 |
| 254 | 0.21 |
| 255 | 30.9 |
| 256 | 2690 |
| 257 | 26.9 |
| 258 | 5.83 |
| 259 | 3.94 |
| 260 | 343 |
| 261 | 68.3 |
| 262 | 348 |
| 263 | 2.71 |
| 264 | 5.77 |
| 265 | 0.28 |
| 266 | 8.16 |
| 267 | 82.4 |
| 268 | 152.73 |
| 269 | 139.97 |
| 270 | 0.39 |
| 271 | 56 |
| 272 | 4.11 |
| 273 | 17.51 |
| 274 | 92.14 |
| 275 | 170.85 |
| 276 | 2.9 |
| 277 | 48.24 |
| 278 | 221.41 |
| 279 | 74.5 |
| 280 | 27.5 |
| 281 | 149 |
| 282 | 10.1 |
| 283 | 14 |
| 284 | 1.73 |
| 285 | 45.1 |
| 286 | 18.1 |
| 287 | 27.1 |
| 288 | 23 |
| 289 | 51.7 |
| 290 | 239 |
| 291 | 9.53 |
| 292 | 0.37 |
| 293 | 1.42 |
| 294 | 1.21 |
| 295 | 9.62 |
| 296 | 28.6 |
| 297 | 8.07 |
| 298 | 12.02 |
| 299 | 27.2 |
| 300 | 9.9 |
| 301 | 6.91 |
| 302 | 16.4 |
| 303 | 10.6 |
| 304 | 3.8 |
| 305 | 251 |
| 306 | 2.82 |
| 307 | 12.5 |
| 308 | 157 |
| 309 | 3.26 |
| 310 | 51.6 |
| 311 | 4.49 |
| 312 | 2.94 |
| 313 | 21.3 |
| 314 | 56.33 |
| 315 | 759 |
| 316 | 38 |

TABLE 2-continued

| Example | IC50 (nM) |
|---------|-----------|
| 317 | 39.1 |
| 318 | 79.5 |
| 319 | 20.3 |
| 320 | 21.97 |
| 321 | 5.75 |
| 322 | 2627 |
| 323 | 226.4 |
| 324 | 96.9 |
| 325 | 314 |
| 326 | 118 |

Biological Example 2: Cell Viability, Proliferation and Survival Assays

Method 2: Generation of OGG1 Knockdown Cell Line

The H460 and A3 cancer cell lines were stably transfected with a containing non-targeting shRNA hairpins or shRNA hairpins targeting OGG1. The following sequences were used to insert the hairpins into the BshTI and EcoRI site of the pRSITEP-U6Tet-(sh)-EF1-TetRep-P2A-Puro-P2A-RFP670 plasmid:

Non-targeting-f:
(SEQ ID NO 3)
CCG GCC TAA GGT TAA GTC GCC CTC GCT CGA GCG AGG
GCG ACT AAC CCT TAA GGT TTT TG, Non-targeting-r:
(SEQ ID NO 4)
AAT TCA AAA ACC TAA GGT TAA GTC GCC CTC GCT CGA
GCG AGG GCG ACT AAC CCT TAG G, shOGG1#1-f:
(SEQ ID NO 5)
CCG GTG GAG TGG TGT ACT AGC GGA TCT CGA GAT CCG
CTA GTA CAC CAC TCC ATT TT TG, shOGG1#1-r:
(SEQ ID NO 6)
AAT TCA AAA ATG GAG TGG TGT ACT AGC GGA TCT CGA
GAT CCG CTA GTA CAC CAC TCC A, shOGG1#2-f:
(SEQ ID NO 7)
CCG GGT GTG CGA CTG CTG CGA CAA GCT CGA GCT TGT
CGC AGC AGT CGC ACA CTT TTT G, shOGG1#2-r:
(SEQ ID NO 8)
AAT TCA AAA AGT GTG CGA CTG CTG CGA CAA GCT CGA
GCT TGT CGC AGC AGT CGC ACA C, shOGG1#3-f:
(SEQ ID NO 9)
CCG GTG TGC CCG TGG ATG TCC ATA TCT CGA GAT ATG
GAC ATC CAC GGG CAC ATT TTT G, shOGG1#3-r:
(SEQ ID NO 10)
AAT TCA AAA ATG TGC CCG TGG ATG TCC ATA TCT CGA
GAT ATG GAC ATC CAC GGG CAC A.

The plasmids were packaged in lentiviral particles and transduced into A3 cells and selected with 1 μg/ml puromycin for 6 days, followed by fluorescence activated cell sorting of the top 15% of the RFP670-positive cell population.

The following sequence was inserted into the SalI and NotI cloning sites of pENTR1A plasmid and shuttled into pLenti PGK Hygro DEST (w530-1) expression vector.

```
                                                      (SEQ ID NO 11)
  1 ATGCCCGCAA GAGCTCTCTT GCCAAGGCGA ATGGGTCATC GAACACTTGC

51 AAGTACCCCG GCCCTGTGGG CATCTATACC TTGCCCACGG TCCGAACTGC

101 GACTGGACCT TGTGTTGCCC AGCGGCCAGA GCTTTAGATG GCGGGAACAA

151 AGCCCCGCAC ATTGGTCAGG AGTCTTGGCA GACCAGGTAT GGACTCTCAC

201 GCAAACTGAG GAGCAGCTCC ATTGCACCGT GTATAGAGGA GATAAGAGTC

251 AAGCCAGCAG GCCCACGCCT GACGAATTGG AAGCAGTCAG AAAATATTTT

301 CAATTGGATG TCACATTGGC GCAGCTTTAC CATCATTGGG GCTCAGTAGA

351 CAGTCATTTT CAGGAAGTAG CACAAAAGTT TCAGGGCGTC AGGTTGTTGA

401 GGCAGGACCC TATTGAGTGC CTGTTCTCAT TCATTTGTAG TTCAAACAAT

451 AATATCGCTA GGATCACTGG AATGGTTGAA AGACTGTGTC AGGCGTTTGG

501 CCCGCGACTT ATTCAATTGG ACGACGTTAC GTATCATGGC TTTCCCTCAC

551 TCCAAGCATT GGCAGGTCCT GAGGTAGAAG CACACCTGCG GAAGCTGGGC

601 TTGGGCTATA GAGCCCGCTA TGTGAGTGCT TCAGCACGCG CAATCCTGGA

651 GGAGCAAGGA GGTCTCGCGT GGCTCCAACA GCTTCGAGAG AGCTCTTATG

701 AAGAAGCACA CAAAGCTCTT TGTATTTTGC CAGGGGTAGG AACCAAGGTC

751 GCGGACTGTA TATGCCTGAT GGCTTTGGAT AAACCACAGG CGGTGCCCGT
```

```
 801 TGACGTACAC ATGTGGCACA TAGCTCAGCG CGACTATTCA TGGCATCCAA

851 CAACAAGTCA AGCAAAAGGG CCAAGTCCGC AAACCAACAA GGAATTGGGA

901 AATTTCTTCC GCTCACTGTG GGGTCCCTAC GCTGGTTGGG CGCAGGCAGG

951 CCTCCTTGGC AATGCATTTG ATGGCCACCA GCTTCTGCGT CCTCTTATCT

1001 TCTGCCAGGA TCACCTCCGA GAAGGCCCCC CTATCGGGAG AGGGGATTCA

1051 CAAGGTGAAG AACTGGAACC CCAGCTTCCC TCCAGCCTCT CCTCCATTCC

1101 CTATGGGTTC TGTGACCACT GCTGGACCAA GGACGTGGAT GACCCTCCCC

1151 TAGTCACTCA TCCATCCCCT GGCTCCAGAG ATGGTCACAT GACCCAGGCC

1201 TGGCCAGTCA AAGTAGTCTC TCCCCTGGCC ACAGTAATTG GTCATGTGAT

1251 GCAAGCCAGC TTACTAGCAC TTGCGGCCGC ACTCGAGATG GACTACAAAG

1301 ACCATGACGG TGATTATAAA GATCATGACA TCGATTACAA GGATGACGAT

1351 GACAAGTAG.
```

The sequence codes for mitochondrial isoform of OGG1 with silent mutations to render it insensitive to all RNAi sequences mentioned above and a c-terminal FLAG-tag. The plasmid was then packaged into lentiviruses and transduced into A3 cells harbouring shRNA constructs as described above and selected with 300 µg/ml hygromycin for 10 days.

Method 3: 96-Well Cell Viability Assay

A dilution series of compound or vehicle are transferred to 96-well plates. Cells are seeded into the plate (500-10,000 cells/well) in suitable media and incubated for five days in 5% $CO_2$ at 37° C. Thereafter, resazurin (diluted in suitable medium or PBS) are added to a final concentration 10 µg/ml resazurin at 37° C. for 2-4 hours before measuring the fluorescence (Ex544/Em590), essentially as described (Riss, Terry L. et al., "Cell Viability Assays." In *Assay Guidance Manual*, ed. G. Sitta Sittampalam, et al. Bethesda (MD): Eli Lilly & Company and the National Center for Advancing Translational Sciences (2004) http://www.ncbi.nlm.nih.gov/books/NBK144065/).

Method 4: 384-Well Cell Viability Assay

The compounds to be tested are nano-dispensed in duplicate in 11 concentrations, directly in 384-well cell plates, with a final DMSO concentration <1%. Cells are seeded in cell plates, pre-dispensed with compounds (200-2500 cells/well in 50 µl). After three or five days culture in 5% CO2, 37° C., resazurin diluted in PBS is added, 10 µl/well, to a final concentration of 10 µg/ml and cells are incubated 2-4 hours before measuring fluorescence (Ex544/Em590), as described (ibid.). Results obtained for selected example compounds described herein on cancer- and non-transformed cell lines are provided in the table below (Table 3) and summarized in FIG. 1. Where indicated, combination indexes was measured with CompuSyn software (www.compusyn.com) by the method of Chou-Talalay (Chou, Ting-Chao., Cancer Research, 70(2), 440-46 (2010)). Table 3 shows the viability $EC_{50}$ values (in M) of selected example compounds on various cancer- and non-transformed cell line viability using methods 2 or 3.

TABLE 3

| Cell line | Type | Cancer/cell type | $EC_{50}$ (M) Ex. 13 | Ex. 28 | Ex. 50 |
|---|---|---|---|---|---|
| 786-0 | Cancer | Renal Cell Adenocarcinoma | 3.0E−05 | 1.5E−05 | 3.3E−05 |
| A3 | Cancer | Acute lymphoblastic leukemia | 1.1E−05 | 7.9E−06 | 9.8E−06 |
| A498 | Cancer | Renal carcinoma | 2.9E−05 | 2.1E−05 | 3.5E−05 |
| A549 | Cancer | Lung carcinoma | 1.2E−05 | 1.1E−05 | 8.5E−06 |
| ACHN | Cancer | Renal Cell Adenocarcinoma | 2.3E−06 | 8.5E−06 | 2.8E−06 |
| BJ Ras | Cancer | Transformed fibroblast | 4.8E−06 | 1.5E−05 | 1.4E−05 |
| BJ Tert | Normal | immortalized fibroblast | 3.4E−05 | 2.4E−05 | 3.1E−05 |
| CCD841 | Normal | fetal epithelial colon | 4.3E−05 | 4.0E−05 | 5.4E−05 |
| CCRF-CEM | Cancer | Acute Lymphoblastic Leukemia | 1.5E−05 | 1.1E−05 | 7.9E−06 |
| Daudi | Cancer | Burkitt's Lymphoma | 1.3E−05 | 1.0E−05 | 1.2E−05 |
| DU145 | Cancer | Prostate carcinoma | 1.3E−05 | 1.1E−05 | 3.1E−06 |
| H460 | Cancer | large cell lung carcinoma | 1.0E−05 | 1.4E−05 | 1.7E−05 |
| HCT116 | Cancer | Colorectal Carcinoma | 1.8E−05 | 1.5E−05 | 2.9E−05 |
| HCT116 + Chr3 | Cancer | Colorectal Carcinoma | 2.1E−05 | 1.7E−05 | 2.0E−05 |
| Hec59 | Cancer | endometrioid adenocarcinoma | 1.7E−05 | 1.1E−05 | ND |
| Hec59 + Chr2 | Cancer | endometrioid adenocarcinoma | 1.6E−05 | 1.7E−05 | ND |
| HeLa | Cancer | Cervical adenocarcinoma | 2.2E−05 | 1.6E−05 | 3.5E−05 |
| HL-60 | Cancer | Acute Promyelocytic Leukemia | 2.2E−05 | 1.4E−05 | 2.4E−05 |
| HT-29 | Cancer | Colorectal Adenocarcinoma | 2.4E−05 | 2.3E−05 | 2.2E−05 |
| Jurkat | Cancer | Acute lymphoblastic leukemia | 1.3E−05 | 1.4E−05 | 1.5E−05 |
| K562 | Cancer | Chronic Myelogenous Leukemia | 2.0E−05 | 2.1E−05 | ND |
| KG1a | Cancer | Acute Myelogenous Leukemia | 1.6E−05 | 1.8E−05 | 1.9E−05 |

TABLE 3-continued

| Cell line | Type | Cancer/cell type | $EC_{50}$ (M) Ex. 13 | Ex. 28 | Ex. 50 |
|---|---|---|---|---|---|
| LCL#1 | Normal | Epstein-Barr-virus-transformed lymphoblastoid cell lines | 3.3E−05 | 3.4E−05 | 4.0E−05 |
| LCL#2 | Normal | Epstein-Barr-virus-transformed lymphoblastoid cell lines | 2.5E−05 | 4.1E−05 | 3.2E−05 |
| M059J | Cancer | Malignant Glioblastoma | 2.6E−05 | 2.1E−05 | 2.9E−05 |
| M059K | Cancer | Malignant Glioblastoma | 2.0E−05 | 1.9E−05 | 2.7E−05 |
| MEF Ogg1 (−/−) | Normal | mouse embryonic fibroblast | 4.8E−05 | 4.6E−05 | 3.4E−05 |
| MOLT4 | Cancer | Acute Lymphoblastic Leukemia | 1.5E−05 | 1.3E−05 | 1.7E−05 |
| MRC5 | Normal | fetal lung fibroblast | 7.5E−05 | 2.1E−05 | 4.7E−05 |
| MV4-11 | Cancer | acute monocytic leukemia | 9.4E−06 | 6.5E−06 | 9.6E−06 |
| NB-4 | Cancer | acute promyelocytic leukemia | 5.0E−06 | 1.1E−05 | ND |
| PC3 | Cancer | Prostate adenocarcinoma | 3.5E−05 | 1.9E−05 | 2.9E−05 |
| PL-21 | Cancer | acute myeloid leukemia | 1.5E−05 | 1.0E−05 | 1.8E−05 |
| Raji | Cancer | Burkitt's Lymphoma | 2.5E−05 | 2.0E−05 | 2.3E−05 |
| Rec1 | Cancer | Mantle Cell Lymphoma | 1.4E−05 | 1.3E−05 | 1.5E−05 |
| Reh | Cancer | Acute Lymphocytic Leukemia | 1.9E−05 | 1.5E−05 | 1.7E−05 |
| RFX393 | Cancer | Renal cancer cell lines | 2.0E−05 | 1.4E−05 | 1.2E−05 |
| SaOS2 | Cancer | Osteosarcoma | 2.1E−05 | 1.6E−05 | 2.0E−05 |
| SW1271 | Cancer | Small Cell Lung Carcinoma | 2.2E−05 | 2.5E−05 | ND |
| SW480 | Cancer | Colorectal Adenocarcinoma | 3.3E−05 | 2.0E−05 | 3.0E−05 |
| T98G | Cancer | Glioblastoma Multiforme | 1.4E−05 | 1.9E−05 | 1.7E−05 |
| THP1 | Cancer | Acute Monocytic Leukemia | 2.3E−05 | 1.9E−05 | ND |
| U2OS | Cancer | Osteosarcoma | 2.0E−05 | 1.6E−05 | 2.5E−05 |
| UO31 | Cancer | Renal carcinoma | 2.9E−06 | 7.1E−06 | 3.2E−06 |
| VH10 | Normal | fibroblast | 3.2E−05 | 2.1E−05 | 4.8E−05 |

Method 5: Suspension Cell Proliferation Assay

Cell proliferation is measured by seeding cells growing in suspension at a density of 200,000 cells/ml in suitable medium. The cells are incubated at 5% $CO_2$, 37° C. with 200 ng/ml doxycycline, 10 µM example compound or vehicle. Dead cells are stained with trypan blue, while viable cells are counted daily or at other fixed intervals. When cell populations exceed 1,000,000 cells/ml they are re-seeded into fresh medium containing fresh doxycycline, example compound or vehicle at 200,000 cells/ml. Results obtained for selected example compounds described herein on the A3 cancer cell line are shown in the FIGS. 4A and 4B.

Method 6: Colony Formation Survival Assay

Example compounds or vehicle are transferred to 6-well plates. Cell lines to be tested are seeded at a density of 200-500 cells/well in suitable media and allowed to grow for 7-11 days in at 5% $CO_2$, 37° C. The medium is removed and replaced with 4% w/v methylene blue in methanol. Following extensive washes in tap water and air drying, colonies with more than 50 colonies are counted, as described in Franken, Nicolaas A. P., et al., *Nature Protocols*, 1(5), 2315-19 (2006). Results obtained for selected example compounds described herein on the normal and cancer cell lines are shown in the FIGS. 5A and 5B.

Biological Example 3: OGG1 Inhibitor Reduce Inflammation

Method 7: OGG1 Inhibitors Preclude Pro-Inflammatory Gene Regulation

MLE-12 cells are maintained in suitable medium and treated with vehicle or 5 µM experimental compound for 48h before stimulation with 20 ng/ml TNFα for 30 minutes. RNA is extracted and reverse-transcribed, followed by quantitative PCR evaluation of a panel of pro-inflammatory regulators (SABiosciences) essentially as described in Ba, Xueqing, et al., The Journal of Immunology, 192(5), 2384-94 (2014). Results obtained a selected example compound described herein on the pro-inflammatory gene regulation are shown in FIG. 6.

Method 8: Evaluation of In Vivo Efficiency

Six- to 8-wk-old BALB/c mice (~20 g; Harlan Sprague Dawley, San Diego, CA) were injected 25 mg/kg intraperitoneally 3h before and at the time of intranasal TNF-α challenge essentially as described in Ba, Xueqing, et al., The Journal of Immunology, 192(5), 2384-94 (2014). To evaluate inflammation, bronchoalveolar lavage fluids (BALF) were collected 16 h after challenge, processed, cytospin slides were stained with Wright-Giemsa, and the number of neutrophils was counted. All experiments were performed according to the National Institutes of Health Guidelines for the Care and Use of Laboratory Animals. Results obtained a selected example compound described herein on the pro-inflammatory gene regulation are shown in FIGS. 7A and 7B.

Biological Example 4: Mouse CCL2 Assay in MLE12 Cells

Assay Principle:

Cisbio mouse CCL2 assay is intended for the quantitative measurement of CCL2 in supernatant using HTRF® technology. The assay is compatible with mouse samples, and is highly specific for CCL2. CCL2 is detected in a sandwich assay format using 2 different specific antibodies, one labeled with Cryptate (donor) and the second with d2 (acceptor). The detection principle is based on HTRF® technology. When the labelled antibodies bind to the same antigen, the excitation of the donor with a light source (laser or flash lamp) triggers a Fluorescence Resonance Energy Transfer (FRET) towards the acceptor, which in turn fluoresces at a specific wavelength (665 nm). The two antibodies bind to the CCL2 present in the sample, thereby generating FRET. Signal intensity is proportional to the number of antigen-antibody complexes formed and therefore to the CCL2 concentration.

Materials:
 Cells: MLE12 (Mouse Lung Epithelial cells, SV40 transformed)
 Medium: DMEM/F12 (Gibco #11330057), FBS 5% (Gibco #10500064), Pen/Strep 50U/50 µg/ml (Gibco #15070063)
 Cell plates: 384-well, black/clear, TC-treated (Corning #3764)
 Source plate: Labcyte LDV 384 (Labcyte #LP-0200)
 Compound dilution plate: V-bottom 384-well PP plate (Greiner #781280)
 Compounds: 10 mM stocks in DMSO HTRF plates: 384-well, white, half area, non-binding (Costar #3824) Mouse CCL2 kit: Cisbio 62MCCL2PEH Other reagents: Trypsin/EDTA 10× (Gibco #15400054), PBS (Gibco #14190169), Resazurin (Sigma-Aldrich #199303), 1 mg/ml in PBS, TNF-α 200 µg/ml in PBS (Peprotech #300-01A)

Instruments:
  Echo liquid handler (Labcyte)
  Multidrop Combi (Thermo Scientific)
  Sense plate reader (Hidex)

Compound Handling:

Stock solutions (10 mM in DMSO) of compounds were dispensed in V-bottom 384-well plates and the following dilutions were prepared: 10 mM and 0.05 mM. The dilutions were transferred to the source plate. Duplicate 6 points dose-response curves of compounds were nano-dispensed in cell plates (CCL2 assay) and in parallel, 11 points DR curves in duplicates were nano-dispensed for the viability assay. The plates were heat sealed and kept at RT until use.

Seeding of Cells:

MLE12 cells in flasks were washed once with PBS, detached with Trypsin/EDTA, resuspended in fresh medium and counted. Cells were diluted to 3×105 cells/ml and seeded with Multidrop Combi in cell plates pre-dispensed with compounds, 25 µl/well (7500 cells/well). The plates were placed, one by one, in a $CO_2$-incubator at 37° C. for 1 hour after which 25 µl/well of TNF-α (final concentration 20 ng/ml) were added. The plates were transferred back to the $CO_2$-incubator placed in a plastic box with wet tissue in the bottom, to avoid evaporation, for 30 hours.

mCCL2 Assay:

After 30 hours incubation, the plates were spun down 5 minutes at 400 g, and 16 µl/well of the supernatants were transferred to the assay plate. A mCCL2 standard curve was prepared according to the kit protocol and 16 µl/well of the standards were also added to the assay plate.

The anti-CCL2 antibody mix was prepared according to the kit protocol, and 4 µl/well were added to the assay plate. The plate was sealed and incubated over night at RT. After incubation the plate was read in Sense plate reader with Time-resolved FRET protocol (Ex330 nm/Em 620 and 665 nm). After data reduction, the delta ratios were imported to an excel template where the IC50 values were calculated.

Cell Viability Assay:

After 24 hours culture, resazurin reagent (stock 1 mg/ml in PBS) diluted 1:17 in PBS was added with Multidrop Combi, 10 µl/well, and plates were incubated for 6 hours. Plates were read in Sense plate reader with resorufin protocol (ex544 nm/em595 nm). The results were imported to an excel template where the EC50 values were calculated using XLfit. The results of the inflammation assay are shown in Table 4.

TABLE 4

| Example | Cell Viability (IC50, nM) | CCL2 (EC50, nM) |
|---|---|---|
| 2 | 10331 | 15400 |
| 13 | 7666 | 18781 |
| 20 | 11526 | 33000 |
| 22 | 13847 | 52700 |
| 23 | 19867 | 29000 |
| 26 | 7702 | 15031 |
| 27 | 7740 | 16300 |
| 28 | 7183 | 17000 |
| 37 | 7025 | 17400 |

TABLE 4-continued

| Example | Cell Viability (IC50, nM) | CCL2 (EC50, nM) |
|---|---|---|
| 39 | 6495 | 15100 |
| 41 | 16617 | 50700 |
| 49 | 5400 | 15200 |
| 50 | 7232 | 15400 |
| 72 | 6310 | 21500 |
| 75 | 10430 | 34100 |
| 75 | 12821 | 39400 |
| 77 | 7397 | 21200 |
| 82 | 17679 | 30848 |
| 83 | 14027 | 34700 |
| 84 | 8136 | 23900 |
| 85 | 17217 | 39200 |
| 86 | 13665 | 19400 |
| 87 | 5255 | 6480 |
| 89 | 25088 | 47100 |
| 91 | 6448 | 12600 |
| 92 | 13735 | 38800 |
| 93 | 21324 | 34900 |
| 94 | 8454 | 20200 |
| 107 | 7405 | 15576 |
| 107 | 7401 | 16700 |
| 117 | 14440 | 65200 |
| 118 | 5390 | 16700 |
| 119 | 5067 | 17700 |
| 121 | 4858 | 13000 |
| 122 | 4499 | 14100 |
| 123 | 10000 | 24200 |
| 124 | 11538 | 31200 |
| 126 | 15663 | 26470 |
| 127 | 16228 | 28700 |
| 129 | 9482 | 21600 |
| 130 | 6356 | 22600 |
| 131 | 17439 | 39200 |
| 135 | 9004 | 23300 |
| 136 | 8857 | 23800 |
| 139 | 10086 | 31800 |
| 140 | 17682 | 34600 |
| 142 | 7963 | 15800 |
| 146 | 9725 | 29559 |
| 147 | 17892 | 32110 |
| 148 | 15740 | 31700 |
| 149 | 16660 | 33700 |
| 150 | 7580 | 18700 |
| 151 | 17137 | 5250 |
| 152 | 6176 | 15400 |
| 153 | 24600 | 44000 |
| 154 | 16138 | 52300 |
| 160 | 8175 | 25600 |
| 164 | 12900 | 33900 |
| 166 | 16400 | 42700 |
| 168 | 14413 | 32600 |
| 171 | 17484 | 41063 |
| 183 | 16953 | 36172 |
| 184 | 7855 | 16771 |
| 187 | 7900 | 13017 |
| 191 | 29793 | 33500 |
| 192 | 15725 | 32900 |
| 194 | 15581 | 33500 |
| 197 | 19489 | 30200 |
| 199 | 7510 | 16500 |
| 201 | 10392 | 18200 |
| 202 | 7968 | 11600 |
| 204 | 7930 | 12900 |
| 206 | 26747 | 33718 |
| 209 | 21453 | 34904 |
| 212 | 16877 | 34167 |
| 221 | 7845 | 15200 |
| 225 | 1712 | 3130 |
| 226 | 17068 | 34100 |
| 227 | 16451 | 27476 |
| 228 | 16390 | 20800 |
| 228 | 10476 | 11200 |
| 229 | 9186 | 12200 |
| 229 | 6667 | 6932 |
| 230 | 2578 | 5840 |
| 237 | 4536 | 31745 |
| 238 | 9175 | 27100 |

TABLE 4-continued

| Example | Cell Viability (IC50, nM) | CCL2 (EC50, nM) |
|---|---|---|
| 240 | 16062 | 21455 |
| 243 | 5740 | 14700 |
| 244 | 13733 | 37339 |
| 245 | 12545 | >33000 |
| 249 | 15729 | 34722 |
| 250 | 25986 | 39900 |
| 257 | 19902 | 34300 |
| 258 | 11339 | 42700 |
| 262 | 19672 | >100000 |
| 263 | 27159 | >33000 |
| 267 | 17930 | 34091 |
| 268 | 13382 | >100000 |
| 269 | 17329 | 31204 |
| 270 | 16751 | 32897 |
| 271 | 4647 | 9445 |
| 272 | 27062 | 35690 |
| 273 | 19238 | 32561 |
| 274 | 18087 | 39018 |
| 276 | 16893 | 54041 |
| 277 | 14992 | 28647 |
| 280 | 16643 | 24677 |
| 281 | 1826 | 8825 |
| 282 | 27521 | 28593 |
| 283 | 19830 | 30753 |
| 285 | 15915 | >33000 |
| 286 | 20295 | >33000 |
| 289 | 24489 | 32073 |
| 295 | 10393 | 11100 |
| 296 | 13450 | 10500 |
| 297 | 28878 | 30800 |
| 298 | 29165 | 36569 |
| 299 | 10232 | 31665 |
| 300 | 1577 | 2110 |
| 301 | 16213 | 43041 |
| 302 | 14378 | 27200 |
| 304 | 8267 | 10600 |
| 305 | 4880 | 8110 |
| 306 | 7152 | 8075 |
| 307 | 28839 | 32044 |
| 308 | 215 | 2043 |
| 309 | 15568 | 27817 |
| 310 | 6129 | 13558 |
| 311 | 13768 | 14541 |
| 312 | 10982 | 28477 |
| 313 | 19546 | 35107 |

Abbreviations

The following abbreviations may be used herein:
APEX1 apurinic/apyrimidinic endodeoxyribonuclease 1
aq aqueous
BINAP 2,2'-bis(diphenylphosphino)-1,1'-binaphthyl
Boc tert-butoxycarbonyl
brine saturated aqueous solution of NaCl
CI combination index
DBU 1,8-diazabicyclo[5.4.0]undec-7-ene
DCM dichloromethane
DIEA N,N-diisopropylethylamine
DMAP 4-dimethylaminopyridine
DMF dimethylformamide
DMSO dimethylsulfoxide
DTT dithiothreitol
EDC•HCl N-(3-dimethylaminopropyl)-N'-ethylcarbodiimide hydrochloride
EtOAc ethyl acetate
EtOH ethanol
Ex example
FAM fluorescein
HATU O-(7-azabenzotriazolyl)-N,N,N',N'-tetramethyluronium hexafluorophosphate
HOBt 1-hydroxybenzotriazole
Int intermediate
LAH lithium aluminium hydride
MeCN acetonitrile
MeOH methanol
NBS N-bromosuccinimide
NMR nuclear magnetic resonance
OGG1 8-oxoguanine-DNA glycosylase 1
$Pd_2(dba)_3$ tris(dibenzylideneacetone)dipalladium(0)
PBS phosphate buffered saline
rac racemic
rt room temperature
tBuOK potassium tert-butoxide
tBuONa sodium tert-butoxide
TBS tris-buffered saline
TFA trifluoroacetic acid
THF tetrahydrofuran
TNFα Tumor necrosis factor alpha
Xantphos 4,5-bis(diphenylphosphino)-9,9-dimethylxanthene
8-oxoA 8-oxo-2'deoxyadenosine

The invention claimed is:

1. A compound of formula I

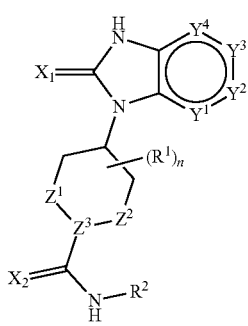

Ic or a pharmaceutically acceptable salt thereof, wherein:
$X^1$ and $X^2$ each independently represent O or S;
each of $Y^1$ to $Y^4$ independently represents CH or $CR^3$,
either $Z^1$ and $Z^2$ both represent methylene optionally linked by an additional ethylene group, or $Z^1$ represents ethylene and $Z^2$ represents methylene;
$Z^3$ represents N;
each $R^1$ independently represents, where possible
(i) halo, oxy, —$NO_2$, —CN, —$R^{1a}$, —$OR^{1b}$, —$S(O)_qR^{1c}$, —$S(O)_r(R^{1d})(R^{1e})$, —$N(R^{1f})S(O)_sR^{1g}$, —$N(R^{1h})(R^{1i})$, —$C(O)OR^{1j}$, or —$C(O)NR^{1k}R^{1l}$,
(ii) aryl optionally substituted by one or more groups independently selected from $A^1$,
(iii) heteroaryl optionally substituted by one or more groups selected from $A^2$, or
(iv) heterocyclyl optionally substituted by one or more groups independently selected from $A^3$;
n represents 0 to 11;
$R^2$ represents
(i) phenyl optionally substituted by one or more groups independently selected from $A^4$,
(ii) 5- or 6-membered monocyclic heteroaryl optionally substituted by one or more groups selected from oxy and $A^5$, or
(iii) phenyl substituted with two adjacent groups which, together with the ring to which they are attached, form a bicyclic heteroaryl optionally substituted by one or more groups selected from oxy and $A^6$;
each $R^3$ independently represents
(i) halo, —$NO_2$, —CN, —$R^{2a}$, —$OR^{2b}$, —$S(O)_qR^{2c}$, —$S(O)_r(R^{2d})(R^{2e})$, —$N(R^{2f})SO_sR^{2g}$, —$N(R^{2h})(R^{2i})$, —$C(O)OR^{2j}$, or —$C(O)NR^{2k}R^{2l}$,
(ii) aryl optionally substituted by one or more groups independently selected from $A^7$,
(iii) heteroaryl optionally substituted by one or more groups selected from $A^8$, or
(iv) heterocyclyl optionally substituted by one or more groups independently selected from $A^9$;
each $R^{1a}$ independently represents
(i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $B^1$;

(ii) aryl optionally substituted by one or more groups independently selected from oxy and $B^2$,
(iii) heteroaryl optionally substituted by one or more groups selected from oxy and $B^3$, or
(iv) heterocyclyl optionally substituted by one or more groups independently selected from oxy and $B^4$;
each $R^{2a}$ independently represents
(i) $C_{1-6}$ alkyl, $C_{2-6}$ alkenyl or $C_{2-6}$ alkynyl, wherein each such alkyl, alkenyl or alkynyl group is substituted by one or more groups independently selected from oxy and $B^1$;
(ii) aryl optionally substituted by one or more groups independently selected from oxy and $B^2$,
(iii) heteroaryl optionally substituted by one or more groups selected from oxy and $B^3$, or
(iv) heterocyclyl optionally substituted by one or more groups independently selected from oxy and $B^4$;
each $R^{1b}$ to $R^{1l}$ and $R^{2b}$ to $R^{2l}$ independently represents H or
(i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $B^1$;
(ii) aryl optionally substituted by one or more groups independently selected from oxy and $B^2$,
(iii) heteroaryl optionally substituted by one or more groups selected from oxy and $B^3$, or
(iv) heterocyclyl optionally substituted by one or more groups independently selected from oxy and $B^4$;
each $A^1$ to $A^9$ independently represents
(i) halo, $NO_2$, —ON, —$R^{3a}$, $OR^{3b}$, $S(O)_qR^{3c}$, $S(O)_rN(R^{3d})(R^{3e})$, $N(R^{3f})SO_sR^{3g}$, —$N(R^{3h})(R^{3i})$, —$C(O)OR^{3j}$, or —$C(O)NR^{3k}R^{3l}$,
(ii) aryl optionally substituted by one or more groups independently selected from oxy and $D^1$,
(iii) heteroaryl optionally substituted by one or more groups selected from oxy and $D^2$, or
(iv) heterocyclyl optionally substituted by one or more groups independently selected from oxy and $D^3$;
each $B^1$ independently represents
(i) halo, $NO_2$, —CN, —$OR^{4b}$, —$S(O)_qR^{4c}$, —$S(O)_rN(R^{4d})(R^{4e})$, —$N(R^{4f})SO_sR^{4g}$, —$N(R^{4h})(R^{4i})$, —$C(O)OR^{4j}$, or —$C(O)NR^{4k}R^{4l}$,
(ii) aryl optionally substituted by one or more groups independently selected from $D^4$,
(iii) heteroaryl optionally substituted by one or more groups selected from $D^5$, or (iv) heterocyclyl optionally substituted by one or more groups independently selected from $D^6$;
each $B^2$ to $B^4$ independently represents
(i) halo, $NO_2$, —CN, —$R^{4a}$, —$OR^{4b}$, —$S(O)_qR^{4c}$, —$S(O)_rN(R^{4d})(R^{4e})$, —$N(R^{4f})SO_sR^{4g}$, —$N(R^{4h})(R^{4i})$, —$C(O)OR^{4j}$, or —$C(O)NR^{4k}R^{4l}$,
(ii) aryl optionally substituted by one or more groups independently selected from oxy and $D^4$,
(iii) heteroaryl optionally substituted by one or more groups selected from oxy and $D^5$, or
(iv) heterocyclyl optionally substituted by one or more groups independently selected from oxy and $D^6$;
each $R^{3a}$ and $R^{4a}$ represent
(i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $E^1$;
(ii) aryl optionally substituted by one or more groups independently selected from oxy and $E^2$,
(iii) heteroaryl optionally substituted by one or more groups selected from oxy and $E^3$, or
(iv) heterocyclyl optionally substituted by one or more groups independently selected from oxy and $E^4$;
each $R^{3b}$ to $R^{3l}$, and $R^{4b}$ to $R^{4l}$ independently represents H or
(i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $E^1$;
(ii) aryl optionally substituted by one or more groups independently selected from oxy and $E^2$,
(iii) heteroaryl optionally substituted by one or more groups selected from oxy and $E^3$, or
(iv) heterocyclyl optionally substituted by one or more groups independently selected from oxy and $E^4$;
each $D^1$ to $D^6$ independently represents
(i) halo, $NO_2$, —CN, —$R^{5a}$, —$OR^{5b}$, —$S(O)_qR^{5c}$, —$S(O)_rN(R^{5d})(R^{5e})$, —$N(R^{5f})SO_sR^{5g}$, —$N(R^{5h})(R^{5i})$, —$C(O)OR^{5j}$, or —$C(O)NR^{5k}R^{5l}$,
(ii) aryl optionally substituted by one or more groups independently selected from oxy and $G^1$,
(iii) heteroaryl optionally substituted by one or more groups selected from oxy and $G^2$, or
(iv) heterocyclyl optionally substituted by one or more groups independently selected from oxy and $G^3$;
each $E^1$ independently represents
(i) halo, $NO_2$, —CN, —$OR^{6b}$, —$S(O)_qR^{6c}$, —$S(O)_rN(R^{6d})(R^{6e})$, —$N(R^{6f})SO_sR^{6g}$, —$N(R^{6h})(R^{6i})$, —$C(O)OR^{6j}$, or —$C(O)NR^{6k}R^{6l}$,
(ii) aryl optionally substituted by one or more groups independently selected from $G^4$,
(iii) heteroaryl optionally substituted by one or more groups selected from $G^5$, or
(iv) heterocyclyl optionally substituted by one or more groups independently selected from $G^6$;
each $E^2$ to $E^4$ independently represents
(i) halo, $NO_2$, —CN, —$R^{6a}$, —$OR^{6b}$, —$S(O)_qR^{6c}$, —$S(O)_rN(R^{6d})(R^{6e})$, —$N(R^{6f})SO_sR^{6g}$, —$N(R^{6h})(R^{6i})$, —$C(O)OR^{6j}$, or —$C(O)NR^{6k}R^{6l}$,
(ii) aryl optionally substituted by one or more groups independently selected from oxy and $G^4$,
(iii) heteroaryl optionally substituted by one or more groups selected from oxy and $G^5$, or
(iv) heterocyclyl optionally substituted by one or more groups independently selected from oxy and $G^6$;
each $R^{5a}$ and $R^{6a}$ represent
(i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $J^1$;
(ii) aryl optionally substituted by one or more groups independently selected from oxy and $J^2$,
(iii) heteroaryl optionally substituted by one or more groups selected from oxy and $J^3$, or
(iv) heterocyclyl optionally substituted by one or more groups independently selected from oxy and $J^4$;
each $R^{5b}$ to $R^{5l}$, and $R^{6b}$ to $R^{6l}$ independently represents H or
(i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $J^1$;
(ii) aryl optionally substituted by one or more groups independently selected from oxy and $J^2$,
(iii) heteroaryl optionally substituted by one or more groups selected from oxy and $J^3$, or

257

(iv) heterocyclyl optionally substituted by one or more groups independently selected from oxy and J$^4$;
each G$^1$ to G$^6$ independently represents
(i) halo, NO$_2$, —CN, —R$^{7a}$, —OR$^{7b}$, —S(O)$_q$R$^{7c}$, —S(O)$_r$N(R$^{7d}$)(R$^{7e}$), —N(R$^{7f}$)SO$_s$R$^{7g}$, —N(R$^{7h}$)(R$^{7i}$), —C(O)OR$^{7j}$, or —C(O)NR$^{7k}$R$^{7l}$,
(ii) aryl optionally substituted by one or more groups independently selected from oxy and L$^1$,
(iii) heteroaryl optionally substituted by one or more groups selected from oxy and L$^2$, or
(iv) heterocyclyl optionally substituted by one or more groups independently selected from oxy and L$^3$;
each J$^1$ independently represents
(i) halo, NO$_2$, —CN, —OR$^{8b}$, —S(O)$_q$R$^{8c}$, —S(O)$_r$N(R$^{8d}$)(R$^{8e}$), —N(R$^{8f}$)SO$_s$R$^{8g}$, —N(R$^{8h}$)(R$^{8i}$), —C(O)OR$^{8j}$, or —C(O)NR$^{8k}$R$^{8l}$,
(ii) aryl optionally substituted by one or more groups independently selected from L$^1$,
(iii) heteroaryl optionally substituted by one or more groups selected from L$^2$, or
(iv) heterocyclyl optionally substituted by one or more groups independently selected from L$^3$;
each J$^2$ to J$^4$ independently represents
(i) halo, NO$_2$, —CN, —R$^{8a}$, —OR$^{8b}$, —S(O)$_q$R$^{8c}$, —S(O)$_r$N(R$^{8d}$)(R$^{8e}$), —N(R$^{8f}$)SO$_s$R$^{8g}$, —N(R$^{8h}$)(R$^{8i}$), —C(O)OR$^{8j}$, or —C(O)NR$^{8k}$R$^{8l}$,
(ii) aryl optionally substituted by one or more groups independently selected from oxy and L$^1$,
(iii) heteroaryl optionally substituted by one or more groups selected from oxy and L$^2$, or
(iv) heterocyclyl optionally substituted by one or more groups independently selected from oxy and L$^3$;
each R$^{7a}$ and R$^{8a}$ represent C$_{1-3}$ alkyl optionally substituted with one or more fluoro;
each R$^{7b}$ to R$^{7l}$, and R$^{8b}$ to R$^{8l}$ independently represents H or C$_{1-3}$ alkyl optionally substituted with one or more fluoro;
each L$^1$ to L$^3$ independently represents halo, NO$_2$, —CN, —R$^{9a}$, —OR$^{9b}$, —S(O)$_q$R$^{9c}$, —S(O)$_r$N(R$^{9d}$)(R$^{9e}$), —N(R$^{9f}$)SO$_s$R$^{9g}$, —N(R$^{9h}$)(R$^{9i}$), —C(O)OR$^{9j}$, or —C(O)NR$^{9k}$R$^{9l}$,
each R$^{9a}$ independently represents C$_{1-3}$ alkyl optionally substituted with one or more fluoro;
each R$^{9b}$ to R$^{9l}$ independently represents H or C$_{1-3}$ alkyl optionally substituted with one or more fluoro; and
each q, r and s independently represents 0, 1 or 2,
with the provisos that:
(a) at least one R$^3$ group is present; and
(b) the compound of formula I is not:
4-(5-chloro-2-oxo-2,3-dihydro-1H-1,3-benzodiazol-1-yl)-N-(4-chlorophenyl)piperidine-1-carbothioamide;
N-(4-chlorophenyl)-4-(5-fluoro-2-oxo-2,3-dihydro-1H-1,3-benzodiazol-1-yl)piperidine-1-carbothioamide;
4-(5-chloro-2-oxo-2,3-dihydro-1H-1,3-benzodiazol-1-yl)-N-(3-chlorophenyl)piperidine-1-carboxamide;
ethyl 4-{[4-(5-chloro-2-oxo-2,3-dihydro-1H-1,3-benzodiazol-1-yl)piperidine-1-carbonyl]amino}benzoate; or
4-(5-chloro-2-oxo-2,3-dihydro-1H-1,3-benzodiazol-1-yl)-N-(2,6-dichloropyridin-4-yl)piperidine-1-carboxamide.

2. A compound as claimed in claim 1, wherein X$^1$ and X$^2$ each represent O; or X$^1$ represents O and X$^2$ represents S.

3. A compound as claimed in claim 1, wherein the compound of formula I is a compound of formula Ib

258

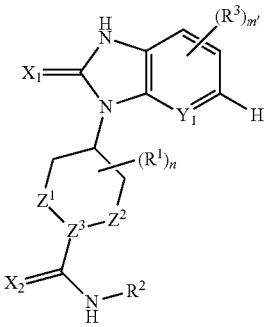

Ib wherein:
Y$^1$ represents CH;
m' represents 1; and
R$^1$ to R$^3$, X$^1$, X$^2$, Z$^1$ to Z$^3$, and n are as defined in claim 1.

4. A compound as claimed in claim 1, wherein n represents 0 or 1.

5. A compound as claimed in claim 1, wherein each R$^1$ independently represents halo, oxy, —NO$_2$, —CN, —R$^{1a}$, —OR$^{1b}$, —S(O)$_q$R$^{1c}$, —S(O)$_r$(R$^{1d}$)(R$^{1e}$), —N(R$^{1f}$)S(O)$_s$R$^{1g}$, N(R$^{1h}$)(R$^{1i}$), —C(O)OR$^{1j}$, or —C(O)NR$^{1k}$R$^{1l}$.

6. A compound as claimed in claim 1, wherein R$^2$ represents:
(i) phenyl optionally substituted by one to three groups independently selected from A$^4$,
(ii) 5- or 6-membered monocyclic heteroaryl optionally substituted by one to three groups selected from oxy and A$^5$, or
(iii) phenyl substituted with two adjacent groups which, together with the ring to which they are attached, form a bicyclic heteroaryl optionally substituted by one to three groups selected from oxy and A$^6$.

7. A compound as claimed in claim 1, wherein each R$^3$ independently represents:
(i) halo, —NO$_2$, —CN, —R$^{2a}$, —OR$^{2b}$, —S(O)$_q$R$^{2c}$, —S(O)$_r$N(R$^{2d}$)(R$^{2e}$), —N(R$^{2f}$)SO$_s$R$^{2g}$, —N(R$^{2h}$)(R$^{2i}$), —C(O)OR$^{2j}$, or —C(O)NR$^{2k}$R$^{2l}$;
(ii) aryl optionally substituted by one or more groups independently selected from A$^7$; or
(iii) heteroaryl optionally substituted by one or more groups selected from A$^8$.

8. A compound as claimed in claim 1, selected from
4-(5-Chloro-2-oxo-2,3-dihydro-1H-1,3-benzodiazol-1-yl)-N-(4-chlorophenyl) piperidine-1-carboxamide,
4-(5-Chloro-2-oxo-2,3-dihydro-1H-1,3-benzodiazol-1-yl)-N-(4-iodophenyl) piperidine-1-carboxamide,
4-(5-Chloro-2-oxo-2,3-dihydro-1H-1,3-benzodiazol-1-yl)-N-(3,4-dichlorophenyl)piperidine-1-carboxamide,
N-(4-iodophenyl)-4-(4-methoxy-2-oxo-2,3-dihydro-1H-1,3-benzodiazol-1-yl)piperidine-1-carboxamide,
4-(4-Hydroxy-2-oxo-2,3-dihydro-1H-1,3-benzodiazol-1-yl)-N-(4-iodophenyl)piperidine-1-carboxamide,
N-(4-chlorophenyl)-4-(4-methoxy-2-oxo-2,3-dihydro-1H-1,3-benzodiazol-1-yl)piperidine-1-carboxamide,
N-(3,4-dichlorophenyl)-4-(4-hydroxy-2-oxo-2,3-dihydro-1H-1,3-benzodiazol-1-yl)piperidine-1-carboxamide,
4-(5-Cyano-2-oxo-2,3-dihydro-1H-1,3-benzodiazol-1-yl)-N-(4-iodophenyl)piperidine-1-carboxamide,
4-(4-Fluoro-2-oxo-2,3-dihydro-1H-1,3-benzodiazol-1-yl)-N-(4-iodophenyl)piperidine-1-carboxamide, 4-(4-Bromo-2-oxo-2,3-dihydro-1H-1,3-benzodiazol-1-yl)-N-(4-iodophenyl)piperidine-1-carboxamide,
N-(4-iodophenyl)-4-(5-methoxy-2-oxo-2,3-dihydro-1H-1,3-benzodiazol-1-yl)piperidine-1-carboxamide,
N-(4-iodophenyl)-4-(5-fluoro-2-oxo-2,3-dihydro-1H-1,3-benzodiazol-1-yl)piperidine-1-carboxamide,
Methyl 2-(1-{1-[(4-iodophenyl)carbamoyl]piperidin-4-yl}-2-oxo-2,3-dihydro-1H-1,3-benzodiazol-4-yl)acetate
4-(5-Chloro-2-oxo-2,3-dihydro-1H-1,3-benzodiazol-1-yl)-N-(3-chloro-4-iodophenyl)piperidine-1-carboxamide,
4-(4-Ethoxy-2-oxo-2,3-dihydro-1H-1,3-benzodiazol-1-yl)-N-(4-iodophenyl)piperidine-1-carboxamide,
N-(4-iodophenyl)-4-[4-(methylamino)-2-oxo-2,3-dihydro-1H-1,3-benzodiazol-1-yl]piperidine-1-carboxamide,
4-(4-Amino-2-oxo-2,3-dihydro-1H-1,3-benzodiazol-1-yl)-N-(4-iodophenyl)piperidine-1-carboxamide,
4-(4-Dimethylamino-2-oxo-2,3-dihydro-1H-1,3-benzodiazol-1-yl)-N-(4-iodophenyl)piperidine-1-carboxamide,
N-(4-iodophenyl)-4-[2-oxo-4-(1H-pyrazol-1-yl)-2,3-dihydro-1H-1,3-benzodiazol-1-yl]piperidine-1-carboxamide,
N-(4-iodophenyl)-4-[2-oxo-4-(1H-1,2,4-triazol-1-yl)-2,3-dihydro-1H-1,3-benzodiazol-1-yl]piperidine-1-carboxamide,
N-(4-iodophenyl)-4-[4-(methylsulfanyl)-2-oxo-2,3-dihydro-1H-1,3-benzodiazol-1-yl]piperidine-1-carboxamide,
N-(4-iodophenyl)-4-[2-oxo-4-(1H-pyrrol-2-yl)-2,3-dihydro-1H-1,3-benzodiazol-1-yl]piperidine-1-carboxamide,
N-(4-iodophenyl)-4-[2-oxo-4-(pyridin-3-yl)-2,3-dihydro-1H-1,3-benzodiazol-1-yl]piperidine-1-carboxamide,
4-(4-Bromo-2-oxo-2,3-dihydro-1H-1,3-benzodiazol-1-yl)-N-(3,4-dichlorophenyl)piperidine-1-carboxamide,
N-(3,4-dichlorophenyl)-4-{4-[6-(hydroxymethyl)pyridin-3-yl]-2-oxo-2,3-dihydro-1H-1,3-benzodiazol-1-yl}piperidine-1-carboxamide,
4-[4-(3-Aminophenyl)-2-oxo-2,3-dihydro-1H-1,3-benzodiazol-1-yl]-N-(3,4-dichlorophenyl)piperidine-1-carboxamide,
4-[4-(2-Hydroxyethyl)-2-oxo-2,3-dihydro-1H-1,3-benzodiazol-1-yl]-N-(4-iodophenyl)piperidine-1-carboxamide,
N-(3,4-dichlorophenyl)-4-[2-oxo-4-(pyridin-4-yl)-2,3-dihydro-1H-1,3-benzodiazol-1-yl]piperidine-1-carboxamide,
4-{4-[4-(Aminomethyl)phenyl]-2-oxo-2,3-dihydro-1H-1,3-benzodiazol-1-yl}-N-(3,4-dichlorophenyl)piperidine-1-carboxamide,
4-(4-Bromo-2-oxo-2,3-dihydro-1H-1,3-benzodiazol-1-yl)-N-(4-iodophenyl)azepane-1-carboxamide,
4-(1-{1-[(3,4-Dichlorophenyl)carbamoyl]piperidin-4-yl}-2-oxo-2,3-dihydro-1H-1,3-benzodiazol-4-yl)benzoic acid,
N-(3,4-dichlorophenyl)-4-(4-{4-[2-(dimethylamino)ethoxy]phenyl}-2-oxo-2,3-dihydro-1H-1,3-benzodiazol-1-yl)piperidine-1-carboxamide,
N-(3,4-dichlorophenyl)-4-[2-oxo-4-(pyrimidin-5-yl)-2,3-dihydro-1H-1,3-benzodiazol-1-yl]piperidine-1-carboxamide,
4-{4-[3,5-Bis(trifluoromethyl)phenyl]-2-oxo-2,3-dihydro-1H-1,3-benzodiazol-1-yl}-N-(3,4-dichlorophenyl)piperidine-1-carboxamide,
4-[4-(6-Aminopyridin-3-yl)-2-oxo-2,3-dihydro-1H-1,3-benzodiazol-1-yl]-N-(3,4-dichlorophenyl)piperidine-1-carboxamide,
N-(3,4-dichlorophenyl)-4-{2-oxo-4-[4-(2,2,2-trifluoroacetyl)phenyl]-2,3-dihydro-1H-1,3-benzodiazol-1-yl}piperidine-1-carboxamide,
4-[4-(4-Bromo-1H-pyrazol-1-yl)-2-oxo-2,3-dihydro-1H-1,3-benzodiazol-1-yl]-N-(4-iodophenyl)piperidine-1-carboxamide,
4-(4-Bromo-2-oxo-2,3-dihydro-1H-1,3-benzodiazol-1-yl)-N-(4-ethylphenyl)piperidine-1-carboxamide,
4-(4-Bromo-2-oxo-2,3-dihydro-1H-1,3-benzodiazol-1-yl)-N-(4-methylphenyl)piperidine-1-carboxamide,
4-(4-Bromo-2-oxo-2,3-dihydro-1H-1,3-benzodiazol-1-yl)-N-(4-methoxyphenyl)piperidine-1-carboxamide,
4-(4-Bromo-2-oxo-2,3-dihydro-1H-1,3-benzodiazol-1-yl)-N-(3,4-dimethoxyphenyl)piperidine-1-carboxamide,
4-(4-Bromo-2-oxo-2,3-dihydro-1H-1,3-benzodiazol-1-yl)-N-(3-chloro-4-methoxyphenyl)piperidine-1-carboxamide,
N-(2H-1,3-benzodioxol-5-yl)-4-(4-bromo-2-oxo-2,3-dihydro-1H-1,3-benzodiazol-1-yl)piperidine-1-carboxamide,
4-(4-Bromo-2-oxo-2,3-dihydro-1H-1,3-benzodiazol-1-yl)-N-(4-bromo-3-methylphenyl)piperidine-1-carboxamide,
4-(4-Bromo-2-oxo-2,3-dihydro-1H-1,3-benzodiazol-1-yl)-N-(4-bromo-3-chlorophenyl)piperidine-1-carboxamide,
4-(4-Bromo-2-oxo-2,3-dihydro-1H-1,3-benzodiazol-1-yl)-N-(4-iodo-3-methylphenyl)piperidine-1-carboxamide,
4-(4-bromo-2-oxo-2,3-dihydro-1H-1,3-benzodiazol-1-yl)-N-(3,4-dichlorophenyl)-3-trans-hydroxypiperidine-1-carboxamide,
4-(5-Hydroxy-2-oxo-2,3-dihydro-1H-1,3-benzodiazol-1-yl)-N-(4-iodophenyl)piperidine-1-carboxamide,
N-(3,4-dichlorophenyl)-4-{2-oxo-4-[2-(trifluoromethyl)pyridin-4-yl]-2,3-dihydro-1H-1,3-benzodiazol-1-yl}piperidine-1-carboxamide,
4-[4-(5-Aminopyridin-3-yl)-2-oxo-2,3-dihydro-1H-1,3-benzodiazol-1-yl]-N-(3,4-dichlorophenyl)piperidine-1-carboxamide,
N-(3,4-dichlorophenyl)-4-[4-(2-ethoxypyridin-3-yl)-2-oxo-2,3-dihydro-1H-1,3-benzodiazol-1-yl]piperidine-1-carboxamide,
N-(3,4-dichlorophenyl)-4-[4-(6-methoxypyridin-3-yl)-2-oxo-2,3-dihydro-1H-1,3-benzodiazol-1-yl]piperidine-1-carboxamide,
4-{4-[3-(Carbamoylmethyl)phenyl]-2-oxo-2,3-dihydro-1H-1,3-benzodiazol-1-yl}-N-(3,4-dichlorophenyl)piperidine-1-carboxamide,
3-(1-{1-[(3,4-Dichlorophenyl)carbamoyl]piperidin-4-yl}-2-oxo-2,3-dihydro-1H-1,3-benzodiazol-4-yl)benzoic acid,
Methyl 3-(1-{1-[(3,4-dichlorophenyl)carbamoyl]piperidin-4-yl}-2-oxo-2,3-dihydro-1H-1,3-benzodiazol-4-yl)benzoate,
N-(3,4-dichlorophenyl)-4-(4-{3-[2-(dimethylamino)ethoxy]phenyl}-2-oxo-2,3-dihydro-1H-1,3-benzodiazol-1-yl)piperidine-1-carboxamide,
N-(3,4-dichlorophenyl)-4-{4-[3-(morpholine-4-carbonyl)phenyl]-2-oxo-2,3-dihydro-1H-1,3-benzodiazol-1-yl}piperidine-1-carboxamide, N-(3,4-dichlorophenyl)-4-(4-{3-[(2-methoxyethyl)carbamoyl]phenyl}-2-oxo-2,3-dihydro-1H-1,3-benzodiazol-1-yl)piperidine-1-carboxamide, N-(3,4-dichlorophenyl)-4-[2-oxo-4-(4-sulfamoylphenyl)-2,3-dihydro-1H-1,3-benzodiazol-1-yl]piperidine-1-carboxamide, N-(3,4-dichlorophenyl)-4-[4-(3-fluorophenyl)-2-oxo-2,3-dihydro-1H-1,3-benzodiazol-1-yl]piperidine-1-carboxamide, 4-{4-[3-(Aminomethyl)phenyl]-2-oxo-2,3-dihydro-1H-1,3-benzodiazol-1-yl}-N-(3,4-dichlorophenyl)piperidine-1-carboxamide, 4-[4-(2-Aminophenyl)-2-oxo-2,3-dihydro-1H-1,3-benzodiazol-1-yl]-N-(3,4-dichlorophenyl)piperidine-1-carboxamide, N-(3,4-dichlorophenyl)-4-(4-{2-[(dimethylamino)methyl]phenyl}-2-oxo-2,3-dihydro-1H-1,3-benzodiazol-1-yl)piperidine-1-carboxamide, 4-(4-Bromo-2-sulfanylidene-2,3-dihydro-1H-1,3-benzodiazol-1-yl)-N-(3,4-dichlorophenyl)piperidine-1-carboxamide, N-(3,4-dichlorophenyl)-4-(7-fluoro-2-oxo-2,3-dihydro-1H-1,3-benzodiazol-1-yl)piperidine-1-carboxamide, 4-(7-Chloro-2-oxo-2,3-dihydro-1H-1,3-benzodiazol-1-yl)-N-(3,4-dichlorophenyl)piperidine-1-carboxamide, 4-(7-Bromo-2-oxo-2,3-dihydro-1H-1,3-benzodiazol-1-yl)-N-(3,4-dichlorophenyl)piperidine-1-carboxamide, 3-(4-Bromo-2-oxo-2,3-dihydro-1H-1,3-benzodiazol-1-yl)-N-(3,4-dichlorophenyl)-(endo)-8-azabicyclo[3.2.1]octane-8-carboxamide, 4-(4-Bromo-2-oxo-2,3-dihydro-1H-1,3-benzodiazol-1-yl)-N-(1H-indol-6-yl)piperidine-1-carboxamide, 4-(4-Bromo-2-oxo-2,3-dihydro-1H-1,3-benzodiazol-1-yl)-N-[4-methyl-3-(trifluoromethyl)phenyl]piperidine-1-carboxamide, 4-(4-Bromo-2-oxo-2,3-dihydro-1H-1,3-benzodiazol-1-yl)-N-(3-methoxy-4-methylphenyl)piperidine-1-carboxamide, 4-(4-Bromo-2-oxo-2,3-dihydro-1H-1,3-benzodiazol-1-yl)-N-(4-fluoro-3-methoxyphenyl)piperidine-1-carboxamide, 4-(4-Bromo-2-oxo-2,3-dihydro-1H-1,3-benzodiazol-1-yl)-N-(4-chloro-3-methoxyphenyl)piperidine-1-carboxamide, 4-(4-Bromo-2-oxo-2,3-dihydro-1H-1,3-benzodiazol-1-yl)-N-(4-chloro-3-fluorophenyl)piperidine-1-carboxamide, 4-(4-Bromo-2-oxo-2,3-dihydro-1H-1,3-benzodiazol-1-yl)-N-(4-fluoro-3-methylphenyl)piperidine-1-carboxamide, 4-(4-Bromo-2-oxo-2,3-dihydro-1H-1,3-benzodiazol-1-yl)-N-[3-chloro-4-(trifluoromethoxy)phenyl]piperidine-1-carboxamide, 4-{4-[6-(Hydroxymethyl)pyridin-3-yl]-2-oxo-2,3-dihydro-1H-1,3-benzodiazol-1-yl}-N-(4-iodo-3-methylphenyl)piperidine-1-carboxamide, 4-{4-[6-(Hydroxymethyl)pyridin-3-yl]-2-oxo-2,3-dihydro-1H-1,3-benzodiazol-1-yl}-N-(3-methoxy-4-methylphenyl)piperidine-1-carboxamide, N-(4-Chloro-3-methoxyphenyl)-4-{4-[6-(hydroxymethyl)pyridin-3-yl]-2-oxo-2,3-dihydro-1H-1,3-benzodiazol-1-yl}piperidine-1-carboxamide, 3-(4-Bromo-2-oxo-2,3-dihydro-1H-1,3-benzodiazol-1-yl)-N-(4-iodo-3-methylphenyl)-(endo)-8-azabicyclo[3.2.1]octane-8-carboxamide, 3-(4-Bromo-2-oxo-2,3-dihydro-1H-1,3-benzodiazol-1-yl)-N-(3-methoxy-4-methylphenyl)-(endo)-8-azabicyclo[3.2.1]octane-8-carboxamide, 3-(4-Bromo-2-oxo-2,3-dihydro-1H-1,3-benzodiazol-1-yl)-N-(4-chloro-3-fluorophenyl)-(endo)-8-azabicyclo[3.2.1]octane-8-carboxamide, 4-{4-[4-(Ethylcarbamoyl)-1H-pyrazol-1-yl]-2-oxo-2,3-dihydro-1H-1,3-benzodiazol-1-yl}-N-(4-iodophenyl)piperidine-1-carboxamide, 4-{4-[4-(Diethylcarbamoyl)-1H-pyrazol-1-yl]-2-oxo-2,3-dihydro-1H-1,3-benzodiazol-1-yl}-N-(4-iodophenyl)piperidine-1-carboxamide, 4-(4-(4-((2-(Dimethylamino)ethyl)carbamoyl)-1H-pyrazol-1-yl)-2-oxo-2,3-dihydro-1H-benzo[d]imidazol-1-yl)-N-(4-iodophenyl)piperidine-1-carboxamide, 2,2,2-trifluoroacetate, 4-(4-{4-[(2,3-Dihydroxypropyl)carbamoyl]-1H-pyrazol-1-yl}-2-oxo-2,3-dihydro-1H-1,3-benzodiazol-1-yl)-N-(4-iodophenyl)piperidine-1-carboxamide, 3-{4-[6-(Hydroxymethyl)pyridin-3-yl]-2-oxo-2,3-dihydro-1H-1,3-benzodiazol-1-yl}-N-(4-iodo-3-methylphenyl)-(endo)-8-azabicyclo[3.2.1]octane-8-carboxamide, 3-{4-[6-(Hydroxymethyl)pyridin-3-yl]-2-oxo-2,3-dihydro-1H-1,3-benzodiazol-1-yl}-N-(3-methoxy-4-methylphenyl)-(endo)-8-azabicyclo[3.2.1]octane-8-carboxamide, N-(4-chloro-3-methoxyphenyl)-3-{4-[6-(hydroxymethyl)pyridin-3-yl]-2-oxo-2,3-dihydro-1H-1,3-benzodiazol-1-yl}-(endo)-8-azabicyclo[3.2.1]octane-8-carboxamide, N-(4-chloro-3-fluorophenyl)-3-{4-[6-(hydroxymethyl)pyridin-3-yl]-2-oxo-2,3-dihydro-1H-1,3-benzodiazol-1-yl}-(endo)-8-azabicyclo[3.2.1]octane-8-carboxamide, N-(3-methoxy-4-methylphenyl)-4-[2-oxo-4-(pyridin-3-yl)-2,3-dihydro-1H-1,3-benzodiazol-1-yl]piperidine-1-carboxamide, 4-[4-(6-Aminopyridin-3-yl)-2-oxo-2,3-dihydro-1H-1,3-benzodiazol-1-yl]-N-(3-methoxy-4-methylphenyl)piperidine-1-carboxamide, 4-[4-(5-Aminopyridin-3-yl)-2-oxo-2,3-dihydro-1H-1,3-benzodiazol-1-yl]-N-(3-methoxy-4-methylphenyl)piperidine-1-carboxamide, N-(3-chloro-4-methoxyphenyl)-4-[2-oxo-4-(pyridin-3-yl)-2,3-dihydro-1H-1,3-benzodiazol-1-yl]piperidine-1-carboxamide, 4-[4-(6-Aminopyridin-3-yl)-2-oxo-2,3-dihydro-1H-1,3-benzodiazol-1-yl]-N-(3-chloro-4-methoxyphenyl)piperidine-1-carboxamide, 4-[4-(5-Aminopyridin-3-yl)-2-oxo-2,3-dihydro-1H-1,3-benzodiazol-1-yl]-N-(3-chloro-4-methoxyphenyl)piperidine-1-carboxamide, N-(3-chloro-4-methoxyphenyl)-4-(2-oxo-4-{1H-pyrazolo[3,4-b]pyridin-5-yl}-2,3-dihydro-1H-1,3-benzodiazol-1-yl)piperidine-1-carboxamide, N-(4-chloro-3-methoxyphenyl)-4-[2-oxo-4-(pyridin-3-yl)-2,3-dihydro-1H-1,3-benzodiazol-1-yl]piperidine-1-carboxamide, 4-[4-(6-Aminopyridin-3-yl)-2-oxo-2,3-dihydro-1H-1,3-benzodiazol-1-yl]-N-(4-chloro-3-methoxyphenyl)piperidine-1-carboxamide, 4-[4-(5-Aminopyridin-3-yl)-2-oxo-2,3-dihydro-1H-1,3-benzodiazol-1-yl]-N-(4-chloro-3-methoxyphenyl)piperidine-1-carboxamide, N-(4-chloro-3-methoxyphenyl)-4-[4-(6-methoxypyridin-3-yl)-2-oxo-2,3-dihydro-1H-1,3-benzodiazol-1-yl]piperidine-1-carboxamide, N-(3-chloro-4-methoxyphenyl)-4-(4-{[2-(dimethylamino)ethyl](methyl)amino}-2-oxo-2,3-dihydro-1H-1,3-benzodiazol-1-yl)piperidine-1-carboxamide, N-(3-chloro-4-methoxyphenyl)-4-(2-oxo-4-{1H,4H,5H,6H-pyrrolo[3,4-c]pyrazol-5-yl}-2,3-dihydro-1H-1,3-benzodiazol-1-yl)piperidine-1-carboxamide, 4-(4-Bromo-2-oxo-2,3-dihydro-1H-1,3-benzodiazol-1-yl)-N-(5,6-dichloropyridin-3-yl)piperidine-1-carboxamide, 4-(4-Bromo-2-oxo-2,3-dihydro-1H-1,3-benzodiazol-1-yl)-N-(6-methoxy-5-methylpyridin-3-yl)piperidine-1-carboxamide, 4-(4-Bromo-2-oxo-2,3-dihydro-1H-1,3-benzodiazol-1-yl)-N-(5-chloro-6-methylpyridin-2-yl)piperidine-1-carboxamide, 4-(4-Bromo-2-oxo-2,3-dihydro-1H-benzo[d]imidazol-1-yl)-N-(3,4-dichlorophenyl)-2-methylpiperidine-1-carboxamide, 4-(4-Bromo-2-oxo-2,3-dihydro-1H-benzo[d]imidazol-1-yl)-N-(3,4-dichlorophenyl)-3-methylpiperidine-1-carboxamide, 4-(4-Chloro-2-oxo-2,3-dihydro-1H-1,3-benzodiazol-1-yl)-N-(3-methoxy-4-methylphenyl)piperidine-1-carboxamide, 4-(4-Methoxy-2-oxo-2,3-dihydro-1H-1,3-benzodiazol-1-yl)-N-(3-methoxy-4-methylphenyl)piperidine-1-carboxamide, N-(3-methoxy-4-methylphenyl)-4-[2-oxo-4-(1H-pyrazol-1-yl)-2,3-dihydro-1H-1,3-benzodiazol-1-yl]piperidine-1-carboxamide, N-(3-Chloro-4-methoxyphenyl)-4-(5-methoxy-2-oxo-2,3-dihydro-1H-1,3-benzodiazol-1-yl)piperidine-1-carboxamide, N-(3-Chloro-4-methoxyphenyl)-4-(5-fluoro-2-oxo-2,3-dihydro-1H-1,3-benzodiazol-1-yl)piperidine-1-carboxamide, 4-(4-Amino-2-oxo-2,3-dihydro-1H-1,3-benzodiazol-1-yl)-N-(3-chloro-4-methoxyphenyl)piperidine-1-carboxamide, N-(3-Chloro-4-methoxyphenyl)-4-[2-oxo-4-(propylamino)-2,3-dihydro-1H-1,3-benzodiazol-1-yl]piperidine-1-carboxamide, N-(3-Chloro-4-methoxyphenyl)-4-[4-(methylsulfanyl)-2-oxo-2,3-dihydro-1H-1,3-benzodiazol-1-yl]piperidine-1-carboxamide, 4-(4-Bromo-2-oxo-2,3-dihydro-1H-1,3-benzodiazol-1-yl)-N-(3-chloro-4-methoxyphenyl)-3-hydroxypiperidine-1-carboxamide, N-(3-Chloro-4-methoxyphenyl)-4-(5-cyano-2-oxo-2,3-dihydro-1H-1,3-benzodiazol-1-yl)piperidine-1-carboxamide, N-(3-Chloro-4-methoxyphenyl)-4-(4-fluoro-2-oxo-2,3-dihydro-1H-1,3-benzodiazol-1-yl)piperidine-1-carboxamide, or a pharmaceutically acceptable salt thereof.

9. A method of treating a cell proliferation disorder comprising administering to a patient in need thereof a therapeutically effective amount of a compound as defined in claim 1, including a pharmaceutically acceptable salt thereof, but without proviso (b).

10. A pharmaceutical composition comprising a compound as defined in claim 1, including a pharmaceutically acceptable salt thereof, but without proviso (b), and optionally one or more pharmaceutically acceptable excipient.

11. A combination product comprising:
(I) a compound as defined in claim 1, including a pharmaceutically acceptable salt thereof, but without proviso (b); and
(II) one or more other therapeutic agent that is useful in the treatment of a cell proliferation disorder,
wherein each of components (I) and (II) is formulated in admixture, optionally with one or more a pharmaceutically acceptable excipient.

12. A kit-of-parts comprising:
(a) a pharmaceutical formulation as defined in claim 10; and
(b) one or more other therapeutic agent that is useful in the treatment of a cell proliferation disorder, optionally in admixture with one or more pharmaceutically acceptable excipient,
which components (a) and (b) are each provided in a form that is suitable for administration in conjunction with the other.

13. A process for the preparation of a compound as defined in claim 1, comprising the step of:
(i) for compounds of formula I wherein $X^1$ represents O, reacting a compound of formula II

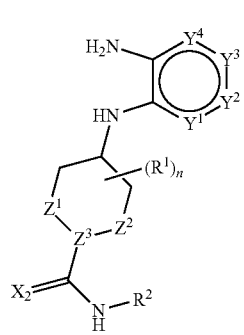

II wherein $R^1$, $R^2$, $X^2$, $Y^1$ to $Y^4$, $Z^1$ to $Z^3$, and n are as defined in claim 1, with phosgene or a suitable equivalent thereof, in the presence of a suitable solvent and a suitable base;
(ii) reaction of a compound of formula III

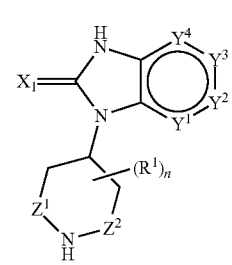

III wherein $R^1$, $X^1$, $Y^1$ to $Y^4$, $Z^1$, $Z^2$, and n are as defined in claim 1, with a compound of formula IV

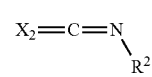

IV or a suitable salt thereof, wherein $X^2$ and $R^2$ are as defined in claim 1, in the presence of a suitable solvent and a suitable base;

(iii) reaction of a compound of formula III as defined herein with a compound of formula V

V wherein $R^2$ is as defined in claim 1, and with phosgene or a suitable equivalent thereof, in the presence of a suitable solvent and a suitable base; or (v) for compounds of formula I wherein at least one $R^3$ group represents an alkyl, aryl, heteroaryl or heterocycloalkyl group, reaction of a corresponding compound of formula I but wherein the relevant $R^3$ group instead represents $LG^1$, wherein $LG^1$ represents a suitable leaving group, with a compound of formula VII

VII wherein $R^3$ is as defined in claim 1 and $LG^2$ represents a suitable leaving group, in the presence of a suitable catalyst, and in the presence of a suitable solvent and a suitable base.

14. A compound as claimed in claim 1, wherein $Z^1$ and $Z^2$ both represent methylene.

15. A compound as claimed in claim 1, wherein $Z^1$ and $Z^2$ both represent methylene linked by an additional ethylene group.

16. A compound as claimed in claim 1, wherein $Z^1$ represents ethylene and $Z^2$ represents methylene.

17. A compound as claimed in claim 1, wherein the compound of formula I is a compound of formula Ic

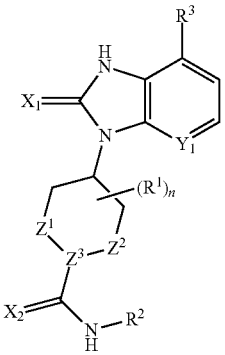

Ic wherein:
$Y^1$ represents CH; and
$R^1$ to $R^3$, $X^1$, $X^2$, $Z^1$ to $Z^3$, and n are as defined in claim 1.

18. A compound as claimed in claim 1, wherein $R^2$ represents:
 (i) phenyl optionally substituted by one to three groups independently selected from $A^4$,
 (ii) 5- or 6-membered monocyclic heteroaryl optionally substituted by one or two groups selected from oxy and $A^5$, or
 (iii) phenyl substituted with two adjacent groups which, together with the ring to which they are attached, form a bicyclic heteroaryl optionally substituted by one group selected from oxy and $A^6$.

19. A compound as claimed in claim 1, wherein each $R^3$ independently represents:
 (i) halo, $-NO_2$, $-CN$, $-R^{2a}$, $-OR^{2b}$, $-S(O)_qR^{2c}$, $-S(O)_rN(R^{2d})(R^{2e})$, $-N(R^{2f})SO_sR^{2g}$, $-N(R^{2h})(R^{2i})$, $-C(O)OR^{2j}$, or $-C(O)NR^{2k}R^{2l}$;
 (ii) phenyl optionally substituted by one or two groups independently selected from $A^7$; or
 (iii) heteroaryl selected from pyridinyl, pyrimidinyl, pyrazolyl, triazolyl, pyrazolopyrimidinyl, and pyrrolopyrazolyl, wherein said heteroaryl is optionally substituted by one or more groups selected from $A^8$.

20. A compound as claimed in claim 19, wherein said heteroaryl is optionally substituted by one group selected from $A^8$.

* * * * *

SEQUENCE LISTING

```
Sequence total quantity: 11
SEQ ID NO: 1             moltype = DNA  length = 23
FEATURE                  Location/Qualifiers
misc_feature             1..23
                         note = fluorophore-modified oligonucleotide containing OGG1
                           substrate
misc_feature             1
                         note = fluorescein substituted
modified_base            8
                         mod_base = OTHER
                         note = 8-oxo-2'deoxyadenosine
source                   1..23
                         mol_type = other DNA
                         organism = synthetic construct
SEQUENCE: 1
tctgccaaca ctgcgtcgac ctg                                                23

SEQ ID NO: 2             moltype = DNA  length = 23
FEATURE                  Location/Qualifiers
misc_feature             1..23
                         note = quencher-modified oligonucleotide
misc_feature             23
```

```
                     note = dabcyl substituted
source               1..23
                     mol_type = other DNA
                     organism = synthetic construct
SEQUENCE: 2
caggtcgacg cagtgctggc agt                                           23

SEQ ID NO: 3         moltype = DNA  length = 58
FEATURE              Location/Qualifiers
misc_feature         1..58
                     note = Non-targeting-f
source               1..58
                     mol_type = other DNA
                     organism = synthetic construct
SEQUENCE: 3
ccggcctaag gttaagtcgc cctcgctcga gcgagggcga cttaacctta ggttttttg    58

SEQ ID NO: 4         moltype = DNA  length = 58
FEATURE              Location/Qualifiers
misc_feature         1..58
                     note = Non-targeting-r
source               1..58
                     mol_type = other DNA
                     organism = synthetic construct
SEQUENCE: 4
aattcaaaaa cctaaggtta agtcgccctc gctcgagcga gggcgactta accttagg    58

SEQ ID NO: 5         moltype = DNA  length = 58
FEATURE              Location/Qualifiers
misc_feature         1..58
                     note = shOGG1#1-f
source               1..58
                     mol_type = other DNA
                     organism = synthetic construct
SEQUENCE: 5
ccggtggagt ggtgtactag cggatctcga gatccgctag tacaccactc catttttg    58

SEQ ID NO: 6         moltype = DNA  length = 58
FEATURE              Location/Qualifiers
misc_feature         1..58
                     note = shOGG1#1-r
source               1..58
                     mol_type = other DNA
                     organism = synthetic construct
SEQUENCE: 6
aattcaaaaa tggagtggtg tactagcgga tctcgagatc cgctagtaca ccactcca    58

SEQ ID NO: 7         moltype = DNA  length = 58
FEATURE              Location/Qualifiers
misc_feature         1..58
                     note = shOGG1#2-f
source               1..58
                     mol_type = other DNA
                     organism = synthetic construct
SEQUENCE: 7
ccgggtgtgc gactgctgcg acaagctcga gcttgtcgca gcagtcgcac actttttg    58

SEQ ID NO: 8         moltype = DNA  length = 58
FEATURE              Location/Qualifiers
misc_feature         1..58
                     note = shOGG1#2-r
source               1..58
                     mol_type = other DNA
                     organism = synthetic construct
SEQUENCE: 8
aattcaaaaa gtgtgcgact gctgcgacaa gctcgagctt gtcgcagcag tcgcacac    58

SEQ ID NO: 9         moltype = DNA  length = 58
FEATURE              Location/Qualifiers
misc_feature         1..58
                     note = shOGG1#3-f
source               1..58
                     mol_type = other DNA
                     organism = synthetic construct
SEQUENCE: 9
ccggtgtgcc cgtggatgtc catatctcga gatatggaca tccacgggca catttttg    58

SEQ ID NO: 10        moltype = DNA  length = 58
FEATURE              Location/Qualifiers
```

```
misc_feature         1..58
                     note = shOGG1#3-r
source               1..58
                     mol_type = other DNA
                     organism = synthetic construct
SEQUENCE: 10
aattcaaaaa tgtgcccgtg gatgtccata tctcgagata tggacatcca cgggcaca    58

SEQ ID NO: 11        moltype = DNA  length = 1359
FEATURE              Location/Qualifiers
misc_feature         1..1359
                     note = Sequence coding for mitochondrial isoform of OGG1
                     with silent mutations and a c-terminal FLAG-tag
source               1..1359
                     mol_type = other DNA
                     organism = synthetic construct
SEQUENCE: 11
atgcccgcaa gagctctctt gccaaggcga atgggtcatc gaacacttgc aagtaccccg    60
gccctgtggg catctatacc ttgcccacgg tccgaactgc gactggacct tgtgttgccc   120
agcggccaga gctttagatg gcgggaacaa agccccgcac attggtcagg agtcttggca   180
gaccaggtat ggactctcac gcaaactgag gagcagctcc attgcaccgt gtatagagga   240
gataagagtc aagccagcag gcccacgcct gacgaattgg aagcagtcag aaaatattt    300
caattggatg tcacattggc gcagctttac catcattggg gctcagtaga cagtcatttt   360
caggaagtag cacaaaagtt tcagggcgtc aggttgttga ggcaggaccc tattgagtgc   420
ctgttctcat tcatttgtag ttcaaacaat aatatcgcta ggatcactgg aatggttgaa   480
agactgtgtc aggcgtttgg cccgcgactt attcaattgg acgacgttac gtatcatgge   540
tttccctcac tccaagcatt ggcaggtcct gaggtagaag cacacctgcg gaagctgggc   600
ttgggctata gagcccgcta tgtgagtgct tcagcacgcg caatcctgga ggagcaagga   660
ggtctcgcgt ggctccaaca gcttcgagag agctcttatg aagaagcaca caagctctt    720
tgtattttgc caggggtagg aaccaaggtc gcggactgta tatgcctgat ggctttgatt   780
aaaccacagg cggtgcccgt tgacgtacac atgtggcaca tagctcagcg cgactattca   840
tggcatccaa caacaagtca agcaaagggg ccaagtccgc aaaccaacaa ggaattggga   900
aatttcttcc gctcactgtg gggtccctac gctggttggg cgcaggcagg cctccttgc   960
aatgcatttg atggccacca gcttctgcgt cctcttatct tctgccagga tcacctccga  1020
gaaggccccc ctatcgggag aggggattca caaggtgaag aactggaacc ccagcttccc  1080
tccagcctct cctccattcc ctatgggttc tgtgaccact gctggaccaa ggacgtggat  1140
gaccctcccc tagtcactca tccatcccct ggctccagag atggtcacat gacccaggcc  1200
tggccagtca aagtagtctc tcccctggcc acagtaattg gtcatgtgat gcaagccagc  1260
ttactagcac ttgcggccgc actcgagatg gactacaaag accatgacgg tgattataaa  1320
gatcatgaca tcgattacaa ggatgacgat gacaagtag                         1359
```